(12) United States Patent
Kristiansen

(10) Patent No.: US 9,072,776 B2
(45) Date of Patent: *Jul. 7, 2015

(54) ANTI-CANCER COMBINATION TREATMENT AND KIT-OF-PARTS

(75) Inventor: Bjørn Kristiansen, Frederikstad (NO)

(73) Assignee: Glycanova AS, Gamle Fredrikstad (NO)

( * ) Notice: Subject to any disclaimer, the term of this patent is extended or adjusted under 35 U.S.C. 154(b) by 424 days.

This patent is subject to a terminal disclaimer.

(21) Appl. No.: 11/917,521

(22) PCT Filed: Jun. 14, 2006

(86) PCT No.: PCT/DK2006/000339
§ 371 (c)(1),
(2), (4) Date: Sep. 12, 2008

(87) PCT Pub. No.: WO2006/133707
PCT Pub. Date: Dec. 21, 2006

(65) Prior Publication Data
US 2009/0143280 A1 Jun. 4, 2009

Related U.S. Application Data

(60) Provisional application No. 60/690,482, filed on Jun. 15, 2005, provisional application No. 60/761,743, filed on Jan. 25, 2006.

(30) Foreign Application Priority Data

Jun. 15, 2005 (DK) ................................. 2005 00882
Jan. 25, 2006 (DK) ................................. 2006 00116

(51) Int. Cl.
*A01N 65/00* (2009.01)
*A01N 43/04* (2006.01)
*A61K 31/70* (2006.01)
*A61K 45/06* (2006.01)

(52) U.S. Cl.
CPC ................ *A61K 45/06* (2013.01); *A61K 31/70* (2013.01)

(58) Field of Classification Search
CPC .... A61K 31/70; A61K 45/06; A61K 2300/00
See application file for complete search history.

(56) References Cited

U.S. PATENT DOCUMENTS

| | | |
|---|---|---|
| 3,943,247 A | 3/1976 | Komatsu |
| 3,987,166 A | 10/1976 | Komatsu |
| 4,163,780 A * | 8/1979 | Ishida et al. ............... 424/116 |
| 4,174,388 A | 11/1979 | McAleer et al. |
| 4,247,541 A | 1/1981 | Ishida et al. |
| 4,454,289 A | 6/1984 | Nakajima et al. |
| 4,461,760 A | 7/1984 | Sugano |
| 4,617,379 A | 10/1986 | Dobkin et al. |
| 4,769,363 A | 9/1988 | Misaki et al. |
| 4,851,395 A | 7/1989 | Ueno et al. |
| 4,962,094 A | 10/1990 | Jamas et al. |
| 5,032,401 A | 7/1991 | Jamas et al. |
| 5,223,491 A | 6/1993 | Donzis |
| 5,322,841 A | 6/1994 | Jamas et al. |
| 5,397,773 A | 3/1995 | Donzis |
| 5,488,040 A | 1/1996 | Jamas et al. |
| 5,504,079 A | 4/1996 | Jamas et al. |
| 5,519,009 A | 5/1996 | Donzis |
| 5,532,223 A | 7/1996 | Jamas et al. |
| 5,576,015 A | 11/1996 | Donzis |
| 5,607,677 A | 3/1997 | Jamas et al. |
| 5,622,939 A | 4/1997 | Jamas et al. |
| 5,622,940 A | 4/1997 | Ostroff |
| 5,633,369 A | 5/1997 | Jamas et al. |
| 5,641,761 A | 6/1997 | Takahashi |
| 5,663,324 A | 9/1997 | James et al. |
| 5,702,719 A | 12/1997 | Donzis |
| 5,705,184 A | 1/1998 | Donzis |
| 5,741,495 A | 4/1998 | Jamas et al. |
| 5,744,187 A | 4/1998 | Gaynor |
| 5,756,318 A | 5/1998 | Kosuna |
| 5,783,569 A | 7/1998 | Jamas et al. |
| 5,811,542 A | 9/1998 | Jamas et al. |
| 5,817,643 A | 10/1998 | Jamas et al. |
| 5,849,720 A | 12/1998 | Jamas et al. |
| 5,934,012 A | 8/1999 | Holtz et al. |
| 6,020,324 A | 2/2000 | Jamas et al. |
| 6,084,092 A | 7/2000 | Wakshull et al. |
| 6,090,938 A | 7/2000 | Wakshull et al. |
| 6,110,692 A | 8/2000 | Wakshull et al. |
| 6,117,850 A | 9/2000 | Patchen et al. |
| 6,120,772 A | 9/2000 | Ito et al. |
| 6,143,731 A | 11/2000 | Jamas et al. |
| 6,294,321 B1 | 9/2001 | Wakshull et al. |
| 6,369,216 B1 | 4/2002 | Patchen et al. |
| 6,413,715 B2 | 7/2002 | Wakshull et al. |
| 6,440,448 B1 | 8/2002 | Intelisano |
| 6,630,310 B1 | 10/2003 | Wakshull et al. |
| 6,692,739 B1 | 2/2004 | Patti et al. |

(Continued)

FOREIGN PATENT DOCUMENTS

| | | |
|---|---|---|
| CN | 1082551 | 2/1994 |
| CN | 1093714 | * 10/1994 |

(Continued)

OTHER PUBLICATIONS

EFSA Panel on Dietetic Products, Nutrition and Allergies (NDA); Scientific Opinion on the safety of "Lentinus edodes extract" as a Novel Food ingredient. EFSA Journal 2010; 8(7):1685.*

(Continued)

*Primary Examiner* — Doug Schultz

(74) *Attorney, Agent, or Firm* — Posternak Blankstein & Lund LLP

(57) ABSTRACT

In one aspect the present invention relates to pharmaceutical kits of parts suitable for treating neoplastic diseases such as cancer comprising an anti-cancer medicament, a Basidiomycete bioactive agent in solid or liquid form, and, optionally instructions for a dosing regime.

10 Claims, 2 Drawing Sheets

(56) References Cited

U.S. PATENT DOCUMENTS

Figure 1:
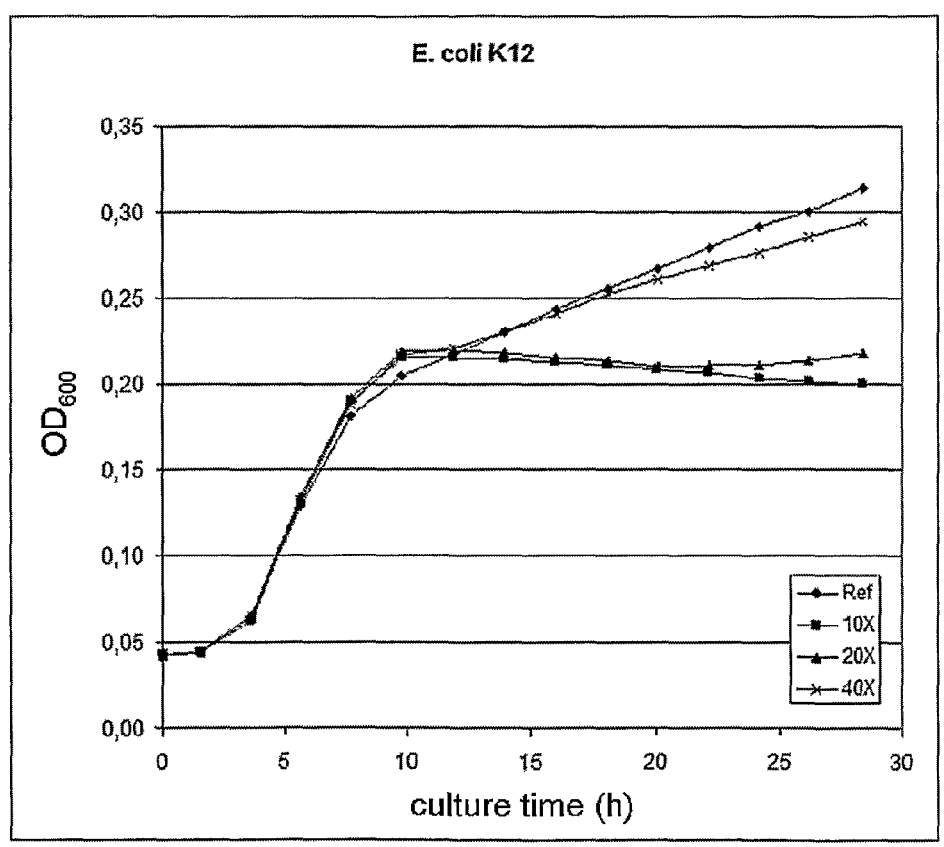

| | | | |
|---|---|---|---|
| 7,022,685 B2 | 4/2006 | Patchen et al. | |
| 7,514,085 B2* | 4/2009 | Kristiansen | 424/195.15 |
| 7,682,615 B2* | 3/2010 | Kristiansen | 424/195.15 |
| 2001/0051717 A1 | 12/2001 | Wakshull et al. | |
| 2002/0164317 A1 | 11/2002 | Gorsek | |
| 2002/0164773 A1 | 11/2002 | Wasser | |
| 2003/0208796 A1 | 11/2003 | Song et al. | |
| 2003/0229068 A1* | 12/2003 | Huang et al. | 514/210.21 |
| 2004/0001856 A1 | 1/2004 | Jin et al. | |
| 2005/0069989 A1 | 3/2005 | Kim et al. | |
| 2005/0158258 A1 | 7/2005 | Fisher | |
| 2005/0245480 A1 | 11/2005 | Ostroff et al. | |
| 2006/0013825 A1 | 1/2006 | Kristiansen | |
| 2008/0063650 A1 | 3/2008 | Yan | |
| 2008/0103112 A1 | 5/2008 | Magee et al. | |
| 2008/0108114 A1 | 5/2008 | Cox et al. | |
| 2008/0167268 A1 | 7/2008 | Yan | |
| 2009/0005340 A1* | 1/2009 | Kristiansen | 514/54 |
| 2010/0086647 A1 | 4/2010 | Kristiansen | |

FOREIGN PATENT DOCUMENTS

| | | |
|---|---|---|
| CN | 1093714 A1 | 10/1994 |
| CN | 1269423 | 11/2000 |
| CN | 1297994 | 6/2001 |
| CN | 1314417 | 9/2001 |
| CN | 1477130 | 2/2004 |
| CN | 1490016 | 4/2004 |
| CN | 1528335 | 9/2004 |
| CN | 1765935 | 3/2006 |
| EP | 0292601 | 11/1988 |
| EP | 0298706 | 1/1989 |
| EP | 0370673 | 5/1990 |
| EP | 1155623 | 11/2001 |
| GB | 133513 | 9/1973 |
| JP | 01132315 | 5/1989 |
| JP | 06172217 | 6/1994 |
| JP | 7173070 | 7/1995 |
| JP | 63296662 | 12/1998 |
| JP | 11080206 | 3/1999 |
| JP | 2001078714 | 3/2001 |
| JP | 2002060344 | 2/2002 |
| JP | 2004300438 | 3/2004 |
| KR | 470734 | 2/2005 |
| KR | 2003097062 | 2/2005 |
| SU | 1244179 | 7/1986 |
| WO | WO 8912106 | 12/1989 |
| WO | WO 9106307 | 5/1991 |
| WO | WO 9615659 | 5/1996 |
| WO | WO 0032212 | 6/2000 |
| WO | WO 0032213 | 6/2000 |
| WO | WO 0054795 | 9/2000 |
| WO | WO 0065029 | 11/2000 |
| WO | WO 0127305 | 4/2001 |
| WO | WO 0151070 | 7/2001 |
| WO | WO 0164057 | 9/2001 |
| WO | WO 0182935 | 11/2001 |
| WO | WO 0207708 | 1/2002 |
| WO | WO 02087603 | 11/2002 |
| WO | WO 02098440 | 12/2002 |
| WO | WO 03020944 | 3/2003 |
| WO | WO 03043440 | 5/2003 |
| WO | WO 03/049117 | 6/2003 |
| WO | WO 03080077 | 10/2003 |
| WO | WO 2004075907 | 9/2004 |
| WO | WO 2004100965 | 11/2004 |
| WO | WO 2005/044182 | 5/2005 |
| WO | WO 2006/007848 | 1/2006 |
| WO | WO 2006/133707 | 12/2006 |

OTHER PUBLICATIONS

Abstract: Liu et al., Fractionation of extracellular polysaccharide from *Agaricus blazei* murill and its antitumor activity, 27(1), pp. 27-29, 2001.

Abstract: Liu et al., "Study on antitumor activity of *Agaricus blazei*", Shipin Gongye Kenji (2001), 22(4), 10-11.
Abstract: Osaki, Y. et al., Antimutagenic and bactericidal substances in the fruit body of a Basidomycete *Agaricus blazei*, Jun. 17, Yakugaku Zasshi, vol. 114(5), pp. 342-50, 1994.
Aoki et al.: "Antibodies to HTVLVI and III in sera from two Japanese patients, one with possible pre-aids" The Lancet, Oct. 20, pp. 936-937,1984.
Aoki, "Lentinan", Immune Modulation Agents and Their Mechanisms, Editors: Fenichel and Chirigos, Marcel Dekker, Inc. 1984, pp. 63-77.
Borchers A., et al. Mushrooms, Tumors, and Immunity: An update., Experimental Biology and Medicine, 229:393-406 (2004).
Brauer et al. Effects of Management on the Yield and High-Molecular-weight Polysaccharide Content of Shiitake (*Lentinus edodes*) Mushrooms. J Agric Food Chem 2002, pp. 5333-5337, vol. 50.
Budavari. The Merck Index an encyclopedia of chemicals, drugs and biologicals. 1996, p. 927, right-hand column.
Chang R. Functional properties of edible mushrooms. Nutrition Reviews, vol. 54, No. 11. Nov. 1996: s91-s93.
Chihara et al., "Fractionation and Purification of the Polysaccharides with Marked Antituniour Activity, Especially Lentinan, from *Lentinan edodes* (Berk.) Sing. (an Edible Mushroom)", Cancer Research 30, 2776-2781, Nov. 1970.
Chihara et al.: "Antitumour Polysaccharide derived Chemically from Natural Glucan (Pachyman)" Nature, vol. 225, pp. 943-944, Mar. 7, 1970.
Chihara, "The antitumor polysaccharide Lentinan: an overview", pp. 1-16, in Aoki, et al.,eds., *Manipulation of Host Defence Mechanisms*, (Excerpta Medica 1981).
Elisashvili et al. Extracellular Polysaccharide Production by Culinary—Medicinal Shiitake Mushroom *Lentinus edodes* (Berk.) Singer and *Pleurotus* (Fr.) P. Karst. Species Depending on Carbon and Nitrogen Source. International Journal of Medicinal Mushrooms, 2004, pp. 165-172, vol. 6.
Fan et al., "Production of polysaccharide by culinary-medicinal mushroom *Agaricus brasiliensis* S. Wasser et al. LPB 03 (Agaricomycetideae) in submerged fermentation and its antitumor effect", International Journal of Medicinal Mushrooms, vol. 5, pp. 17-23, 2003.
Fan et al: "Effect of nutritional and environmental conditions on the production of exo-polysaccharide of *Agaricus brasiliensis* by submerged fermentation and its antitumor activity" LWT, vol. 40, Oct. 20, 2005, pp. 30-35.
Fujii T. et al., "Isolation and characterization of a new antitumour polysaccharide, KS-2, extracted from culture mycelia of *Lentinus edodes*", The Journal of Antibiotics. vol. 31, No. 11, pp. 1079-1090.
Fujimiya et al., Selective Tumoricial effect of soluble proteoglucan extracted from the basidiomycete, *Agaricus blazei* Murill, mediated via natural killer cell activation and apoptosis, Cancer Immunol Immunother (1998) 46: 147-159.
Fujimiya et al., Tumor-specific cytocidal and immunopotentiating effects of relatively low molecular weight products derived from the basidiomycete, *Agaricus blazei* Murill. Anticancer Res. Jan.-Feb. 1999;19(1A):113-8.
Gonzaga et al., "Isolation and characterisation of polysaccharides from *Agaricus blazei* Murill", Carbohydrate polymers 2005, vol. 60, Iss 1, p. 43-49.
Griffin et al., "Free lipids and carbohydrates of *Agaricus bisporus* mycelium", Biochem J. Sep. 1970; 119(3):11P-12P.
Guo et al. Effects of mushroom and herb polysaccharides, as alternatives for an antibiotic, on growth performance of broilers. British Poultry Science vol. 45, No. 5, p. 684-694, Oct. 2004.
Guo et al., "Immunoactive, medicinal properties of mushroom and herb polysaccharides and their potential use in chicken diets", Worlds poultry science journal 59 (4): 427-440 Dec. 2003 (Abstract).
Guo FC, et al."Effects of mushroom and herb polysaccharides, as alternatives for an antibiotic, on the cecal microbial ecosystm in broiler chickens" Poultry Science 83(2): 175-182 Feb. 2004 (abstract).
Hamuro J. et al., "carboxymethylpachymaran, a New Water Soluble Polysaccharide with Marked Antitumour Activity", Nature vol. 233, Oct. 15, pp. 486-488, 1971.

(56) References Cited

OTHER PUBLICATIONS

Harvey, L et al. Production of Lentinan by submerged cultivation of *Lentinus edodes* (Berk.) Sing. Int. Jour. of Medicinal Mushrooms, vol. 3, p. 161 (2001) Abstract.

Hatvani N. Antibacterial effect of the culture fluid of *Lentinus edodes* mycelium grown in submerged liquid culture. Int J. Antimicrob Agents, 17, 1, 71-74, 2001.

Hideo Matsuoka, et al. Lentinan potentiates immunity and prolongs the survival time of some patients. Anticancer Research 17: 2751-2756 (1997).

Hsieh et al. Production of polysaccharides of *Ganoderma lucidum* (CCRC36021) by reusing thin stillage. Process Biochemistry 2005 vol. 40, No. 2, Feb. 2005, pp. 909-916.

Ito et al., "Antitumor effects of a new polysaccharide-protein complex (ATOM) prepared from *Agaricus blazei* (Iwade strain 101) "Himematsutake" and its mechanisms in tumor-bearing mice", Anti-cancer research 17:277-284 (1997).

Jin Y et al., "Antitumor activities of heteropolysaccharides of *Poria cocos* mycelia from different strains and culture media", Carbohydrate Research 2003, 338: 1517-1521.

Jong SC and Birmingham JM. Medicinal Benefits of the Mushroom Ganoderma. Advances in applied Microbiology, 1992, vol. 37, p. 101-134.

Jong, S.C., and Birmingham, J.M. "Medicinal and Therapeutic Value of the Shiitake Mushroom", Advances in applied microbiology, 1993, vol. 39, pp. 153-184.

Kawagishi et al., Formolysis of a potent antitumor (1-6)-beta-D-glucan-protein complex from *Agaricus blazei* fruiting bodies and antitumor activity of the resulting products. Carbohydr polymers 12:393-403, 1990.

Kawazoe T, et al. "Influence of an excessive supply of vitamin D-1 fortified shiitake mushroom on laying hens" Journal of the Japanese Society for food and science technology—Nippon Shokuhin Kagaku Kaishi 44(4) :300-305, 1997 (Abstract).

Khondkar et al. Sugar profile of extracellular polysaccharides from different *Tremella* species. International Journal of Food Microbiology, 2002, pp. 121-129, vol. 79, Elsevier.

Kim D-H et al: "Production of a hypoglycemic, extracellular polysaccharide from.the submerged culture of the mushroom, *Phellinus linteus*" Biotechnology Letters, Kew, Surrey, GB, vol. 23, Apr. 2001, pp. 513-517.

Kimura et al., "Isolation of an anti-angiogenic substance from *Agaricus blazei* Murill: Its antitumor and antimetastatic actions", Cancer Science 2004, vol. 95, Iss 9, p. 758-764.

Kimura, Y: In Vivo 2005, vol. 19, Iss 1, p. 37-60; "New Anticancer agents: In Vitro and In Vivo Evaluation of the antitumor and Antimetastatic Actions of Various Compounds Isolated from Medicinal Plants".

Kobayashi et al., "Suppressing effects of daily oral supplementation of beta-glucan extracted from *Agaricus blazei* Murill on spontaneous and peritoneal disseminated metastasis in mouse model", J Cancer Res Clin Oncol. May 10, 2005, vol. 131, pp. 527-538.

Kuo et al., Journal of Laboratory and clinical medicine 2002, vol. 140, Iss 3, p. 176-187; "Cell Cycle progression and cytokine gene expression of human peripheral blood mononuclear cells modulated by *Agaricus blazei*".

Lee et al. Submerged culture conditions for the production of mycehal biomass and exopolysaccharides by the edible Basidiomycete *Grifola frondosa*. Enzyme and Microbial Technology 2004, pp. 369-376, vol. 35, Elsevier.

Lee, et al. "Structural Analysis of the Antitumor Active Exo-polysaccharide Produced by Submerged Cultivation of *Ganoderma lucidum* Mycelium", The Korean Journal of Mycology, vol. 27, No. 1, pp. 76-81, Feb. 1999. English abstract.

Li, et al., "Isolation, Purification and Bioactivities of Exopoly Saccharides from Fermented Broth of *Ganoderma lucidum*", Acta Microbiologica Sinica, vol. 40, No. 2, pp. 217-220, Apr. 2000. English abstract only.

Liu et al., "Fractionation of extracellular polysaccharide from *Agaricus blazei* murill and its antitumor activity", Shipin Yu Fajiao Gongye (2001), 27(11), 27-29, Abstract.

Lobanok et al. Composition and biological activity of submerged mycelium of the xylotrophic basidiomycete *Lentinus edodes*. Applied Biochemistry and microbiology, vol. 39, No. 1, 2003, p. 60-64 (translated from Priki Biokhi Mikkrobiol Jan.-Feb. 2003, 39(1):69-73 (abstract)).

MediMush Science Documents. C. Immune modifiers from the shiitake mushroom. Downloaded from Medimush website Jun. 2005, pp. 1-9, Oct. 2004.

MediMush Science Documents. H. Lentinan taken orally. Downloaded from Medimush website Jun. 2005 (www.medimush.dk), pp. 1-5, Oct. 2004.

MediMush Science Documents. K. Tuberculosis. Downloaded from Medimush website Jun. 2005 (www.medimush.dk), pp. 1-2, Oct. 2004.

MediMush Science Documents. L. HIV/AIDS. Downloaded from Medimush website Jun. 2005 (www.medimush.dk), pp. 1-3, Oct. 2004.

Mizuno et al., "Anti-tumor polysaccharide from the mycelium of liquid-cultured *Agaricus blazei* mill", Biochem Mol Biol Int. Apr. 1999;47(4):707-14.

Mizuno T. The extraction and development of antitumor-active polysaccharides from medicinal mushrooms in Japan [Review]. International Journal of Medicinal Mushrooms 1999;1:9-29.

Nikl L et al. "Influence of 7 immunostimulants on the immne-response of Coho Salmon to *Aeromonas-salmonicida*", Diseases of Aquatic organisms 12(1): 7-12 Dec. 5, 1991 (Abstract only).

Ohno et al., Antitumor beta glucan from the cultured fruit body of *Agaricus blazei*. Biol Pharm Bull. Jul. 2001:24(7):820-8.

Ooi et al., Current Medicinal Chemistry 2000, vol. 7, Iss 7, p. 715-729; "Immunomodulation and Anti-Cancer Activity of Polysaccharide-Protein Complexes".

Peng Y et al, "Structure and antitumor activity of extracellular polysaccharides from mycelium", Carbohydrate Polymers 2003, 54, 297-303.

S. W. Kim, et al. Mycelial growth and exo-biopolymer production by submerged culture of various edible mushrooms under different media. Letters in applied microbiology 2002, 34, 56-61.

Sasaki et al.: "Further study of the structure of lentinan, an anti-tumor polysaccharide from *Lentinus edodes*" Carbohydrate Research, 47 (1976) 99-104.

Sermanni, et al. The production of exo-enzymes by *Lentinus edodes* and *pleurotus ostreatus* and their use for upgrading corn straw. Bioresour-technol, 48, 2, 173-178 1994.

Shu CH; Wen BJ; Lin KJ "Monitoring the polysaccharide quality of *Agaricus blazei* in submerged culture by examining molecular weight distribution and TNF-alpha release capability of macrophage cell line RAW 264.7" Biotechnology Letters 2003, vol. 25, Iss 24, pp. 2061-2064.

Shu et al: "Effects of culture pH on the production of bioactive polysaccharides by *Agaricus blazei* in batch cultures" Journal of Chemical Technology and Biotechnology, vol. 79, 2004, pp. 998-1002.

Song CH, et al. Anti-complementary activity of endo-polymers produced from submerged mycelial culture of higher fungi with particular reference to *Lentinus edodes*. Biotechnology Letters, vol. 20, No. 8, Aug. 1998, pp. 741-744.

Sorimachi et al., Cell structure and function 2001, vol. 26, Iss 2, p. 103-108, "Secretion of TNF-alpha, IL-8 and Nitric Oxide by Macrophages Activated with *Agaricus blazei* Murill fractions in vitro".

Suzuki et al., "Structural Characterization of the Immunoactive and Antiviral Water-solubilized Lignin in an Extract of the Culture Medium of Lentinus edodes Mycelia (LEM)", Agric. Biol. Chem., 54 (2), 479-487, 1990.

Suzuki et al.: "Induction of endogenous lymphokine-activated killer activity by combined administration of lentinan and interleukin 2" Int. J. Immunopharmac., vol. 12, No. 6, pp. 613-623, 1990.

Smith, et al., *Medicinal Mushrooms: Their therapeutic properties and current medical usage with special emphasis on cancer treat-*

(56) References Cited

OTHER PUBLICATIONS

*ments*, "Chapter 5: Extraction, development and chemistry of anticancer compounds from medical mushrooms", pp. 80-105, 2001.

Takaku et al., Isolation of an antitumor compound from *Agaricus blazei* Murill and its mechanism of action. J Nutr. May 2001;131(5):1409-13.

Tan YH and Moore D "Comienient and effective methods for in vitro cultivation of mycelium and fruiting bodies of *Lentinus edodes*" Mycol. Res., 1992, 96(12): 1077-1084, abstract, materials & methods, and results & discussion.

The term "Extracellular"—Merriam-Webster Online Dictionary, at www.m-w.com. p. 1.

Togami M et al., "Studies on basidiomycetes I antitumor polysaccharide from bagasse medium on which mycelia of *Lentinus edodes* (Berk.) Sing. had been grown", Chem Pharm Bull 1982, 30: 1134-1140.

Tokimoto, K.: "Lysis of the mycelium of *Lentinus edodes* caused by mycolytic enzymes of *Trichoderma harzianum* when the two fungi were in an antagonistic state", Trans. Mycol. Soc. Japan 23: 13-20, 1982.

Van Nevel et al. "The influence of *Lentinus edodes* (Shiitake muhroom) preparations on bacteriological and morphological aspects of the small intestine in piglets" Archives of animal nutrition—archive fur tierernahrung 57(6):399-412, Dec. 2003 (abstract).

Wang H et al, "Lectins from mushrooms", Mycol Res 1998; 102:897-906.

Wang, Tze-Hua, et al., "*Lentinus* Products and Patents in China". Medimush internal document, compiled from information retrieved from internet Aug.-Sep. 2006.

Wasser SP and Weis AL, Medicinal properties of substances occurring in higher basidiomyces mushrooms: current perspectives (Review). International Journal of Medicinal Muchrooms, 1999, vol. 1 : 31-62.

Wasser: "Medical mushrooms as a source of antitumor and immunomodulating polysaccharides" Applied Microbial Biotechnology, vol. 60, 2002, pp. 258-274.

Xueyu Z, et al. The study of the effect of LNT and HEP of *Lentinus edodes* on the immune of normal mice. (Guangxi institute of traditional Chinese medicine and material medica).

Yang, et al. Hypoglycemic Effect of a *Lentinus edodes* exo-polymer produced from a submerged mycelial culture. Biosci Biotechnol Biochem, 66, 5, 937-42, 2002.

Yang, et al., "Hepatoprotective Effect of exo-polysaccharide Produced from Submerged Mycelial Culture of *Ganoderma lucidum* WK-003 by using Industrial Grade Medium", The Korean journal of Mycology, vol. 27, No. 1, pp. 82-86, Feb. 1999. English abstract.

Yang, et al., "The influence of environmental conditions on polysaccharide formation by *Ganoderma lucidum* in submerged cultures", Process Biochemistry, vol. 33, No. 5, pp. 547-553, 1998.

Yoshiki Yamamoto, et al., Immunopotentiating activity of the water-soluble ligning rich fraction prepared from LEM—the extract of the solid culture medium of *Lentinus edodes* mycelia. Biosci, biotech, biochem., 61 (11), 1909-1912, 1997.

Zhang M et al., "Molecular weight and anti-tumor activity of the water-soluble polysaccharides isolated by hot water and ultrasonic treatment from the sclerotia and mycelia of pleurotus tuber-regium", Carbohydrate Polymers, available online Mar. 12, 2004, 56:123-128.

Zhang, L., et al. "Correlation between antitumor activity, molecular weight, and conformation of lentinan" Carbohydrate Research, 340, (2005), 1515-1521.

Zheng Xueyu et al. Zhongcaoyao, abstract, vol. 16, No. 11, 1985, p. 494-497.

Zhou Weidong et al. Junwu Xitong, vol. 16, No. 3, 1997, p. 202-207.

Zorn et al. Enzymatic hydrolysis of carotenoid esters of marigold lowers (*Tagetes erecta* L.) and red paprika (*Capsicum annuum* L.) by commercial lipases and Pleurotus sapidus extracellular lipase. Enzyme and Microbial Technology, 2003, pp. 623-628, vol. 32.

Kristiansen, Preliminary Amendment, U.S. Appl. No. 11/914,318, mailed Dec. 1, 2009.

Kristiansen, Preliminary Amendment, U.S. Appl. No. 11/917,516, mailed Jul. 31, 2008.

WIPO, International Preliminary Report on Patentability, PCT/DK2006/000339, Dec. 17, 2007.

Yu, et al., "Macrophage Stimulating Activity of Exo-Biopolymer from Submerged Culture of *Lentinus edodes* with Rice Bran", *J. Microbtol. Biotechnol.*, vol. 14(4), pp. 658-664, 2004.

USPTO, Non-Final Office Action, mailed Apr. 15, 2011 on Application of Kristiansen, U.S. Appl. No. 11/917,516.

Chihara, "Fractionation and Purification of the Polysaccharides with Marked Antitumor Activity, Especially Lentinan, from *Lentinus edodes* (Berk.) Sing. (an Edible Mushroom)," National Cancer Center Research Institute, vol. 30, pp. 2776-2781 (1970).

\* cited by examiner

ANTI-CANCER COMBINATION TREATMENT AND KIT-OF-PARTS

All patent and non-patent references cited in the present application are hereby incorporated by reference in their entirety.

TECHNICAL FIELD OF THE INVENTION

The present invention relates to pharmaceutical kits of parts suitable for treating neoplastic diseases such as cancer.

BACKGROUND OF THE INVENTION

Medicinal Mushrooms

Mushrooms have been used for medicinal purposes for centuries in many cultures. Several members of the Basidiomycete mushroom class, such as for e.g. members of the *Agaricus* mushroom family have been used for medicinal and health-related purposes.

A number of researchers have suggested anticancer, antitumour or antimutagenic properties of e.g. *Agaricus* mushrooms (Kimura, Y: In Vivo 2005, Vol 19, Iss 1, p 37-60; Kim et al., Food Science and Biotechnology 2004, vol 13, Iss 6, p 852; Kim et al., Food Science and Biotechnology 2004, vol 13, Iss 3, p 347-352; Guterrez et al., Texicology in Vitro 2004, Vol 18, Iss 3, p 301-309; Ribeiro et al., Mutation Research Reviews in Mutation Research 2003, Vol 54, Iss 2-3, p 195.201; Pinheiro et al., Food and Chemical Toxicology 2003, Vol. 41, Iss 11, p 1543-1550; (Inhibiting tumour growth) Lee et al., Experimental Animals 2003, Vol. 52, p 371-375; Luiz et al., Mutation research-Fundamental and Molecular Mechanisms of Mutagenesis 2003, Vol. 528, Iss 1-2, p 75-79; Bellini et al., Texicology in Vitro 2003, Vol 17, Iss 4, p 465-469; Ashida et al., Food Factors in Health Promotion and Disease Prevention 2003, Vol. 851, p 235-248; (antigenotoxic effect) de Oliveira et al., Food and Chemical Toxicology 2002, Vol. 40, Iss 12, p 1775-1780; Kuo et al., Journal of Laboratory and clinical medicine 2002, Vol. 140, Iss 3, p 176-187; Oshiman et al., Planta Medica 2002, Vol. 68, Iss 7, p 610-614; Meloni et al., Mutation Research—Genetic Toxicology and Environmental Mutagenesis 2001, Vol. 496, Iss 1-2, p 5-13; Osaki et al., Yakugaku Zasshi—Journal of the Pharmaceutical Society of Japan 1994, Vol. 114, Iss 5, p 342-350; Itoh et al., Japanese Journal of Pharmacology 1994, Vol. 66, Iss 2, p 265-271.; Ito et al., Anticancer Research 1997, Vol. 17, Iss 1A, p 277-284; Fujimiya et al., Cancer Immunology Immunotherapy 1998, Vol. 46, Iss 3, p 147-159; Fujimiya et al., Journal of the Japanese Society for Food Science and Technology—Nippon Shokuhin Kagaku Kogaku Kaishi 1998., Vol 45, Iss 4, p 246-252; Ebina et al., Biotherapy 1998, Vol. 11, Iss 4, p 259-265; Fujimiya et al., Anticancer Research 1999, Vol. 19, Iss 1A, p 113-118; Mizuno et al., Biochemistry and Molecular Biology International 1999, Vol. 47, Iss 4, p 707-717; Takaku et al., Journal of Nutrition 2001, Vol. 131, Iss 5, p 1409-1413; Ohno et al., Biological and Pharmaceutical Bulletin 2001, Vol. 24, Iss 7, p 820-828; Delmanto et al., Mutation Research—Genetic Toxicology and Environmental Mutagenesis 2001, Vol. 496, Iss 1-2, p 15-21).

There is however a surprising paucity of epidemiologic and experimental studies that address the biologic activities of mushrooms after oral administration to animals or humans (Borchers et al., "Mushrooms, Tumors and Immunity: an update", Experimental Biology and Medicine 229:393-406).

SUMMARY OF THE INVENTION

The present invention relates to a pharmaceutical kit of parts comprising
 a) an anti-cancer medicament,
 b) a Basidiomycete bioactive agent in solid or liquid form, and, optionally
 c) instructions for a dosage regime for said kits of parts.

In another aspect, the present invention relates to a method of treatment comprising the step of administering said pharmaceutical kit of parts simultaneously (optionally in a co-formulation) or sequentially according to a set dosage regime.

Another aspect of the present invention relates to use of a medicament, such as an anti-cancer medicament, and a Basidiomycete bioactive agent in solid or liquid form in the manufacture of a kit of parts for the treatment of an individual in need thereof, such as an individual suffering from, or at risk of suffering from, a neoplastic disease such as cancer.

Another aspect of the present invention relates to a method for enhancing a therapeutic effect of an anti-cancer drug, comprising co-administering (simultaneously or in any order) with said anti-cancer drug (such as any of the anti-cancer drugs described herein) a Basidiomycete bioactive agent (such as any of the Basidiomycete bioactive agents described herein).

Bioactive agents produced by *Agaricus* sp. (any basidiomycetous fungal species of the genus *agaricus* of the family agaricaceae and the order agaricales and the subclass agaricomycetidae), *Schizophyllum* sp. (any basidiomycetous fungal species of the genus *schizophyllum* of the family schizophyllaceae and the order agaricales and the subclass agaricomycetidae), *Lentinus* sp. (any basidiomycetous fungal species of the genus *lentinus* of the family polyporaceae and the order polyporales and the subclass agaricomycetidae (*L. edodes* is also termed *Lentinula edodes*, which is placed in the family Marasmiaceae, in the order Agaricales and the subclass agaricomycetidae)), *Trametes* sp. (any basidiomycetous fungal species of the genus *trametes* of the family polyporaceae and the order polyporales and the subclass agaricomycetidae), *Ganoderma* sp. (any basidiomycetous fungal species of the genus *ganoderma* of the family ganodermataceae and the order polyporales and the subclass agaricomycetidae), and *Grifola* sp. (any basidiomycetous fungal species of the genus *grifola* of the family meripilaceae and the order polyporales and the subclass agaricomycetidae) are preferred in one embodiment of the present invention.

FIGURE LEGENDS

FIG. 1: bacteriostatic effect of different dilutions (1:10, 1:20 and 1:40) of the bioactive agent obtained by the method as described in example 1 on *E. coli* K12. A culture without the bioactive agent was used as control (Ref). The experiment is described in detail in Example 4.

Figure 2:
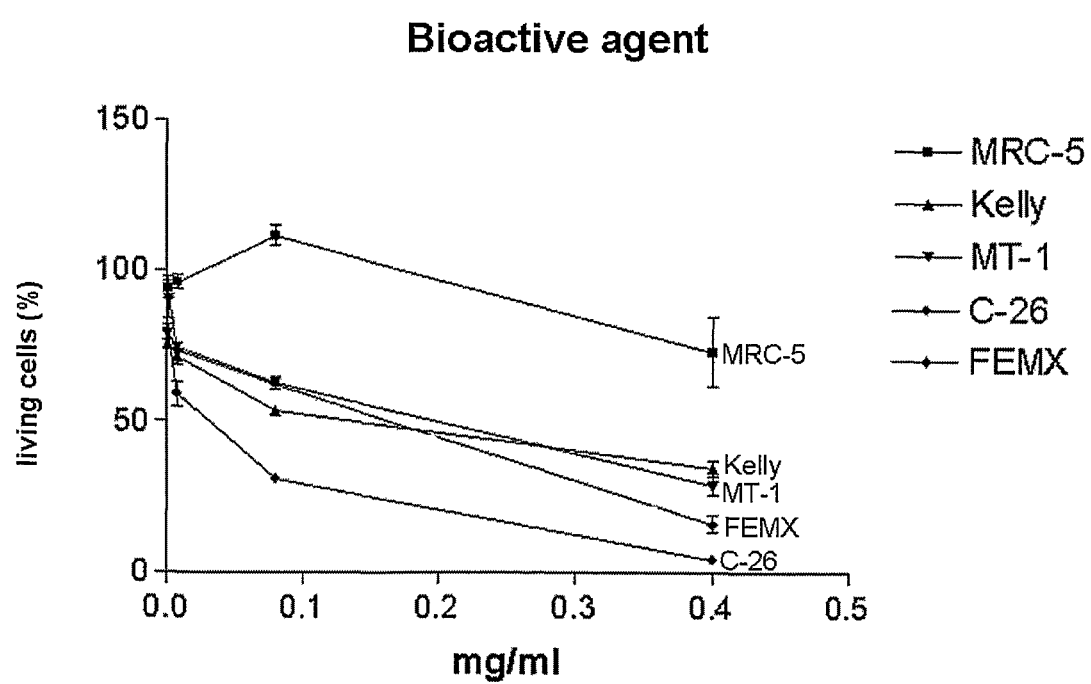

FIG. 2: cancer-cell specific cytotoxicity of different concentrations of Lentinex—comprising an embodiment of the bioactive agent of the present invention—on 4 different human and mouse cancer cell lines. The MRC-5 cell line from normal human fetal lung fibroblasts was used as control. The experiment is described in detail in Example 5.

DEFINITIONS

Mycelium: Mass of hyphae constituting the body (thallus) of the fungus.

*Agaricus* sp.: A basidiomycetous fungal species of the genus *agaricus* of the family agaricaceae and the order agaricales and the subclass agaricomycetidae.

*Schizophyllum* sp.: A basidiomycetous fungal species of the genus *schizophyllum* of the family schizophyllaceae and the order agaricales and the subclass agaricomycetidae.

*Lentinus* sp.: A basidiomycetous fungal species of the genus *lentinus* of the family polyporaceae and the order polyporales and the subclass agaricomycetidae. *L. edodes* is also termed *Lentinula edodes*, which is placed in the family Marasmiaceae, in the order Agaricales and the subclass agaricomycetidae.

*Trametes* sp.: A basidiomycetous fungal species of the genus *trametes* of the family polyporaceae and the order polyporales and the subclass agaricomycetidae.

*Ganoderma* sp.: A basidiomycetous fungal species of the genus *ganoderma* of the family ganodermataceae and the order polyporales and the subclass agaricomycetidae.

*Grifola* sp.: A basidiomycetous fungal species of the genus *grifola* of the family meripilaceae and the order polyporales and the subclass agaricomycetidae.

Fruiting bodies or fruit bodies: Any one of a variety of complex, spore-bearing fungal structures.

Basidiomycete cell: A cell from a fungus of the class Basidiomycete of the Phylum Basidiomycota, wherein the cell can be derived from any part of the fungus, such as fruiting body, hyphae, spores and mycelium. The Basidiomycete cell can be a single hyphae, spores, aggregates of mycelium, or partly differentiated mycelium, or comprised in fungal mycelium.

Bioactive agent: Any agent, drug, compound, composition of matter or mixture which provides some pharmacologic, often beneficial, effect that can be demonstrated in-vivo or in vitro. As used herein, this term further includes any physiologically or pharmacologically active substance that produces a localized or systemic effect in a patient. Further examples of bioactive agents include, but are not limited to, agents comprising or consisting of an oligosaccharide, agents comprising or consisting of a polysaccharide, agents comprising or consisting of an optionally glycosylated peptide, agents comprising or consisting of an optionally glycosylated polypeptide, agents comprising or consisting of an oligonucleotide, agents comprising or consisting of a polynucleotide, agents comprising or consisting of a lipid, agents comprising or consisting of a fatty acid, agents comprising or consisting of a fatty acid ester and agents comprising or consisting of secondary metabolites.

Anti-cancer medicament: a medicament comprising an anti-cancer activity or anti-neoplastic activity, i.e. effective in treating or preventing a cancer. Often the efficacy is tested in a clinical trial to test whether a new treatment has an anti-cancer effect, for example, whether it shrinks a tumour or improves blood test results, and whether it works against a certain type of cancer.

Bioactive agents comprising an immune stimulating activity: Agents effective in the stimulation or restoration of the ability of the immune system to fight infection and disease. Also included are agents capable of reducing or eliminating any side effect(s) that may be caused by some cancer treatments.

Neoplasm: tissue composed of cells that grow in an abnormal way. Neoplasms may be benign or malignant (metastatic). Benign tumors remain localized as a discrete mass. A system has been devised to classify malignant tissue according to the degree of malignancy, from grade 1, barely malignant, to grade 4, highly malignant. One preferred neoplasm type treated is a cancer. An individual suffering from a neoplastic disease is defined as having at least one neoplasm. Neoplastic diseases as used herein includes any abnormal and uncontrolled cell growth (mitosis) that results in the production of a tumour (i.e. a neoplasm).

Kit of parts: a kit of parts as used in the present invention provides the Basidiomycete bioactive agent and anti-cancer medicament for administration in combination. By the phrase "in combination" with another substance(s) and/or therapeutic method(s) is meant herein the Basidiomycete bioactive agent is administered to the individual thus treated before, during (including concurrently with—preferably co-formulated with) and/or after treatment of an individual with the anti-cancer medicament. The combined active substances may be used for simultaneous, sequential or separate administration. In all cases, it is preferred that any of the herein-mentioned medicaments and bioactive agents are administered in pharmaceutically effective amounts, i.e. an administration involving a total amount of each active component of the medicament or pharmaceutical composition or method that is sufficient to show a meaningful patient benefit. The formulations may conveniently be presented in unit dosage form by methods known to those skilled in the art. It is preferred that the kit may for example contain the active compounds in dosage forms for administration. A dosage form contains a sufficient amount of one or more of the active compound(s) such that a desirable effect can be obtained when administered to a subject. Thus, it is preferred that the medical packaging comprises an amount of dosage units corresponding to the relevant dosage regimen. Accordingly, in one embodiment, the medical packaging comprises a pharmaceutical composition comprising the compounds as defined above or a pharmaceutically acceptable salt thereof and pharmaceutically acceptable carriers, vehicles and/or excipients, said packaging having from 7 to 21 dosage units, or multiples thereof, thereby having dosage units for one week of administration or several weeks of administration. The medical packaging may be in any suitable form—for example for oral or parenteral administration. In another preferred embodiment the packaging is in the form of a cartridge, such as a cartridge for an injection pen, the injection pen being such as an injection pen known from insulin treatment. Preferably, the kit-of-parts contains instructions indicating the use of the dosage form to achieve a desirable affect and the amount of dosage form to be taken over a specified time period. Accordingly, in one embodiment the medical packaging comprises instructions for administering the pharmaceutical composition. It is envisaged that at least one (such as 2 or 3) anti-cancer medicament(s) and at least one (such as 2 or 3) Basidiomycete bioactive agents may be used for the manufacture of any of the "kit of parts" described herein for administration to an individual in need thereof. Preferably, said kit of parts is for treatment or prophylaxis of a neoplastic disease, such as cancer.

Polysaccharides: the term "polysaccharide" as used herein covers polysaccharides as well as polysaccharides containing and/or covalently linked to peptides, polypeptides or the like, such as proteopolysaccharides.

Polysaccharides comprising monosaccharides: A polysaccharide is said to comprise monosaccharides, wherein said monosaccharides are covalently linked to form said polysaccharide. Hydrolysing a polysaccharide will yield the monosaccharides that formed said polysaccharide in free form. The monosaccharide content of a polysaccharide can thus be determined by hydrolysing the polysaccharide and measuring the presence of individual monosaccharides. The monosaccharide content of a mixture of polysaccharides is determined by determining the monosaccharide content of the entire mixture.

Polypeptide: the term "polypeptide" as used herein covers proteins, peptides and polypeptides, wherein said proteins, peptides or polypeptides may or may not have been post-translationally modified. Post-translational modification may for example be phosphorylation, methylation, glucosylation, Ratio: A polysaccharide or a mixture of polysaccharides are said to comprise e.g. galactose, mannose, and glucose in a given ratio, when hydrolysation of said polysaccharide or said mixture of polysaccharide yields galactose, mannose and glucose in said given ratio. Galactose, mannose, and glucose in the ratio 1:a to b:c to d, means that for every part galactose, mannose is present in the range of a to b parts and glucose is present in the range of c to d parts, wherein a, b, c and d indicates numerical values. Thus, by way of example a polysaccharide mixture comprising galactose, mannose, and glucose in the ratio 1:5 to 25:1 to 50, means that for every part galactose, the polysaccharide mixture comprises in the range of 5 to 25 parts mannose and in the range if 1 to 50 part glucose

DETAILED DESCRIPTION OF THE INVENTION

Anti-Cancer Medicament

In one aspect, the present invention relates to a kit of parts comprising:
 a) an anti-cancer medicament,
 b) a Basidiomycete bioactive agent in solid or liquid form, and, optionally
 c) instructions for a dosing regime.

Said anti-cancer medicament may be any medicament with an anti-cancer effect in the individual thus treated.

Thus, said anti-cancer medicament may for example be selected from the group consisting of:
 Aldesleukin/Proleukin (Chiron Corp)
 Alemtuzumab/Campath (Millennium and ILEX Partners, LP)
 alitretinoin/Panretin (Ligand Pharmaceuticals)
 allopurinol/Zyloprim (GlaxoSmithKline)
 altretamine/Hexylen (US Bioscience)
 amifostine/Ethyol (US Bioscience)
 anastrozole/Arimidex (AstraZeneca)
 arsenic trioxide/Trisenox (Cell Therapeutic)
 Asparaginase/Elspar (Merck & Co, Inc)
 BCG Live/TICE BCG (Organon Teknika Corp)
 bexarotene capsules/Targretin (Ligand Pharmaceuticals)
 bleomycin/Blenoxane (Bristol-Myers Squibb)
 busulfan/Busulfex (GlaxoSmithKline)
 calusterone/Methosarb (Pharmacia & Upjohn Company)
 capecitabine/Xeloda (Roche)
 carboplatin/Paraplatin (Bristol-Myers Squibb)
 carmustine/BCNU, BiCNU (Bristol-Myers Squibb)
 carmustine with Polifeprosan 20 Implant/Gliadel Wafer (Guilford Pharmaceuticals Inc.)
 celecoxib/Celebrex (Searle)
 chlorambucil/Leukeran (GlaxoSmithKline)
 cisplatin/Platinol (Bristol-Myers Squibb)
 cladribine/Leustatin, 2-CdA (R. W. Johnson Pharmaceutical Research Institute)
 cyclophosphamide Cytoxan/Neosar (Bristol-Myers Squibb)
 cytarabine/Cytosar-U (Pharmacia & Upjohn Company)
 dacarbazine/DTIC-Dome (Bayer)
 dactinomycin/actinomycin D Cosmegen (Merck)
 Darbepoetin alfa/Aranesp (Amgen, Inc)
 daunorubicin/daunomycin/Daunorubicin (Bedford Labs)
 daunorubicin/daunomycin/Cerubidine (Wyeth Ayerst)
 Denileukin/diftitox/Ontak (Seragen, Inc)
 dexrazoxane/Zinecard (Pharmacia & Upjohn Company)
 docetaxel/Taxotere (Aventis Pharmaceutical)
 doxorubicin Adriamycin/Rubex (Pharmacia & Upjohn Company)
 DROMOSTANOLONE PROPIONATE/MASTERONE INJECTION (SYNTEX)
 Elliott's B Solution (Orphan Medical, Inc)
 epirubicin/Ellence (Pharmacia & Upjohn Company)
 etoposide phosphate (Bristol-Myers Squibb)
 etoposide/VP-16/Vepesid (Bristol-Myers Squibb)
 exemestane/Aromasin (Pharmacia & Upjohn Company)
 Filgrastim/Neupogen (Amgen, Inc)
 floxuridine/FUDR (Roche)
 fludarabine/Fludara (Berlex Laboratories Inc.)
 fluorouracil/5-FU/Adrucil (ICN Puerto Rico)
 fulvestrant/Faslodex (IPR)
 gemcitabine/Gemzar (Eli Lilly)
 gemtuzumab/ozogamicin/Mylotarg (Wyeth Ayerst)
 goserelin acetate/Zoladex Implant (AstraZeneca Pharmaceuticals)
 hydroxyurea/Hydrea (Bristol-Myers Squibb)
 Ibritumomab Tiuxetan/Zevalin (IDEC Pharmaceuticals Corp)
 idarubicin/Idamycin (Adria Laboratories)
 ifosfamide/IFEX (Bristol-Myers Squibb)
 imatinib mesylate/Gleevec (Novartis)
 Interferon alfa-2a/Roferon-A (Hoffmann-La Roche Inc)
 Interferon alfa-2b/Intron A (Schering Corp)
 irinotecan/Camptosar (Pharmacia & Upjohn Company)
 letrozole/Femara (Novartis)
 leucovorin Welicovorin/Leucovorin (Immunex Corporation)
 levamisole/Ergamisol (Janssen Research Foundation)
 lomustine/CCNU/CeeBU (Bristol-Myers Squibb)
 mechlorethamine/nitrogen mustard/Mustargen (Merck)
 megestrol acetate/Megace (Bristol-Myers Squibb)
 melphalan/L-PAM/Alkeran (GlaxoSmithKline)
 mercaptopurine/6-MP Purinethol (GlaxoSmithKline)
 mesna/Mesnex (Asta Medica)
 methotrexate (Lederle Laboratories)
 methoxsalen/Uvadex (Therakos)
 mitomycin C/Mutamycin (Bristol-Myers Squibb)
 mitomycin C/Mitozytrex (Supergen)
 mitotane/Lysodren (Bristol-Myers Squibb)
 mitoxantrone/Novantrone (Lederle Laboratories)
 nandrolone phenpropionate/Durabolin-50 (Organon)
 Nofetumomab/Verluma (Boehringer Ingelheim Pharma KG (formerly Dr. Karl Thomae GmbH))
 Oprelvekin/Neumega (Genetics Institute)
 oxaliplatin/Eloxatin (Sanofi Synthelabo)
 paclitaxel/Taxol (Bristol-Myers Squibb)
 pamidronate/Aredia (Novartis)
 pegademase/Adagen (Pegademase Bovine) (Enzon)
 Pegaspargase/Oncaspar (Enzon, Inc)
 Pegfilgrastim/Neulasta (Amgen, Inc)
 pentostatin/Nipent (Parke-Davis Pharmaceutical Co.)
 pipobroman/Vercyte (Abbott Labs)
 plicamycin/mithramycin/Mithracin (Pfizer Labs)
 porfimer sodium/Photofrin (QLT Phototherapeutics Inc.)
 procarbazine/Matulane (Sigma Tau Pharms)
 quinacrine/Atabrine (Abbott Labs)
 Rasburicase/Elitek (Sanofi-Synthelabo, Inc)

Rituximab/Rituxan (Genentech, Inc)
Sargramostim/Prokine (Immunex Corp)
streptozocin/Zanosar (Pharmacia & Upjohn Company)
talc/Sclerosol (Bryan)
tamoxifen/Nolvadex (AstraZeneca Pharmaceuticals)
temozolomide/Temodar (Schering)
teniposide/VM-26/Vumon (Bristol-Myers Squibb)
testolactone/Teslac (Bristol-Myers Squibb)
thioguanine/6-TG/Thioguanine (GlaxoSmithKline)
thiotepa/Thioplex (Lederle Laboratories)
topotecan/Hycamtin (GlaxoSmithKline)
topotecan/Hycamtin (GlaxoSmithKline)
toremifene/Fareston (Orion Corp)
Tositumomab/Bexxar (Corixa Corporation)
Trastuzumab/Herceptin (Genentech, Inc)
tretinoin/ATRA/Vesanoid (Roche)
Uracil Mustard (Roberts Labs)
valrubicin/Valstar (Medeva)
vinblastine/Velban (Eli Lilly)
vincristine/Oncovin (Eli Lilly)
vinorelbine/Navelbine (GlaxoSmithKline), and
zoledronate/Zometa (Novartis)

In a preferred embodiment of the present invention, said anti-cancer drug is Aldesleukin/Proleukin (Chiron Corp)

In another preferred embodiment of the present invention, said anti-cancer drug is Alemtuzumab/Campath (Millennium and ILEX Partners, LP), such as for the treatment or prophylaxis of B-cell chronic lymphocytic leukaemia (B-CLL).

In another preferred embodiment of the present invention, said anti-cancer drug is alitretinoin/Panretin (Ligand Pharmaceuticals), such as for the treatment or prophylaxis of cutaneous lesions in sarcoma patients, such as in patients suffering from AIDS-related Kaposi's sarcoma.

In another preferred embodiment of the present invention, said anti-cancer drug is allopurinol/Zyloprim (GlaxoSmithKline), such as for the treatment of patients with leukaemia and/or lymphoma and/or one or more solid tumor malignancies who are receiving cancer therapy which causes elevations of serum and urinary uric acid levels.

In another preferred embodiment of the present invention, said anti-cancer drug is altretamine/Hexylen (US Bioscience), such as for treatment or prophylaxis of ovarian cancer.

In another preferred embodiment of the present invention, said anti-cancer drug is amifostine/Ethyol (US Bioscience), such as for treatment or prophylaxis of post-radiation xerostomia for e.g. head and neck cancer and/or ovarian cancer (preferably advanced) and/or non-small cell lung cancer.

In another preferred embodiment of the present invention, said anti-cancer drug is anastrozole/Arimidex (AstraZeneca), such as for the treatment of breast cancer, for example hormone receptor positive early breast cancer, advanced breast cancer, locally advanced or metastatic breast cancer.

In another preferred embodiment of the present invention, said anti-cancer drug is trioxide/Trisenox (Cell Therapeutic).

In another preferred embodiment of the present invention, said anti-cancer drug is Asparaginase/Elspar (Merck & Co, Inc), such as for the treatment of pediatric patients.

In another preferred embodiment of the present invention, said anti-cancer drug is Live/TICE BCG (Organon Teknika Corp).

In another preferred embodiment of the present invention, said anti-cancer drug is bexarotene capsules/Targretin (Ligand Pharmaceuticals), such as for treatment of cutaneous manifestations of cutaneous T-cell lymphoma, preferably via oral administration.

In another preferred embodiment of the present invention, said anti-cancer drug is bleomycin/Blenoxane (Bristol-Myers Squibb), such as for treatment of malignant pleural effusion (MPE) and prevention of recurrent pleural effusions.

In another preferred embodiment of the present invention, said anti-cancer drug is busulfan/Busulfex (GlaxoSmithKline), such as prior to hematopoietic progenitor cell transplantation for chronic myelogenous leukemia, preferably via oral administration.

In another preferred embodiment of the present invention, said anti-cancer drug is calusterone/Methosarb (Pharmacia & Upjohn Company).

In another preferred embodiment of the present invention, said anti-cancer drug is capecitabine/Xeloda (Roche), such as for treatment of breast cancer, preferably metastatic breast cancer, or colorectal carcinoma, preferably metastatic colorectal carcinoma.

In another preferred embodiment of the present invention, said anti-cancer drug is Carboplatin/Paraplatin (Bristol-Myers Squibb), such as for treatment of ovarian carcinoma.

In another preferred embodiment of the present invention, said anti-cancer drug is carmustine/BCNU, BiCNU (Bristol-Myers Squibb)

In another preferred embodiment of the present invention, said anti-cancer drug is carmustine with Polifeprosan 20 Implant/Gliadel Wafer (Guilford Pharmaceuticals Inc.), such as to prolong survival in patients with recurrent glioblastoma multiforme who qualify for surgery.

In another preferred embodiment of the present invention, said anti-cancer drug is celecoxib/Celebrex (Searle), such as for treatment of familial adenomatous polyposis.

In another preferred embodiment of the present invention, said anti-cancer drug is chlorambucil/Leukeran (GlaxoSmithKline), such as for treatment of chronic lymphocytic leukaemia.

In another preferred embodiment of the present invention, said anti-cancer drug is cisplatin/Platinol (Bristol-Myers Squibb), such as for treatment of ovarian tumour preferably metastatic ovarian tumour, testicular tumour, preferably testicular tumour, transitional cell bladder cancer.

In another preferred embodiment of the present invention, said anti-cancer drug is cladribine/Leustatin, 2-CdA (R. W. Johnson Pharmaceutical Research Institute), such as for treatment of active hairy cell leukaemia.

In another preferred embodiment of the present invention, said anti-cancer drug is cyclophosphamide Cytoxan/Neosar (Bristol-Myers Squibb)

In another preferred embodiment of the present invention, said anti-cancer drug is cytarabine/Cytosar-U (Pharmacia & Upjohn Company)

In another preferred embodiment of the present invention, said anti-cancer drug is dacarbazine/DTIC-Dome (Bayer).

In another preferred embodiment of the present invention, said anti-cancer drug is dactinomycin/actinomycin D Cosmegen (Merck)

In another preferred embodiment of the present invention, said anti-cancer drug is Darbepoetin alfa/Aranesp (Amgen, Inc), such as for treatment of anemia associated with chemotherapeutic regimes.

In another preferred embodiment of the present invention, said anti-cancer drug is daunorubicin/daunomycin/Daunorubicin (Bedford Labs), such as in liposomal form, for example for the treatment of HIV-related Kaposi's sarcoma.

In another preferred embodiment of the present invention, said anti-cancer drug is daunorubicin/daunomycin/Cerubidine (Wyeth Ayerst), such as for treatment of leukaemia.

In another preferred embodiment of the present invention, said anti-cancer drug is Denileukin/diftitox/Ontak (Seragen, Inc), such as for treatment of T-cell lymphoma, preferably of individuals whose malignant cells express the CDC25 component of the IL-2 receptor.

In another preferred embodiment of the present invention, said anti-cancer drug is dexrazoxane/Zinecard (Pharmacia & Upjohn Company), such as to aid in reducing the severity of cardiomyopathy associated with doxorubicin administration in women with metastatic breast cancer.

In another preferred embodiment of the present invention, said anti-cancer drug is docetaxel/Taxotere (Aventis Pharmaceutical), such as for treatment of breast cancer, preferably locally advanced or metastatic breast cancer, or non-small cell lung cancer, preferably locally advanced or metastatic non-small cell lung cancer.

In another preferred embodiment of the present invention, said anti-cancer drug is doxorubicin/Adriamycin Rubex (Pharmacia & Upjohn Company), such as for treatment of AIDS-related Kaposi's sarcoma or metastatic carcinoma of the ovary.

In another preferred embodiment of the present invention, said anti-cancer drug is Dromostanolone propionate/Masterone injection (SYNTEX).

In another preferred embodiment of the present invention, said anti-cancer drug is Elliott's B Solution (Orphan Medical, Inc), such as for treatment or prophylaxis of miningeal leukaemia or lymphocytic lymphoma.

In another preferred embodiment of the present invention, said anti-cancer drug is Epirubicin/Ellence (Pharmacia & Upjohn Company), such as for treatment or prophylaxis of breast cancer.

In another preferred embodiment of the present invention, said anti-cancer drug is etoposide phosphate (Bristol-Myers Squibb), such as for treatment or prophylaxis of refractory testicular tumours, small cell lung cancer.

In another preferred embodiment of the present invention, said anti-cancer drug is etoposide/VP-16/Vepesid (Bristol-Myers Squibb), such as for treatment or prophylaxis of refractory testicular tumours, small cell lung cancer.

In another preferred embodiment of the present invention, said anti-cancer drug is exemestane/Aromasin (Pharmacia & Upjohn Company), such as for treatment or prophylaxis of breast cancer, preferably for treatment of advanced breast cancer.

In another preferred embodiment of the present invention, said anti-cancer drug is Filgrastim/Neupogen (Amgen, Inc), such as for treatment of nonmyeloid malignancies undergoing myeloablative chemotherapy followed by marrow transplantation.

In another preferred embodiment of the present invention, said anti-cancer drug is floxuridine/FUDR (Roche)

In another preferred embodiment of the present invention, said anti-cancer drug is fludarabine/Fludara (Berlex Laboratories Inc.), such as for treatment or prophylaxis of B-cell lymphocytic leukaemia.

In another preferred embodiment of the present invention, said anti-cancer drug is fluorouracil/5-FU/Adrucil (ICN Puerto Rico), such as to prolong survival.

In another preferred embodiment of the present invention, said anti-cancer drug is fulvestrant/Faslodex (IPR), such as for treatment or prophylaxis of breast cancer, preferably in post-menopausal women.

In another preferred embodiment of the present invention, said anti-cancer drug is gemcitabine/Gemzar (Eli Lilly), such as for treatment or prophylaxis of adenocarcinoma of the pancreas or non-small cell lung cancer, preferably locally advanced or metastatic adenocarcinoma of the pancreas or non-small cell lung cancer.

In another preferred embodiment of the present invention, said anti-cancer drug is gemtuzumab/ozogamicin/Mylotarg (Wyeth Ayerst), such as for treatment or prophylaxis of CD33 positive acute myeloid leukaemia in patients who are preferably 60 years of age or older.

In another preferred embodiment of the present invention, said anti-cancer drug is goserelin acetate/Zoladex Implant (AstraZeneca Pharmaceuticals), such as for treatment or prophylaxis of breast cancer, preferably advanced stage breast cancer.

In another preferred embodiment of the present invention, said anti-cancer drug is hydroxyurea/Hydrea (Bristol-Myers Squibb).

In another preferred embodiment of the present invention, said anti-cancer drug is Ibritumomab Tiuxetan/Zevalin (IDEC Pharmaceuticals Corp), such as for treatment or prophylaxis of non-Hodgkin's lymphoma, for example patients with Rituximab refractory follicular non-Hodgkin's lymphoma.

In another preferred embodiment of the present invention, said anti-cancer drug is idarubicin/Idamycin (Adria Laboratories), such as for treatment or prophylaxis of acute myeloid leukaemia, for example in adults.

In another preferred embodiment of the present invention, said anti-cancer drug is ifosfamide/IFEX (Bristol-Myers Squibb), such as for treatment of germ cell testicular cancer.

In another preferred embodiment of the present invention, said anti-cancer drug is imatinib mesylate/Gleevec (Novartis), such as for treatment of chronic myelogeneous leukaemia or gastrointestinal stromal tumours.

In another preferred embodiment of the present invention, said anti-cancer drug is Interferon alfa-2a/Roferon-A (Hoffmann-La Roche Inc), such as for treatment or prophylaxis of malignant melanoma, Non-Hodgkin's Lymphoma, condylomata acuminate, hairy cell leukaemia or AIDS-related Kaposi's sarcoma.

In another preferred embodiment of the present invention, said anti-cancer drug is Interferon alfa-2b/Intron A (Schering Corp).

In another preferred embodiment of the present invention, said anti-cancer drug is irinotecan/Camptosar (Pharmacia & Upjohn Company), such as for treatment or prophylaxis of carcinoma of the colon or rectum, preferably metastatic carcinoma of the colon or rectum.

In another preferred embodiment of the present invention, said anti-cancer drug is letrozole/Femara (Novartis), carcinoma of the colon or rectum, such as for treatment or prophylaxis of breast cancer, preferably in post-menopausal women.

In another preferred embodiment of the present invention, said anti-cancer drug is Leucovorin/Wellcovorin (Immunex Corporation), such as for treatment or prophylaxis of colorectal cancer, preferably advanced colorectal cancer.

In another preferred embodiment of the present invention, said anti-cancer drug is levamisole/Ergamisol (Janssen Research Foundation), such as for treatment or prophylaxis of colon cancer, preferably after surgical resection.

In another preferred embodiment of the present invention, said anti-cancer drug is lomustine/CCNU/CeeBU (Bristol-Myers Squibb).

In another preferred embodiment of the present invention, said anti-cancer drug is meclorethamine/nitrogen mustard/Mustargen (Merck)

In another preferred embodiment of the present invention, said anti-cancer drug is megestrol acetate/Megace (Bristol-Myers Squibb)

In another preferred embodiment of the present invention, said anti-cancer drug is melphalan/L-PAM/Alkeran (GlaxoSmithKline), such as for treatment or prophylaxis of multiple myeloma.

In another preferred embodiment of the present invention, said anti-cancer drug is mercaptopurine/6-MP Purinethol (GlaxoSmithKline)

In another preferred embodiment of the present invention, said anti-cancer drug is mesna/Mesnex (Asta Medica) such as for treatment or prophylaxis of ifosfamide-induced hemorrhagic cystitis.

In another preferred embodiment of the present invention, said anti-cancer drug is methotrexate (Lederle Laboratories), such as for treatment or prophylaxis of osteosarcoma.

In another preferred embodiment of the present invention, said anti-cancer drug is methoxsalen/Uvadex (Therakos), such as for treatment or prophylaxis of skin manifestations of cutaneous T-cell lymphoma (CTCL).

In another preferred embodiment of the present invention, said anti-cancer drug is mitomycin C/Mutamycin (Bristol-Myers Squibb).

In another preferred embodiment of the present invention, said anti-cancer drug is mitomycin C/Mitozytrex (Supergen), such as for treatment or prophylaxis of disseminated adenocarcinoma of the stomach or pancreas.

In another preferred embodiment of the present invention, said anti-cancer drug is mitotane/Lysodren (Bristol-Myers Squibb)

In another preferred embodiment of the present invention, said anti-cancer drug is mitoxantrone/Novantrone (Lederle Laboratories), such as for treatment or prophylaxis of prostrate cancer or acute nonlymphocytic leukaemia (ANLL) in adults.

In another preferred embodiment of the present invention, said anti-cancer drug is nandrolone phenpropionate/Durabolin-50 (Organon).

In another preferred embodiment of the present invention, said anti-cancer drug is Nofetumomab/Verluma (Boehringer Ingelheim Pharma KG (formerly Dr. Karl Tomae GmbH).

In another preferred embodiment of the present invention, said anti-cancer drug is doxorubicin/Adriamycin PFS.

In another preferred embodiment of the present invention, said anti-cancer drug is Oprelvekin/Neumega (Genetics Institute), preferably administered after myelosuppressive chemotherapy in patients with nonmyeloid malignancies In another preferred embodiment of the present invention, said anti-cancer drug is oxaliplatin/Eloxatin (Sanofi Synthelabo), such as for treatment or prophylaxis of carcinoma of the colon, preferably metastatic carcinoma of the colon.

In another preferred embodiment of the present invention, said anti-cancer drug is paclitaxel/Taxol/Paxene (Bristol-Myers Squibb), such as for treatment or prophylaxis of advanced AIDS-related Kaposi's sarcoma, breast cancer, metastatic breast cancer, carcinoma of the ovary, AIDS-related Kaposi's sarcoma, metastatic carcinoma of the ovary, non-small cell lung cancer or node-positive breast cancer.

In another preferred embodiment of the present invention, said anti-cancer drug is pamidronate/Aredia (Novartis), such as for treatment or prophylaxis of osteolytic bone metastases of breast cancer.

In another preferred embodiment of the present invention, said anti-cancer drug is pegademase/Adagen (Pegademase Bovine) (Enzon).

In another preferred embodiment of the present invention, said anti-cancer drug is Pegaspargase/Oncaspar (Enzon, Inc).

In another preferred embodiment of the present invention, said anti-cancer drug is Pegfilgrastim/Neulasta (Amgen, Inc), such as for treatment or prophylaxis of non-myeloid malignancies.

In another preferred embodiment of the present invention, said anti-cancer drug is pentostatin/Nipent (Parke-Davis Pharmaceutical Co.), such as for treatment or prophylaxis of hairy cell leukaemia, for example alpha interferon refractory hairy cell leukaemia.

In another preferred embodiment of the present invention, said anti-cancer drug is pipobroman/Vercyte (Abbott Labs)

In another preferred embodiment of the present invention, said anti-cancer drug is plicamycin/mithramycin/Mithracin (Pfizer Labs)

In another preferred embodiment of the present invention, said anti-cancer drug is porfimer sodium/Photofrin (QLT Phototherapeutics Inc.), such as for the treatment or prophylaxis of partially obstructing or completely obstructing esophogeal cancer.

In another preferred embodiment of the present invention, said anti-cancer drug is procarbazine/Matulane (Sigma Tau Pharms)

In another preferred embodiment of the present invention, said anti-cancer drug is quinacrine/Atabrine (Abbott Labs)

In another preferred embodiment of the present invention, said anti-cancer drug is Rasburicase/Elitek (Sanofi-Synthelabo, Inc), such as for the treatment or prophylaxis of patients suffering from leukaemia, lymphoma or solid tumor malignancies.

In another preferred embodiment of the present invention, said anti-cancer drug is Rituximab/Rituxan (Genentech, Inc)

In another preferred embodiment of the present invention, said anti-cancer drug is Sargramostim/Prokine (Immunex Corp)

In another preferred embodiment of the present invention, said anti-cancer drug is streptozocin/Zanosar (Pharmacia & Upjohn Company)

In another preferred embodiment of the present invention, said anti-cancer drug is talc/Sclerosol (Bryan), such as for the treatment or prophylaxis of malignant pleural effusion in symptomatic patients.

In another preferred embodiment of the present invention, said anti-cancer drug is tamoxifen/Nolvadex (AstraZeneca Pharmaceuticals), such as for the treatment or prophylaxis of breast cancer, for example following mastectomy and axillary dissection in postmenopausal women, or for metastatic breast cancer, for example in men.

In another preferred embodiment of the present invention, said anti-cancer drug is temozolomide/Temodar (Schering), such as for the treatment or prophylaxis of refractory anaplastic astrocytma.

In another preferred embodiment of the present invention, said anti-cancer drug is teniposide/VM-26/Vumon (Bristol-Myers Squibb), such as for the treatment or prophylaxis of refractory childhood acute lymphoblastic leukaemia.

In another preferred embodiment of the present invention, said anti-cancer drug is testolactone/Teslac (Bristol-Myers Squibb)

In another preferred embodiment of the present invention, said anti-cancer drug is thioguanine/6-TG/Thioguanine (GlaxoSmithKline)

In another preferred embodiment of the present invention, said anti-cancer drug is thiotepa/Thioplex (Lederle Laboratories)

In another preferred embodiment of the present invention, said anti-cancer drug is topotecan/Hycamtin (GlaxoSmithKline), such as for the treatment or prophylaxis of metastatic carcinoma of the ovary, or small cell lung cancer.

In another preferred embodiment of the present invention, said anti-cancer drug is toremifene/Fareston (Orion Corp), such as for the treatment or prophylaxis of advanced breast cancer in postmenopausal women.

In another preferred embodiment of the present invention, said anti-cancer drug is Tositumomab/Bexxar (Corixa Corporation), such as for the treatment or prophylaxis of non-Hodgkin's lymphoma.

In another preferred embodiment of the present invention, said anti-cancer drug is Trastuzumab/Herceptin (Genentech, Inc), such as for the treatment or prophylaxis of metastatic breast cancer.

In another preferred embodiment of the present invention, said anti-cancer drug is tretinoin/ATRA/Vesanoid (Roche), such as for the treatment or prophylaxis of acute promyeocytic leukaemia.

In another preferred embodiment of the present invention, said anti-cancer drug is Uracil Mustard (Roberts Labs)

In another preferred embodiment of the present invention, said anti-cancer drug is valrubicin/Valstar (Medeva), such as for the treatment or prophylaxis of BCG-refractory carcinoma in situ (CIS) of the urinary bladder.

In another preferred embodiment of the present invention, said anti-cancer drug is vinblastine/Velban (Eli Lilly)

In another preferred embodiment of the present invention, said anti-cancer drug is vincristine/Oncovin (Eli Lilly)

In another preferred embodiment of the present invention, said anti-cancer drug is vinorelbine/Navelbine (GlaxoSmithKline), such as for the treatment or prophylaxis of non-small cell lung cancer, such as unresectable, advanced non-small cell lung cancer.

In another preferred embodiment of the present invention, said anti-cancer drug is zoledronate/Zometa (Novartis), such as for the treatment or prophylaxis of multiple myeloma or patients with documented bone metastases from solid tumours.

In one preferred embodiment of the present invention, the anti-cancer drug is not carboplatin.

In one aspect of the present invention, the Basidiomycete bioactive agent is administered in combination with a chemotherapeutic agent, such as any of the following: an alkylating agent, a Nitrosourea, an antimetabolite, Anthracycline or a related drug, a topoisomerase II inhibitor, a mitotic inhibitor, a corticosteroid hormone.

Thus, in one preferred embodiment, the Basidiomycete bioactive agent is administered in combination with an alkylating agent, such as one or more of the following: busulfan, cisplatin, carboplatin, chlorambucil, cyclophosphamide, ifosfamide, dacarbazine (DTIC), mechlorethamine (nitrogen mustard), melphalan, and temozolomide.

In another preferred embodiment, the Basidiomacete bioactive agent is administered in combination with a Nitrosourea, such as one or more of the following: carmustine (BCNU) and lomustine (CCNU).

In another preferred embodiment, the Basidiomycete bioactive agent is administered in combination with an antimetabolite, such as one or more of the following: 5-fluorouracil, capecitabine, 6-mercaptopurine, methotrexate, gemcitabine, cytarabine (ara-C), fludarabine, and pemetrexed.

In another preferred embodiment, the Basidiomycete bioactive agent is administered in combination with an Anthracycline or a related drug, such as one or more of the following: daunorubicin, doxorubicin (Adriamycin), epirubicin, idarubicin, and mitoxantrone.

In another preferred embodiment, the Basidiomycete bioactive agent is administered in combination with a topoisomerase II inhibitor, such as one or more of the following: topotecan, irinotecan, etoposide (VP-16), and teniposide.

In another preferred embodiment, the Basidiomycete bioactive agent is administered in combination with a mitotic inhibitor, such as one or more of the following: a taxane (for example paclitaxel, docetaxel), a vinca alkaloid (vinblastine, vincristine, and vinorelbine).

In another preferred embodiment, the Basidiomycete bioactive agent is administered in combination with a corticosteroid hormone, such as one or more of the following: prednisone or dexamethasone.

In another preferred embodiment, the Basidiomycete bioactive agent is administered in combination with a targeted therapy, such as one or more of the following: imatinib (Gleevec), gefitinib (Iressa), erlotinib (Tarceva), rituximab (Rituxan), and bevacizumab (Avastin).

In another preferred embodiment, the Basidiomycete bioactive agent is administered in combination with a sexhormone, such as one or more of the following: anti-estrogens (such as tamoxifen, fulvestrant), aromatase inhibitors (such as anastrozole, exemestane, letrozole), progestins (such as megestrol acetate), anti-androgens (such as bicalutamide, flutamide), and LHRH agonists (such as leuprolide, goserelin).

In another preferred embodiment, the Basidiomycete bioactive agent is administered in combination with one or more of the following: L-asparaginase, dactinomycin, thalidomide, and tretinoin.

Disease Treated

The methods, uses, and kit-of-parts described herein may be used to treat any individual suffering from, or at risk of suffering from, a neoplastic disease.

In one embodiment of the present invention, said neoplastic disease is benign. In another embodiment of the present invention, said neoplastic disease is metastatic, such as stage 3-4 metastatic disease.

In one preferred embodiment of the present invention, the neoplastic disease is selected from the group consisting of: Acute Lymphoblastic Leukemia, Acute Myeloid Leukemia, Adrenocortical Carcinoma, AIDS-Related Cancers, AIDS-Related Lymphoma, Anal Cancer, Astrocytoma (e.g. Childhood Cerebellar or Childhood Cerebral), Basal Cell Carcinoma, Extrahepatic Bile Duct Cancer, Bladder Cancer, Bone Cancer, Osteosarcoma/Malignant Fibrous Histiocytoma, Brain Stem Glioma, Brain Tumor, Breast Cancer, Male Breast Cancer, Bronchial Adenomas/Carcinoids, Burkitt's Lymphoma, Carcinoid Tumor, Carcinoma of Unknown Primary, Primary Central Nervous System Lymphoma, Cerebral Astrocytoma/Malignant Glioma, Cervical Cancer, Childhood Cancers, Chronic Lymphocytic Leukemia, Chronic Myelogenous Leukemia, Chronic Myeloproliferative Disorders, Colon Cancer, Cutaneous T-Cell Lymphoma, Endometrial Cancer, Ependymoma (such as Childhood Ependymoma), Esophageal Cancer, Ewing's Family of Tumors, Extracranial Germ Cell Tumor (such as Childhood Extracranial Germ Cell Tumor), Extragonadal Germ Cell Tumor, Eye Cancer (Intraocular Melanoma or Retinoblastoma), Gallbladder Cancer, Gastric (Stomach) Cancer, Gastrointestinal Carcinoid Tumor, Gestational Trophoblastic Tumor, Glioma, Hairy Cell Leukemia, Head and Neck Cancer, Hepatocellular (Liver) Cancer, Hodgkin's Lymphoma, Hypopharyngeal Cancer, Hypothalamic and Visual Pathway Glioma (such as Childhood Hypothalamic and Visual Pathway Glioma), Intraocular Melanoma, Islet Cell Carcinoma (Endocrine Pancreas), Kaposi's Sarcoma, Kidney (Renal Cell) Cancer, Laryngeal Cancer, Lip and Oral Cavity Cancer, Lung Cancer (Non-Small Cell or Small Cell), Lymphoma (such as AIDS-Related Lymphoma, Burkitt's Lymphoma, Cutaneous T-Cell Lymphoma, Non-Hodgkin's Lymphoma), Macroglobulinemia (such as Waldenström's Macroglobulinemia), Malignant Fibrous Histiocytoma of Bone/Osteosarcoma, Medulloblastoma (such as Childhood Medulloblastoma), Melanoma, Merkel Cell Carcinoma, Mesothelioma (such as Adult Malignant Mesothelioma or childhood Mesothelioma), Metastatic Squamous Neck Cancer with Occult Primary, Multiple Endocrine Neoplasia Syndrome (such as occurring in childhood), Multiple Myeloma/Plasma Cell Neoplasm, Mycosis Fungoides, Myelodysplastic Syndromes, Myelodysplastic/Myeloproliferative Diseases, Myeloma (such as Multiple Myeloma), Chronic myeloproliferative disorders, Nasal Cavity and Paranasal Sinus Cancer, Nasopharyngeal Cancer, Nasopharyngeal Cancer (such as Childhood Nasopharyngeal Cancer), Neuroblastoma, Oropharyngeal Cancer, Osteosarcoma/Malignant Fibrous Histiocytoma of Bone, Ovarian Cancer (such as Childhood Ovarian Cancer), Ovarian Epithelial Cancer, Ovarian Germ Cell Tumor, Ovarian Low Malignant Potential Tumor, Pancreatic Cancer, Pancreatic Cancer, Paranasal Sinus and Nasal Cavity Cancer, Parathyroid Cancer, Penile Cancer, Pheochromocytoma, Pineoblastoma and Supratentorial Primitive Neuroectodermal Tumors, Pituitary Tumor, Pleuropulmonary Blastoma, Prostate Cancer, Renal Pelvis and Ureter Transitional Cell Cancer, Retinoblastoma, Rhabdomyosarcoma (such as Childhood Rhabdomyosarcoma), Salivary Gland Cancer, Adult-onset soft tissue Sarcoma, Soft Tissue Sarcoma (such as Childhood Soft Tissue Sarcoma), uterine Sarcoma, Sezary Syndrome, Skin Cancer (such as non-Melanoma skin cancer), Merkel Cell Skin Carcinoma, Small Intestine Cancer, Supratentorial Primitive Neuroectodermal Tumors (such as occurring in Childhood), Cutaneous T-Cell Lymphoma, Testicular Cancer, Thymoma and Thymic Carcinoma, Thyroid Cancer, Transitional Cell Cancer of the Renal Pelvis and Ureter, Trophoblastic Tumor (such as Gestational Trophoblastic Tumor), Urethral Cancer, Endometrial uterine cancer, Uterine Sarcoma, Vaginal Cancer, Visual Pathway and Hypothalamic Glioma (such as Childhood Visual Pathway and Hypothalamic Glioma), Waldenström's Macroglobulinemia or Wilms' Tumor.

One aspect of the present invention relates to the palliative treatment of terminal cancer states in an individual in need thereof, such as wherein said individual is suffering from advanced-stage cancer, preferably terminal cancer.

In accordance with the above, in one aspect of the present invention, the kit-of-parts is suitable for treating or preventing any of the following aerodigestive tract cancer forms:
Pancreatic cancer
cancer of the upper GI tract, such as stomach cancer and/or esophagus cancer.
head and neck cancer, in particular cancer of the thyroid or cancer of the salivary glands.
lung cancer, in particular small lung cell cancer.

In another preferred embodiment of the present invention, the kit of parts according to the present invention is for the treatment or prevention of lower GI cancer, such as colorectal cancers, in particular colon cancer.

In another preferred embodiment of the present invention, the kit-of-parts is for the treatment or prevention of an endocrine cancer, i.e. a cancer in an endocrine organ of an individual's body.

In one preferred embodiment, said cancer is liver cancer.

The invention is also useful for treating individuals suffering from the following cancer forms:
cancer of the ovaries
breast cancer.

In a further preferred embodiment of the present invention, the treatment with Basidiomycete bioactive agent is for the treatment or prevention of undesirable side-effects caused in whole or in part by an anti-cancer treatment, such as chemotherapy or radiotherapy or combinations thereof.

In one embodiment it is preferred that the Basidiomycete bioactive agent is administered before the anti-cancer treatment (for example prophylactically). In this embodiment the treatment may be started before any anti-cancer treatment initiates. It may be administered continuously during the anti-cancer treatment or it may be administered at intervals, for example between periods with anti-cancer therapy. By administering during and in particular between the periods of anti-cancer therapy, the risk that the treated individual acquires infections and other complications may be reduced due to the better health conditions.

*Helicobacter pylori*

*Helicobacter* is a gram-negative bacterium with polar flagella, using oxygen as an electron acceptor, which cannot utilize carbohydrates as an energy source. *Helicobacter* is used herein interchangeably with "*Helicobacter* sp.". In a preferred embodiment the *Helicobacter* sp. is *Helicobacter pylori*.

In one embodiment, the present invention provides methods for preventing or inhibiting or reducing the growth of *Helicobacter* by administering the bioactive agent according to the present invention. The bioactive agent can be administered to an individual in need thereof alone or in combination with other therapeutic agents like antibiotics and inhibitors of acid secretion. By the phrase "in combination" with therapeutic agents is meant herein that one or more bioactive agent(s) according to the present invention is administered to the individual thus treated before and/or during (including concurrently with) and/or after treatment of an individual with one or more therapeutic agents. In all cases of combination treatment described herein, the bioactive agent can be administered in the form of food. In all cases of combination treatment described herein, the combination may be in the form of kit-in-part systems, wherein the combined active substances may be used for simultaneous, sequential or separate administration. In all cases, it is preferred that any of the herein-mentioned medicaments are administered in pharmaceutically effective amounts, i.e. an administration involving a total amount of each active component of the medicament or pharmaceutical composition or method that is sufficient to show a meaningful patient benefit. The combination of a bioactive agent according to the present invention and therapeutic agents provide improvements over therapy with the therapeutic agent alone, in particular for patients that do not respond to therapy with the therapeutic agent alone or in combination with other treatment regimes.

Thus, the present invention provides a method of treating an infection with *Helicobacter* in a subject, particularly human subjects, comprising administering a therapeutically effective amount of a bioactive agent according to the present invention alone or in combination with other therapeutic agents.

In one embodiment, the other therapeutic agent is an antibiotic. In another embodiment the antibiotic is amoxicillin. In a further embodiment the antibiotic is clarithromycin. In yet another embodiment the antibiotic is metronidazole. In another embodiment the therapeutic agent is an inhibitor of acid secretion like an $H_2$ inhibitor or a proton pump inhibitor.

In a further embodiment the $H_2$ inhibitor is omeprazol. Further embodiments of the invention provide methods where one or more antibiotic is co-administered with an inhibitor of acid secretion.

In one embodiment of the invention the subject having a *Helicobacter* infection is suffering from a peptic ulcer. Peptic ulcers, as contemplated in the current invention include, but are not limited to, circumscribed breaks in the continuity of the mucosal layer of the gastrointestinal tract. These breaks in the continuity of the mucosal layer can include breaks that do not extend below the epithelium, also referred to as "erosions" or breaks that do extend below the epithelium. The peptic ulcers may be acute, or chronic. Further, peptic ulcers can be located in any part of the gastrointestinal tract that is exposed to acid-pepsin gastric juice, including esophagus, stomach, duodenum and after gastroenterostomy, the jejunum.

In another embodiment the subject having the *Helicobacter* infection is suffering from, or at risk of developing, cancer of the gastrointestinal tract. As stated above, the portions of the gastrointestinal tract where cancer may be present or may develop are any areas where the gastrointestinal tract is exposed to acid-pepsin gastric juice, including esophagus, stomach, duodenum and after gastroenterostomy, the jejunum. As used herein the term "cancer of the gastrointestinal tract" is used as one of ordinary skill in the art would recognize the term. Examples of "cancer of the gastrointestinal tract" include, but are not limited to, neoplasias (or neoplasms), hyperplasias, dysplasias, metaplasias or hypertrophies. The neoplasms may be benign or malignant, and they may originate from any cell type, including but not limited to epithelial cells of various origin, muscle cells and endothelial cells.

The treatment can be used for patients with a pre-existing *Helicobacter* infection, or for patients pre-disposed to a *Helicobacter* infection. Additionally, the bioactive agent of the present invention can be used to alleviate symptoms of a *Helicobacter* infection in patients, or as a preventative measure in patients.

As used herein, the phrase *Helicobacter* infection is used to mean an interaction between *Helicobacter* and the host organism (subject). The infections may be localized, meaning that the *Helicobacter* grows and remains near the point of initial interaction. The infection may also be generalized, where the *Helicobacter* may become more widespread beyond the initial point of interaction, including spreading to the surrounding tissue or organ and even being distributed and growing throughout the entire host organism. As used herein the term interaction (of a host and *Helicobacter*) is used to mean a process where the *Helicobacter* grows in or around a particular tissue. *Helicobacter* is considered to have infected the subject if the bacteria is able to penetrate the surface of cells of a particular tissue and grow within the cells of the tissue. An example of this type of infection includes, but is not limited to *Helicobacter* penetrating and growing within the epithelial cells lining the lumen of the stomach. Additionally, the *Helicobacter* can also be said to have infected the host organism by growing extracellularly to the tissue cells.

The method of the current invention comprises administering an antibacterially effective amount of the bioactive agent to treat a *Helicobacter* infection. As used herein, "an antibacterially effective amount to treat a *Helicobacter* infection" is intended to mean an amount affective to prevent, inhibit, retard or reverse the growth of *Helicobacter*, and/or reduce the number of viable *Helicobacter* cells within the stomach or at a site of infection. "Antibacterially effective amount to treat a *Helicobacter* infection" is also used to mean an amount effective to kill, reduce or ameliorate any existing infections of *Helicobacter*. Thus, according to the present invention, an "antibacterially effective amount to treat a *Helicobacter* infection" of the bioactive agent of the present invention can be used as a treatment of a pre-existing *Helicobacter* infection. Effective amounts for use in these treatments can completely or partially prevent a pre-existing *Helicobacter* infection from spreading to surrounding tissue and beyond, and they can also be used to slow the growth and/or spread rate of the *Helicobacter* in the subject. Furthermore, the "antibacterially effective amounts to treat a *Helicobacter* infection" of the bioactive agent of the current invention can prevent a *Helicobacter* infection in subjects. Another aspect of an "antibacterially effective amount to treat a *Helicobacter* infection", as used in the current invention, means that the bioactive agent administered to the subject is capable of preventing or reducing the cellular or physiological damage to the infected or surrounding tissue, caused by the toxins produced by the *Helicobacter*. In still another aspect, the phrase "antibacterially effective amount to treat a *Helicobacter* infection" can be used to mean an amount of the administered bioactive agent that can reduce or prevent the formation or efficacy of the virulence of the *Helicobacter*. By virulence is meant the ability of the *Helicobacter* to combat the host organism's or cells natural defenses to the *Helicobacter* infection.

Antibody Therapy

In one embodiment, the present invention provides methods for enhancing the antitumor activity of antibody therapy by administering a bioactive agent according to the present invention in combination with the antibody therapy. By the phrase "in combination" with antibody therapy is meant herein that one or more bioactive agent(s) according to the present invention is administered to the individual thus treated before and/or during (including concurrently with) and/or after treatment of an individual with a therapeutic antibody. In all cases of combination treatment described herein, the bioactive agent can be administered in the form of food. In all cases of combination treatment described herein, the combination may be in the form of kit-in-part systems, wherein the combined active substances may be used for simultaneous, sequential or separate administration. In all cases, it is preferred that any of the herein-mentioned medicaments are administered in pharmaceutically effective amounts, i.e. an administration involving a total amount of each active component of the medicament or pharmaceutical composition or method that is sufficient to show a meaningful patient benefit. The combination of a bioactive agent according to the present invention and therapeutic monoclonal antibodies provide improvements over monoclonal antibody therapy alone, in particular for patients that do not respond to monoclonal antibody therapy alone or in combination with other treatment regimes.

Thus, the present invention provides a method of treating cancer in a subject, particularly human subjects, comprising co-administering a therapeutically effective amount of a monoclonal antibody and a therapeutically effective amount of a bioactive agent according to the present invention.

In one embodiment, the monoclonal antibody is an anti-CD20 monoclonal antibody. In another embodiment, the monoclonal antibody is rituximab. In another embodiment, methods of the present invention treat non-Hodgkin's lymphoma. Further embodiments of the present invention provide methods where monoclonal antibody rituximab and a bioactive agent according to the present invention are administered once weekly for e.g. up to eight consecutive weeks. In another embodiment, the rituximab is administered once weekly and the a bioactive agent according to the present invention is administered up to five times weekly for up to eight consecutive weeks. Another embodiment of present invention provides that the bioactive agent dose is from 10 to 500 [mu]g/kg/dose. In certain embodiments of the present invention, the patient has previously been treated with rituximab and showed no appreciable tumor remission or regression. In other embodiments, the patient has relapsed after receiving rituximab therapy.

In another aspect, the present invention provides a method of treating cancer in a subject comprising co-administering a therapeutically effective amount of an anti-CD20 monoclonal antibody and a therapeutically effective amount of a bioactive agent according to the present invention, wherein administering the bioactive agent results in an optimal immunological response.

In another aspect, the present invention provides a method for treating cancer in a subject comprising co-administering a monoclonal antibody that binds to a Her-2/neu receptor and a bioactive agent according to the present invention. In one embodiment, the subject is a human patient. The monoclonal antibody can e.g. be trastuzumab.

One aspect of the present invention provides a method of treating cancer in a subject comprising co-administering a monoclonal antibody that binds to a cytotoxic T lymphocyte-associated antigen 4 (CTLA-4) and a bioactive agent according to the present invention. In certain embodiments, the subject is a human patient. In one embodiment of the present invention, the anti-CTLA-4 monoclonal antibody is administered at a dose of 3 mg/kg every three weeks for four cycles and the bioactive agent is administered one to five times weekly for up to eight weeks. The present invention also provides embodiments where the dose of the bioactive agent is from 10 to 500 [mu]g/kg/dose.

One of the mechanisms associated with the antitumor activity of monoclonal antibody therapy is antibody dependent cellular cytotoxicity (ADCC). In ADCC, monoclonal antibodies bind to a target cell (e.g. cancer cell) and specific effector cells expressing receptors for the monoclonal antibody (e.g. NK cells, monocytes and granulocytes) bind the monoclonal antibody/target cell complex resulting in target cell death. A bioactive agent according to the present invention is believed to enhance effector cell function, thereby increasing monoclonal antibody therapy efficacy. Thus, the dose and schedule of bioactive agent administration in combination with MAbs can be based on the ability of the bioactive agent to elevate parameters associated with differentiation and functional activity of cell populations mediating ADCC, including but not limited to, NK cells, macrophages and neutrophils. These parameters can be evaluated using assays of NK, macrophage and neutrophil cell cytotoxicity, ADCC (NK cell fraction or total mononuclear cells, or effector molecules essential to the ability of cells to implement ADCC (e.g., FasL, granzymes and perforin).

Combination therapy with a bioactive agent according to the present invention and a monoclonal antibody may in one embodiment be indicated when a first line treatment has failed and may be considered as a second line treatment. However, based on the enhanced antitumor activity of the bioactive agent in combination with a monoclonal antibody, the present invention also provides using the combination as a first line treatment in patient populations that are newly diagnosed and have not been previously treated with anticancer agents "de novo patients" and patients that have not previously received any monoclonal antibody therapy "naive patients."

A bioactive agent according to the present invention is also useful in combination therapy with monoclonal antibodies in the absence of any direct antibody mediated ADCC of tumor cells. Antibodies that block an inhibitory signal in the immune system can lead to augmented immune responses. Examples include (1) antibodies against molecules of the B7R family that have inhibitory function such as, cytotoxic T lymphocyte-associated antigen 4 (CTLA-4), programmed death-1 (PD-1), B and T lymphocyte attenuator (BTLA); (2) antibodies against inhibitory cytokines like IL-10, TGFP; and (3) antibodies that deplete or inhibit functions of suppressive cells like anti-CD25 or CTLA-4. For example, anti-CTLA4 mAbs in both mice and humans are thought to either suppress function of immune-suppressive regulatory T cells (Tregs) or inhibit the inhibitory signal transmitted through binding of CTLA-4 on T cells to B7-1 or B7-2 molecules on APCs or tumor cells. CTLA-4 is expressed transiently on the surface of activated T cells and constitutively expressed on Treg cells. Cross-linking CTLA-4 leads to an inhibitory signal on activated T cells, and antibodies against CTLA-4 block the inhibitory signal on T cells leading to sustained T cell activation (Phan et al., PNAS, 100:8372-8377, 2003.)

Preferred Antibodies for Use in the Combination Therapy:

Although monoclonal antibodies are preferred, any of the embodiments described herein may also use polyclonal antibodies instead of, or in combination with, monoclonal antibodies. In one embodiment of the combination invention, naked antibodies (i.e. antibodies without any drug or radioactive material attached to them) are used. In another embodiment of the present invention, conjugated antibodies are used (joined e.g. to one or more of: a chemotherapy drug, a radioactive particle, or a toxin). For example, the antibody used may be a conjugated monoclonal antibody. Another preferred embodiment uses one or more of: a chemolabeled monoclonal antibody, a monoclonal antibody with radioactive particles attached, an immunotoxin.

Preferred immunotoxins include, but are not restricted to, an antibody attached to one or more of: a bacterial toxins such as diphtherial toxin (DT) or pseudomonal exotoxin (PE40), a plant toxin such as ricin A or saporin. Preferred is e.g. gemtuzumab ozogamicin (Mylotarg) or other antibodies attached to calicheamicin, or BL22.

It is preferred that the antibody is targeted to a molecule known to be associated with cancerous processes. For example, the antibody may bind specifically one or more of the following targets: vascular endothelial growth factor-A (VEGF-A), epidermal growth factor receptor (EGFR), CD20 antigen, the HER2 protein, the CD52 antigen, the VEGF protein, erbB-2, EGFR, erbB-2, cathepsin L, cyclin E, Ras, p53, BCR-ABL, Bcl-2, caspase-3.

Table 1 is a non-exclusive list of monoclonal antibodies approved or being tested for which combination therapy with a bioactive agent according to the present invention is possible. Other preferred antibodies may be selected from, but are not restricted to, the group consisting of:

Alemtuzumab (Campath), bevacizumab (Avastin, Genentech Inc.), OncoScint (such as for colorectal and ovarian cancer), ProstaScint (such as for prostate cancer), Tositumomab (Bexxar), Cetuximab (Erbitux, ImClone Systems Inc.), Gemtuzumab ozogamicin (Mylotarg), Rituximab (Rituxan, Roche/Genentech), anti-erbB-2 scFv, Ibritumomab tiuxetan (Zevalin), Panitumumab (formerly known as "ABX-EGF", Abgenix, Fremont Calif.), Ibritumomab tiuxetan (Zevalin), EMD 72000 (Vanhoefer et al., J Clin Oncol 2004; 22:175-184), Ibritumomab Tioxetan, and Trastuzumab (Herceptin).

Further suitable antibodies and protocols for use of any of the antibodies described herein can be found in e.g. US 2005/0244413 (Adolf et al.) and US 2005/0265966 (Wane et al.), U.S. Pat. No. 5,338,661 (Jensenius), and "Recombinant Polyclonal Antibodies for Cancer Therapy" (Sharon et al., Journal of Cellular Biochemistry 96:305-313 (2005)), all of which are incorporated herein by reference).  P450s are a class of drug- and xenobiotic-metabolizing enzymes mainly expressed in the liver. Carcinogens such as polyaromatic hydrocarbons and hetero-

TABLE 1

| Target | Drug Name | Clinical Indication | Company |
|---|---|---|---|
| IL-2Rα(CD25) | Zenapax | transplant | Roche |
| IL-1R | AMG108 | osteoarthritis | Amgen |
| RANK-L | AMG162 | osteoporosis | Amgen |
| Blys | LympoSTAT-B | SLE, RA | HGS |
| CD40L (CD39) | InitiatedAID | Celltech/IDEC | |
| TRAIL-R1 | HGS-ETR1 | cancers | HGS |
| TRAIL-R2 | HGS-ETR2 | solid tumors | HGS |
| CD30 | SGN30 | NHL | Seattle Genetics |
| CD40 | SGN40 | MM | Seattle Genetics |
| HER2 | Herceptin | Breast cancer | Genentech |
| EGF-R | ABX-EGF | CRC, NSCLC, RCC | Abgenix |
| | EMD72000 | solid tumors | Merck |
| | MDX-214 | EGF-R-positive tumors | Medarex |
| | Erbitux | CRC | Imclone |
| VEGF-R | CDP791 | solid tumors | Celltech |
| PDGF-R | CDP860 | solid tumors | Celltech/ZymoGenetics |
| CD11a (αL) | Raptiva | psoriasis | Genentech |
| α4-integrin | Antegrin | CD, MS | PDL, Biogen-IDEC |
| α4β7 integrin | MLM02 | CD, UC | Millenium |
| α5β3 integrin | Vitaxin | psoriasis, prostate cancer | AME/Lilly |
| CD2 (LFA3/Fc) | Amevive | psoriasis | Biogen/IDEC |
| CD152 | CTLA-4/lg | RA | Bristol Meyers |
| CD152 | CTLA-4 | cancers | Medarex |
| CD49a | Integrin α1 | RA/Luous | Biogen/IDEC |
| CD49e | Integrin α5 | cancers | Protein Design Labs |
| MUC1 | | | Theragyn |
| MUC18 (TIM-like) | ABX-MA1 | melanoma | |
| TAG-72 Mucin | Anatumomab | cancers | |
| CD3 | Ecromeximab | melanoma | Kyowa Hakko |
| | TRX4 | type1 IDDM | TolerRx |
| | Nuvion | UC | PDL |
| | OrthoCloneOKT3 | organ transplant | Ortho biotech |
| CD4 | HuMax-CD4 | T-cell lymphoma | GenMab |
| CD19 | MT103 | NHL | Medimmune |
| CD64 (Fc GR1) | AntiCD64 | cancers | Medarex |
| CD33 | MyloTarg | AML | Celltch/Whyeth |
| | ZAmyl | AML | Protein Design Labs |
| CD22 | lymphocide | NHL, AID | Immunomedics |
| CEA | CEA-Cide | cancers | Immunomedics |
| CD20 | Rituxan | NHL | Genentech |
| CD52 | Campath | MS, NHL, T-cell lymph | Genzyme, IDEX |
| CD44 | Bivatuzumab | cancers | Boehringer Ingelhelm |
| CD23 (Fc Ep R) | IDEC152 | allerhic asthma, rhinitis LRR: | Biogen/IDEC |
| CD14 | ICOSIC14 | sepsis | ICOS |
| EpCAM | Panorex | colorectal cancer | Centocor |
| Lewis-Y—Ag | SGN15 | cancers | Seattle Genetics |
| CD80 | B7.1 | psoriasis/NHL | Biogen/IDEC |

Dosage of the bioactive agent may be varied as known to one skilled in the art and as disclosed in detail elsewhere herein. Preferably, administration is intravenous administration or oral administration. Antibodies may also be given intravenously in one embodiment, for example co-formulated with the bioactive agent.

For example, the antibody and/or bioactive agent may be given at a dosage of 5 mg/kg, every other week, or may be administered with a 400 mg/m² loading dose and weekly doses of 250 mg/m² over 1 hour.

Cytochrome P450

It has been shown, that the polysaccharide Lentinan from *Lentinus edodes* and polysaccharides from *Agaricus blazei* can suppress the expression of cytochrome P450s (CYPs) and thus can prevent cancer (Hashimoto et al. Biosci. Biotechnol. Biochem. 2004, 66 (7) 1610-1614 and Okamoto et al. Biofactors 2004 21 (1-4) 407-09 both of which are incorporated cyclic amines are metabolized to their carcinogenic forms by CYPs. Moreover the suppression of P450 caused by polysaccharides, such as Lentinan, is advantageous for chemotherapy patients, as it prolongs the duration and intensifies the action of drugs.

Thus in one embodiment the present invention is directed to a bioactive agent capable of suppressing the expression of P450s. In a further embodiment the bioactive agent of the present invention is used in a combination therapy with a chemotherapeutic drug. In all cases of combination therapy described herein, the bioactive agent can be administered in the form of food.

Dendritic Cells

It has been demonstrated that chemoimmunotherapy using S-1, an oral fluoropyrimidine anticancer drug, combined with lentinan is effective in modifying dendritic cells (DCs) in vivo and in vitro (Mushiake et al. Cancer Immunol. Immunother. 2005 February; 54 (2) 120-128).

The survival period of Colon-26-bearing mice treated with S-1 and Lentinan was significantly more prolonged than that of mice treated with S-1 alone (P<0.05). The frequency of CD86+ DCs infiltrated into Colon-26 was increased in mice treated with S-1 and lentinan, and splenic DCs harvested from mice treated with S-1+LNT showed more potent T-cell proliferation activity than that of DCs from mice treated with S-1 alone (P<0.05).

Furthermore, the activity of cytotoxic T lymphocytes (CTLs) in splenocytes of mice treated with S-1 and Lentinan was specific and more potent than that of CTLs from mice treated with S-1 alone (P<0.05).

The results suggest that modulation of specific immunity with Lentinan has a significant role in enhanced anti-tumour effects through the modification of DC function. The combination therapy of S-1 and bioactive agents according to the invention presents a promising chemoimmunotherapy, which may lead to better survival for cancer patients. Thus in one embodiment the present invention is directed to a combination therapy of S-1 and the bioactive agent according to this invention in cancer patients. In all cases of combination therapy described herein, the bioactive agent can be administered in the form of food.

Bioactive Species According to the Invention

In one aspect there is provided a bioactive agent as disclosed in the items herein below:

1. The bioactive agent according to a first item comprises or consists of an agent selected from an oligosaccharide, a polysaccharide and an optionally glycosylated polypeptide.
2. The bioactive agent according to item 1, wherein the bioactive agent comprises or consists of a polysaccharide.
3. The bioactive agent according to item 1, wherein the bioactive agent comprises or consists of an oligosaccharide.
4. The bioactive agent according to item 1, wherein the bioactive agent comprises or consists of an optionally glycosylated polypeptide.
5. The bioactive agent according to item 2, wherein the polysaccharide is a homopolymer.
6. The bioactive agent according to item 2, wherein the polysaccharide is a heteropolymer.
7. The bioactive agent according to items 2, wherein the polysaccharide comprises glucose monosaccharide units, optionally in combination with further monosaccharide units selected from the group of units consisting of glucuronic acid, galactose, mannose, arabinose and xylose, including any combination thereof.
8. The bioactive agent according to item 7, wherein the further monosaccharide units are all glucuronic acid.
9. The bioactive agent according to item 7, wherein the further monosaccharide units are all galactose.
10. The bioactive agent according to item 7, wherein the further monosaccharide units are all mannose.
11. The bioactive agent according to item 7, wherein the further monosaccharide units are all arabinose.
12. The bioactive agent according to item 7, wherein the further monosaccharide units are all xylose.
13. The bioactive agent according to item 7, wherein the further monosaccharide units are glucuronic acid and galactose.
14. The bioactive agent according to item 7, wherein the further monosaccharide units are glucuronic acid and mannose.
15. The bioactive agent according to item 7, wherein the further monosaccharide units are glucuronic acid and arabinose.
16. The bioactive agent according to item 7, wherein the further monosaccharide units are glucuronic acid and xylose.
17. The bioactive agent according to item 7, wherein the further monosaccharide units are galactose and mannose.
18. The bioactive agent according to item 7, wherein the further monosaccharide units are galactose and arabinose.
19. The bioactive agent according to item 7, wherein the further monosaccharide units are galactose and xylose.
20. The bioactive agent according to item 7, wherein the further monosaccharide units are mannose and arabinose.
21. The bioactive agent according to item 7, wherein the further monosaccharide units are mannose and xylose.
22. The bioactive agent according to item 7, wherein the further monosaccharide units are arabinose and xylose.
23. The bioactive agent according to item 7, wherein the further monosaccharide units are glucuronic acid, galactose and mannose.
24. The bioactive agent according to item 7, wherein the further monosaccharide units are glucuronic acid, galactose and arabinose.
25. The bioactive agent according to item 7, wherein the further monosaccharide units are glucuronic acid, galactose and xylose.
26. The bioactive agent according to item 7, wherein the further monosaccharide units are glucuronic acid, mannose and arabinose.
27. The bioactive agent according to item 7, wherein the further monosaccharide units are glucuronic acid mannose and xylose.
28. The bioactive agent according to item 7, wherein the further monosaccharide units are glucuronic acid, arabinose and xylose.
29. The bioactive agent according to item 7, wherein the further monosaccharide units are galactose, mannose and arabinose.
30. The bioactive agent according to item 7, wherein the further monosaccharide units are galactose, mannose and xylose.
31. The bioactive agent according to item 7, wherein the further monosaccharide units are galactose, arabinose and xylose.
32. The bioactive agent according to item 7, wherein the further monosaccharide units are mannose, arabinose and xylose.
33. The bioactive agent according to item 7, wherein the further monosaccharide units are glucuronic acid, galactose, mannose and arabinose.
34. The bioactive agent according to item 7, wherein the further monosaccharide units are glucuronic acid, galactose, mannose and xylose.
35. The bioactive agent according to item 7, wherein the further monosaccharide units are glucuronic acid, galactose, arabinose and xylose.
36. The bioactive agent according to item 7, wherein the further monosaccharide units are glucuronic acid, mannose, arabinose and xylose.
37. The bioactive agent according to item 7, wherein the further monosaccharide units are galactose, mannose, arabinose and xylose.
38. The bioactive agent according to item 2, wherein the backbone of the polysaccharide comprises glucose monosaccharide units in combination with further monosaccharide units selected from the group of units consisting of glucuronic acid, galactose, mannose, arabinose and xylose, including any combination thereof.

39. The bioactive agent according to item 38, wherein the further monosaccharide units are all glucuronic acid.
40. The bioactive agent according to item 38, wherein the further monosaccharide units are all galactose.
41. The bioactive agent according to item 38, wherein the further monosaccharide units are all mannose.
42. The bioactive agent according to item 38, wherein the further monosaccharide units are all arabinose.
43. The bioactive agent according to item 38, wherein the further monosaccharide units are all xylose.
44. The bioactive agent according to item 38, wherein the further monosaccharide units are glucuronic acid and galactose.
45. The bioactive agent according to item 38, wherein the further monosaccharide units are glucuronic acid and mannose.
46. The bioactive agent according to item 38, wherein the further monosaccharide units are glucuronic acid and arabinose.
47. The bioactive agent according to item 38, wherein the further monosaccharide units are glucuronic acid and xylose.
48. The bioactive agent according to item 38, wherein the further monosaccharide units are galactose and mannose.
49. The bioactive agent according to item 38, wherein the further monosaccharide units are galactose and arabinose.
50. The bioactive agent according to item 38, wherein the further monosaccharide units are galactose and xylose.
51. The bioactive agent according to item 38, wherein the further monosaccharide units are mannose and arabinose.
52. The bioactive agent according to item 38, wherein the further monosaccharide units are mannose and xylose.
53. The bioactive agent according to item 38, wherein the further monosaccharide units are arabinose and xylose.
54. The bioactive agent according to item 38, wherein the further monosaccharide units are glucuronic acid, galactose and mannose.
55. The bioactive agent according to item 38, wherein the further monosaccharide units are glucuronic acid, galactose and arabinose.
56. The bioactive agent according to item 38, wherein the further monosaccharide units are glucuronic acid, galactose and xylose.
57. The bioactive agent according to item 38, wherein the further monosaccharide units are glucuronic acid, mannose and arabinose.
58. The bioactive agent according to item 38, wherein the further monosaccharide units are glucuronic acid mannose and xylose.
59. The bioactive agent according to item 38, wherein the further monosaccharide units are glucuronic acid, arabinose and xylose.
60. The bioactive agent according to item 38, wherein the further monosaccharide units are galactose, mannose and arabinose.
61. The bioactive agent according to item 38, wherein the further monosaccharide units are galactose, mannose and xylose.
62. The bioactive agent according to item 38, wherein the further monosaccharide units are galactose, arabinose and xylose.
63. The bioactive agent according to item 38, wherein the further monosaccharide units are mannose, arabinose and xylose.
64. The bioactive agent according to item 38, wherein the further monosaccharide units are glucuronic acid, galactose, mannose and arabinose.
65. The bioactive agent according to item 38, wherein the further monosaccharide units are glucuronic acid, galactose, mannose and xylose.
66. The bioactive agent according to item 38, wherein the further monosaccharide units are glucuronic acid, galactose, arabinose and xylose.
67. The bioactive agent according to item 38, wherein the further monosaccharide units are glucuronic acid, mannose, arabinose and xylose.
68. The bioactive agent according to item 38, wherein the further monosaccharide units are galactose, mannose, arabinose and xylose.
69. The bioactive agent according to item 2, wherein the backbone of the polysaccharide comprises a plurality of monosaccharide units, and wherein the side chains of the polysaccharide comprises further monosaccharide units selected from the group of units consisting of glucuronic acid, galactose, mannose, arabinose xylose and glucose, including any combination thereof.
70. The bioactive agent according to item 69, wherein the further monosaccharide units are all glucuronic acid.
71. The bioactive agent according to item 69, wherein the further monosaccharide units are all galactose.
72. The bioactive agent according to item 69, wherein the further monosaccharide units are all mannose.
73. The bioactive agent according to item 69, wherein the further monosaccharide units are all arabinose.
74. The bioactive agent according to item 69, wherein the further monosaccharide units are all xylose.
75. The bioactive agent according to item 69, wherein the further monosaccharide units are all glucose.
76. The bioactive agent according to item 69, wherein the further monosaccharide units are glucuronic acid and galactose.
77. The bioactive agent according to item 69, wherein the further monosaccharide units are glucuronic acid and mannose.
78. The bioactive agent according to item 69, wherein the further monosaccharide units are glucuronic acid and arabinose.
79. The bioactive agent according to item 69, wherein the further monosaccharide units are glucuronic acid and xylose.
80. The bioactive agent according to item 69, wherein the further monosaccharide units are glucuronic acid and glucose.
81. The bioactive agent according to item 69, wherein the further monosaccharide units are galactose and mannose.
82. The bioactive agent according to item 69, wherein the further monosaccharide units are galactose and arabinose.
83. The bioactive agent according to item 69, wherein the further monosaccharide units are galactose and xylose.
84. The bioactive agent according to item 69, wherein the further monosaccharide units are galactose and glucose.
85. The bioactive agent according to item 69, wherein the further monosaccharide units are mannose and arabinose.
86. The bioactive agent according to item 69, wherein the further monosaccharide units are mannose and xylose.
87. The bioactive agent according to item 69, wherein the further monosaccharide units are mannose and glucose.
88. The bioactive agent according to item 69, wherein the further monosaccharide units are arabinose and xylose.
89. The bioactive agent according to item 69, wherein the further monosaccharide units are arabinose and glucose.
90. The bioactive agent according to item 69, wherein the further monosaccharide units are xylose and glucose.

91. The bioactive agent according to item 69, wherein the further monosaccharide units are glucuronic acid, galactose and mannose.
92. The bioactive agent according to item 69, wherein the further monosaccharide units are glucuronic acid, galactose and arabinose.
93. The bioactive agent according to item 69, wherein the further monosaccharide units are glucuronic acid, galactose and xylose.
94. The bioactive agent according to item 69, wherein the further monosaccharide units are glucuronic acid, galactose and glucose.
95. The bioactive agent according to item 69, wherein the further monosaccharide units are glucuronic acid, mannose and arabinose.
96. The bioactive agent according to item 69, wherein the further monosaccharide units are glucuronic acid mannose and xylose.
97. The bioactive agent according to item 69, wherein the further monosaccharide units are glucuronic acid mannose and glucose.
98. The bioactive agent according to item 69, wherein the further monosaccharide units are glucuronic acid, arabinose and xylose.
99. The bioactive agent according to item 69, wherein the further monosaccharide units are glucuronic acid, arabinose and glucose.
100. The bioactive agent according to item 69, wherein the further monosaccharide units are glucuronic acid, xylose and glucose.
101. The bioactive agent according to item 69, wherein the further monosaccharide units are galactose, mannose and arabinose.
102. The bioactive agent according to item 69, wherein the further monosaccharide units are galactose, mannose and xylose.
103. The bioactive agent according to item 69, wherein the further monosaccharide units are galactose, mannose and glucose.
104. The bioactive agent according to item 69, wherein the further monosaccharide units are galactose, arabinose and xylose.
105. The bioactive agent according to item 69, wherein the further monosaccharide units are galactose, arabinose and glucose.
106. The bioactive agent according to item 69, wherein the further monosaccharide units are galactose, xylose and glucose.
107. The bioactive agent according to item 69, wherein the further monosaccharide units are mannose, arabinose and xylose.
108. The bioactive agent according to item 69, wherein the further monosaccharide units are mannose, arabinose and glucose.
109. The bioactive agent according to item 69, wherein the further monosaccharide units are mannose, xylose and glucose.
110. The bioactive agent according to item 69, wherein the further monosaccharide units are arabinose, xylose and glucose.
111. The bioactive agent according to item 69, wherein the further monosaccharide units are glucuronic acid, galactose, mannose and arabinose.
112. The bioactive agent according to item 69, wherein the further monosaccharide units are glucuronic acid, galactose, mannose and xylose.
113. The bioactive agent according to item 69, wherein the further monosaccharide units are glucuronic acid, galactose, mannose and glucose.
114. The bioactive agent according to item 69, wherein the further monosaccharide units are glucuronic acid, galactose, arabinose and xylose.
115. The bioactive agent according to item 69, wherein the further monosaccharide units are glucuronic acid, galactose, arabinose and glucose.
116. The bioactive agent according to item 69, wherein the further monosaccharide units are glucuronic acid, galactose, xylose and glucose.
117. The bioactive agent according to item 69, wherein the further monosaccharide units are glucuronic acid, mannose, arabinose and xylose.
118. The bioactive agent according to item 69, wherein the further monosaccharide units are glucuronic acid, mannose, arabinose and glucose.
119. The bioactive agent according to item 69, wherein the further monosaccharide units are glucuronic acid, mannose, xylose and glucose.
120. The bioactive agent according to item 69, wherein the further monosaccharide units are glucuronic acid, arabinose, xylose and glucose.
121. The bioactive agent according to item 69, wherein the further monosaccharide units are galactose, mannose, arabinose and xylose.
122. The bioactive agent according to item 69, wherein the further monosaccharide units are galactose, mannose, arabinose and glucose.
123. The bioactive agent according to item 69, wherein the further monosaccharide units are galactose, mannose, xylose and glucose.
124. The bioactive agent according to item 69, wherein the further monosaccharide units are galactose, arabinose, xylose and glucose.
125. The bioactive agent according to item 69, wherein the further monosaccharide units are mannose, arabinose, xylose and glucose.
126. The bioactive agent according to item 69, wherein the further monosaccharide units are glucuronic acid, galactose, mannose, arabinose and xylose.
127. The bioactive agent according to item 69, wherein the further monosaccharide units are glucuronic acid, galactose, mannose, arabinose and glucose.
128. The bioactive agent according to item 69, wherein the further monosaccharide units are glucuronic acid, galactose, mannose, xylose and glucose.
129. The bioactive agent according to item 69, wherein the further monosaccharide units are glucuronic acid, galactose, arabinose xylose and glucose.
130. The bioactive agent according to item 69, wherein the further monosaccharide units are glucuronic acid, mannose, arabinose xylose and glucose.
131. The bioactive agent according to item 69, wherein the further monosaccharide units are galactose, mannose, arabinose xylose and glucose.
132. The bioactive agent according to item 2, wherein the polysaccharide comprises a repetitive backbone macromomer comprising from 2 to 6, such as 2, 3, 4, 5 or 6 different monosaccharide units and having from 1 to 3 monosaccharide units selected from glucose, mannose and galactose.
133. The bioactive agent according to item 2, wherein the polysaccharide comprises an average of from 1 to 1000 monosaccharide units in the backbone between each branching point, such as from 2 to 1000 monosaccharide units, for example from 3 to 1000 monosaccharide units, such as from 4 to 1000 monosaccharide units, for example from 5 to 1000 monosaccharide units, such as from 6 to 1000 monosaccharide units, for example from 7 to 1000 monosaccharide units, such as from 8 to 1000 monosaccharide units, for example from 9 to 1000 monosaccharide units, such as from 10 to 1000 monosaccharide units, for example from 11 to 1000 monosaccharide units, such as from 12 to 1000 monosaccharide units, for example from 13 to 1000 monosaccharide units, such as from 14 to 1000 monosaccharide units, for example from 15 to 1000 monosaccharide units, such as from 20 to 1000 monosaccharide units, for example from 25 to 1000 monosaccharide units, such as from 30 to 1000 monosaccharide units, for example from 40 to 1000 monosaccharide units, such as from 50 to 1000 monosaccharide units, for example from 60 to 1000 monosaccharide units, such as from 70 to 1000 monosaccharide units, for example from 80 to 1000 monosaccharide units, such as from 90 to 1000 monosaccharide units, for example from 100 to 1000 monosaccharide units, such as from 2 to 500 monosaccharide units, for example from 3 to 500 monosaccharide units, such as from 4 to 500 monosaccharide units, for example from 5 to 500 monosaccharide units, such as from 6 to 500 monosaccharide units, for example from 7 to 500 monosaccharide units, such as from 8 to 500 monosaccharide units, for example from 9 to 500 monosaccharide units, such as from 10 to 500 monosaccharide units, for example from 11 to 500 monosaccharide units, such as from 12 to 500 monosaccharide units, for example from 13 to 500 monosaccharide units, such as from 14 to 500 monosaccharide units, for example from 15 to 500 monosaccharide units, such as from 20 to 500 monosaccharide units, for example from 25 to 500 monosaccharide units, such as from 30 to 500 monosaccharide units, for example from 40 to 500 monosaccharide units, such as from 50 to 500 monosaccharide units, for example from 60 to 500 monosaccharide units, such as from 70 to 500 monosaccharide units, for example from 80 to 500 monosaccharide units, such as from 90 to 500 monosaccharide units, for example from 100 to 500 monosaccharide units, such as from 2 to 250 monosaccharide units, for example from 3 to 250 monosaccharide units, such as from 4 to 250 monosaccharide units, for example from 5 to 250 monosaccharide units, such as from 6 to 250 monosaccharide units, for example from 7 to 250 monosaccharide units, such as from 8 to 250 monosaccharide units, for example from 9 to 250 monosaccharide units, such as from 10 to 250 monosaccharide units, for example from 11 to 250 monosaccharide units, such as from 12 to 250 monosaccharide units, for example from 13 to 250 monosaccharide units, such as from 14 to 250 monosaccharide units, for example from 15 to 250 monosaccharide units, such as from 20 to 250 monosaccharide units, for example from 25 to 250 monosaccharide units, such as from 30 to 250 monosaccharide units, for example from 40 to 250 monosaccharide units, such as from 50 to 250 monosaccharide units, for example from 60 to 250 monosaccharide units, such as from 70 to 250 monosaccharide units, for example from 80 to 250 monosaccharide units, such as from 90 to 250 monosaccharide units, for example from 100 to 250 monosaccharide units, such as from 2 to 100 monosaccharide units, for example from 3 to 100 monosaccharide units, such as from 4 to 100 monosaccharide units, for example from 5 to 100 monosaccharide units, such as from 6 to 100 monosaccharide units, for example from 7 to 100 monosaccharide units, such as from 8 to 100 monosaccharide units, for example from 9 to 100 monosaccharide units, such as from 10 to 100 monosaccharide units, for example from 11 to 100 monosaccharide units, such as from 12 to 100 monosaccharide units, for example from 13 to 100 monosaccharide units, such as from 14 to 100 monosaccharide units, for example from 15 to 100 monosaccharide units, such as from 20 to 100 monosaccharide units, for example from 25 to 100 monosaccharide units, such as from 30 to 100 monosaccharide units, for example from 40 to 100 monosaccharide units, such as from 50 to 100 monosaccharide units, for example from 60 to 100 monosaccharide units, such as from 70 to 100 monosaccharide units, for example from 80 to 100 monosaccharide units, such as from 90 to 100 monosaccharide units, such as from 2 to 50 monosaccharide units, for example from 3 to 50 monosaccharide units, such as from 4 to 50 monosaccharide units, for example from 5 to 50 monosaccharide units, such as from 6 to 50 monosaccharide units, for example from 7 to 50 monosaccharide units, such as from 8 to 50 monosaccharide units, for example from 9 to 50 monosaccharide units, such as from 10 to 50 monosaccharide units, for example from 11 to 50 monosaccharide units, such as from 12 to 50 monosaccharide units, for example from 13 to 50 monosaccharide units, such as from 14 to 50 monosaccharide units, for example from 15 to 50 monosaccharide units, such as from 20 to 50 monosaccharide units, for example from 25 to 50 monosaccharide units, such as from 30 to 50 monosaccharide units, for example from 40 to 50 monosaccharide units, such as from 2 to 25 monosaccharide units, for example from 3 to 25 monosaccharide units, such as from 4 to 25 monosaccharide units, for example from 5 to 25 monosaccharide units, such as from 6 to 25 monosaccharide units, for example from 7 to 25 monosaccharide units, such as from 8 to 25 monosaccharide units, for example from 9 to 25 monosaccharide units, such as from 10 to 25 monosaccharide units, for example from 11 to 25 monosaccharide units, such as from 12 to 25 monosaccharide units, for example from 13 to 25 monosaccharide units, such as from 14 to 25 monosaccharide units, for example from 15 to 25 monosaccharide units, such as from 20 to 25 monosaccharide units, such as from 2 to 20 monosaccharide units, for example from 3 to 20 monosaccharide units, such as from 4 to 20 monosaccharide units, for example from 5 to 20 monosaccharide units, such as from 6 to 20 monosaccharide units, for example from 7 to 20 monosaccharide units, such as from 8 to 20 monosaccharide units, for example from 9 to 20 monosaccharide units, such as from 10 to 20 monosaccharide units, for example from 11 to 20 monosaccharide units, such as from 12 to 20 monosaccharide units, for example from 13 to 20 monosaccharide units, such as from 14 to 20 monosaccharide units, for example from 15 to 20 monosaccharide units, such as from 2 to 18 monosaccharide units, for example from 3 to 18 monosaccharide units, such as from 4 to 18 monosaccharide units, for example from 5 to 18 monosaccharide units, such as from 6 to 18 monosaccharide units, for example from 7 to 18 monosaccharide units, such as from 8 to 18 monosaccharide units, for example from 9 to 18 monosaccharide units, such as from 10 to 18 monosaccharide units, for example from 11 to 18 monosaccharide units, such as from 12 to 18 monosaccharide units, for example from 13 to 18 monosaccharide units, such as from 14 to 18 monosaccharide units, for example from 15 to 18 monosaccharide units, such as from 2 to 16 monosaccharide units, for example from 3 to 16 monosaccharide units, such as from 4 to 16 monosaccharide units, for example from 5 to 16 monosaccharide units, such as from 6 to 16 monosaccharide units, for example from 7 to 16 monosaccharide units, such as from 8 to 16 monosaccharide units, for example from 9 to 16 monosaccharide units, such as from 10 to 16 monosaccharide units, for example from 11 to 16 monosaccharide units, such as from 12 to 16 monosaccharide units, for example from 13 to 16 monosaccharide units, such as from 14 to 16 monosaccharide units, for example from 15 to 16 monosaccharide units, such as from 2 to 14 monosaccharide units, for example from 3 to 14 monosaccharide units, such as from 4 to 14 monosaccharide units, for example from 5 to 14 monosaccharide units, such as from 6 to 14 monosaccharide units, for example from 7 to 14 monosaccharide units, such as from 8 to 14 monosaccharide units, for example from 9 to 14 monosaccharide units, such as from 10 to 14 monosaccharide units, for example from 11 to 14 monosaccharide units, such as from 12 to 14 monosaccharide units, for example from 13 to 14 monosaccharide units, such as from 2 to 12 monosaccharide units, for example from 3 to 12 monosaccharide units, such as from 4 to 12 monosaccharide units, for example from 5 to 12 monosaccharide units, such as from 6 to 12 monosaccharide units, for example from 7 to 12 monosaccharide units, such as from 8 to 12 monosaccharide units, for example from 9 to 12 monosaccharide units, such as from 10 to 12 monosaccharide units, for example from 11 to 12 monosaccharide units, such as from 2 to 10 monosaccharide units, for example from 3 to 10 monosaccharide units, such as from 4 to 10 monosaccharide units, for example from 5 to 10 monosaccharide units, such as from 6 to 10 monosaccharide units, for example from 7 to 10 monosaccharide units, such as from 8 to 10 monosaccharide units, for example from 9 to 10 monosaccharide units, such as from 2 to 8 monosaccharide units, for example from 3 to 8 monosaccharide units, such as from 4 to 8 monosaccharide units, for example from 5 to 8 monosaccharide units, such as from 6 to 8 monosaccharide units, for example from 7 to 8 monosaccharide units in the backbone between each branching point.

134. The bioactive agent according to item 2, wherein the polysaccharide has a molecular weight in the range of from 5,000 g/mol to about 1,000,000 g/mol, such as a molecular weight in the range of from 5,000 g/mol to about 900,000 g/mol, for example a molecular weight in the range of from 5,000 g/mol to about 800,000 g/mol, such as a molecular weight in the range of from 5,000 g/mol to about 900,000 g/mol, for example a molecular weight in the range of from 5,000 g/mol to about 800,000 g/mol, such as a molecular weight in the range of from 5,000 g/mol to about 750,000 g/mol, for example a molecular weight in the range of from 5,000 g/mol to about 700,000 g/mol, such as a molecular weight in the range of from 5,000 g/mol to about 1270,000 g/mol, for example a molecular weight in the range of from 5,000 g/mol to about 600,000 g/mol, such as a molecular weight in the range of from 5,000 g/mol to about 550,000 g/mol, for example a molecular weight in the range of from 5,000 g/mol to about 500,000 g/mol, such as a molecular weight in the range of from 5,000 g/mol to about 450,000 g/mol, for example a molecular weight in the range of from 5,000 g/mol to about 400,000 g/mol, such as a molecular weight in the range of from 5,000 g/mol to about 350,000 g/mol, for example a molecular weight in the range of from 5,000 g/mol to about 300,000 g/mol, such as a molecular weight in the range of from 5,000 g/mol to about 250,000 g/mol, for example a molecular weight in the range of from 5,000 g/mol to about 200,000 g/mol, such as a molecular weight in the range of from 5,000 g/mol to about 100,000 g/mol, for example a molecular weight in the range of from 5,000 g/mol to about 80,000 g/mol, such as a molecular weight in the range of from 5,000 g/mol to about 60,000 g/mol, for example a molecular weight in the range of from 5,000 g/mol to about 50,000 g/mol, such as a molecular weight in the range of from 5,000 g/mol to about 40,000 g/mol, for example a molecular weight in the range of from 5,000 g/mol to about 35.000 g/mol, such as a molecular weight in the range of from 5,000 g/mol to about 30,000 g/mol, for example a molecular weight in the range of from 5,000 g/mol to about 25.000 g/mol, such as a molecular weight in the range of from 5,000 g/mol to about 20,000 g/mol, for example a molecular weight in the range of from 5,000 g/mol to about 15.000 g/mol, such as a molecular weight in the range of from 5,000 g/mol to about 10,000 g/mol, for example a molecular weight in the range of from 10,000 g/mol to about 1,000,000 g/mol, such as a molecular weight in the range of from 10,000 g/mol to about 900,000 g/mol, for example a molecular weight in the range of from 10,000 g/mol to about 800,000 g/mol, such as a molecular weight in the range of from 10,000 g/mol to about 900,000 g/mol, for example a molecular weight in the range of from 10,000 g/mol to about 800,000 g/mol, such as a molecular weight in the range of from 10,000 g/mol to about 750,000 g/mol, for example a molecular weight in the range of from 10,000 g/mol to about 700,000 g/mol, such as a molecular weight in the range of from 10,000 g/mol to about 1270,000 g/mol, for example a molecular weight in the range of from 10,000 g/mol to about 600,000 g/mol, such as a molecular weight in the range of from 10,000 g/mol to about 550,000 g/mol, for example a molecular weight in the range of from 10,000 g/mol to about 500,000 g/mol, such as a molecular weight in the range of from 10,000 g/mol to about 450,000 g/mol, for example a molecular weight in the range of from 10,000 g/mol to about 400,000 g/mol, such as a molecular weight in the range of from 10,000 g/mol to about 350,000 g/mol, for example a molecular weight in the range of from 10,000 g/mol to about 300,000 g/mol, such as a molecular weight in the range of from 10,000 g/mol to about 250,000 g/mol, for example a molecular weight in the range of from 10,000 g/mol to about 200,000 g/mol, such as a molecular weight in the range of from 10,000 g/mol to about 100,000 g/mol, for example a molecular weight in the range of from 10,000 g/mol to about 80,000 g/mol, such as a molecular weight in the range of from 10,000 g/mol to about 60,000 g/mol, for example a molecular weight in the range of from 10,000 g/mol to about 50,000 g/mol, such as a molecular weight in the range of from 10,000 g/mol to about 40,000 g/mol, for example a molecular weight in the range of from 10,000 g/mol to about 35.000 g/mol, such as a molecular weight in the range of from 10,000 g/mol to about 30,000 g/mol, for example a molecular weight in the range of from 10,000 g/mol to about 25.000 g/mol, such as a molecular weight in the range of from 10,000 g/mol to about 20,000 g/mol, for example a molecular weight in the range of from 10,000 g/mol to about 15.000 g/mol, such as a molecular weight in the range of from 15,000 g/mol to about 1,000,000 g/mol, such as a molecular weight in the range of from 15,000 g/mol to about 900,000 g/mol, for example a molecular weight in the range of from 15,000 g/mol to about 800,000 g/mol, such as a molecular weight in the range of from 15,000 g/mol to about 900,000 g/mol, for example a molecular weight in the range of from 15,000 g/mol to about 800,000 g/mol, such as a molecular weight in the range of from 15,000 g/mol to about 750,000 g/mol, for example a molecular weight in the range of from 15,000 g/mol to about 700,000 g/mol, such as a molecular weight in the range of from 15,000 g/mol to about 1270,000 g/mol, for example a molecular weight in the range of from 15,000 g/mol to about 600,000 g/mol, such as a molecular weight in the range of from 15,000 g/mol to about 550,000 g/mol, for example a molecular weight in the range of from 15,000 g/mol to about 500,000 g/mol, such as a molecular weight in the range of from 15,000 g/mol to about 450,000 g/mol, for example a molecular weight in the range of from 15,000 g/mol to about 400,000 g/mol, such as a molecular weight in the range of from 15,000 g/mol to about 350,000 g/mol, for example a molecular weight in the range of from 15,000 g/mol to about 300,000 g/mol, such as a molecular weight in the range of from 15,000 g/mol to about 250,000 g/mol, for example a molecular weight in the range of from 15,000 g/mol to about 200,000 g/mol, such as a molecular weight in the range of from 15,000 g/mol to about 100,000 g/mol, for example a molecular weight in the range of from 15,000 g/mol to about 80,000 g/mol, such as a molecular weight in the range of from 15,000 g/mol to about 60,000 g/mol, for example a molecular weight in the range of from 15,000 g/mol to about 50,000 g/mol, such as a molecular weight in the range of from 15,000 g/mol to about 40,000 g/mol, for example a molecular weight in the range of from 15,000 g/mol to about 35.000 g/mol, such as a molecular weight in the range of from 15,000 g/mol to about 30,000 g/mol, for example a molecular weight in the range of from 15,000 g/mol to about 25.000 g/mol, such as a molecular weight in the range of from 15,000 g/mol to about 20,000 g/mol, for example a molecular weight in the range of from 20,000 g/mol to about 1,000,000 g/mol, such as a molecular weight in the range of from 20,000 g/mol to about 900,000 g/mol, for example a molecular weight in the range of from 20,000 g/mol to about 800,000 g/mol, such as a molecular weight in the range of from 20,000 g/mol to about 900,000 g/mol, for example a molecular weight in the range of from 20,000 g/mol to about 800,000 g/mol, such as a molecular weight in the range of from 20,000 g/mol to about 750,000 g/mol, for example a molecular weight in the range of from 20,000 g/mol to about 700,000 g/mol, such as a molecular weight in the range of from 20,000 g/mol to about 1270,000 g/mol, for example a molecular weight in the range of from 20,000 g/mol to about 600,000 g/mol, such as a molecular weight in the range of from 20,000 g/mol to about 550,000 g/mol, for example a molecular weight in the range of from 20,000 g/mol to about 500,000 g/mol, such as a molecular weight in the range of from 20,000 g/mol to about 450,000 g/mol, for example a molecular weight in the range of from 20,000 g/mol to about 400,000 g/mol, such as a molecular weight in the range of from 20,000 g/mol to about 350,000 g/mol, for example a molecular weight in the range of from 20,000 g/mol to about 300,000 g/mol, such as a molecular weight in the range of from 20,000 g/mol to about 250,000 g/mol, for example a molecular weight in the range of from 20,000 g/mol to about 200,000 g/mol, such as a molecular weight in the range of from 20,000 g/mol to about 100,000 g/mol, for example a molecular weight in the range of from 20,000 g/mol to about 80,000 g/mol, such as a molecular weight in the range of from 20,000 g/mol to about 60,000 g/mol, for example a molecular weight in the range of from 20,000 g/mol to about 50,000 g/mol, such as a molecular weight in the range of from 20,000 g/mol to about 40,000 g/mol, for example a molecular weight in the range of from 20,000 g/mol to about 35.000 g/mol, such as a molecular weight in the range of from 20,000 g/mol to about 30,000 g/mol, for example a molecular weight in the range of from 20,000 g/mol to about 25.000 g/mol, such as a molecular weight in the range of from 25,000 g/mol to about 1,000,000 g/mol, such as a molecular weight in the range of from 25,000 g/mol to about 900,000 g/mol, for example a molecular weight in the range of from 25,000 g/mol to about 800,000 g/mol, such as a molecular weight in the range of from 25,000 g/mol to about 900,000 g/mol, for example a molecular weight in the range of from 25,000 g/mol to about 800,000 g/mol, such as a molecular weight in the range of from 25,000 g/mol to about 750,000 g/mol, for example a molecular weight in the range of from 25,000 g/mol to about 700,000 g/mol, such as a molecular weight in the range of from 25,000 g/mol to about 1270,000 g/mol, for example a molecular weight in the range of from 25,000 g/mol to about 600,000 g/mol, such as a molecular weight in the range of from 25,000 g/mol to about 550,000 g/mol, for example a molecular weight in the range of from 25,000 g/mol to about 500,000 g/mol, such as a molecular weight in the range of from 25,000 g/mol to about 450,000 g/mol, for example a molecular weight in the range of from 25,000 g/mol to about 400,000 g/mol, such as a molecular weight in the range of from 25,000 g/mol to about 350,000 g/mol, for example a molecular weight in the range of from 25,000 g/mol to about 300,000 g/mol, such as a molecular weight in the range of from 25,000 g/mol to about 250,000 g/mol, for example a molecular weight in the range of from 25,000 g/mol to about 200,000 g/mol, such as a molecular weight in the range of from 25,000 g/mol to about 100,000 g/mol, for example a molecular weight in the range of from 25,000 g/mol to about 80,000 g/mol, such as a molecular weight in the range of from 25,000 g/mol to about 60,000 g/mol, for example a molecular weight in the range of from 25,000 g/mol to about 50,000 g/mol, such as a molecular weight in the range of from 25,000 g/mol to about 40,000 g/mol, for example a molecular weight in the range of from 25,000 g/mol to about 35.000 g/mol, such as a molecular weight in the range of from 25,000 g/mol to about 30,000 g/mol, for example a molecular weight in the range of from 30,000 g/mol to about 1,000,000 g/mol, such as a molecular weight in the range of from 30,000 g/mol to about 900,000 g/mol, for example a molecular weight in the range of from 30,000 g/mol to about 800,000 g/mol, such as a molecular weight in the range of from 30,000 g/mol to about 900,000 g/mol, for example a molecular weight in the range of from 30,000 g/mol to about 800,000 g/mol, such as a molecular weight in the range of from 30,000 g/mol to about 750,000 g/mol, for example a molecular weight in the range of from 30,000 g/mol to about 700,000 g/mol, such as a molecular weight in the range of from 30,000 g/mol to about 1270,000 g/mol, for example a molecular weight in the range of from 30,000 g/mol to about 600,000 g/mol, such as a molecular weight in the range of from 30,000 g/mol to about 550,000 g/mol, for example a molecular weight in the range of from 30,000 g/mol to about 500,000 g/mol, such as a molecular weight in the range of from 30,000 g/mol to about 450,000 g/mol, for example a molecular weight in the range of from 30,000 g/mol to about 400,000 g/mol, such as a molecular weight in the range of from 30,000 g/mol to about 350,000 g/mol, for example a molecular weight in the range of from 30,000 g/mol to about 300,000 g/mol, such as a molecular weight in the range of from 30,000 g/mol to about 250,000 g/mol, for example a molecular weight in the range of from 30,000 g/mol to about 200,000 g/mol, such as a molecular weight in the range of from 30,000 g/mol to about 100,000 g/mol, for example a molecular weight in the range of from 30,000 g/mol to about 80,000 g/mol, such as a molecular weight in the range of from 30,000 g/mol to about 60,000 g/mol, for example a molecular weight in the range of from 30,000 g/mol to about 50,000 g/mol, such as a molecular weight in the range of from 30,000 g/mol to about 40,000 g/mol, for example a molecular weight in the range of from 30,000 g/mol to about 35.000 g/mol, such as a molecular weight in the range of from 40,000 g/mol to about 1,000,000 g/mol, such as a molecular weight in the range of from 40,000 g/mol to about 900,000 g/mol, for example a molecular weight in the range of from 40,000 g/mol to about 800,000 g/mol, such as a molecular weight in the range of from 40,000 g/mol to about 900,000 g/mol, for example a molecular weight in the range of from 40,000 g/mol to about 800,000 g/mol, such as a molecular weight in the range of from 40,000 g/mol to about 750,000 g/mol, for example a molecular weight in the range of from 40,000 g/mol to about 700,000 g/mol, such as a molecular weight in the range of from 40,000 g/mol to about 1270,000 g/mol, for example a molecular weight in the range of from 40,000 g/mol to about 600,000 g/mol, such as a molecular weight in the range of from 40,000 g/mol to about 550,000 g/mol, for example a molecular weight in the range of from 40,000 g/mol to about 500,000 g/mol, such as a molecular weight in the range of from 40,000 g/mol to about 450,000 g/mol, for example a molecular weight in the range of from 40,000 g/mol to about 400,000 g/mol, such as a molecular weight in the range of from 40,000 g/mol to about 350,000 g/mol, for example a molecular weight in the range of from 40,000 g/mol to about 300,000 g/mol, such as a molecular weight in the range of from 40,000 g/mol to about 250,000 g/mol, for example a molecular weight in the range of from 40,000 g/mol to about 200,000 g/mol, such as a molecular weight in the range of from 40,000 g/mol to about 100,000 g/mol, for example a molecular weight in the range of from 40,000 g/mol to about 80,000 g/mol, such as a molecular weight in the range of from 40,000 g/mol to about 60,000 g/mol, for example a molecular weight in the range of from 40,000 g/mol to about 50,000 g/mol, such as a molecular weight in the range of from 50,000 g/mol to about 1,000,000 g/mol, such as a molecular weight in the range of from 50,000 g/mol to about 900,000 g/mol, for example a molecular weight in the range of from 50,000 g/mol to about 800,000 g/mol, such as a molecular weight in the range of from 50,000 g/mol to about 900,000 g/mol, for example a molecular weight in the range of from 50,000 g/mol to about 800,000 g/mol, such as a molecular weight in the range of from 50,000 g/mol to about 750,000 g/mol, for example a molecular weight in the range of from 50,000 g/mol to about 700,000 g/mol, such as a molecular weight in the range of from 50,000 g/mol to about 1270,000 g/mol, for example a molecular weight in the range of from 50,000 g/mol to about 600,000 g/mol, such as a molecular weight in the range of from 50,000 g/mol to about 550,000 g/mol, for example a molecular weight in the range of from 50,000 g/mol to about 500,000 g/mol, such as a molecular weight in the range of from 50,000 g/mol to about 450,000 g/mol, for example a molecular weight in the range of from 50,000 g/mol to about 400,000 g/mol, such as a molecular weight in the range of from 50,000 g/mol to about 350,000 g/mol, for example a molecular weight in the range of from 50,000 g/mol to about 300,000 g/mol, such as a molecular weight in the range of from 50,000 g/mol to about 250,000 g/mol, for example a molecular weight in the range of from 50,000 g/mol to about 200,000 g/mol, such as a molecular weight in the range of from 50,000 g/mol to about 100,000 g/mol, for example a molecular weight in the range of from 50,000 g/mol to about 80,000 g/mol, such as a molecular weight in the range of from 50,000 g/mol to about 60,000 g/mol, for example a molecular weight in the range of from 75,000 g/mol to about 1,000,000 g/mol, such as a molecular weight in the range of from 75,000 g/mol to about 900,000 g/mol, for example a molecular weight in the range of from 75,000 g/mol to about 800,000 g/mol, such as a molecular weight in the range of from 75,000 g/mol to about 900,000 g/mol, for example a molecular weight in the range of from 75,000 g/mol to about 800,000 g/mol, such as a molecular weight in the range of from 75,000 g/mol to about 750,000 g/mol, for example a molecular weight in the range of from 75,000 g/mol to about 700,000 g/mol, such as a molecular weight in the range of from 75,000 g/mol to about 1270,000 g/mol, for example a molecular weight in the range of from 75,000 g/mol to about 600,000 g/mol, such as a molecular weight in the range of from 75,000 g/mol to about 550,000 g/mol, for example a molecular weight in the range of from 75,000 g/mol to about 500,000 g/mol, such as a molecular weight in the range of from 75,000 g/mol to about 450,000 g/mol, for example a molecular weight in the range of from 75,000 g/mol to about 400,000 g/mol, such as a molecular weight in the range of from 75,000 g/mol to about 350,000 g/mol, for example a molecular weight in the range of from 75,000 g/mol to about 300,000 g/mol, such as a molecular weight in the range of from 75,000 g/mol to about 250,000 g/mol, for example a molecular weight in the range of from 75,000 g/mol to about 200,000 g/mol, such as a molecular weight in the range of from 75,000 g/mol to about 100,000 g/mol, for example a molecular weight in the range of from 75,000 g/mol to about 80,000 g/mol, a molecular weight in the range of from 100,000 g/mol to about 1,000,000 g/mol, such as a molecular weight in the range of from 100,000 g/mol to about 900,000 g/mol, for example a molecular weight in the range of from 100,000 g/mol to about 800,000 g/mol, such as a molecular weight in the range of from 100,000 g/mol to about 900,000 g/mol, for example a molecular weight in the range of from 100,000 g/mol to about 800,000 g/mol, such as a molecular weight in the range of from 100,000 g/mol to about 750,000 g/mol, for example a molecular weight in the range of from 100,000 g/mol to about 700,000 g/mol, such as a molecular weight in the range of from 100,000 g/mol to about 1270,000 g/mol, for example a molecular weight in the range of from 100,000 g/mol to about 600,000 g/mol, such as a molecular weight in the range of from 100,000 g/mol to about 550,000 g/mol, for example a molecular weight in the range of from 100,000 g/mol to about 500,000 g/mol, such as a molecular weight in the range of from 100,000 g/mol to about 450,000 g/mol, for example a molecular weight in the range of from 100,000 g/mol to about 400,000 g/mol, such as a molecular weight in the range of from 100,000 g/mol to about 350,000 g/mol, for example a molecular weight in the range of from 100,000 g/mol to about 300,000 g/mol, such as a molecular weight in the range of from 100,000 g/mol to about 250,000 g/mol, for example a molecular weight in the range of from 100,000 g/mol to about 200,000 g/mol, such as a molecular weight in the range of from 200,000 g/mol to about 300,000 g/mol, for example a molecular weight in the range of from 300,000 g/mol to about 400,000 g/mol, such as a molecular weight in the range of from 400,000 g/mol to about 500,000 g/mol, for example a molecular weight in the range of from 500,000 g/mol to about 600,000 g/mol, such as a molecular weight in the range of from 700,000 g/mol to about 800,000 g/mol, for example a molecular weight in the range of from 800,000 g/mol to about 900,000 g/mol, such as a molecular weight in the range of from 900,000 g/mol to about 1,000,000 g/mol.

135. The bioactive agent according to item 2, wherein the polysaccharide comprises a structural component selected from the group of components consisting of
(1-3)-alpha-D-glucan;
(1-3)-alpha-D-glucan with (1-6)-beta branching;
(1-3)-alpha-D-glucan with (1-6)-alpha branching;
(1-3)-alpha-D-glucan with (1-4)-beta branching;
(1-3)-alpha-D-glucan with (1-4)-alpha branching;
(1-3)-beta-D-glucan;
(1-3)-beta-D-glucan with (1-6)-beta branching;
(1-3)-beta-D-glucan with (1-6)-alpha branching;
(1-3)-beta-D-glucan with (1-4)-beta branching;
(1-3)-beta-D-glucan with (1-4)-alpha branching;
(1-4)-alpha-D-glucan;
(1-4)-alpha-D-glucan with (1-6)-beta branching;
(1-4)-alpha-D-glucan with (1-6)-alpha branching;
(1-4)-alpha-D-glucan with (1-4)-beta branching;
(1-4)-alpha-D-glucan with (1-4)-alpha branching;
(1-4)-beta-D-glucan;
(1-4)-beta-D-glucan with (1-6)-beta branching;
(1-4)-beta-D-glucan with (1-6)-alpha branching;
(1-4)-beta-D-glucan with (1-4)-beta branching;
(1-4)-beta-D-glucan with (1-4)-alpha branching;
(1-6)-beta-D-glucan;
(1-6)-beta-D-glucan with (1-6)-beta branching;
(1-6)-beta-D-glucan with (1-6)-alpha branching;
(1-6)-beta-D-glucan with (1-4)-beta branching;
(1-6)-beta-D-glucan with (1-4)-alpha branching;
(1-6)-alpha-D-glucan;
(1-6)-alpha-D-glucan with (1-6)-beta branching;
(1-6)-alpha-D-glucan with (1-6)-alpha branching;
(1-6)-alpha-D-glucan with (1-4)-beta branching;
(1-6)-alpha-D-glucan with (1-4)-alpha branching;

136. The bioactive agent according to item 2, wherein the polysaccharide comprises a structural component comprising (1-3)-alpha-D-glucan.

137. The bioactive agent according to item 2, wherein the polysaccharide comprises a structural component comprising (1-3)-alpha-D-glucan with (1-6)-beta branching.

138. The bioactive agent according to item 2, wherein the polysaccharide comprises a structural component comprising (1-3)-alpha-D-glucan with (1-6)-alpha branching.

139. The bioactive agent according to item 2, wherein the polysaccharide comprises a structural component comprising (1-3)-alpha-D-glucan with (1-4)-beta branching.

140. The bioactive agent according to item 2, wherein the polysaccharide comprises a structural component comprising (1-3)-alpha-D-glucan with (1-4)-alpha branching.

141. The bioactive agent according to item 2, wherein the polysaccharide comprises a structural component comprising (1-3)-beta-D-glucan.

142. The bioactive agent according to item 2, wherein the polysaccharide comprises a structural component comprising (1-3)-beta-D-glucan with (1-6)-beta branching.

143. The bioactive agent according to item 2, wherein the polysaccharide comprises a structural component comprising (1-3)-beta-D-glucan with (1-6)-alpha branching.

144. The bioactive agent according to item 2, wherein the polysaccharide comprises a structural component comprising (1-3)-beta-D-glucan with (1-4)-beta branching.

145. The bioactive agent according to item 2, wherein the polysaccharide comprises a structural component comprising (1-3)-beta-D-glucan with (1-4)-alpha branching.

146. The bioactive agent according to item 2, wherein the polysaccharide comprises a structural component comprising (1-4)-alpha-D-glucan.

147. The bioactive agent according to item 2, wherein the polysaccharide comprises a structural component comprising (1-4)-alpha-D-glucan with (1-6)-beta branching.

148. The bioactive agent according to item 2, wherein the polysaccharide comprises a structural component comprising (1-4)-alpha-D-glucan with (1-6)-alpha branching.

149. The bioactive agent according to item 2, wherein the polysaccharide comprises a structural component comprising (1-4)-alpha-D-glucan with (1-4)-beta branching.

150. The bioactive agent according to item 2, wherein the polysaccharide comprises a structural component comprising (1-4)-alpha-D-glucan with (1-4)-alpha branching.

151. The bioactive agent according to item 2, wherein the polysaccharide comprises a structural component comprising (1-4)-beta-D-glucan.

152. The bioactive agent according to item 2, wherein the polysaccharide comprises a structural component comprising (1-4)-beta-D-glucan with (1-6)-beta branching.

153. The bioactive agent according to item 2, wherein the polysaccharide comprises a structural component comprising (1-4)-beta-D-glucan with (1-6)-alpha branching.

154. The bioactive agent according to item 2, wherein the polysaccharide comprises a structural component comprising (1-4)-beta-D-glucan with (1-4)-beta branching.

155. The bioactive agent according to item 2, wherein the polysaccharide comprises a structural component comprising (1-4)-beta-D-glucan with (1-4)-alpha branching.

156. The bioactive agent according to item 2, wherein the polysaccharide comprises a structural component comprising (1-6)-beta-D-glucan.

157. The bioactive agent according to item 2, wherein the polysaccharide comprises a structural component comprising (1-6)-beta-D-glucan with (1-6)-beta branching.

158. The bioactive agent according to item 2, wherein the polysaccharide comprises a structural component comprising (1-6)-beta-D-glucan with (1-6)-alpha branching.

159. The bioactive agent according to item 2, wherein the polysaccharide comprises a structural component comprising (1-6)-beta-D-glucan with (1-4)-beta branching.

160. The bioactive agent according to item 2, wherein the polysaccharide comprises a structural component comprising (1-6)-beta-D-glucan with (1-4)-alpha branching.

161. The bioactive agent according to item 2, wherein the polysaccharide comprises a structural component comprising (1-6)-alpha-D-glucan.

162. The bioactive agent according to item 2, wherein the polysaccharide comprises a structural component comprising (1-6)-alpha-D-glucan with (1-6)-beta branching.

163. The bioactive agent according to item 2, wherein the polysaccharide comprises a structural component comprising (1-6)-alpha-D-glucan with (1-6)-alpha branching.

164. The bioactive agent according to item 2, wherein the polysaccharide comprises a structural component comprising (1-6)-alpha-D-glucan with (1-4)-beta branching.

165. The bioactive agent according to item 2, wherein the polysaccharide comprises a structural component comprising (1-6)-alpha-D-glucan with (1-4)-alpha branching.

166. The bioactive agent according to item 2, wherein the polysaccharide backbone comprises a plurality of monosaccharide units linked by a chemical bond selected from the group consisting of (1-6)-beta bonds, (1-4)-beta bonds, (1-3)-beta bonds, (1-2)-beta bonds, (1-1)-beta bonds, 1-beta-1-alpha bonds, 1-alpha-1-alpha bonds, 1-alpha-1-beta bonds, (1-2)-alpha bonds, (1-3)-alpha bonds, (1-4)-alpha bonds and (1-6)-alpha bonds.
167. The bioactive agent according to item 2, wherein the polysaccharide backbone comprises a plurality of monosaccharide units linked by (1-6)-beta bonds.
168. The bioactive agent according to item 2, wherein the polysaccharide backbone comprises a plurality of monosaccharide units linked by (1-4)-beta bonds.
169. The bioactive agent according to item 2, wherein the polysaccharide backbone comprises a plurality of monosaccharide units linked by (1-3)-beta bonds.
170. The bioactive agent according to item 2, wherein the polysaccharide backbone comprises a plurality of monosaccharide units linked by (1-2)-beta bonds.
171. The bioactive agent according to item 2, wherein the polysaccharide backbone comprises a plurality of monosaccharide units linked by (1-1)-beta bonds.
172. The bioactive agent according to item 2, wherein the polysaccharide backbone comprises a plurality of monosaccharide units linked by 1-beta-1-alpha bonds.
173. The bioactive agent according to item 2, wherein the polysaccharide backbone comprises a plurality of monosaccharide units linked by 1-alpha-1-alpha bonds.
174. The bioactive agent according to item 2, wherein the polysaccharide backbone comprises a plurality of monosaccharide units linked by 1-alpha-1-beta bonds.
175. The bioactive agent according to item 2, wherein the polysaccharide backbone comprises a plurality of monosaccharide units linked by (1-2)-alpha bonds.
176. The bioactive agent according to item 2, wherein the polysaccharide backbone comprises a plurality of monosaccharide units linked by (1-3)-alpha bonds.
177. The bioactive agent according to item 2, wherein the polysaccharide backbone comprises a plurality of monosaccharide units linked by (1-4)-alpha bonds.
178. The bioactive agent according to item 2, wherein the polysaccharide backbone comprises a plurality of monosaccharide units linked by (1-6)-alpha bonds.
179. The bioactive agent according to any of items 166 to 178, wherein the polysaccharide further comprises side chains comprising a plurality of monosaccharides selected from the group consisting of (1-6)-beta bonds, (1-4)-beta bonds, (1-3)-beta bonds, (1-2)-beta bonds, (1-1)-beta bonds, 1-beta-1-alpha bonds, 1-alpha-1-alpha bonds, 1-alpha-1-beta bonds, (1-2)-alpha bonds, (1-3)-alpha bonds, (1-4)-alpha bonds and (1-6)-alpha bonds.
180. The bioactive agent according to any of items 166 to 178, wherein the polysaccharide side chains comprise a plurality of monosaccharide units linked by (1-6)-beta bonds.
181. The bioactive agent according to any of items 166 to 178, wherein the polysaccharide side chains comprise a plurality of monosaccharide units linked by (1-4)-beta bonds.
182. The bioactive agent according to any of items 166 to 178, wherein the polysaccharide side chains comprise a plurality of monosaccharide units linked by (1-3)-beta bonds.
183. The bioactive agent according to any of items 166 to 178, wherein the polysaccharide side chains comprise a plurality of monosaccharide units linked by (1-2)-beta bonds.
184. The bioactive agent according to any of items 166 to 178, wherein the polysaccharide side chains comprise a plurality of monosaccharide units linked by (1-1)-beta bonds.
185. The bioactive agent according to any of items 166 to 178, wherein the polysaccharide side chains comprise a plurality of monosaccharide units linked by 1-beta-1-alpha bonds.
186. The bioactive agent according to any of items 166 to 178, wherein the polysaccharide side chains comprise a plurality of monosaccharide units linked by 1-alpha-1-alpha bonds.
187. The bioactive agent according to any of items 166 to 178, wherein the polysaccharide side chains comprise a plurality of monosaccharide units linked by 1-alpha-1-beta bonds.
188. The bioactive agent according to any of items 166 to 178, wherein the polysaccharide side chains comprise a plurality of monosaccharide units linked by (1-2)-alpha bonds.
189. The bioactive agent according to any of items 166 to 178, wherein the polysaccharide side chains comprise a plurality of monosaccharide units linked by (1-3)-alpha bonds.
190. The bioactive agent according to any of items 166 to 178, wherein the polysaccharide side chains comprise a plurality of monosaccharide units linked by (1-4)-alpha bonds.
191. The bioactive agent according to any of items 166 to 178, wherein the polysaccharide side chains comprise a plurality of monosaccharide units linked by (1-6)-alpha bonds.
192. The bioactive agent according to any of items 2 to 191, wherein the polysaccharide is a heteropolymer comprising two or more different monosaccharides in the main chain, such as 3 different monosaccharides in the main chain, for example 4 different monosaccharides in the main chain, such as 5 different monosaccharides in the main chain, for example 6 different monosaccharides in the main chain.
193. The bioactive agent according to item 192, wherein the polysaccharide further comprises two or more different monosaccharides in the side chains, such as 3 different monosaccharides in the side chains, for example 4 different monosaccharides in the side chains, such as 5 different monosaccharides in the side chains, for example 6 different monosaccharides in the side chains.
194. The bioactive agent according to any of items 7, 38 and 69, wherein the ratio R=a/b between a) the number of glucose monosaccharides and b) the number of further monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; such as from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1, such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

195. The bioactive agent according to any of items 7, 38 and 69, wherein the ratio R=b/a between a) the number of glucose monosaccharides and b) the number of further monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

196. The bioactive agent according to any of items 7, 38 and 69, wherein the ratio R=a/b between a) the number of glucose monosaccharides and b) the number of glucuronic acid monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

197. The bioactive agent according to any of items 7, 38 and 69, wherein the ratio R=b/a between a) the number of glucose monosaccharides and b) the number of glucuronic acid monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

198. The bioactive agent according to any of items 7, 38 and 69, wherein the ratio R=a/b between a) the number of glucose monosaccharides and b) the number of galactose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

199. The bioactive agent according to any of items 7, 38 and 69, wherein the ratio R=b/a between a) the number of glucose monosaccharides and b) the number of galactose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

200. The bioactive agent according to any of items 7, 38 and 69, wherein the ratio R=a/b between a) the number of glucose monosaccharides and b) the number of mannose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

201. The bioactive agent according to any of items 7, 38 and 69, wherein the ratio R=b/a between a) the number of glucose monosaccharides and b) the number of mannose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

202. The bioactive agent according to any of items 7, 38 and 69, wherein the ratio R=a/b between a) the number of glucose monosaccharides and b) the number of arabinose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

203. The bioactive agent according to any of items 7, 38 and 69, wherein the ratio R=b/a between a) the number of glucose monosaccharides and b) the number of arabinose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

204. The bioactive agent according to any of items 7, 38 and 69, wherein the ratio R=a/b between a) the number of glucose monosaccharides and b) the number of xylose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

205. The bioactive agent according to any of items 7, 38 and 69, wherein the ratio R=b/a between a) the number of glucose monosaccharides and b) the number of xylose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

206. The bioactive agent according to item 2, wherein the polysaccharide comprises a structural component in the back bone comprising beta-1,2-linked D-mannopyranosyl residues and a structural component in the side chains comprising beta-D-glucopyranosyl-3-O-beta-D-glucopyranosyl residues.

207. The bioactive agent according to item 2, wherein the polysaccharide is a complex comprising a (1,4)-alpha-D-glucan and a (1,6)-beta glucan.

208. The bioactive agent according to item 2, wherein the polysaccharide is a complex comprising a (1,4)-alpha-D-glucan and a (1,6)-alpha glucan.

209. The bioactive agent according to any of the above items 1 to 208, wherein said bioactive agent is produced by liquid cultivation of a Basidiomycete cell selected from the group consisting of cells belonging to the subclasses of Agaricomycetidae, Exobasidiomycetidae, Tremellomycetidae and Ustilaginomycetidae.

210. The bioactive agent according to item 209, wherein the Basidiomycete cell is selected form the subclass of Agaricomycetidae.

211. The bioactive agent according to item 209, wherein the Basidiomycete cell is selected form the subclass of Exobasidiomycetidae.

212. The bioactive agent according to item 209, wherein the Basidiomycete cell is selected form the subclass of Tremellomyceditae.

213. The bioactive agent according to item 209, wherein the Basidiomycete cell is selected form the subclass of Ustilaginomycetidae.

214. The bioactive agent according to item 1 to 208, wherein said bioactive agent is produced by liquid cultivation of a Basidiomycete cell selected from the group consisting of cells belonging to the orders of Agaricales, Boletales, Cantheralles, Ceratobasidiales, Dacrymycetales, Hymenochaetales, Phallales, Polyporales, Poriales, Russulales, Thelphorales, Auriculariales, Christianseniales, Cystofilobasidiales, Filobasidiales, Tremellales, Tulasenellales and Urocystales.

215. The bioactive agent according to item 214, wherein the Basidiomycete cell is selected from the order of Agaricales.

216. The bioactive agent according to item 215, wherein said Basidiomycete cell belongs to a family selected from the group consisting of Agaricaceae, Bolbitiaceae, Broomeiaceae, Clavariaceae, Coprinaceae, Cortinariaceae, Entolomataceae, Fistulinaceae, Gigaspermaceae, Hemigasteraceae, Hydnangiaceae, Lycoperdaceae, Marasmiaceae, Mesophelliaceae, Mycenastraceae, Niaceae, Nidulariaceae, Phelloriniaceae, Pleurotaceae, Pluteaceae, Pterulaceae, Schizophyllaceae, Stromatocyphaceae, Strophariaceae, Tricholomataceae, Tulostomataceae, Typhulaceae and Xerulaceae.

217. The bioactive agent according to item 216, wherein Basidiomycete cell is selected from the family of Agaricaceae.

218. The bioactive agent according to item 216, wherein Basidiomycete cell is selected from the family of Bolbitiaceae.

219. The bioactive agent according to item 216, wherein Basidiomycete cell is selected from the family of Broomeiaceae.

220. The bioactive agent according to item 216, wherein Basidiomycete cell is selected from the family of Clavariaceae.

221. The bioactive agent according to item 216, wherein Basidiomycete cell is selected from the family of Coprinaceae.

222. The bioactive agent according to item 216, wherein Basidiomycete cell is selected from the family of Cortinariaceae.

223. The bioactive agent according to item 216, wherein Basidiomycete cell is selected from the family of Entolomataceae.

224. The bioactive agent according to item 216, wherein Basidiomycete cell is selected from the family of Fistulinaceae.

225. The bioactive agent according to item 216, wherein Basidiomycete cell is selected from the family of Gigaspermaceae.

226. The bioactive agent according to item 216, wherein Basidiomycete cell is selected from the family of Hemigasteraceae.

227. The bioactive agent according to item 216, wherein Basidiomycete cell is selected from the family of Hydnangiaceae.

228. The bioactive agent according to item 216, wherein Basidiomycete cell is selected from the family of Lycoperdaceae.

229. The bioactive agent according to item 216, wherein Basidiomycete cell is selected from the family of Marasmiaceae.

230. The bioactive agent according to item 216, wherein Basidiomycete cell is selected from the family of Mesophelliaceae.

231. The bioactive agent according to item 216, wherein Basidiomycete cell is selected from the family of Mycenastraceae.

232. The bioactive agent according to item 216, wherein Basidiomycete cell is selected from the family of Niaceae.

233. The bioactive agent according to item 216, wherein Basidiomycete cell is selected from the family of Nidulariaceae.

234. The bioactive agent according to item 216, wherein Basidiomycete cell is selected from the family of Phelloriniaceae.

235. The bioactive agent according to item 216, wherein Basidiomycete cell is selected from the family of Pleurotaceae.

236. The bioactive agent according to item 216, wherein Basidiomycete cell is selected from the family of Pluteaceae.

237. The bioactive agent according to item 216, wherein Basidiomycete cell is selected from the family of Pterulaceae.

238. The bioactive agent according to item 216, wherein Basidiomycete cell is selected from the family of Schizophyllaceae.

239. The bioactive agent according to item 216, wherein Basidiomycete cell is selected from the family of Stromatocyphaceae.

240. The bioactive agent according to item 216, wherein Basidiomycete cell is selected from the family of Strophariaceae.

241. The bioactive agent according to item 216, wherein Basidiomycete cell is selected from the family of Tricholomataceae.

242. The bioactive agent according to item 216, wherein Basidiomycete cell is selected from the family of Tulostomataceae.

243. The bioactive agent according to item 216, wherein Basidiomycete cell is selected from the family of Typhulaceae.

244. The bioactive agent according to item 216, wherein Basidiomycete cell is selected from the family of Xerulaceae.

245. The bioactive agent according to item 214, wherein the Basidiomycete cell is selected from the order of Polyporales.

246. The bioactive agent according to item 245, wherein said Basidiomycete cell belongs to a family selected from the group consisting of Albatrellaceae, Atheliaceae, Boreostereaceae, Corticiaceae, Cyphellaceae, Cystostereaceae, Epitheliaceae, Fomitopsidaceae, Ganodermataceae, Gloeophyllaceae, Grammotheleaceae, Hapalopilaceae, Hyphodermataceae, Meripilaceae, Meruliaceae, Phanerochaetaceae, Podoscyphaceae, Polyporaceae, Sistotremataceae, Sparassidaceae, Steccherinaceae, Tubulicrinaceae and Xenasmataceae.

247. The bioactive agent according to item 246, wherein Basidiomycete cell is selected from the family of Albatrellaceae.

248. The bioactive agent according to item 246, wherein Basidiomycete cell is selected from the family of Atheliaceae.

249. The bioactive agent according to item 246, wherein Basidiomycete cell is selected from the family of Boreostereaceae.

250. The bioactive agent according to item 246, wherein Basidiomycete cell is selected from the family of Corticiaceae.

251. The bioactive agent according to item 246, wherein Basidiomycete cell is selected from the family of Cyphellaceae.

252. The bioactive agent according to item 246, wherein Basidiomycete cell is selected from the family of Cystostereaceae.

253. The bioactive agent according to item 246, wherein Basidiomycete cell is selected from the family of Epitheliaceae.
254. The bioactive agent according to item 246, wherein Basidiomycete cell is selected from the family of Fomitopsidaceae.
255. The bioactive agent according to item 246, wherein Basidiomycete cell is selected from the family of Ganodermataceae.
256. The bioactive agent according to item 246, wherein Basidiomycete cell is selected from the family of Gloeophyllaceae.
257. The bioactive agent according to item 246, wherein Basidiomycete cell is selected from the family of Grammotheleaceae.
258. The bioactive agent according to item 246, wherein Basidiomycete cell is selected from the family of Hapalopilaceae.
259. The bioactive agent according to item 246, wherein Basidiomycete cell is selected from the family of Hyphodermataceae.
260. The bioactive agent according to item 246, wherein Basidiomycete cell is selected from the family of Meripilaceae.
261. The bioactive agent according to item 246, wherein Basidiomycete cell is selected from the family of Meruliaceae.
262. The bioactive agent according to item 246, wherein Basidiomycete cell is selected from the family of Phanerochaetaceae.
263. The bioactive agent according to item 246, wherein Basidiomycete cell is selected from the family of Podoscyphaceae.
264. The bioactive agent according to item 246, wherein Basidiomycete cell is selected from the family of Polyporaceae.
265. The bioactive agent according to item 246, wherein Basidiomycete cell is selected from the family of Sistotremataceae.
266. The bioactive agent according to item 246, wherein Basidiomycete cell is selected from the family of Sparassidaceae.
267. The bioactive agent according to item 246, wherein Basidiomycete cell is selected from the family of Steccherinaceae.
268. The bioactive agent according to item 246, wherein Basidiomycete cell is selected from the family of Tubulicrinaceae.
269. The bioactive agent according to item 246, wherein Basidiomycete cell is selected from the family of Xenasmataceae.
270. The bioactive agent according to item 214, wherein the Basidiomycete cell is selected from the order of Boletales.
271. The bioactive agent according to item 270, wherein said Basidiomycete cell belongs to a family selected from the group consisting of Boletaceae, Boletinellaceae, Coniophoraceae, Diplocystaceae, Gasterellaceae, Gastrosporiaceae, Gomphidiaceae, Gyroporaceae, Hygrophoropsidaceae, Hymenogasteraceae, Leucogastraceae, Melanogastraceae, Octavianiaceae, Octavianinaceae, Paxillaceae, Protogastraceae, Rhizopogonaceae, Sclerodermataceae and Suillaceae.
272. The bioactive agent according to item 271, wherein Basidiomycete cell is selected from the family of Boletaceae.
273. The bioactive agent according to item 271, wherein Basidiomycete cell is selected from the family of Boletinellaceae.
274. The bioactive agent according to item 271, wherein Basidiomycete cell is selected from the family of Coniophoraceae.
275. The bioactive agent according to item 271, wherein Basidiomycete cell is selected from the family of Diplocystaceae.
276. The bioactive agent according to item 271, wherein Basidiomycete cell is selected from the family of Gasterellaceae.
277. The bioactive agent according to item 271, wherein Basidiomycete cell is selected from the family of Gastrosporiaceae.
278. The bioactive agent according to item 271, wherein Basidiomycete cell is selected from the family of Gomphidiaceae.
279. The bioactive agent according to item 271, wherein Basidiomycete cell is selected from the family of Gyroporaceae.
280. The bioactive agent according to item 271, wherein Basidiomycete cell is selected from the family of Hygrophoropsidaceae.
281. The bioactive agent according to item 271, wherein Basidiomycete cell is selected from the family of Hymenogasteraceae.
282. The bioactive agent according to item 271, wherein Basidiomycete cell is selected from the family of Leucogastraceae.
283. The bioactive agent according to item 271, wherein Basidiomycete cell is selected from the family of Melanogastraceae.
284. The bioactive agent according to item 271, wherein Basidiomycete cell is selected from the family of Octavianiaceae.
285. The bioactive agent according to item 271, wherein Basidiomycete cell is selected from the family of Octavianinaceae.
286. The bioactive agent according to item 271, wherein Basidiomycete cell is selected from the family of Paxillaceae.
287. The bioactive agent according to item 271, wherein Basidiomycete cell is selected from the family of Protogastraceae.
288. The bioactive agent according to item 271, wherein Basidiomycete cell is selected from the family of Rhizopogonaceae.
289. The bioactive agent according to item 271, wherein Basidiomycete cell is selected from the family of Sclerodermataceae.
290. The bioactive agent according to item 271, wherein Basidiomycete cell is selected from the family of Suillaceae.
291. The bioactive agent according to item 214, wherein the Basidiomycete cell is selected from the order of Cantheralles.
292. The bioactive agent according to item 291, wherein said Basidiomycete cell belongs to a family selected from the group consisting of Aphelariaceae, Botryobasidiaceae, Cantharellaceae, Clavulinaceae, and Hydnaceae.
293. The bioactive agent according to item 271, wherein Basidiomycete cell is selected from the family of Aphelariaceae.
294. The bioactive agent according to item 271, wherein Basidiomycete cell is selected from the family of Botryobasidiaceae.

295. The bioactive agent according to item 271, wherein Basidiomycete cell is selected from the family of Cantharellaceae.
296. The bioactive agent according to item 271, wherein Basidiomycete cell is selected from the family of Clavulinaceae.
297. The bioactive agent according to item 271, wherein Basidiomycete cell is selected from the family of Hydnaceae.
298. The bioactive agent according to item 214, wherein the Basidiomycete cell is selected from the order of Ceratobasidiales.
299. The bioactive agent according to item 298, wherein said Basidiomycete cell belongs to a family selected from the group consisting of Ceratobasidiaceae and Oliveoniaceae.
300. The bioactive agent according to item 299, wherein Basidiomycete cell is selected from the family of Ceratobasidiaceae.
301. The bioactive agent according to item 299, wherein Basidiomycete cell is selected from the family of Oliveoniaceae.
302. The bioactive agent according to item 214, wherein the Basidiomycete cell is selected from the order of Dacrymycetales.
303. The bioactive agent according to item 302, wherein said Basidiomycete cell belongs to a family selected from the group consisting of Cerinomycetaceae and Dacrymycetaceae.
304. The bioactive agent according to item 303, wherein Basidiomycete cell is selected from the family of Cerinomycetaceae.
305. The bioactive agent according to item 303, wherein Basidiomycete cell is selected from the family of Dacrymycetaceae.
306. The bioactive agent according to item 214, wherein the Basidiomycete cell is selected from the order of Hymenochaetales.
307. The bioactive agent according to item 306, wherein said Basidiomycete cell belongs to a family selected from the group consisting of Asterostromataceae, Hymenochaetaceae and Schizoporaceae.
308. The bioactive agent according to item 307, wherein Basidiomycete cell is selected from the family of Asterostromataceae.
309. The bioactive agent according to item 307, wherein Basidiomycete cell is selected from the family of Hymenochaetaceae.
310. The bioactive agent according to item 307, wherein Basidiomycete cell is selected from the family of Schizoporaceae.
311. The bioactive agent according to item 214, wherein the Basidiomycete cell is selected from the order of Phallales.
312. The bioactive agent according to item 311, wherein said Basidiomycete cell belongs to a family selected from the group consisting of Geastraceae, Gomphaceae, Hysterangiaceae, Phallaceae and Ramariaceae.
313. The bioactive agent according to item 312, wherein Basidiomycete cell is selected from the family of Geastraceae.
314. The bioactive agent according to item 312, wherein Basidiomycete cell is selected from the family of Gomphaceae.
315. The bioactive agent according to item 312, wherein Basidiomycete cell is selected from the family of Hysterangiaceae.
316. The bioactive agent according to item 312, wherein Basidiomycete cell is selected from the family of Phallaceae.
317. The bioactive agent according to item 312, wherein Basidiomycete cell is selected from the family of Ramariaceae.
318. The bioactive agent according to item 214, wherein the Basidiomycete cell is selected from the order of Poriales.
319. The bioactive agent according to item 318, wherein said Basidiomycete cell belongs to a family of Polyporaceae.
320. The bioactive agent according to item 214, wherein the Basidiomycete cell is selected from the order of Russulales.
321. The bioactive agent according to item 320, wherein said Basidiomycete cell belongs to a family selected from the group consisting of Auriscalpiaceae, Bondarzewiaceae, Echinodontiaceae, Hericiaceae, Hybogasteraceae, Lachnocladiaceae, Peniophoraceae, Phanerochaetaceae, Russulaceae, Stephanosporaceae and Stereaceae.
322. The bioactive agent according to item 321, wherein Basidiomycete cell is selected from the family of Auriscalpiaceae.
323. The bioactive agent according to item 321, wherein Basidiomycete cell is selected from the family of Bondarzewiaceae.
324. The bioactive agent according to item 321, wherein Basidiomycete cell is selected from the family of Echinodontiaceae.
325. The bioactive agent according to item 321, wherein Basidiomycete cell is selected from the family of Hericiaceae.
326. The bioactive agent according to item 321, wherein Basidiomycete cell is selected from the family of Hybogasteraceae.
327. The bioactive agent according to item 321, wherein Basidiomycete cell is selected from the family of Lachnocladiaceae.
328. The bioactive agent according to item 321, wherein Basidiomycete cell is selected from the family of Peniophoraceae.
329. The bioactive agent according to item 321, wherein Basidiomycete cell is selected from the family of Phanerochaetaceae.
330. The bioactive agent according to item 321, wherein Basidiomycete cell is selected from the family of Russulaceae.
331. The bioactive agent according to item 321, wherein Basidiomycete cell is selected from the family of Stephanosporaceae.
332. The bioactive agent according to item 321, wherein Basidiomycete cell is selected from the family of Stereaceae.
333. The bioactive agent according to item 214, wherein the Basidiomycete cell is selected from the order of Thelophorales.
334. The bioactive agent according to item 333, wherein said Basidiomycete cell belongs to a family selected from the group consisting of Bankeraceae and Thelephoraceae.
335. The bioactive agent according to item 334, wherein Basidiomycete cell is selected from the family of Bankeraceae.
336. The bioactive agent according to item 334, wherein Basidiomycete cell is selected from the family of Thelephoraceae.
337. The bioactive agent according to item 214, wherein the Basidiomycete cell is selected from the order of Auriculariales.

338. The bioactive agent according to item 337, wherein Basidiomycete cell is selected from the family of Auriculariaceae.
339. The bioactive agent according to item 214, wherein the Basidiomycete cell is selected from the order of Christianseniales.
340. The bioactive agent according to item 339, wherein Basidiomycete cell is selected from the family of Christianseniaceae.
341. The bioactive agent according to item 214, wherein the Basidiomycete cell is selected from the order of Cystofilobasidiales.
342. The bioactive agent according to item 341, wherein Basidiomycete cell is selected from the family of Cystofilobasidiaceae.
343. The bioactive agent according to item 214, wherein the Basidiomycete cell is selected from the order of Filobasidiales.
344. The bioactive agent according to item 343, wherein Basidiomycete cell is selected from the family of Filobasidiaceae.
345. The bioactive agent according to item 214, wherein the Basidiomycete cell is selected from the order of Tremellales.
346. The bioactive agent according to item 345, wherein said Basidiomycete cell belongs to a family selected from the group consisting of Aporpiaceae, Cuniculitremaceae, Exidiaceae, Hyaloriaceae, Phragmoxenidiaceae, Rhynchogastremataceae, Sirobasidiaceae, Syzygosporaceae, Tetragoniomycetaceae, Tremellaceae and Tremellodendropsidaceae.
347. The bioactive agent according to item 346, wherein Basidiomycete cell is selected from the family of Aporpiaceae.
348. The bioactive agent according to item 346, wherein Basidiomycete cell is selected from the family of Cuniculitremaceae.
349. The bioactive agent according to item 346, wherein Basidiomycete cell is selected from the family of Exidiaceae.
350. The bioactive agent according to item 346, wherein Basidiomycete cell is selected from the family of Hyaloriaceae.
351. The bioactive agent according to item 346, wherein Basidiomycete cell is selected from the family of Phragmoxenidiaceae.
352. The bioactive agent according to item 346, wherein Basidiomycete cell is selected from the family of Rhynchogastremataceae.
353. The bioactive agent according to item 346, wherein Basidiomycete cell is selected from the family of Sirobasidiaceae.
354. The bioactive agent according to item 346, wherein Basidiomycete cell is selected from the family of Syzygosporaceae.
355. The bioactive agent according to item 346, wherein Basidiomycete cell is selected from the family of Tetragoniomycetaceae.
356. The bioactive agent according to item 346, wherein Basidiomycete cell is selected from the family of Tremellaceae.
357. The bioactive agent according to item 346, wherein Basidiomycete cell is selected from the family of Tremellodendropsidaceae.
358. The bioactive agent according to item 214, wherein the Basidiomycete cell is selected from the order of Tulasenellales.
359. The bioactive agent according to item 358, wherein Basidiomycete cell is selected from the family of Tulasnellaceae.
360. The bioactive agent according to item 214, wherein the Basidiomycete cell is selected from the order of Urocystales.
361. The bioactive agent according to item 360, wherein Basidiomycete cell is selected from the family of Urocystaceae.
362. The bioactive agent according to item 217, wherein said Basidiomycete cell belongs to a genus selected from the group consisting of *Agaricus, Amanita, Amylolepiota, Araneosa, Artymenium, Attamyces, Barcheria, Cauloglossum, Chainoderma, Chamaemyces, Chitonia, Chitoniella, Chitonis, Chlorolepiota, Chlorophyllum, Chlorosperma, Chlorospora, Clarkeinda, Clavogaster, Coccobotrys, Crucispora, Cystoagaricus, Cystolepiota, Drosella, Endolepiotula, Fungus, Fusispora, Gasterellopsis, Glaucospora, Gymnogaster, Gyrophragmium, Heinemannomyces, Herculea, Hiatulopsis, Holocotylon, Horakia, Hymenagaricus, Hypogaea, Hypophyllum, Lepidotus, Lepiotella, Lepiotula, Leucoagaricus, Leucobolbitius, Leucocoprinus, Longia, Longula, Macrolepiota, Mastocephalus, Melanophylium, Metraria, Metrodia, Micropsalliota, Montagnea, Montagnites, Morobia, Myces, Neosecotium, Notholepiota, Panaeolopsis, Phaeopholiota, Phlebonema, Phyllogaster, Podaxis, Polyplocium, Pseudoauricularia, Pulverolepiota, Rickella, Rugosospora, Schinzinia, Schulzeria, Schweinitzia, Secotium, Sericeomyces, Singerina, Smithiogaster, Smithiomyces, Stellifera, Termiticola, Verrucospora, Volvigerum, Volvolepiota* and *Xanthagaricus*.
363. The bioactive agent according to item 362, wherein Basidiomycete cell is selected from the genus of *Agaricus*.
364. The bioactive agent according to item 362, wherein Basidiomycete cell is selected from the genus of *Amanita*.
365. The bioactive agent according to item 362, wherein Basidiomycete cell is selected from the genus of *Amylolepiota*.
366. The bioactive agent according to item 362, wherein Basidiomycete cell is selected from the genus of *Araneosa*.
367. The bioactive agent according to item 362, wherein Basidiomycete cell is selected from the genus of *Artymenium*.
368. The bioactive agent according to item 362, wherein Basidiomycete cell is selected from the genus of *Attamyces*.
369. The bioactive agent according to item 362, wherein Basidiomycete cell is selected from the genus of *Barcheria*.
370. The bioactive agent according to item 362, wherein Basidiomycete cell is selected from the genus of *Cauloglossum*.
371. The bioactive agent according to item 362, wherein Basidiomycete cell is selected from the genus of *Chainoderma*.
372. The bioactive agent according to item 362, wherein Basidiomycete cell is selected from the genus of *Chamaemyces*.
373. The bioactive agent according to item 362, wherein Basidiomycete cell is selected from the genus of *Chitonia*.
374. The bioactive agent according to item 362, wherein Basidiomycete cell is selected from the genus of *Chitoniella*.
375. The bioactive agent according to item 362, wherein Basidiomycete cell is selected from the genus of *Chitonis*.

376. The bioactive agent according to item 362, wherein Basidiomycete cell is selected from the genus of *Chlorolepiota*.
377. The bioactive agent according to item 362, wherein Basidiomycete cell is selected from the genus of *Chlorophyllum*.
378. The bioactive agent according to item 362, wherein Basidiomycete cell is selected from the genus of *Chlorosperma*.
379. The bioactive agent according to item 362, wherein Basidiomycete cell is selected from the genus of *Chlorospora*.
380. The bioactive agent according to item 362, wherein Basidiomycete cell is selected from the genus of *Clarkeinda*.
381. The bioactive agent according to item 362, wherein Basidiomycete cell is selected from the genus of *Clavogaster*.
382. The bioactive agent according to item 362, wherein Basidiomycete cell is selected from the genus of *Coccobotrys*.
383. The bioactive agent according to item 362, wherein Basidiomycete cell is selected from the genus of *Crucispora*.
384. The bioactive agent according to item 362, wherein Basidiomycete cell is selected from the genus of *Cystoagaricus*.
385. The bioactive agent according to item 362, wherein Basidiomycete cell is selected from the genus of *Cystolepiota*.
386. The bioactive agent according to item 362, wherein Basidiomycete cell is selected from the genus of *Drosella*.
387. The bioactive agent according to item 362, wherein Basidiomycete cell is selected from the genus of *Endolepiotula*.
388. The bioactive agent according to item 362, wherein Basidiomycete cell is selected from the genus of *Fungus*.
389. The bioactive agent according to item 362, wherein Basidiomycete cell is selected from the genus of *Fusispora*.
390. The bioactive agent according to item 362, wherein Basidiomycete cell is selected from the genus of *Gasterellopsis*.
391. The bioactive agent according to item 362, wherein Basidiomycete cell is selected from the genus of *Glaucospora*.
392. The bioactive agent according to item 362, wherein Basidiomycete cell is selected from the genus of *Gymnogaster*.
393. The bioactive agent according to item 362, wherein Basidiomycete cell is selected from the genus of *Gyrophragmium*.
394. The bioactive agent according to item 362, wherein Basidiomycete cell is selected from the genus of *Heinemannomyces*.
395. The bioactive agent according to item 362, wherein Basidiomycete cell is selected from the genus of *Herculea*.
396. The bioactive agent according to item 362, wherein Basidiomycete cell is selected from the genus of *Hiatulopsis*.
397. The bioactive agent according to item 362, wherein Basidiomycete cell is selected from the genus of *Holocotylon*.
398. The bioactive agent according to item 362, wherein Basidiomycete cell is selected from the genus of *Horakia*.
399. The bioactive agent according to item 362, wherein Basidiomycete cell is selected from the genus of *Hymenagaricus*.
400. The bioactive agent according to item 362, wherein Basidiomycete cell is selected from the genus of *Hypogaea*.
401. The bioactive agent according to item 362, wherein Basidiomycete cell is selected from the genus of *Hypophyllum*.
402. The bioactive agent according to item 362, wherein Basidiomycete cell is selected from the genus of *Lepidotus*.
403. The bioactive agent according to item 362, wherein Basidiomycete cell is selected from the genus of *Lepiotella*.
404. The bioactive agent according to item 362, wherein Basidiomycete cell is selected from the genus of *Lepiotula*.
405. The bioactive agent according to item 362, wherein Basidiomycete cell is selected from the genus of *Leucoagaricus*.
406. The bioactive agent according to item 362, wherein Basidiomycete cell is selected from the genus of *Leucobolbitius*.
407. The bioactive agent according to item 362, wherein Basidiomycete cell is selected from the genus of *Leucocoprinus*.
408. The bioactive agent according to item 362, wherein Basidiomycete cell is selected from the genus of *Longia*.
409. The bioactive agent according to item 362, wherein Basidiomycete cell is selected from the genus of *Longula*.
410. The bioactive agent according to item 362, wherein Basidiomycete cell is selected from the genus of *Macrolepiota*.
411. The bioactive agent according to item 362, wherein Basidiomycete cell is selected from the genus of *Mastocephalus*.
412. The bioactive agent according to item 362, wherein Basidiomycete cell is selected from the genus of *Melanophyllum*.
413. The bioactive agent according to item 362, wherein Basidiomycete cell is selected from the genus of *Metraria*.
414. The bioactive agent according to item 362, wherein Basidiomycete cell is selected from the genus of *Metrodia*.
415. The bioactive agent according to item 362, wherein Basidiomycete cell is selected from the genus of *Micropsalliota*.
416. The bioactive agent according to item 362, wherein Basidiomycete cell is selected from the genus of *Montagnea*.
417. The bioactive agent according to item 362, wherein Basidiomycete cell is selected from the genus of *Montagnites*.
418. The bioactive agent according to item 362, wherein Basidiomycete cell is selected from the genus of *Morobia*.
419. The bioactive agent according to item 362, wherein Basidiomycete cell is selected from the genus of *Myces*.
420. The bioactive agent according to item 362, wherein Basidiomycete cell is selected from the genus of *Neosecotium*.
421. The bioactive agent according to item 362, wherein Basidiomycete cell is selected from the genus of *Notholepiota*.
422. The bioactive agent according to item 362, wherein Basidiomycete cell is selected from the genus of *Panaeolopsis*.
423. The bioactive agent according to item 362, wherein Basidiomycete cell is selected from the genus of *Phaeopholiota*.

424. The bioactive agent according to item 362, wherein Basidiomycete cell is selected from the genus of *Phlebonema*.
425. The bioactive agent according to item 362, wherein Basidiomycete cell is selected from the genus of *Phyllogaster*.
426. The bioactive agent according to item 362, wherein Basidiomycete cell is selected from the genus of *Podaxis*.
427. The bioactive agent according to item 362, wherein Basidiomycete cell is selected from the genus of *Polyplocium*.
428. The bioactive agent according to item 362, wherein Basidiomycete cell is selected from the genus of *Pseudoauricularia*.
429. The bioactive agent according to item 362, wherein Basidiomycete cell is selected from the genus of *Pulverolepiota*.
430. The bioactive agent according to item 362, wherein Basidiomycete cell is selected from the genus of *Rickella*.
431. The bioactive agent according to item 362, wherein Basidiomycete cell is selected from the genus of *Rugosospora*.
432. The bioactive agent according to item 362, wherein Basidiomycete cell is selected from the genus of *Schinzinia*.
433. The bioactive agent according to item 362, wherein Basidiomycete cell is selected from the genus of *Schulzeria*.
434. The bioactive agent according to item 362, wherein Basidiomycete cell is selected from the genus of *Schweinitzia*.
435. The bioactive agent according to item 362, wherein Basidiomycete cell is selected from the genus of *Secotium*.
436. The bioactive agent according to item 362, wherein Basidiomycete cell is selected from the genus of *Sericeomyces*.
437. The bioactive agent according to item 362, wherein Basidiomycete cell is selected from the genus of *Singerina*.
438. The bioactive agent according to item 362, wherein Basidiomycete cell is selected from the genus of *Smithiogaster*.
439. The bioactive agent according to item 362, wherein Basidiomycete cell is selected from the genus of *Smithiomyces*.
440. The bioactive agent according to item 362, wherein Basidiomycete cell is selected from the genus of *Stellifera*.
441. The bioactive agent according to item 362, wherein Basidiomycete cell is selected from the genus of *Termiticola*.
442. The bioactive agent according to item 362, wherein Basidiomycete cell is selected from the genus of *Verrucospora*.
443. The bioactive agent according to item 362, wherein Basidiomycete cell is selected from the genus of *Volvigerum*.
444. The bioactive agent according to item 362, wherein Basidiomycete cell is selected from the genus of *Volvolepiota*.
445. The bioactive agent according to item 362, wherein Basidiomycete cell is selected from the genus of *Xanthagaricus*.
446. The bioactive agent according to item 218, wherein said Basidiomycete cell belongs to a genus selected from the group consisting of *Acetabularia, Agrocybe, Agrogaster, Alnicola, Anellaria, Bolbitius, Bulla, Campanularius, Chalymmota, Conocybe, Copelandia, Coprinarius, Cyclocybe, Cyclopus, Cyphellopus, Cyttarophyllopsis, Cyttarophyllum, Galerella, Galeropsis, Gastrocybe, Gymnoglossum, Hebeloma, Hebelomatis, Hylophila, Myxocybe, Naucoria, Panaeolina, Panaeolus, Pholiotella, Pholiotina, Picromyces, Pluteolus, Psammomyces, Pseudoconocybe, Pseudodeconica, Ptychella, Raddetes, Roumeguerites, Sarcoloma, Setchelliogaster, Togaria, Tubariella, Tubariopsis, Tympanella* and *Wielandomyces*.
447. The bioactive agent according to item 446, wherein Basidiomycete cell is selected from the genus of *Acetabularia*.
448. The bioactive agent according to item 446, wherein Basidiomycete cell is selected from the genus of *Agrocybe*.
449. The bioactive agent according to item 446, wherein Basidiomycete cell is selected from the genus of *Agrogaster*.
450. The bioactive agent according to item 446, wherein Basidiomycete cell is selected from the genus of *Alnicola*.
451. The bioactive agent according to item 446, wherein Basidiomycete cell is selected from the genus of *Anellaria*.
452. The bioactive agent according to item 446, wherein Basidiomycete cell is selected from the genus of *Bolbitius*.
453. The bioactive agent according to item 446, wherein Basidiomycete cell is selected from the genus of *Bulla*.
454. The bioactive agent according to item 446, wherein Basidiomycete cell is selected from the genus of *Campanularius*.
455. The bioactive agent according to item 446, wherein Basidiomycete cell is selected from the genus of *Chalymmota*.
456. The bioactive agent according to item 446, wherein Basidiomycete cell is selected from the genus of *Conocybe*.
457. The bioactive agent according to item 446, wherein Basidiomycete cell is selected from the genus of *Copelandia*.
458. The bioactive agent according to item 446, wherein Basidiomycete cell is selected from the genus of *Coprinarius*.
459. The bioactive agent according to item 446, wherein Basidiomycete cell is selected from the genus of *Cyclocybe*.
460. The bioactive agent according to item 446, wherein Basidiomycete cell is selected from the genus of *Cyclopus*.
461. The bioactive agent according to item 446, wherein Basidiomycete cell is selected from the genus of *Cyphellopus*.
462. The bioactive agent according to item 446, wherein Basidiomycete cell is selected from the genus of *Cyttarophyllopsis*.
463. The bioactive agent according to item 446, wherein Basidiomycete cell is selected from the genus of *Cyttarophyllum*.
464. The bioactive agent according to item 446, wherein Basidiomycete cell is selected from the genus of *Galerella*.
465. The bioactive agent according to item 446, wherein Basidiomycete cell is selected from the genus of *Galeropsis*.
466. The bioactive agent according to item 446, wherein Basidiomycete cell is selected from the genus of *Gastrocybe*.
467. The bioactive agent according to item 446, wherein Basidiomycete cell is selected from the genus of *Gymnoglossum*.
468. The bioactive agent according to item 446, wherein Basidiomycete cell is selected from the genus of *Hebeloma*.

469. The bioactive agent according to item 446, wherein Basidiomycete cell is selected from the genus of *Hebelomatis*.
470. The bioactive agent according to item 446, wherein Basidiomycete cell is selected from the genus of *Hylophila*.
471. The bioactive agent according to item 446, wherein Basidiomycete cell is selected from the genus of *Myxocybe*.
472. The bioactive agent according to item 446, wherein Basidiomycete cell is selected from the genus of *Naucoria*.
473. The bioactive agent according to item 446, wherein Basidiomycete cell is selected from the genus of *Panaeolina*.
474. The bioactive agent according to item 446, wherein Basidiomycete cell is selected from the genus of *Panaeolus*.
475. The bioactive agent according to item 446, wherein Basidiomycete cell is selected from the genus of *Pholiotella*.
476. The bioactive agent according to item 446, wherein Basidiomycete cell is selected from the genus of *Pholiotina*.
477. The bioactive agent according to item 446, wherein Basidiomycete cell is selected from the genus of *Picromyces*.
478. The bioactive agent according to item 446, wherein Basidiomycete cell is selected from the genus of *Pluteolus*.
479. The bioactive agent according to item 446, wherein Basidiomycete cell is selected from the genus of *Psammomyces*.
480. The bioactive agent according to item 446, wherein Basidiomycete cell is selected from the genus of *Pseudoconocybe*.
481. The bioactive agent according to item 446, wherein Basidiomycete cell is selected from the genus of *Pseudodeconica*.
482. The bioactive agent according to item 446, wherein Basidiomycete cell is selected from the genus of *Ptychella*.
483. The bioactive agent according to item 446, wherein Basidiomycete cell is selected from the genus of *Raddetes*.
484. The bioactive agent according to item 446, wherein Basidiomycete cell is selected from the genus of *Roumeguerites*.
485. The bioactive agent according to item 446, wherein Basidiomycete cell is selected from the genus of *Sarcoloma*.
486. The bioactive agent according to item 446, wherein Basidiomycete cell is selected from the genus of *Setchelliogaster*.
487. The bioactive agent according to item 446, wherein Basidiomycete cell is selected from the genus of *Togaria*.
488. The bioactive agent according to item 446, wherein Basidiomycete cell is selected from the genus of *Tubariella*.
489. The bioactive agent according to item 446, wherein Basidiomycete cell is selected from the genus of *Tubariopsis*.
490. The bioactive agent according to item 446, wherein Basidiomycete cell is selected from the genus of *Tympanella*.
491. The bioactive agent according to item 446, wherein Basidiomycete cell is selected from the genus of *Wielandomyces*.
492. The bioactive agent according to item 219, wherein Basidiomycete cell is selected from the genus of *Broomeia*.
493. The bioactive agent according to item 220, wherein said Basidiomycete cell belongs to a genus selected from the group consisting of *Capitoclavaria, Clavaria, Clavulinopsis, Cornicularia, Donkella, Holocoryne, Macrotyphula, Manina, Multiclavula, Podostrombium, Ramaria, Ramariopsis, Scytinopogon, Setigeroclavula* and *Stichoclavaria*.
494. The bioactive agent according to item 493, wherein Basidiomycete cell is selected from the genus of *Capitoclavaria*.
495. The bioactive agent according to item 493, wherein Basidiomycete cell is selected from the genus of *Clavaria*.
496. The bioactive agent according to item 493, wherein Basidiomycete cell is selected from the genus of *Clavulinopsis*.
497. The bioactive agent according to item 493, wherein Basidiomycete cell is selected from the genus of *Cornicularia*.
498. The bioactive agent according to item 493, wherein Basidiomycete cell is selected from the genus of *Donkella*.
499. The bioactive agent according to item 493, wherein Basidiomycete cell is selected from the genus of *Holocoryne*.
500. The bioactive agent according to item 493, wherein Basidiomycete cell is selected from the genus of *Macrotyphula*.
501. The bioactive agent according to item 493, wherein Basidiomycete cell is selected from the genus of *Manina*.
502. The bioactive agent according to item 493, wherein Basidiomycete cell is selected from the genus of *Multiclavula*.
503. The bioactive agent according to item 493, wherein Basidiomycete cell is selected from the genus of *Podostrombium*.
504. The bioactive agent according to item 493, wherein Basidiomycete cell is selected from the genus of *Ramaria*.
505. The bioactive agent according to item 493, wherein Basidiomycete cell is selected from the genus of *Ramariopsis*.
506. The bioactive agent according to item 493, wherein Basidiomycete cell is selected from the genus of *Scytinopogon*.
507. The bioactive agent according to item 493, wherein Basidiomycete cell is selected from the genus of *Setigeroclavula*.
508. The bioactive agent according to item 493, wherein Basidiomycete cell is selected from the genus of *Stichoclavaria*.
509. The bioactive agent according to item 221, wherein said Basidiomycete cell belongs to a genus selected from the group consisting of *Annularius, Astylospora, Coprinellus, Coprinopsis, Coprinus, Coprinusella, Cortiniopsis, Drosophila, Ephemerocybe, Gasteroagaricoides, Glyptospora, Gymnochilus, Homophron, Hypholomopsis, Lacrymaria, Lentispora, Macrometrula, Onchopus, Palaeocybe, Pannucia, Parasola, Pluteopsis, Psalliotina, Psammocoparius, Psathyra, Psathyrella, Pselliophora, Pseudocoprinus, Psilocybe, Rhacophyllus, Xerocoprinus* and *Zerovaemyces*.
510. The bioactive agent according to item 509, wherein Basidiomycete cell is selected from the genus of *Annularius*.
511. The bioactive agent according to item 509, wherein Basidiomycete cell is selected from the genus of *Astylospora*.
512. The bioactive agent according to item 509, wherein Basidiomycete cell is selected from the genus of *Coprinellus*.

513. The bioactive agent according to item 509, wherein Basidiomycete cell is selected from the genus of *Coprinopsis*.
514. The bioactive agent according to item 509, wherein Basidiomycete cell is selected from the genus of *Coprinus*.
515. The bioactive agent according to item 509, wherein Basidiomycete cell is selected from the genus of *Coprinusella*.
516. The bioactive agent according to item 509, wherein Basidiomycete cell is selected from the genus of *Cortiniopsis*.
517. The bioactive agent according to item 509, wherein Basidiomycete cell is selected from the genus of *Drosophila*.
518. The bioactive agent according to item 509, wherein Basidiomycete cell is selected from the genus of *Ephemerocybe*.
519. The bioactive agent according to item 509, wherein Basidiomycete cell is selected from the genus of *Gasteroagaricoides*.
520. The bioactive agent according to item 509, wherein Basidiomycete cell is selected from the genus of *Glyptospora*.
521. The bioactive agent according to item 509, wherein Basidiomycete cell is selected from the genus of *Gymnochilus*.
522. The bioactive agent according to item 509, wherein Basidiomycete cell is selected from the genus of *Homophron*.
523. The bioactive agent according to item 509, wherein Basidiomycete cell is selected from the genus of *Hypholomopsis*.
524. The bioactive agent according to item 509, wherein Basidiomycete cell is selected from the genus of *Lacrymaria*.
525. The bioactive agent according to item 509, wherein Basidiomycete cell is selected from the genus of *Lentispora*.
526. The bioactive agent according to item 509, wherein Basidiomycete cell is selected from the genus of *Macrometrula*.
527. The bioactive agent according to item 509, wherein Basidiomycete cell is selected from the genus of *Onchopus*.
528. The bioactive agent according to item 509, wherein Basidiomycete cell is selected from the genus of *Palaeocybe*.
529. The bioactive agent according to item 509, wherein Basidiomycete cell is selected from the genus of *Pannucia*.
530. The bioactive agent according to item 509, wherein Basidiomycete cell is selected from the genus of *Parasola*.
531. The bioactive agent according to item 509, wherein Basidiomycete cell is selected from the genus of *Pluteopsis*.
532. The bioactive agent according to item 509, wherein Basidiomycete cell is selected from the genus of *Psalliotina*.
533. The bioactive agent according to item 509, wherein Basidiomycete cell is selected from the genus of *Psammocoparius*.
534. The bioactive agent according to item 509, wherein Basidiomycete cell is selected from the genus of *Psathyra*.
535. The bioactive agent according to item 509, wherein Basidiomycete cell is selected from the genus of *Psathyrella*.
536. The bioactive agent according to item 509, wherein Basidiomycete cell is selected from the genus of *Pselliophora*.
537. The bioactive agent according to item 509, wherein Basidiomycete cell is selected from the genus of *Pseudocoprinus*.
538. The bioactive agent according to item 509, wherein Basidiomycete cell is selected from the genus of *Psilocybe*.
539. The bioactive agent according to item 509, wherein Basidiomycete cell is selected from the genus of *Rhacophyllus*.
540. The bioactive agent according to item 509, wherein Basidiomycete cell is selected from the genus of *Xerocoprinus*.
541. The bioactive agent according to item 509, wherein Basidiomycete cell is selected from the genus of *Zerovaemyces*.
542. The bioactive agent according to item 222, wherein said Basidiomycete cell belongs to a genus selected from the group consisting of *Agmocybe, Anamika, Aroramyces, Astrosporina, Bulbopodium, Calathinus, Cereicium, Chromocyphella, Clypeus, Cortinarius, Crepidotus, Cribbea, Cuphocybe, Cyanicium, Cymbella, Cyphellathelia, Cystocybe, Dermocybe, Descolea, Dochmiopus, Epicorticium, Epiphaeria, Flammulaster, Flocculina, Fulvidula, Galera, Galerina, Galerula, Gomphos, Gymnopilus, Hebelomina, Horakomyces, Hydrocybe, Hydrocybium, Hydrotelamonia, Hygramaricium, Hygromyxacium, Inocibium, Inocybe, Inocybella, Inoloma, Kjeldsenia, Leucocortinarius, Leucopus, Locellina, Mackintoshia, Marasmiopsis, Melanomphalia, Meliderma, Mycolevis, Myxacium, Myxopholis, Nanstelocephala, Octojuga, Pellidiscus, Phaeocarpus, Phaeocollybia, Phaeocyphella, Phaeogalera, Phaeoglabrotricha, Phaeomarasmius, Phaeosolenia, Phialocybe, Phlegmacium, Pholidotopsis, Pleurotellus, Pseudodescolea, Pseudogymnopilus, Pyrrhoglossum, Quercella, Ramicola, Rapacea, Raphanozon, Rozites, Sericeocybe, Simocybe, Sphaerotrachys, Squamaphlegma, Stagnicola, Stephanopus, Telamonia, Thaxterogaster, Tremellastrum, Tremellopsis, Tubaria, Velomycena* and *Weinzettlia*.
543. The bioactive agent according to item 542, wherein Basidiomycete cell is selected from the genus of *Agmocybe*.
544. The bioactive agent according to item 542, wherein Basidiomycete cell is selected from the genus of *Anamika*.
545. The bioactive agent according to item 542, wherein Basidiomycete cell is selected from the genus of *Aroramyces*.
546. The bioactive agent according to item 542, wherein Basidiomycete cell is selected from the genus of *Astrosporina*.
547. The bioactive agent according to item 542, wherein Basidiomycete cell is selected from the genus of *Bulbopodium*.
548. The bioactive agent according to item 542, wherein Basidiomycete cell is selected from the genus of *Calathinus*.
549. The bioactive agent according to item 542, wherein Basidiomycete cell is selected from the genus of *Cereicium*.
550. The bioactive agent according to item 542, wherein Basidiomycete cell is selected from the genus of *Chromocyphella*.
551. The bioactive agent according to item 542, wherein Basidiomycete cell is selected from the genus of *Clypeus*.

552. The bioactive agent according to item 542, wherein Basidiomycete cell is selected from the genus of *Cortinarius*.
553. The bioactive agent according to item 542, wherein Basidiomycete cell is selected from the genus of *Crepidotus*.
554. The bioactive agent according to item 542, wherein Basidiomycete cell is selected from the genus of *Cribbea*.
555. The bioactive agent according to item 542, wherein Basidiomycete cell is selected from the genus of *Cuphocybe*.
556. The bioactive agent according to item 542, wherein Basidiomycete cell is selected from the genus of *Cyanicium*.
557. The bioactive agent according to item 542, wherein Basidiomycete cell is selected from the genus of *Cymbella*.
558. The bioactive agent according to item 542, wherein Basidiomycete cell is selected from the genus of *Cyphellathelia*.
559. The bioactive agent according to item 542, wherein Basidiomycete cell is selected from the genus of *Cystocybe*.
560. The bioactive agent according to item 542, wherein Basidiomycete cell is selected from the genus of *Dermocybe*.
561. The bioactive agent according to item 542, wherein Basidiomycete cell is selected from the genus of *Descolea*.
562. The bioactive agent according to item 542, wherein Basidiomycete cell is selected from the genus of *Dochmiopus*.
563. The bioactive agent according to item 542, wherein Basidiomycete cell is selected from the genus of *Epicorticium*.
564. The bioactive agent according to item 542, wherein Basidiomycete cell is selected from the genus of *Episphaeria*.
565. The bioactive agent according to item 542, wherein Basidiomycete cell is selected from the genus of *Flammulaster*.
566. The bioactive agent according to item 542, wherein Basidiomycete cell is selected from the genus of *Flocculina*.
567. The bioactive agent according to item 542, wherein Basidiomycete cell is selected from the genus of *Fulvidula*.
568. The bioactive agent according to item 542, wherein Basidiomycete cell is selected from the genus of *Galera*.
569. The bioactive agent according to item 542, wherein Basidiomycete cell is selected from the genus of *Galerina*.
570. The bioactive agent according to item 542, wherein Basidiomycete cell is selected from the genus of *Galerula*.
571. The bioactive agent according to item 542, wherein Basidiomycete cell is selected from the genus of *Gomphos*.
572. The bioactive agent according to item 542, wherein Basidiomycete cell is selected from the genus of *Gymnopilus*.
573. The bioactive agent according to item 542, wherein Basidiomycete cell is selected from the genus of *Hebelomina*.
574. The bioactive agent according to item 542, wherein Basidiomycete cell is selected from the genus of *Horakomyces*.
575. The bioactive agent according to item 542, wherein Basidiomycete cell is selected from the genus of *Hydrocybe*.
576. The bioactive agent according to item 542, wherein Basidiomycete cell is selected from the genus of *Hydrocybium*.
577. The bioactive agent according to item 542, wherein Basidiomycete cell is selected from the genus of *Hydrotelamonia*.
578. The bioactive agent according to item 542, wherein Basidiomycete cell is selected from the genus of *Hygramaricium*.
579. The bioactive agent according to item 542, wherein Basidiomycete cell is selected from the genus of *Hygromyxacium*.
580. The bioactive agent according to item 542, wherein Basidiomycete cell is selected from the genus of *Inocibium*.
581. The bioactive agent according to item 542, wherein Basidiomycete cell is selected from the genus of *Inocybe*.
582. The bioactive agent according to item 542, wherein Basidiomycete cell is selected from the genus of *Inocybella*.
583. The bioactive agent according to item 542, wherein Basidiomycete cell is selected from the genus of *Inoloma*.
584. The bioactive agent according to item 542, wherein Basidiomycete cell is selected from the genus of *Kjeldsenia*.
585. The bioactive agent according to item 542, wherein Basidiomycete cell is selected from the genus of *Leucocortinarius*.
586. The bioactive agent according to item 542, wherein Basidiomycete cell is selected from the genus of *Leucopus*.
587. The bioactive agent according to item 542, wherein Basidiomycete cell is selected from the genus of *Locellina*.
588. The bioactive agent according to item 542, wherein Basidiomycete cell is selected from the genus of *Mackintoshia*.
589. The bioactive agent according to item 542, wherein Basidiomycete cell is selected from the genus of *Marasmiopsis*.
590. The bioactive agent according to item 542, wherein Basidiomycete cell is selected from the genus of *Melanomphalia*.
591. The bioactive agent according to item 542, wherein Basidiomycete cell is selected from the genus of *Meliderma*.
592. The bioactive agent according to item 542, wherein Basidiomycete cell is selected from the genus of *Mycolevis*.
593. The bioactive agent according to item 542, wherein Basidiomycete cell is selected from the genus of *Myxacium*.
594. The bioactive agent according to item 542, wherein Basidiomycete cell is selected from the genus of *Myxopholis*.
595. The bioactive agent according to item 542, wherein Basidiomycete cell is selected from the genus of *Nanstelocephala*.
596. The bioactive agent according to item 542, wherein Basidiomycete cell is selected from the genus of *Octojuga*.
597. The bioactive agent according to item 542, wherein Basidiomycete cell is selected from the genus of *Pellidiscus*.
598. The bioactive agent according to item 542, wherein Basidiomycete cell is selected from the genus of *Phaeocarpus*.
599. The bioactive agent according to item 542, wherein Basidiomycete cell is selected from the genus of *Phaeocollybia*.
600. The bioactive agent according to item 542, wherein Basidiomycete cell is selected from the genus of *Phaeocyphella*.

601. The bioactive agent according to item 542, wherein Basidiomycete cell is selected from the genus of *Phaeogalera*.
602. The bioactive agent according to item 542, wherein Basidiomycete cell is selected from the genus of *Phaeoglabrotricha*.
603. The bioactive agent according to item 542, wherein Basidiomycete cell is selected from the genus of *Phaeomarasmius*.
604. The bioactive agent according to item 542, wherein Basidiomycete cell is selected from the genus of *Phaeosolenia*.
605. The bioactive agent according to item 542, wherein Basidiomycete cell is selected from the genus of *Phialocybe*.
606. The bioactive agent according to item 542, wherein Basidiomycete cell is selected from the genus of *Phlegmacium*.
607. The bioactive agent according to item 542, wherein Basidiomycete cell is selected from the genus of *Pholidotopsis*.
608. The bioactive agent according to item 542, wherein Basidiomycete cell is selected from the genus of *Pleurotellus*.
609. The bioactive agent according to item 542, wherein Basidiomycete cell is selected from the genus of *Pseudodescolea*.
610. The bioactive agent according to item 542, wherein Basidiomycete cell is selected from the genus of *Pseudogymnopilus*.
611. The bioactive agent according to item 542, wherein Basidiomycete cell is selected from the genus of *Pyrrhoglossum*.
612. The bioactive agent according to item 542, wherein Basidiomycete cell is selected from the genus of *Quercella*.
613. The bioactive agent according to item 542, wherein Basidiomycete cell is selected from the genus of *Ramicola*.
614. The bioactive agent according to item 542, wherein Basidiomycete cell is selected from the genus of *Rapacea*.
615. The bioactive agent according to item 542, wherein Basidiomycete cell is selected from the genus of *Raphanozon*.
616. The bioactive agent according to item 542, wherein Basidiomycete cell is selected from the genus of *Rozites*.
617. The bioactive agent according to item 542, wherein Basidiomycete cell is selected from the genus of *Sericeocybe*.
618. The bioactive agent according to item 542, wherein Basidiomycete cell is selected from the genus of *Simocybe*.
619. The bioactive agent according to item 542, wherein Basidiomycete cell is selected from the genus of *Sphaerotrachys*.
620. The bioactive agent according to item 542, wherein Basidiomycete cell is selected from the genus of *Squamaphlegma*.
621. The bioactive agent according to item 542, wherein Basidiomycete cell is selected from the genus of *Stagnicola*.
622. The bioactive agent according to item 542, wherein Basidiomycete cell is selected from the genus of *Stephanopus*.
623. The bioactive agent according to item 542, wherein Basidiomycete cell is selected from the genus of *Telamonia*.
624. The bioactive agent according to item 542, wherein Basidiomycete cell is selected from the genus of *Thaxterogaster*.
625. The bioactive agent according to item 542, wherein Basidiomycete cell is selected from the genus of *Tremellastrum*.
626. The bioactive agent according to item 542, wherein Basidiomycete cell is selected from the genus of *Tremellopsis*.
627. The bioactive agent according to item 542, wherein Basidiomycete cell is selected from the genus of *Tubaria*.
628. The bioactive agent according to item 542, wherein Basidiomycete cell is selected from the genus of *Velomycena*.
629. The bioactive agent according to item 542, wherein Basidiomycete cell is selected from the genus of *Weinzettlia*.
630. The bioactive agent according to item 223, wherein said Basidiomycete cell belongs to a genus selected from the group consisting of *Alboleptonia, Arenicola, Calliderma, Claudopus, Clitopiloidea, Clitopilopsis, Clitopilus, Eccilia, Entoloma, Fibropilus, Hexajuga, Hirneola, Inocephalus, Inopilus, Lanolea, Latzinaea, Leptonia, Leptoniella, Nigropogon, Nolanea, Omphaliopsis, Orcella, Paraeccilia, Paraleptonia, Paxillopsis, Pouzarella, Pouzaromyces, Rhodocybe, Rhodocybella, Rhodogaster, Rhodophana, Rhodophyllus, Richoniella* and *Trichopilus*.
631. The bioactive agent according to item 630, wherein Basidiomycete cell is selected from the genus of *Alboleptonia*.
632. The bioactive agent according to item 630, wherein Basidiomycete cell is selected from the genus of *Arenicola*.
633. The bioactive agent according to item 630, wherein Basidiomycete cell is selected from the genus of *Calliderma*.
634. The bioactive agent according to item 630, wherein Basidiomycete cell is selected from the genus of *Claudopus*.
635. The bioactive agent according to item 630, wherein Basidiomycete cell is selected from the genus of *Clitopiloidea*.
636. The bioactive agent according to item 630, wherein Basidiomycete cell is selected from the genus of *Clitopilopsis*.
637. The bioactive agent according to item 630, wherein Basidiomycete cell is selected from the genus of *Clitopilus*.
638. The bioactive agent according to item 630, wherein Basidiomycete cell is selected from the genus of *Eccilia*.
639. The bioactive agent according to item 630, wherein Basidiomycete cell is selected from the genus of *Entoloma*.
640. The bioactive agent according to item 630, wherein Basidiomycete cell is selected from the genus of *Fibropilus*.
641. The bioactive agent according to item 630, wherein Basidiomycete cell is selected from the genus of *Hexajuga*.
642. The bioactive agent according to item 630, wherein Basidiomycete cell is selected from the genus of *Hirneola*.
643. The bioactive agent according to item 630, wherein Basidiomycete cell is selected from the genus of *Inocephalus*.
644. The bioactive agent according to item 630, wherein Basidiomycete cell is selected from the genus of *Inopilus*.
645. The bioactive agent according to item 630, wherein Basidiomycete cell is selected from the genus of *Lanolea*.
646. The bioactive agent according to item 630, wherein Basidiomycete cell is selected from the genus of *Latzinaea*.

647. The bioactive agent according to item 630, wherein Basidiomycete cell is selected from the genus of *Leptonia*.
648. The bioactive agent according to item 630, wherein Basidiomycete cell is selected from the genus of *Leptoniella*.
649. The bioactive agent according to item 630, wherein Basidiomycete cell is selected from the genus of *Nigropogon*.
650. The bioactive agent according to item 630, wherein Basidiomycete cell is selected from the genus of *Nolanea*.
651. The bioactive agent according to item 630, wherein Basidiomycete cell is selected from the genus of *Omphaliopsis*.
652. The bioactive agent according to item 630, wherein Basidiomycete cell is selected from the genus of *Orcella*.
653. The bioactive agent according to item 630, wherein Basidiomycete cell is selected from the genus of *Paraeccilia*.
654. The bioactive agent according to item 630, wherein Basidiomycete cell is selected from the genus of *Paraleptonia*.
655. The bioactive agent according to item 630, wherein Basidiomycete cell is selected from the genus of *Paxillopsis*.
656. The bioactive agent according to item 630, wherein Basidiomycete cell is selected from the genus of *Pouzarella*.
657. The bioactive agent according to item 630, wherein Basidiomycete cell is selected from the genus of *Pouzaromyces*.
658. The bioactive agent according to item 630, wherein Basidiomycete cell is selected from the genus of *Rhodocybe*.
659. The bioactive agent according to item 630, wherein Basidiomycete cell is selected from the genus of *Rhodocybella*.
660. The bioactive agent according to item 630, wherein Basidiomycete cell is selected from the genus of *Rhodogaster*.
661. The bioactive agent according to item 630, wherein Basidiomycete cell is selected from the genus of *Rhodophana*.
662. The bioactive agent according to item 630, wherein Basidiomycete cell is selected from the genus of *Rhodophyllus*.
663. The bioactive agent according to item 630, wherein Basidiomycete cell is selected from the genus of *Richoniella*.
664. The bioactive agent according to item 630, wherein Basidiomycete cell is selected from the genus of *Trichopilus*.
665. The bioactive agent according to item 224, wherein said Basidiomycete cell belongs to a genus selected from the group consisting of *Agarico-carnis, Buglossus, Confistulina, Fistulina, Hypodrys* and *Pseudofistulina*.
666. The bioactive agent according to item 665, wherein Basidiomycete cell is selected from the genus of *Agarico-carnis*.
667. The bioactive agent according to item 665, wherein Basidiomycete cell is selected from the genus of *Buglossus*.
668. The bioactive agent according to item 665, wherein Basidiomycete cell is selected from the genus of *Confistulina*.
669. The bioactive agent according to item 665, wherein Basidiomycete cell is selected from the genus of *Fistulina*.
670. The bioactive agent according to item 665, wherein Basidiomycete cell is selected from the genus of *Hypodrys*.
671. The bioactive agent according to item 665, wherein Basidiomycete cell is selected from the genus of *Pseudofistulina*.
672. The bioactive agent according to item 225, wherein Basidiomycete cell is selected from the genus of *Gigasperma*.
673. The bioactive agent according to item 226, wherein Basidiomycete cell is selected from the genus of *Hemigaster*.
674. The bioactive agent according to item 227, wherein said Basidiomycete cell belongs to a genus selected from the group consisting of *Hydnangium, Laccaria, Maccagnia, Podohydnangium* and *Russuliopsis*.
675. The bioactive agent according to item 674, wherein Basidiomycete cell is selected from the genus of *Hydnangium*.
676. The bioactive agent according to item 674, wherein Basidiomycete cell is selected from the genus of *Laccaria*.
677. The bioactive agent according to item 674, wherein Basidiomycete cell is selected from the genus of *Maccagnia*.
678. The bioactive agent according to item 674, wherein Basidiomycete cell is selected from the genus of *Podohydnangium*.
679. The bioactive agent according to item 674, wherein Basidiomycete cell is selected from the genus of *Russuliopsis*.
680. The bioactive agent according to item 228, wherein said Basidiomycete cell belongs to a genus selected from the group consisting of *Abstoma, Acutocapillitium, Arachnion, Arachniopsis, Bovista, Bovistaria, Bovistella, Bovistina, Calbovista, Calvatia, Calvatiella, Calvatiopsis, Capillaria, Catastoma, Cerophora, Disciseda, Enteromyxa, Eriosphaera, Gastropila, Globaria, Glyptoderma, Handkea, Hippoperdon, Hypoblema, Japonogaster, Langermannia, Lanopila, Lasiosphaera, Lycogalopsis, Lycoperdon, Lycoperdopsis, Morganella, Omalycus, Piemycus, Piesmycus, Pila, Priapus, Pseudolycoperdon, Sackea, Scoleciocarpus, Sufa, Utraria* and *Vascellum*.
681. The bioactive agent according to item 680, wherein Basidiomycete cell is selected from the genus of *Abstoma*.
682. The bioactive agent according to item 680, wherein Basidiomycete cell is selected from the genus of *Acutocapillitium*.
683. The bioactive agent according to item 680, wherein Basidiomycete cell is selected from the genus of *Arachnion*.
684. The bioactive agent according to item 680, wherein Basidiomycete cell is selected from the genus of *Arachniopsis*.
685. The bioactive agent according to item 680, wherein Basidiomycete cell is selected from the genus of *Bovista*.
686. The bioactive agent according to item 680, wherein Basidiomycete cell is selected from the genus of *Bovistaria*.
687. The bioactive agent according to item 680, wherein Basidiomycete cell is selected from the genus of *Bovistella*.
688. The bioactive agent according to item 680, wherein Basidiomycete cell is selected from the genus of *Bovistina*.
689. The bioactive agent according to item 680, wherein Basidiomycete cell is selected from the genus of *Calbovista*.
690. The bioactive agent according to item 680, wherein Basidiomycete cell is selected from the genus of *Calvatia*.

691. The bioactive agent according to item 680, wherein Basidiomycete cell is selected from the genus of *Calvatiella*.
692. The bioactive agent according to item 680, wherein Basidiomycete cell is selected from the genus of *Calvatiopsis*.
693. The bioactive agent according to item 680, wherein Basidiomycete cell is selected from the genus of *Capillaria*.
694. The bioactive agent according to item 680, wherein Basidiomycete cell is selected from the genus of *Catastoma*.
695. The bioactive agent according to item 680, wherein Basidiomycete cell is selected from the genus of *Cerophora*.
696. The bioactive agent according to item 680, wherein Basidiomycete cell is selected from the genus of *Disciseda*.
697. The bioactive agent according to item 680, wherein Basidiomycete cell is selected from the genus of *Enteromyxa*.
698. The bioactive agent according to item 680, wherein Basidiomycete cell is selected from the genus of *Eriosphaera*.
699. The bioactive agent according to item 680, wherein Basidiomycete cell is selected from the genus of *Gastropila*.
700. The bioactive agent according to item 680, wherein Basidiomycete cell is selected from the genus of *Globaria*.
701. The bioactive agent according to item 680, wherein Basidiomycete cell is selected from the genus of *Glyptoderma*.
702. The bioactive agent according to item 680, wherein Basidiomycete cell is selected from the genus of *Handkea*.
703. The bioactive agent according to item 680, wherein Basidiomycete cell is selected from the genus of *Hippoperdon*.
704. The bioactive agent according to item 680, wherein Basidiomycete cell is selected from the genus of *Hypoblema*.
705. The bioactive agent according to item 680, wherein Basidiomycete cell is selected from the genus of *Japonogaster*.
706. The bioactive agent according to item 680, wherein Basidiomycete cell is selected from the genus of *Langermannia*.
707. The bioactive agent according to item 680, wherein Basidiomycete cell is selected from the genus of *Lanopila*.
708. The bioactive agent according to item 680, wherein Basidiomycete cell is selected from the genus of *Lasiosphaera*.
709. The bioactive agent according to item 680, wherein Basidiomycete cell is selected from the genus of *Lycogalopsis*.
710. The bioactive agent according to item 680, wherein Basidiomycete cell is selected from the genus of *Lycoperdon*.
711. The bioactive agent according to item 680, wherein Basidiomycete cell is selected from the genus of *Lycoperdopsis*.
712. The bioactive agent according to item 680, wherein Basidiomycete cell is selected from the genus of *Morganella*.
713. The bioactive agent according to item 680, wherein Basidiomycete cell is selected from the genus of *Omalycus*.
714. The bioactive agent according to item 680, wherein Basidiomycete cell is selected from the genus of *Piemycus*.
715. The bioactive agent according to item 680, wherein Basidiomycete cell is selected from the genus of *Piesmycus*.
716. The bioactive agent according to item 680, wherein Basidiomycete cell is selected from the genus of *Pila*.
717. The bioactive agent according to item 680, wherein Basidiomycete cell is selected from the genus of *Priapus*.
718. The bioactive agent according to item 680, wherein Basidiomycete cell is selected from the genus of *Pseudolycoperdon*.
719. The bioactive agent according to item 680, wherein Basidiomycete cell is selected from the genus of *Sackea*.
720. The bioactive agent according to item 680, wherein Basidiomycete cell is selected from the genus of *Scoleciocarpus*.
721. The bioactive agent according to item 680, wherein Basidiomycete cell is selected from the genus of *Sufa*.
722. The bioactive agent according to item 680, wherein Basidiomycete cell is selected from the genus of *Utraria*.
723. The bioactive agent according to item 680, wherein Basidiomycete cell is selected from the genus of *Vascellum*.
724. The bioactive agent according to item 229, wherein said Basidiomycete cell belongs to a genus selected from the group consisting of *Amyloflagellula, Anastrophella, Androsaceus, Anthracophyllum, Aphotistus, Aphyllotus, Armillaria, Armillariella, Baeospora, Baumanniella, Calathella, Campanella, Cephaloscypha, Chaetocalathus, Chamaeceras, Collybidium, Collybiopsis, Coprinopsis, Cymatella, Cymatellopsis, Cyphellopsis, Cyptotrama, Dactylosporina, Deigloria, Discocyphella, Eoagaricus, Epicnaphus, Favolaschia, Fissolimbus, Flagelloscypha, Flammulina, Galeromycena, Gerronema, Glabrocyphella, Gloiocephala, Heliomyces, Hispidocalyptella, Hologloea, Hormomitaria, Hymenoconidium, Hymenogloea, Hymenomarasmius, Lachnella, Laschia, Lecanocybe, Lentinula, Libellus, Macrocystidia, Macrocystis, Manuripia, Marasmiellus, Marasmius, Merismodes, Micromphale, Monodelphus, Mucidula, Mycetinis, Mycomedusa, Myxocollybia, Nochascypha, Omphalotus, Oudemansia, Oudemansiella, Phaeocyphellopsis, Phaeodepas, Phaeolimacium, Physalacria, Plagiotus, Polymarasmius, Polymyces, Poroauricula, Porolaschia, Protomarasmius, Pseudodasyscypha, Pseudotyphula, Pterospora, Rhizomorpha, Rhodocollybia, Scorteus, Setulipes, Shitaker, Skepperiella, Stipitocyphella, Strobilurus, Stromatocyphella, Sympodia, Tephrophana, Tetrapyrgos, Vanromburghia, Xerula* and *Xerulina*.
725. The bioactive agent according to item 724, wherein Basidiomycete cell is selected from the genus of *Amyloflagellula*.
726. The bioactive agent according to item 724, wherein Basidiomycete cell is selected from the genus of *Anastrophella*.
727. The bioactive agent according to item 724, wherein Basidiomycete cell is selected from the genus of *Androsaceus*.
728. The bioactive agent according to item 724, wherein Basidiomycete cell is selected from the genus of *Anthracophyllum*.
729. The bioactive agent according to item 724, wherein Basidiomycete cell is selected from the genus of *Aphotistus*.
730. The bioactive agent according to item 724, wherein Basidiomycete cell is selected from the genus of *Aphyllotus*.

731. The bioactive agent according to item 724, wherein Basidiomycete cell is selected from the genus of *Armillaria*.
732. The bioactive agent according to item 724, wherein Basidiomycete cell is selected from the genus of *Armillariella*.
733. The bioactive agent according to item 724, wherein Basidiomycete cell is selected from the genus of *Baeospora*.
734. The bioactive agent according to item 724, wherein Basidiomycete cell is selected from the genus of *Baumanniella*.
735. The bioactive agent according to item 724, wherein Basidiomycete cell is selected from the genus of *Calathella*.
736. The bioactive agent according to item 724, wherein Basidiomycete cell is selected from the genus of *Campanella*.
737. The bioactive agent according to item 724, wherein Basidiomycete cell is selected from the genus of *Cephaloscypha*.
738. The bioactive agent according to item 724, wherein Basidiomycete cell is selected from the genus of *Chaetocalathus*.
739. The bioactive agent according to item 724, wherein Basidiomycete cell is selected from the genus of *Chamaeceras*.
740. The bioactive agent according to item 724, wherein Basidiomycete cell is selected from the genus of *Collybidium*.
741. The bioactive agent according to item 724, wherein Basidiomycete cell is selected from the genus of *Collybiopsis*.
742. The bioactive agent according to item 724, wherein Basidiomycete cell is selected from the genus of *Coprinopsis*.
743. The bioactive agent according to item 724, wherein Basidiomycete cell is selected from the genus of *Cymatella*.
744. The bioactive agent according to item 724, wherein Basidiomycete cell is selected from the genus of *Cymatellopsis*.
745. The bioactive agent according to item 724, wherein Basidiomycete cell is selected from the genus of *Cyphellopsis*.
746. The bioactive agent according to item 724, wherein Basidiomycete cell is selected from the genus of *Cyptotrama*.
747. The bioactive agent according to item 724, wherein Basidiomycete cell is selected from the genus of *Dactylosporina*.
748. The bioactive agent according to item 724, wherein Basidiomycete cell is selected from the genus of *Deigloria*.
749. The bioactive agent according to item 724, wherein Basidiomycete cell is selected from the genus of *Discocyphella*.
750. The bioactive agent according to item 724, wherein Basidiomycete cell is selected from the genus of *Eoagaricus*.
751. The bioactive agent according to item 724, wherein Basidiomycete cell is selected from the genus of *Epicnaphus*.
752. The bioactive agent according to item 724, wherein Basidiomycete cell is selected from the genus of *Favolaschia*.
753. The bioactive agent according to item 724, wherein Basidiomycete cell is selected from the genus of *Fissolimbus*.
754. The bioactive agent according to item 724, wherein Basidiomycete cell is selected from the genus of *Flagelloscypha*.
755. The bioactive agent according to item 724, wherein Basidiomycete cell is selected from the genus of *Flammulina*.
756. The bioactive agent according to item 724, wherein Basidiomycete cell is selected from the genus of *Galeromycena*.
757. The bioactive agent according to item 724, wherein Basidiomycete cell is selected from the genus of *Gerronema*.
758. The bioactive agent according to item 724, wherein Basidiomycete cell is selected from the genus of *Glabrocyphella*.
759. The bioactive agent according to item 724, wherein Basidiomycete cell is selected from the genus of *Gloiocephala*.
760. The bioactive agent according to item 724, wherein Basidiomycete cell is selected from the genus of *Heliomyces*.
761. The bioactive agent according to item 724, wherein Basidiomycete cell is selected from the genus of *Hispidocalyptella*.
762. The bioactive agent according to item 724, wherein Basidiomycete cell is selected from the genus of *Hologloea*.
763. The bioactive agent according to item 724, wherein Basidiomycete cell is selected from the genus of *Hormomitaria*.
764. The bioactive agent according to item 724, wherein Basidiomycete cell is selected from the genus of *Hymenoconidium*.
765. The bioactive agent according to item 724, wherein Basidiomycete cell is selected from the genus of *Hymenogloea*.
766. The bioactive agent according to item 724, wherein Basidiomycete cell is selected from the genus of *Hymenomarasmius*.
767. The bioactive agent according to item 724, wherein Basidiomycete cell is selected from the genus of *Lachnella*.
768. The bioactive agent according to item 724, wherein Basidiomycete cell is selected from the genus of *Laschia*.
769. The bioactive agent according to item 724, wherein Basidiomycete cell is selected from the genus of *Lecanocybe*.
770. The bioactive agent according to item 724, wherein Basidiomycete cell is selected from the genus of *Lentinula*.
771. The bioactive agent according to item 724, wherein Basidiomycete cell is selected from the genus of *Libellus*.
772. The bioactive agent according to item 724, wherein Basidiomycete cell is selected from the genus of *Macrocystidia*.
773. The bioactive agent according to item 724, wherein Basidiomycete cell is selected from the genus of *Macrocystis*.
774. The bioactive agent according to item 724, wherein Basidiomycete cell is selected from the genus of *Manuripia*.
775. The bioactive agent according to item 724, wherein Basidiomycete cell is selected from the genus of *Marasmiellus*.

776. The bioactive agent according to item 724, wherein Basidiomycete cell is selected from the genus of *Marasmius*.
777. The bioactive agent according to item 724, wherein Basidiomycete cell is selected from the genus of *Merismodes*.
778. The bioactive agent according to item 724, wherein Basidiomycete cell is selected from the genus of *Micromphale*.
779. The bioactive agent according to item 724, wherein Basidiomycete cell is selected from the genus of *Monodelphus*.
780. The bioactive agent according to item 724, wherein Basidiomycete cell is selected from the genus of *Mucidula*.
781. The bioactive agent according to item 724, wherein Basidiomycete cell is selected from the genus of *Mycetinis*.
782. The bioactive agent according to item 724, wherein Basidiomycete cell is selected from the genus of *Mycomedusa*.
783. The bioactive agent according to item 724, wherein Basidiomycete cell is selected from the genus of *Myxocollybia*.
784. The bioactive agent according to item 724, wherein Basidiomycete cell is selected from the genus of *Nochascypha*.
785. The bioactive agent according to item 724, wherein Basidiomycete cell is selected from the genus of *Omphalotus*.
786. The bioactive agent according to item 724, wherein Basidiomycete cell is selected from the genus of *Oudemansia*.
787. The bioactive agent according to item 724, wherein Basidiomycete cell is selected from the genus of *Oudemansiella*.
788. The bioactive agent according to item 724, wherein Basidiomycete cell is selected from the genus of *Phaeocyphellopsis*.
789. The bioactive agent according to item 724, wherein Basidiomycete cell is selected from the genus of *Phaeodepas*.
790. The bioactive agent according to item 724, wherein Basidiomycete cell is selected from the genus of *Phaeolimacium*.
791. The bioactive agent according to item 724, wherein Basidiomycete cell is selected from the genus of *Physalacria*.
792. The bioactive agent according to item 724, wherein Basidiomycete cell is selected from the genus of *Plagiotus*.
793. The bioactive agent according to item 724, wherein Basidiomycete cell is selected from the genus of *Polymarasmius*.
794. The bioactive agent according to item 724, wherein Basidiomycete cell is selected from the genus of *Polymyces*.
795. The bioactive agent according to item 724, wherein Basidiomycete cell is selected from the genus of *Poroauricula*.
796. The bioactive agent according to item 724, wherein Basidiomycete cell is selected from the genus of *Porolaschia*.
797. The bioactive agent according to item 724, wherein Basidiomycete cell is selected from the genus of *Protomarasmius*.
798. The bioactive agent according to item 724, wherein Basidiomycete cell is selected from the genus of *Pseudodasyscypha*.
799. The bioactive agent according to item 724, wherein Basidiomycete cell is selected from the genus of *Pseudotyphula*.
800. The bioactive agent according to item 724, wherein Basidiomycete cell is selected from the genus of *Pterospora*.
801. The bioactive agent according to item 724, wherein Basidiomycete cell is selected from the genus of *Rhizomorpha*.
802. The bioactive agent according to item 724, wherein Basidiomycete cell is selected from the genus of *Rhodocollybia*.
803. The bioactive agent according to item 724, wherein Basidiomycete cell is selected from the genus of *Scorteus*.
804. The bioactive agent according to item 724, wherein Basidiomycete cell is selected from the genus of *Setulipes*.
805. The bioactive agent according to item 724, wherein Basidiomycete cell is selected from the genus of *Shitaker*.
806. The bioactive agent according to item 724, wherein Basidiomycete cell is selected from the genus of *Skepperiella*.
807. The bioactive agent according to item 724, wherein Basidiomycete cell is selected from the genus of *Stipitocyphella*.
808. The bioactive agent according to item 724, wherein Basidiomycete cell is selected from the genus of *Strobilurus*.
809. The bioactive agent according to item 724, wherein Basidiomycete cell is selected from the genus of *Stromatocyphella*.
810. The bioactive agent according to item 724, wherein Basidiomycete cell is selected from the genus of *Sympodia*.
811. The bioactive agent according to item 724, wherein Basidiomycete cell is selected from the genus of *Tephrophana*.
812. The bioactive agent according to item 724, wherein Basidiomycete cell is selected from the genus of *Tetrapyrgos*.
813. The bioactive agent according to item 724, wherein Basidiomycete cell is selected from the genus of *Vanromburghia*.
814. The bioactive agent according to item 724, wherein Basidiomycete cell is selected from the genus of *Xerula*.
815. The bioactive agent according to item 724, wherein Basidiomycete cell is selected from the genus of *Xerulina*.
816. The bioactive agent according to item 230, wherein said Basidiomycete cell belongs to a genus selected from the group consisting of *Andebbia, Castoreum, Gummiglobus, Gummivena, Inoderma, Malajczukia, Mesophellia, Nothocastoreum* and *Potoromyces*.
817. The bioactive agent according to item 816, wherein Basidiomycete cell is selected from the genus of *Andebbia*.
818. The bioactive agent according to item 816, wherein Basidiomycete cell is selected from the genus of *Castoreum*.
819. The bioactive agent according to item 816, wherein Basidiomycete cell is selected from the genus of *Gummiglobus*.
820. The bioactive agent according to item 816, wherein Basidiomycete cell is selected from the genus of *Gummivena*.
821. The bioactive agent according to item 816, wherein Basidiomycete cell is selected from the genus of *Inoderma*.
822. The bioactive agent according to item 816, wherein Basidiomycete cell is selected from the genus of *Malajczukia*.

823. The bioactive agent according to item 816, wherein Basidiomycete cell is selected from the genus of *Mesophellia*.
824. The bioactive agent according to item 816, wherein Basidiomycete cell is selected from the genus of *Nothocastoreum*.
825. The bioactive agent according to item 816, wherein Basidiomycete cell is selected from the genus of *Potoromyces*.
826. The bioactive agent according to item 231, wherein said Basidiomycete cell belongs to a genus selected from the group consisting of *Endonevrum, Mycenastrum* and *Pachyderma*.
827. The bioactive agent according to item 826, wherein Basidiomycete cell is selected from the genus of *Endonevrum*.
828. The bioactive agent according to item 826, wherein Basidiomycete cell is selected from the genus of *Mycenastrum*.
829. The bioactive agent according to item 826, wherein Basidiomycete cell is selected from the genus of *Pachyderma*.
830. The bioactive agent according to item 232, wherein Basidiomycete cell is selected from the genus of *Nia*.
831. The bioactive agent according to item 233, wherein said Basidiomycete cell belongs to a genus selected from the group consisting of *Crucibulum, Cyathia, Cyathodes, Cyathus, Granularia, Mycocalia, Nidula, Nidularia* and *Peziza*.
832. The bioactive agent according to item 831, wherein Basidiomycete cell is selected from the genus of *Crucibulum*.
833. The bioactive agent according to item 831, wherein Basidiomycete cell is selected from the genus of *Cyathia*.
834. The bioactive agent according to item 831, wherein Basidiomycete cell is selected from the genus of *Cyathodes*.
835. The bioactive agent according to item 831, wherein Basidiomycete cell is selected from the genus of *Cyathus*.
836. The bioactive agent according to item 831, wherein Basidiomycete cell is selected from the genus of *Granularia*.
837. The bioactive agent according to item 831, wherein Basidiomycete cell is selected from the genus of *Mycocalia*.
838. The bioactive agent according to item 831, wherein Basidiomycete cell is selected from the genus of *Nidula*.
839. The bioactive agent according to item 831, wherein Basidiomycete cell is selected from the genus of *Nidularia*.
840. The bioactive agent according to item 831, wherein Basidiomycete cell is selected from the genus of *Peziza*.
841. The bioactive agent according to item 234, wherein said Basidiomycete cell belongs to a genus selected from the group consisting of *Areolaria, Battareopsis, Cyphellomyces, Dictyocephalos, Phellorinia, Whetstonia* and *Xylopodium*.
842. The bioactive agent according to item 841, wherein Basidiomycete cell is selected from the genus of *Areolaria*.
843. The bioactive agent according to item 841, wherein Basidiomycete cell is selected from the genus of *Battareopsis*.
844. The bioactive agent according to item 841, wherein Basidiomycete cell is selected from the genus of *Cyphellomyces*.
845. The bioactive agent according to item 841, wherein Basidiomycete cell is selected from the genus of *Dictyocephalos*.
846. The bioactive agent according to item 841, wherein Basidiomycete cell is selected from the genus of *Phellorinia*.
847. The bioactive agent according to item 841, wherein Basidiomycete cell is selected from the genus of *Whetstonia*.
848. The bioactive agent according to item 841, wherein Basidiomycete cell is selected from the genus of *Xylopodium*.
849. The bioactive agent according to item 235, wherein said Basidiomycete cell belongs to a genus selected from the group consisting of *Acanthocystis, Agaricochaete, Crepidopus, Cyclopleurotus, Gelona, Geopetalum, Hohenbuehelia, Lentodiopsis, Pleurotus, Pterophyllus* and *Scieroma*.
850. The bioactive agent according to item 849, wherein Basidiomycete cell is selected from the genus of *Acanthocystis*.
851. The bioactive agent according to item 849, wherein Basidiomycete cell is selected from the genus of *Agaricochaete*.
852. The bioactive agent according to item 849, wherein Basidiomycete cell is selected from the genus of *Crepidopus*.
853. The bioactive agent according to item 849, wherein Basidiomycete cell is selected from the genus of *Cyclopleurotus*.
854. The bioactive agent according to item 849, wherein Basidiomycete cell is selected from the genus of *Gelona*.
855. The bioactive agent according to item 849, wherein Basidiomycete cell is selected from the genus of *Geopetalum*.
856. The bioactive agent according to item 849, wherein Basidiomycete cell is selected from the genus of *Hohenbuehelia*.
857. The bioactive agent according to item 849, wherein Basidiomycete cell is selected from the genus of *Lentodiopsis*.
858. The bioactive agent according to item 849, wherein Basidiomycete cell is selected from the genus of *Pleurotus*.
859. The bioactive agent according to item 849, wherein Basidiomycete cell is selected from the genus of *Pterophyllus*.
860. The bioactive agent according to item 849, wherein Basidiomycete cell is selected from the genus of *Scleroma*.
861. The bioactive agent according to item 236, wherein said Basidiomycete cell belongs to a genus selected from the group consisting of *Agaricus, Amanita, Amanitaria, Amanitella, Amanitina, Amanitopsis, Amarrendia, Amidella, Amplariella, Annularia, Ariella, Aspidella, Boletium, Chamaeota, Gilbertia, Hyporrhodius, Lepidella, Leucomyces, Limacella, Myxoderma, Pluteus, Pseudofarinaceus, Rhodosporus, Termitosphaera, Torrendia, Vaginaria, Vaginarius, Vaginata, Venenarius, Volva, Volvaria, Volvariella, Volvariopsis, Volvarius, Volvella, Volvoamanita* and *Volvoboletus*.
862. The bioactive agent according to item 861, wherein Basidiomycete cell is selected from the genus of *Agaricus*.
863. The bioactive agent according to item 861, wherein Basidiomycete cell is selected from the genus of *Amanita*.
864. The bioactive agent according to item 861, wherein Basidiomycete cell is selected from the genus of *Amanitaria*.
865. The bioactive agent according to item 861, wherein Basidiomycete cell is selected from the genus of *Amanitella*.

866. The bioactive agent according to item 861, wherein Basidiomycete cell is selected from the genus of *Amanitina*.
867. The bioactive agent according to item 861, wherein Basidiomycete cell is selected from the genus of *Amanitopsis*.
868. The bioactive agent according to item 861, wherein Basidiomycete cell is selected from the genus of *Amarrendia*.
869. The bioactive agent according to item 861, wherein Basidiomycete cell is selected from the genus of *Amidella*.
870. The bioactive agent according to item 861, wherein Basidiomycete cell is selected from the genus of *Amplariella*.
871. The bioactive agent according to item 861, wherein Basidiomycete cell is selected from the genus of *Annularia*.
872. The bioactive agent according to item 861, wherein Basidiomycete cell is selected from the genus of *Ariella*.
873. The bioactive agent according to item 861, wherein Basidiomycete cell is selected from the genus of *Aspidella*.
874. The bioactive agent according to item 861, wherein Basidiomycete cell is selected from the genus of *Boletium*.
875. The bioactive agent according to item 861, wherein Basidiomycete cell is selected from the genus of *Chamaeota*.
876. The bioactive agent according to item 861, wherein Basidiomycete cell is selected from the genus of *Gilbertia*.
877. The bioactive agent according to item 861, wherein Basidiomycete cell is selected from the genus of *Hyporhodius*.
878. The bioactive agent according to item 861, wherein Basidiomycete cell is selected from the genus of *Lepidella*.
879. The bioactive agent according to item 861, wherein Basidiomycete cell is selected from the genus of *Leucomyces*.
880. The bioactive agent according to item 861, wherein Basidiomycete cell is selected from the genus of *Limacella*.
881. The bioactive agent according to item 861, wherein Basidiomycete cell is selected from the genus of *Myxoderma*.
882. The bioactive agent according to item 861, wherein Basidiomycete cell is selected from the genus of *Pluteus*.
883. The bioactive agent according to item 861, wherein Basidiomycete cell is selected from the genus of *Pseudofarinaceus*.
884. The bioactive agent according to item 861, wherein Basidiomycete cell is selected from the genus of *Rhodosporus*.
885. The bioactive agent according to item 861, wherein Basidiomycete cell is selected from the genus of *Termitosphaera*.
886. The bioactive agent according to item 861, wherein Basidiomycete cell is selected from the genus of *Torrendia*.
887. The bioactive agent according to item 861, wherein Basidiomycete cell is selected from the genus of *Vaginaria*.
888. The bioactive agent according to item 861, wherein Basidiomycete cell is selected from the genus of *Vaginarius*.
889. The bioactive agent according to item 861, wherein Basidiomycete cell is selected from the genus of *Vaginata*.
890. The bioactive agent according to item 861, wherein Basidiomycete cell is selected from the genus of *Venenarius*.
891. The bioactive agent according to item 861, wherein Basidiomycete cell is selected from the genus of *Volva*.
892. The bioactive agent according to item 861, wherein Basidiomycete cell is selected from the genus of *Volvaria*.
893. The bioactive agent according to item 861, wherein Basidiomycete cell is selected from the genus of *Volvariella*.
894. The bioactive agent according to item 861, wherein Basidiomycete cell is selected from the genus of *Volvariopsis*.
895. The bioactive agent according to item 861, wherein Basidiomycete cell is selected from the genus of *Volvarius*.
896. The bioactive agent according to item 861, wherein Basidiomycete cell is selected from the genus of *Volvella*.
897. The bioactive agent according to item 861, wherein Basidiomycete cell is selected from the genus of *Volvoamanita*.
898. The bioactive agent according to item 861, wherein Basidiomycete cell is selected from the genus of *Volvoboletus*.
899. The bioactive agent according to item 237, wherein said Basidiomycete cell belongs to a genus selected from the group consisting of *Actiniceps, Allantula, Ceratella, Deflexula, Dimorphocystis, Parapterulicium, Penicillaria, Phaeopterula, Pterula* and *Pterulicium*.
900. The bioactive agent according to item 899, wherein Basidiomycete cell is selected from the genus of *Actiniceps*.
901. The bioactive agent according to item 899, wherein Basidiomycete cell is selected from the genus of *Allantula*.
902. The bioactive agent according to item 899, wherein Basidiomycete cell is selected from the genus of *Ceratella*.
903. The bioactive agent according to item 899, wherein Basidiomycete cell is selected from the genus of *Deflexula*.
904. The bioactive agent according to item 899, wherein Basidiomycete cell is selected from the genus of *Dimorphocystis*.
905. The bioactive agent according to item 899, wherein Basidiomycete cell is selected from the genus of *Parapterulicium*.
906. The bioactive agent according to item 899, wherein Basidiomycete cell is selected from the genus of *Penicillaria*.
907. The bioactive agent according to item 899, wherein Basidiomycete cell is selected from the genus of *Phaeopterula*.
908. The bioactive agent according to item 899, wherein Basidiomycete cell is selected from the genus of *Pterula*.
909. The bioactive agent according to item 899, wherein Basidiomycete cell is selected from the genus of *Pterulicium*.
910. The bioactive agent according to item 238, wherein said Basidiomycete cell belongs to a genus selected from the group consisting of *Apus, Auriculariopsis, Cytidiella, Ditiola, Flabellaria, Henningsomyces, Hyponevris, Petrona, Phaeoschizophyllum, Porotheleum, Rectipilus, Rhipidium, Scaphophoeum, Schizonia, Schizophyllum* and *Solenia*.
911. The bioactive agent according to item 910, wherein Basidiomycete cell is selected from the genus of *Apus*.
912. The bioactive agent according to item 910, wherein Basidiomycete cell is selected from the genus of *Auriculariopsis*.
913. The bioactive agent according to item 910, wherein Basidiomycete cell is selected from the genus of *Cytidiella*.
914. The bioactive agent according to item 910, wherein Basidiomycete cell is selected from the genus of *Ditiola*.

915. The bioactive agent according to item 910, wherein Basidiomycete cell is selected from the genus of *Flabellaria*.
916. The bioactive agent according to item 910, wherein Basidiomycete cell is selected from the genus of *Henningsomyces*.
917. The bioactive agent according to item 910, wherein Basidiomycete cell is selected from the genus of *Hyponevris*.
918. The bioactive agent according to item 910, wherein Basidiomycete cell is selected from the genus of *Petrona*.
919. The bioactive agent according to item 910, wherein Basidiomycete cell is selected from the genus of *Phaeoschizophyllum*.
920. The bioactive agent according to item 910, wherein Basidiomycete cell is selected from the genus of *Porotheleum*.
921. The bioactive agent according to item 910, wherein Basidiomycete cell is selected from the genus of *Rectipilus*.
922. The bioactive agent according to item 910, wherein Basidiomycete cell is selected from the genus of *Rhipidium*.
923. The bioactive agent according to item 910, wherein Basidiomycete cell is selected from the genus of *Scaphophoeum*.
924. The bioactive agent according to item 910, wherein Basidiomycete cell is selected from the genus of *Schizonia*.
925. The bioactive agent according to item 910, wherein Basidiomycete cell is selected from the genus of *Schizophyllum*.
926. The bioactive agent according to item 910, wherein Basidiomycete cell is selected from the genus of *Solenia*.
927. The bioactive agent according to item 239, wherein Basidiomycete cell is selected from the genus of *Stromatoscypha*.
928. The bioactive agent according to item 240, wherein said Basidiomycete cell belongs to a genus selected from the group consisting of *Cytophyllopsis, Deconica, Delitescor, Derminus, Dryophila, Flammopsis, Flammula, Galeropsina, Geophila, Gymnocybe, Hemipholiota, Hypholoma, Hypodendrum, Kuehneromyces, Le-Ratia, Leratiomyces, Melanotus, Mythicomyces, Nematoloma, Nemecomyces, Nivatogastrium, Pachylepyrium, Phaeonematoloma, Pholiota, Pleuroflammula, Psilocybe, Ryssospora, Stropharia, Stropholoma, Visculus* and *Weraroa*.
929. The bioactive agent according to item 928, wherein Basidiomycete cell is selected from the genus of *Cytophyllopsis*.
930. The bioactive agent according to item 928, wherein Basidiomycete cell is selected from the genus of *Deconica*.
931. The bioactive agent according to item 928, wherein Basidiomycete cell is selected from the genus of *Delitescor*.
932. The bioactive agent according to item 928, wherein Basidiomycete cell is selected from the genus of *Derminus*.
933. The bioactive agent according to item 928, wherein Basidiomycete cell is selected from the genus of *Dryophila*.
934. The bioactive agent according to item 928, wherein Basidiomycete cell is selected from the genus of *Flammopsis*.
935. The bioactive agent according to item 928, wherein Basidiomycete cell is selected from the genus of *Flammula*.
936. The bioactive agent according to item 928, wherein Basidiomycete cell is selected from the genus of *Galeropsina*.
937. The bioactive agent according to item 928, wherein Basidiomycete cell is selected from the genus of *Geophila*.
938. The bioactive agent according to item 928, wherein Basidiomycete cell is selected from the genus of *Gymnocybe*.
939. The bioactive agent according to item 928, wherein Basidiomycete cell is selected from the genus of *Hemipholiota*.
940. The bioactive agent according to item 928, wherein Basidiomycete cell is selected from the genus of *Hypholoma*.
941. The bioactive agent according to item 928, wherein Basidiomycete cell is selected from the genus of *Hypodendrum*.
942. The bioactive agent according to item 928, wherein Basidiomycete cell is selected from the genus of *Kuehneromyces*.
943. The bioactive agent according to item 928, wherein Basidiomycete cell is selected from the genus of *Le-Ratia*.
944. The bioactive agent according to item 928, wherein Basidiomycete cell is selected from the genus of *Leratiomyces*.
945. The bioactive agent according to item 928, wherein Basidiomycete cell is selected from the genus of *Melanotus*.
946. The bioactive agent according to item 928, wherein Basidiomycete cell is selected from the genus of *Mythicomyces*.
947. The bioactive agent according to item 928, wherein Basidiomycete cell is selected from the genus of *Nematoloma*.
948. The bioactive agent according to item 928, wherein Basidiomycete cell is selected from the genus of *Nemecomyces*.
949. The bioactive agent according to item 928, wherein Basidiomycete cell is selected from the genus of *Nivatogastrium*.
950. The bioactive agent according to item 928, wherein Basidiomycete cell is selected from the genus of *Pachylepyrium*.
951. The bioactive agent according to item 928, wherein Basidiomycete cell is selected from the genus of *Phaeonematoloma*.
952. The bioactive agent according to item 928, wherein Basidiomycete cell is selected from the genus of *Pholiota*.
953. The bioactive agent according to item 928, wherein Basidiomycete cell is selected from the genus of *Pleuroflammula*.
954. The bioactive agent according to item 928, wherein Basidiomycete cell is selected from the genus of *Psilocybe*.
955. The bioactive agent according to item 928, wherein Basidiomycete cell is selected from the genus of *Ryssospora*.
956. The bioactive agent according to item 928, wherein Basidiomycete cell is selected from the genus of *Stropharia*.
957. The bioactive agent according to item 928, wherein Basidiomycete cell is selected from the genus of *Stropholoma*.
958. The bioactive agent according to item 928, wherein Basidiomycete cell is selected from the genus of *Visculus*.
959. The bioactive agent according to item 928, wherein Basidiomycete cell is selected from the genus of *Weraroa*.

960. The bioactive agent according to item 241, wherein said Basidiomycete cell belongs to a genus selected from the group consisting of *Aeruginospora, Amparoina, Ampulloclitocybe, Arrhenia, Arthrosporella, Asproinocybe, Aspropaxillus, Asterophora, Asterotrichum, Asterotus, Austroclitocybe, Austroomphaliaster, Bactroboletus, Basidopus, Bertrandia, Bertrandiella, Biannularia, Boehmia, Botrydina, Caesposus, Callistodermatium, Callistosporium, Calocybe, Calyptella, Camarophyllopsis, Camarophyllus, Campanophyllum, Cantharellopsis, Cantharellula, Cantharocybe, Catathelasma, Catatrama, Caulorhiza, Cellypha, Chemonophyllum, Chromosera, Chrysobostrychodes, Chrysomphalina, Clavicybe, Clavomphalia, Clitocybe, Clitocybula, Collopus, Collybia, Conchomyces, Coolia, Coriscium, Corniola, Corrugaria, Cortinellus, Crinipellis, Cuphophyllus, Cynema, Cyphellocalathus, Cystoderma, Cystodermella, Decapitatus, Delicatula, Dendrocollybia, Dennisiomyces, Dermoloma, Dictyolus, Dictyopanus, Dictyoploca, Dissoderma, Echinosporella, Eomycenella, Fayodia, Filoboletus, Flabellimycena, Floccularia, Galactopus, Gamundia, Geotus, Gerhardtia, Gliophorus, Glutinaster, Godfrinia, Gymnopus, Gyroflexus, Gyrophila, Haasiella, Heimiomyces, Helotium, Hemimycena, Heterosporula, Hiatula, Hodophilus, Humidicutis, Hydrophorus, Hydropus, Hygroaster, Hygrocybe, Hygrophorus, Hygrotrama, Hypsizygus, Infundibulicybe, Insiticia, Jacobia, Lactocollybia, Lampteromyces, Leiopoda, Lepista, Leptoglossum, Leptomyces, Leptotus, Leucoinocybe, Leucopaxillus, Leucopholiota, Lichenomphalia, Limacinus, Limacium, Linopodium, Lulesia, Lyophyllopsis, Lyophyllum, Macrocybe, Maireina, Mastoleucomyces, Megacollybia, Megatricholoma, Melaleuca, Melanoleuca, Metulocyphella, Microcollybia, Microcollybia, Mniopetalum, Moniliophthora, Monomyces, Mycena, Mycenella, Mycenoporella, Mycenopsis, Mycenula, Mycoalvimia, Myxomphalia, Nematoctonus, Neoclitocybe, Neohygrocybe, Neohygrophorus, Neonothopanus, Nothoclavulina, Nothopanus, Nyctalis, Omphalia, Omphalia, Omphaliaster, Omphalina, Omphalius, Omphalopsis, Ossicaulis, Palaeocephala, Panellus, Paralepista, Peglerochaete, Pegleromyces, Perona, Phaeolepiota, Phaeomycena, Phaeotellus, Phalomia, Phlebomarasmius, Phlebomycena, Phlebophora, Phyllotopsis, Phyllotremella, Phyllotus, Physocystidium, Phytoconis, Pleurella, Pleurocollybia, Pleurocybella, Pleuromycenula, Pleurotopsis, Podabrella, Poromycena, Porpoloma, Prunulus, Psammospora, Pseudoarmillariella, Pseudobaeospora, Pseudoclitocybe, Pseudohiatula, Pseudohygrocybe, Pseudohygrophorus, Pseudolyophyllum, Pseudomycena, Pseudoomphalina, Rajapa, Resinomycena, Resupinatus, Retocybe, Rhodocyphella, Rhodopaxillus, Rhodotus, Rickenella, Rimbachia, Ripartitella, Ripartites, Roridomyces, Rubeolarius, Rugosomyces, Sarcomyxa, Sclerostilbum, Scytinotopsis, Scytinotus, Semiomphalina, Singerella, Singerocybe, Sinotermitomyces, Sphaerocephalus, Squamanita, Stachyomphalina, Stanglomyces, Stereopodium, Stigmatolemma, Tectella, Tephrocybe, Termitomyces, Tilachlidiopsis, Tilotus, Tomentifolium, Tricholoma, Tricholomella, Tricholomopsis, Tricholosporum, Trigonipes, Trogia, Ugola, Urceolus, Urospora, Urosporellina, Valentinia, Xeromphalina* and *Zephirea*.

961. The bioactive agent according to item 960, wherein Basidiomycete cell is selected from the genus of *Aeruginospora*.

962. The bioactive agent according to item 960, wherein Basidiomycete cell is selected from the genus of *Amparoina*.

963. The bioactive agent according to item 960, wherein Basidiomycete cell is selected from the genus of *Ampulloclitocybe*.

964. The bioactive agent according to item 960, wherein Basidiomycete cell is selected from the genus of *Ampulloclitocybe*.

965. The bioactive agent according to item 960, wherein Basidiomycete cell is selected from the genus of *Arrhenia*.

966. The bioactive agent according to item 960, wherein Basidiomycete cell is selected from the genus of *Arthrosporella*.

967. The bioactive agent according to item 960, wherein Basidiomycete cell is selected from the genus of *Asproinocybe*.

968. The bioactive agent according to item 960, wherein Basidiomycete cell is selected from the genus of *Aspropaxillus*.

969. The bioactive agent according to item 960, wherein Basidiomycete cell is selected from the genus of *Asterophora*.

970. The bioactive agent according to item 960, wherein Basidiomycete cell is selected from the genus of *Asterotrichum*.

971. The bioactive agent according to item 960, wherein Basidiomycete cell is selected from the genus of *Asterotus*.

972. The bioactive agent according to item 960, wherein Basidiomycete cell is selected from the genus of *Austroclitocybe*.

973. The bioactive agent according to item 960, wherein Basidiomycete cell is selected from the genus of *Austroomphaliaster*.

974. The bioactive agent according to item 960, wherein Basidiomycete cell is selected from the genus of *Bactroboletus*.

975. The bioactive agent according to item 960, wherein Basidiomycete cell is selected from the genus of *Basidopus*.

976. The bioactive agent according to item 960, wherein Basidiomycete cell is selected from the genus of *Bertrandia*.

977. The bioactive agent according to item 960, wherein Basidiomycete cell is selected from the genus of *Bertrandiella*.

978. The bioactive agent according to item 960, wherein Basidiomycete cell is selected from the genus *Biannularia*.

979. The bioactive agent according to item 960, wherein Basidiomycete cell is selected from the genus of *Boehmia*.

980. The bioactive agent according to item 960, wherein Basidiomycete cell is selected from the genus of *Botrydina*.

981. The bioactive agent according to item 960, wherein Basidiomycete cell is selected from the genus of *Caesposus*.

982. The bioactive agent according to item 960, wherein Basidiomycete cell is selected from the genus of *Callistodermatium*.

983. The bioactive agent according to item 960, wherein Basidiomycete cell is selected from the genus of *Callistosporium*.

984. The bioactive agent according to item 960, wherein Basidiomycete cell is selected from the genus of *Calocybe*.

985. The bioactive agent according to item 960, wherein Basidiomycete cell is selected from the genus of *Calyptella*.

986. The bioactive agent according to item 960, wherein Basidiomycete cell is selected from the genus of *Camarophyllopsis*.
987. The bioactive agent according to item 960, wherein Basidiomycete cell is selected from the genus of *Camarophyllus*.
988. The bioactive agent according to item 960, wherein Basidiomycete cell is selected from the genus of *Campanophyllum*.
989. The bioactive agent according to item 960, wherein Basidiomycete cell is selected from the genus of *Cantharellopsis*.
990. The bioactive agent according to item 960, wherein Basidiomycete cell is selected from the genus of *Cantharellula*.
991. The bioactive agent according to item 960, wherein Basidiomycete cell is selected from the genus of *Cantharocybe*.
992. The bioactive agent according to item 960, wherein Basidiomycete cell is selected from the genus of *Catathelasma*.
993. The bioactive agent according to item 960, wherein Basidiomycete cell is selected from the genus of *Catatrama*.
994. The bioactive agent according to item 960, wherein Basidiomycete cell is selected from the genus of *Caulorhiza*.
995. The bioactive agent according to item 960, wherein Basidiomycete cell is selected from the genus of *Cellypha*.
996. The bioactive agent according to item 960, wherein Basidiomycete cell is selected from the genus of *Chemonophyllum*.
997. The bioactive agent according to item 960, wherein Basidiomycete cell is selected from the genus of *Chromosera*.
998. The bioactive agent according to item 960, wherein Basidiomycete cell is selected from the genus of *Chrysobostrychodes*.
999. The bioactive agent according to item 960, wherein Basidiomycete cell is selected from the genus of *Chrysomphalina*.
1000. The bioactive agent according to item 960, wherein Basidiomycete cell is selected from the genus of *Clavicybe*.
1001. The bioactive agent according to item 960, wherein Basidiomycete cell is selected from the genus of *Clavomphalia*.
1002. The bioactive agent according to item 960, wherein Basidiomycete cell is selected from the genus of *Clitocybe*.
1003. The bioactive agent according to item 960, wherein Basidiomycete cell is selected from the genus of *Clitocybula*.
1004. The bioactive agent according to item 960, wherein Basidiomycete cell is selected from the genus of *Collopus*.
1005. The bioactive agent according to item 960, wherein Basidiomycete cell is selected from the genus of *Collybia*.
1006. The bioactive agent according to item 960, wherein Basidiomycete cell is selected from the genus of *Conchomyces*.
1007. The bioactive agent according to item 960, wherein Basidiomycete cell is selected from the genus of *Coolia*.
1008. The bioactive agent according to item 960, wherein Basidiomycete cell is selected from the genus of *Coriscium*.
1009. The bioactive agent according to item 960, wherein Basidiomycete cell is selected from the genus of *Corniola*.
1010. The bioactive agent according to item 960, wherein Basidiomycete cell is selected from the genus of *Corrugaria*.
1011. The bioactive agent according to item 960, wherein Basidiomycete cell is selected from the genus of *Cortinellus*.
1012. The bioactive agent according to item 960, wherein Basidiomycete cell is selected from the genus of *Crinipellis*.
1013. The bioactive agent according to item 960, wherein Basidiomycete cell is selected from the genus of *Cuphophyllus*.
1014. The bioactive agent according to item 960, wherein Basidiomycete cell is selected from the genus of *Cynema*.
1015. The bioactive agent according to item 960, wherein Basidiomycete cell is selected from the genus of *Cyphellocalathus*.
1016. The bioactive agent according to item 960, wherein Basidiomycete cell is selected from the genus of *Cystoderma*.
1017. The bioactive agent according to item 960, wherein Basidiomycete cell is selected from the genus of *Cystodermella*.
1018. The bioactive agent according to item 960, wherein Basidiomycete cell is selected from the genus of *Decapitatus*.
1019. The bioactive agent according to item 960, wherein Basidiomycete cell is selected from the genus of *Delicatula*.
1020. The bioactive agent according to item 960, wherein Basidiomycete cell is selected from the genus of *Dendrocollybia*.
1021. The bioactive agent according to item 960, wherein Basidiomycete cell is selected from the genus of *Dennisiomyces*.
1022. The bioactive agent according to item 960, wherein Basidiomycete cell is selected from the genus of *Dermoloma*.
1023. The bioactive agent according to item 960, wherein Basidiomycete cell is selected from the genus of *Dictyolus*.
1024. The bioactive agent according to item 960, wherein Basidiomycete cell is selected from the genus of *Dictyopanus*.
1025. The bioactive agent according to item 960, wherein Basidiomycete cell is selected from the genus of *Dictyoploca*.
1026. The bioactive agent according to item 960, wherein Basidiomycete cell is selected from the genus of *Dissoderma*.
1027. The bioactive agent according to item 960, wherein Basidiomycete cell is selected from the genus of *Echinosporella*.
1028. The bioactive agent according to item 960, wherein Basidiomycete cell is selected from the genus of *Eomycenella*.
1029. The bioactive agent according to item 960, wherein Basidiomycete cell is selected from the genus of *Fayodia*.
1030. The bioactive agent according to item 960, wherein Basidiomycete cell is selected from the genus of *Filoboletus*.
1031. The bioactive agent according to item 960, wherein Basidiomycete cell is selected from the genus of *Flabellimycena*.
1032. The bioactive agent according to item 960, wherein Basidiomycete cell is selected from the genus of *Floccularia*.

1033. The bioactive agent according to item 960, wherein Basidiomycete cell is selected from the genus of *Galactopus*.
1034. The bioactive agent according to item 960, wherein Basidiomycete cell is selected from the genus of *Gamundia*.
1035. The bioactive agent according to item 960, wherein Basidiomycete cell is selected from the genus of *Geotus*.
1036. The bioactive agent according to item 960, wherein Basidiomycete cell is selected from the genus of *Gerhardtia*.
1037. The bioactive agent according to item 960, wherein Basidiomycete cell is selected from the genus of *Gliophorus*.
1038. The bioactive agent according to item 960, wherein Basidiomycete cell is selected from the genus of *Glutinaster*.
1039. The bioactive agent according to item 960, wherein Basidiomycete cell is selected from the genus of *Godfrinia*.
1040. The bioactive agent according to item 960, wherein Basidiomycete cell is selected from the genus of *Gymnopus*.
1041. The bioactive agent according to item 960, wherein Basidiomycete cell is selected from the genus of *Gyroflexus*.
1042. The bioactive agent according to item 960, wherein Basidiomycete cell is selected from the genus of *Gyrophila*.
1043. The bioactive agent according to item 960, wherein Basidiomycete cell is selected from the genus of *Haasiella*.
1044. The bioactive agent according to item 960, wherein Basidiomycete cell is selected from the genus of *Heimiomyces*.
1045. The bioactive agent according to item 960, wherein Basidiomycete cell is selected from the genus of *Helotium*.
1046. The bioactive agent according to item 960, wherein Basidiomycete cell is selected from the genus of *Hemimycena*.
1047. The bioactive agent according to item 960, wherein Basidiomycete cell is selected from the genus of *Heterosporula*.
1048. The bioactive agent according to item 960, wherein Basidiomycete cell is selected from the genus of *Hiatula*.
1049. The bioactive agent according to item 960, wherein Basidiomycete cell is selected from the genus of *Hodophilus*.
1050. The bioactive agent according to item 960, wherein Basidiomycete cell is selected from the genus of *Humidicutis*.
1051. The bioactive agent according to item 960, wherein Basidiomycete cell is selected from the genus of *Hydrophorus*.
1052. The bioactive agent according to item 960, wherein Basidiomycete cell is selected from the genus of *Hydropus*.
1053. The bioactive agent according to item 960, wherein Basidiomycete cell is selected from the genus of *Hygroaster*.
1054. The bioactive agent according to item 960, wherein Basidiomycete cell is selected from the genus of *Hygrocybe*.
1055. The bioactive agent according to item 960, wherein Basidiomycete cell is selected from the genus of *Hygrophorus*.
1056. The bioactive agent according to item 960, wherein Basidiomycete cell is selected from the genus of *Hygrotrama*.
1057. The bioactive agent according to item 960, wherein Basidiomycete cell is selected from the genus of *Hypsizygus*.
1058. The bioactive agent according to item 960, wherein Basidiomycete cell is selected from the genus of *Infundibulicybe*.
1059. The bioactive agent according to item 960, wherein Basidiomycete cell is selected from the genus of *Insiticia*.
1060. The bioactive agent according to item 960, wherein Basidiomycete cell is selected from the genus of *Jacobia*.
1061. The bioactive agent according to item 960, wherein Basidiomycete cell is selected from the genus of *Lactocollybia*.
1062. The bioactive agent according to item 960, wherein Basidiomycete cell is selected from the genus of *Lampteromyces*.
1063. The bioactive agent according to item 960, wherein Basidiomycete cell is selected from the genus of *Leiopoda*.
1064. The bioactive agent according to item 960, wherein Basidiomycete cell is selected from the genus of *Lepista*.
1065. The bioactive agent according to item 960, wherein Basidiomycete cell is selected from the genus of *Leptoglossum*.
1066. The bioactive agent according to item 960, wherein Basidiomycete cell is selected from the genus of *Leptotus*.
1067. The bioactive agent according to item 960, wherein Basidiomycete cell is selected from the genus of *Leucoinocybe*.
1068. The bioactive agent according to item 960, wherein Basidiomycete cell is selected from the genus of *Leucopaxillus*.
1069. The bioactive agent according to item 960, wherein Basidiomycete cell is selected from the genus of *Leucopholiota*.
1070. The bioactive agent according to item 960, wherein Basidiomycete cell is selected from the genus of *Lichenomphalia*.
1071. The bioactive agent according to item 960, wherein Basidiomycete cell is selected from the genus of *Limacinus*.
1072. The bioactive agent according to item 960, wherein Basidiomycete cell is selected from the genus of *Limacium*.
1073. The bioactive agent according to item 960, wherein Basidiomycete cell is selected from the genus of *Linopodium*.
1074. The bioactive agent according to item 960, wherein Basidiomycete cell is selected from the genus of *Lulesia*.
1075. The bioactive agent according to item 960, wherein Basidiomycete cell is selected from the genus of *Lyophyllopsis*.
1076. The bioactive agent according to item 960, wherein Basidiomycete cell is selected from the genus of *Lyophyllum*.
1077. The bioactive agent according to item 960, wherein Basidiomycete cell is selected from the genus of *Macrocybe*.
1078. The bioactive agent according to item 960, wherein Basidiomycete cell is selected from the genus of *Maireina*.
1079. The bioactive agent according to item 960, wherein Basidiomycete cell is selected from the genus of *Mastoleucomyces*.
1080. The bioactive agent according to item 960, wherein Basidiomycete cell is selected from the genus of *Megacollybia*.

1081. The bioactive agent according to item 960, wherein Basidiomycete cell is selected from the genus of *Megatricholoma*.
1082. The bioactive agent according to item 960, wherein Basidiomycete cell is selected from the genus of *Melaleuca*.
1083. The bioactive agent according to item 960, wherein Basidiomycete cell is selected from the genus of *Melanoleuca*.
1084. The bioactive agent according to item 960, wherein Basidiomycete cell is selected from the genus of *Metulocyphella*.
1085. The bioactive agent according to item 960, wherein Basidiomycete cell is selected from the genus of *Microcolybia*.
1086. The bioactive agent according to item 960, wherein Basidiomycete cell is selected from the genus of *Mniopetalum*.
1087. The bioactive agent according to item 960, wherein Basidiomycete cell is selected from the genus of *Moniliophthora*.
1088. The bioactive agent according to item 960, wherein Basidiomycete cell is selected from the genus of *Monomyces*.
1089. The bioactive agent according to item 960, wherein Basidiomycete cell is selected from the genus of *Mycena*.
1090. The bioactive agent according to item 960, wherein Basidiomycete cell is selected from the genus of *Mycenella*.
1091. The bioactive agent according to item 960, wherein Basidiomycete cell is selected from the genus of *Mycenoporella*.
1092. The bioactive agent according to item 960, wherein Basidiomycete cell is selected from the genus of *Mycenopsis*.
1093. The bioactive agent according to item 960, wherein Basidiomycete cell is selected from the genus of *Mycenula*.
1094. The bioactive agent according to item 960, wherein Basidiomycete cell is selected from the genus of *Mycoalvimia*.
1095. The bioactive agent according to item 960, wherein Basidiomycete cell is selected from the genus of *Myxomphalia*.
1096. The bioactive agent according to item 960, wherein Basidiomycete cell is selected from the genus of *Nematoctonus*.
1097. The bioactive agent according to item 960, wherein Basidiomycete cell is selected from the genus of *Neoclitocybe*.
1098. The bioactive agent according to item 960, wherein Basidiomycete cell is selected from the genus of *Neohygrocybe*.
1099. The bioactive agent according to item 960, wherein Basidiomycete cell is selected from the genus of *Neohygrophorus*.
1100. The bioactive agent according to item 960, wherein Basidiomycete cell is selected from the genus of *Neonothopanus*.
1101. The bioactive agent according to item 960, wherein Basidiomycete cell is selected from the genus of *Nothoclavulina*.
1102. The bioactive agent according to item 960, wherein Basidiomycete cell is selected from the genus of *Nothopanus*.
1103. The bioactive agent according to item 960, wherein Basidiomycete cell is selected from the genus of *Nyctalis*.
1104. The bioactive agent according to item 960, wherein Basidiomycete cell is selected from the genus of *Omphalia*.
1105. The bioactive agent according to item 960, wherein Basidiomycete cell is selected from the genus of *Omphaliaster*.
1106. The bioactive agent according to item 960, wherein Basidiomycete cell is selected from the genus of *Omphalina*.
1107. The bioactive agent according to item 960, wherein Basidiomycete cell is selected from the genus of *Omphalius*.
1108. The bioactive agent according to item 960, wherein Basidiomycete cell is selected from the genus of *Omphalopsis*.
1109. The bioactive agent according to item 960, wherein Basidiomycete cell is selected from the genus of *Ossicaulis*.
1110. The bioactive agent according to item 960, wherein Basidiomycete cell is selected from the genus of *Palaeocephala*.
1111. The bioactive agent according to item 960, wherein Basidiomycete cell is selected from the genus of *Panellus*.
1112. The bioactive agent according to item 960, wherein Basidiomycete cell is selected from the genus of *Paralepista*.
1113. The bioactive agent according to item 960, wherein Basidiomycete cell is selected from the genus of *Peglerochaete*.
1114. The bioactive agent according to item 960, wherein Basidiomycete cell is selected from the genus of *Pegleromyces*.
1115. The bioactive agent according to item 960, wherein Basidiomycete cell is selected from the genus of *Perona*.
1116. The bioactive agent according to item 960, wherein Basidiomycete cell is selected from the genus of *Phaeolepiota*.
1117. The bioactive agent according to item 960, wherein Basidiomycete cell is selected from the genus of *Phaeomycena*.
1118. The bioactive agent according to item 960, wherein Basidiomycete cell is selected from the genus of *Phaeotellus*.
1119. The bioactive agent according to item 960, wherein Basidiomycete cell is selected from the genus of *Phalomia*.
1120. The bioactive agent according to item 960, wherein Basidiomycete cell is selected from the genus of *Phlebomarasmius*.
1121. The bioactive agent according to item 960, wherein Basidiomycete cell is selected from the genus of *Phlebomycena*.
1122. The bioactive agent according to item 960, wherein Basidiomycete cell is selected from the genus of *Phlebophora*.
1123. The bioactive agent according to item 960, wherein Basidiomycete cell is selected from the genus of *Phyllotopsis*.
1124. The bioactive agent according to item 960, wherein Basidiomycete cell is selected from the genus of *Phyllotremella*.
1125. The bioactive agent according to item 960, wherein Basidiomycete cell is selected from the genus of *Phyllotus*.
1126. The bioactive agent according to item 960, wherein Basidiomycete cell is selected from the genus of *Physocystidium*.

1127. The bioactive agent according to item 960, wherein Basidiomycete cell is selected from the genus of *Phytoconis*.
1128. The bioactive agent according to item 960, wherein Basidiomycete cell is selected from the genus of *Pleurella*.
1129. The bioactive agent according to item 960, wherein Basidiomycete cell is selected from the genus of *Pleurocollybia*.
1130. The bioactive agent according to item 960, wherein Basidiomycete cell is selected from the genus of *Pleurocybella*.
1131. The bioactive agent according to item 960, wherein Basidiomycete cell is selected from the genus of *Pleuromycenula*.
1132. The bioactive agent according to item 960, wherein Basidiomycete cell is selected from the genus of *Pleurotopsis*.
1133. The bioactive agent according to item 960, wherein Basidiomycete cell is selected from the genus of *Podabrella*.
1134. The bioactive agent according to item 960, wherein Basidiomycete cell is selected from the genus of *Poromycena*.
1135. The bioactive agent according to item 960, wherein Basidiomycete cell is selected from the genus of *Porpoloma*.
1136. The bioactive agent according to item 960, wherein Basidiomycete cell is selected from the genus of *Prunulus*.
1137. The bioactive agent according to item 960, wherein Basidiomycete cell is selected from the genus of *Psammospora*.
1138. The bioactive agent according to item 960, wherein Basidiomycete cell is selected from the genus of *Pseudoarmillariella*.
1139. The bioactive agent according to item 960, wherein Basidiomycete cell is selected from the genus of *Pseudobaeospora*.
1140. The bioactive agent according to item 960, wherein Basidiomycete cell is selected from the genus of *Pseudoclitocybe*.
1141. The bioactive agent according to item 960, wherein Basidiomycete cell is selected from the genus of *Pseudohiatula*.
1142. The bioactive agent according to item 960, wherein Basidiomycete cell is selected from the genus of *Pseudohygrocybe*.
1143. The bioactive agent according to item 960, wherein Basidiomycete cell is selected from the genus of *Pseudohygrophorus*.
1144. The bioactive agent according to item 960, wherein Basidiomycete cell is selected from the genus of *Pseudolyophyllum*.
1145. The bioactive agent according to item 960, wherein Basidiomycete cell is selected from the genus of *Pseudomycena*.
1146. The bioactive agent according to item 960, wherein Basidiomycete cell is selected from the genus of *Pseudoomphalina*.
1147. The bioactive agent according to item 960, wherein Basidiomycete cell is selected from the genus of *Rajapa*.
1148. The bioactive agent according to item 960, wherein Basidiomycete cell is selected from the genus of *Resinomycena*.
1149. The bioactive agent according to item 960, wherein Basidiomycete cell is selected from the genus of *Resupinatus*.
1150. The bioactive agent according to item 960, wherein Basidiomycete cell is selected from the genus of *Retocybe*.
1151. The bioactive agent according to item 960, wherein Basidiomycete cell is selected from the genus of *Rhodocyphella*.
1152. The bioactive agent according to item 960, wherein Basidiomycete cell is selected from the genus of *Rhodopaxillus*.
1153. The bioactive agent according to item 960, wherein Basidiomycete cell is selected from the genus of *Rhodotus*.
1154. The bioactive agent according to item 960, wherein Basidiomycete cell is selected from the genus of *Rickenella*.
1155. The bioactive agent according to item 960, wherein Basidiomycete cell is selected from the genus of *Rimbachia*.
1156. The bioactive agent according to item 960, wherein Basidiomycete cell is selected from the genus of *Ripartitella*.
1157. The bioactive agent according to item 960, wherein Basidiomycete cell is selected from the genus of *Ripartites*.
1158. The bioactive agent according to item 960, wherein Basidiomycete cell is selected from the genus of *Roridomyces*.
1159. The bioactive agent according to item 960, wherein Basidiomycete cell is selected from the genus of *Rubeolarius*.
1160. The bioactive agent according to item 960, wherein Basidiomycete cell is selected from the genus of *Rugosomyces*.
1161. The bioactive agent according to item 960, wherein Basidiomycete cell is selected from the genus of *Sarcomyxa*.
1162. The bioactive agent according to item 960, wherein Basidiomycete cell is selected from the genus of *Sclerostilbum*.
1163. The bioactive agent according to item 960, wherein Basidiomycete cell is selected from the genus of *Scytinotopsis*.
1164. The bioactive agent according to item 960, wherein Basidiomycete cell is selected from the genus of *Scytinotus*.
1165. The bioactive agent according to item 960, wherein Basidiomycete cell is selected from the genus of *Semiomphalina*.
1166. The bioactive agent according to item 960, wherein Basidiomycete cell is selected from the genus of *Singerella*.
1167. The bioactive agent according to item 960, wherein Basidiomycete cell is selected from the genus of *Singerocybe*.
1168. The bioactive agent according to item 960, wherein Basidiomycete cell is selected from the genus of *Sinotermitomyces*.
1169. The bioactive agent according to item 960, wherein Basidiomycete cell is selected from the genus of *Sphaerocephalus*.
1170. The bioactive agent according to item 960, wherein Basidiomycete cell is selected from the genus of *Squamanita*.
1171. The bioactive agent according to item 960, wherein Basidiomycete cell is selected from the genus of *Stachyomphalina*.
1172. The bioactive agent according to item 960, wherein Basidiomycete cell is selected from the genus of *Stanglomyces*.

1173. The bioactive agent according to item 960, wherein Basidiomycete cell is selected from the genus of *Stereopodium*.
1174. The bioactive agent according to item 960, wherein Basidiomycete cell is selected from the genus of *Stigmatolemma*.
1175. The bioactive agent according to item 960, wherein Basidiomycete cell is selected from the genus of *Tectella*.
1176. The bioactive agent according to item 960, wherein Basidiomycete cell is selected from the genus of *Tephrocybe*.
1177. The bioactive agent according to item 960, wherein Basidiomycete cell is selected from the genus of *Termitomyces*.
1178. The bioactive agent according to item 960, wherein Basidiomycete cell is selected from the genus of *Tilachlidiopsis*.
1179. The bioactive agent according to item 960, wherein Basidiomycete cell is selected from the genus of *Tilotus*.
1180. The bioactive agent according to item 960, wherein Basidiomycete cell is selected from the genus of *Tomentifolium*.
1181. The bioactive agent according to item 960, wherein Basidiomycete cell is selected from the genus of *Tricholoma*.
1182. The bioactive agent according to item 960, wherein Basidiomycete cell is selected from the genus of *Tricholomella*.
1183. The bioactive agent according to item 960, wherein Basidiomycete cell is selected from the genus of *Tricholomopsis*.
1184. The bioactive agent according to item 960, wherein Basidiomycete cell is selected from the genus of *Tricholosporum*.
1185. The bioactive agent according to item 960, wherein Basidiomycete cell is selected from the genus of *Trigonipes*.
1186. The bioactive agent according to item 960, wherein Basidiomycete cell is selected from the genus of *Trogia*.
1187. The bioactive agent according to item 960, wherein Basidiomycete cell is selected from the genus of *Ugola*.
1188. The bioactive agent according to item 960, wherein Basidiomycete cell is selected from the genus of *Urceolus*.
1189. The bioactive agent according to item 960, wherein Basidiomycete cell is selected from the genus of *Urospora*.
1190. The bioactive agent according to item 960, wherein Basidiomycete cell is selected from the genus of *Urosporellina*.
1191. The bioactive agent according to item 960, wherein Basidiomycete cell is selected from the genus of *Valentinia*.
1192. The bioactive agent according to item 960, wherein Basidiomycete cell is selected from the genus of *Xeromphalina*.
1193. The bioactive agent according to item 960, wherein Basidiomycete cell is selected from the genus of *Zephirea*.
1194. The bioactive agent according to item 242, wherein said Basidiomycete cell belongs to a genus selected from the group consisting of *Battarraeastrum, Battarrea, Battarreoides, Chlamydopus, Dendromyces, Queletia, Schizostoma, Sphaericeps, Tulasnodea* and *Tulostoma*.
1195. The bioactive agent according to item 1195, wherein Basidiomycete cell is selected from the genus of *Battarraeastrum*.
1196. The bioactive agent according to item 1195, wherein Basidiomycete cell is selected from the genus of *Battarrea*.
1197. The bioactive agent according to item 1195, wherein Basidiomycete cell is selected from the genus of *Battarreoides*.
1198. The bioactive agent according to item 1195, wherein Basidiomycete cell is selected from the genus of *Chlamydopus*.
1199. The bioactive agent according to item 1195, wherein Basidiomycete cell is selected from the genus of *Dendromyces*.
1200. The bioactive agent according to item 1195, wherein Basidiomycete cell is selected from the genus of *Queletia*.
1201. The bioactive agent according to item 1195, wherein Basidiomycete cell is selected from the genus of *Schizostoma*.
1202. The bioactive agent according to item 1195, wherein Basidiomycete cell is selected from the genus of *Sphaericeps*.
1203. The bioactive agent according to item 1195, wherein Basidiomycete cell is selected from the genus of *Tulasnodea*.
1204. The bioactive agent according to item 1195, wherein Basidiomycete cell is selected from the genus of *Tulostoma*.
1205. The bioactive agent according to item 243, wherein said Basidiomycete cell belongs to a genus selected from the group consisting of *Apiosporium, Astoma, Bromicolla, Cnazonaria, Coccopleum, Dacryopsella, Gliocoryne, Lutypha, Phacorhiza, Pistillaria, Pistillina, Scleromitra, Sclerotiomyces, Sclerotium, Sphaerula, Typhula* and *Xylochoeras*.
1206. The bioactive agent according to item 1205, wherein Basidiomycete cell is selected from the genus of *Apiosporium*.
1207. The bioactive agent according to item 1205, wherein Basidiomycete cell is selected from the genus of *Astoma*.
1208. The bioactive agent according to item 1205, wherein Basidiomycete cell is selected from the genus of *Bromicolla*.
1209. The bioactive agent according to item 1205, wherein Basidiomycete cell is selected from the genus of *Cnazonaria*.
1210. The bioactive agent according to item 1205, wherein Basidiomycete cell is selected from the genus of *Coccopleum*.
1211. The bioactive agent according to item 1205, wherein Basidiomycete cell is selected from the genus of *Dacryopsella*.
1212. The bioactive agent according to item 1205, wherein Basidiomycete cell is selected from the genus of *Gliocoryne*.
1213. The bioactive agent according to item 1205, wherein Basidiomycete cell is selected from the genus of *Lutypha*.
1214. The bioactive agent according to item 1205, wherein Basidiomycete cell is selected from the genus of *Phacorhiza*.
1215. The bioactive agent according to item 1205, wherein Basidiomycete cell is selected from the genus of *Pistillaria*.
1216. The bioactive agent according to item 1205, wherein Basidiomycete cell is selected from the genus of *Pistillina*.
1217. The bioactive agent according to item 1205, wherein Basidiomycete cell is selected from the genus of *Scleromitra*.
1218. The bioactive agent according to item 1205, wherein Basidiomycete cell is selected from the genus of *Sclerotiomyces*.

1219. The bioactive agent according to item 1205, wherein Basidiomycete cell is selected from the genus of *Sclerotium*.
1220. The bioactive agent according to item 1205, wherein Basidiomycete cell is selected from the genus of *Sphaerula*.
1221. The bioactive agent according to item 1205, wherein Basidiomycete cell is selected from the genus of *Typhula*.
1222. The bioactive agent according to item 1205, wherein Basidiomycete cell is selected from the genus of *Xylochoeras*.
1223. The bioactive agent according to item 244, wherein Basidiomycete cell is selected from the genus of *Rhizomarasmius*.
1224. The bioactive agent according to item 247, wherein said Basidiomycete cell belongs to a genus selected from the group consisting of *Albatrellopsis, Albatrellus, Jahnoporus, Ovinus, Polyporoletus* and *Scutiger*.
1225. The bioactive agent according to item 1225, wherein Basidiomycete cell is selected from the genus of *Albatrellopsis*.
1226. The bioactive agent according to item 1225, wherein Basidiomycete cell is selected from the genus of *Albatrellus*.
1227. The bioactive agent according to item 1225, wherein Basidiomycete cell is selected from the genus of *Jahnoporus*.
1228. The bioactive agent according to item 1225, wherein Basidiomycete cell is selected from the genus of *Ovinus*.
1229. The bioactive agent according to item 1225, wherein Basidiomycete cell is selected from the genus of *Polyporoletus*.
1230. The bioactive agent according to item 1225, wherein Basidiomycete cell is selected from the genus of *Scutiger*.
1231. The bioactive agent according to item 248, wherein said Basidiomycete cell belongs to a genus selected from the group consisting of *Amphinema, Amyloathelia, Amylocorticium, Athelia, Athelicium, Athelidium, Athelopsis, Butlerelfia, Byssocorticium, Byssocristella, Byssoporia, Caerulicium, Cora, Coraemyces, Corella, Cristinia, Dacryobasidium, Dichonema, Dictyonema, Dictyonematomyces, Digitatispora, Diplonema, Fibulomyces, Fibulorhizoctonia, Gyrolophium, Hypochnella, Hypochniciellum, Irpicodon, Laudatea, Leptosporomyces, Lobulicium, Luellia, Meizericium, Mycostigma, Piloderma, Plicatura, Plicaturopsis, Rhipidonema, Rhipidonematomyces, Rhizonema, Taeniospora, Tomentellopsis, Tylosperma, Tylospora* and *Wainiocora*.
1232. The bioactive agent according to item 1231, wherein Basidiomycete cell is selected from the genus of *Amphinema*.
1233. The bioactive agent according to item 1231, wherein Basidiomycete cell is selected from the genus of *Amyloathelia*.
1234. The bioactive agent according to item 1231, wherein Basidiomycete cell is selected from the genus of *Amylocorticium*.
1235. The bioactive agent according to item 1231, wherein Basidiomycete cell is selected from the genus of *Athelia*.
1236. The bioactive agent according to item 1231, wherein Basidiomycete cell is selected from the genus of *Athelicium*.
1237. The bioactive agent according to item 1231, wherein Basidiomycete cell is selected from the genus of *Athelidium*.
1238. The bioactive agent according to item 1231, wherein Basidiomycete cell is selected from the genus of *Athelopsis*.
1239. The bioactive agent according to item 1231, wherein Basidiomycete cell is selected from the genus of *Butlerelfia*.
1240. The bioactive agent according to item 1231, wherein Basidiomycete cell is selected from the genus of *Byssocorticium*.
1241. The bioactive agent according to item 1231, wherein Basidiomycete cell is selected from the genus of *Byssocristella*.
1242. The bioactive agent according to item 1231, wherein Basidiomycete cell is selected from the genus of *Byssoporia*.
1243. The bioactive agent according to item 1231, wherein Basidiomycete cell is selected from the genus of *Caerulicium*.
1244. The bioactive agent according to item 1231, wherein Basidiomycete cell is selected from the genus of *Cora*.
1245. The bioactive agent according to item 1231, wherein Basidiomycete cell is selected from the genus of *Coraemyces*.
1246. The bioactive agent according to item 1231, wherein Basidiomycete cell is selected from the genus of *Corella*.
1247. The bioactive agent according to item 1231, wherein Basidiomycete cell is selected from the genus of *Cristinia*.
1248. The bioactive agent according to item 1231, wherein Basidiomycete cell is selected from the genus of *Dacryobasidium*.
1249. The bioactive agent according to item 1231, wherein Basidiomycete cell is selected from the genus of *Dichonema*.
1250. The bioactive agent according to item 1231, wherein Basidiomycete cell is selected from the genus of *Dictyonema*.
1251. The bioactive agent according to item 1231, wherein Basidiomycete cell is selected from the genus of *Dictyonematomyces*.
1252. The bioactive agent according to item 1231, wherein Basidiomycete cell is selected from the genus of *Digitatispora*.
1253. The bioactive agent according to item 1231, wherein Basidiomycete cell is selected from the genus of *Diplonema*.
1254. The bioactive agent according to item 1231, wherein Basidiomycete cell is selected from the genus of *Fibulomyces*.
1255. The bioactive agent according to item 1231, wherein Basidiomycete cell is selected from the genus of *Fibulorhizoctonia*.
1256. The bioactive agent according to item 1231, wherein Basidiomycete cell is selected from the genus of *Gyrolophium*.
1257. The bioactive agent according to item 1231, wherein Basidiomycete cell is selected from the genus of *Hypochnella*.
1258. The bioactive agent according to item 1231, wherein Basidiomycete cell is selected from the genus of *Hypochniciellum*.
1259. The bioactive agent according to item 1231, wherein Basidiomycete cell is selected from the genus of *Irpicodon*.
1260. The bioactive agent according to item 1231, wherein Basidiomycete cell is selected from the genus of *Laudatea*.

1261. The bioactive agent according to item 1231, wherein Basidiomycete cell is selected from the genus of *Amphinema, Amyloathelia, Amylocorticium, Athelia, Leptosporomyces.*

1262. The bioactive agent according to item 1231, wherein Basidiomycete cell is selected from the genus of *Lobulicium.*

1263. The bioactive agent according to item 1231, wherein Basidiomycete cell is selected from the genus of *Luellia.*

1264. The bioactive agent according to item 1231, wherein Basidiomycete cell is selected from the genus of *Meizericium.*

1265. The bioactive agent according to item 1231, wherein Basidiomycete cell is selected from the genus of *Mycostigma.*

1266. The bioactive agent according to item 1231, wherein Basidiomycete cell is selected from the genus of *Piloderma.*

1267. The bioactive agent according to item 1231, wherein Basidiomycete cell is selected from the genus of *Plicatura.*

1268. The bioactive agent according to item 1231, wherein Basidiomycete cell is selected from the genus of *Plicaturopsis.*

1269. The bioactive agent according to item 1231, wherein Basidiomycete cell is selected from the genus of *Rhipidonema.*

1270. The bioactive agent according to item 1231, wherein Basidiomycete cell is selected from the genus of *Rhipidonematomyces.*

1271. The bioactive agent according to item 1231, wherein Basidiomycete cell is selected from the genus of *Rhizonema.*

1272. The bioactive agent according to item 1231, wherein Basidiomycete cell is selected from the genus of *Taeniospora.*

1273. The bioactive agent according to item 1231, wherein Basidiomycete cell is selected from the genus of *Tomentellopsis.*

1274. The bioactive agent according to item 1231, wherein Basidiomycete cell is selected from the genus of *Tylosperma.*

1275. The bioactive agent according to item 1231, wherein Basidiomycete cell is selected from the genus of *Tylospora.*

1276. The bioactive agent according to item 1231, wherein Basidiomycete cell is selected from the genus of *Wainiocora.*

1277. The bioactive agent according to item 249, wherein said Basidiomycete cell belongs to a genus selected from the group consisting *Boreostereum, Chaetocarpus, Chaetodermella, Columnocystis, Grandinioides, Hirneola, Mycobonia, Mycothele* and *Veluticeps.*

1278. The bioactive agent according to item 1277, wherein Basidiomycete cell is selected from the genus of *Boreostereum.*

1279. The bioactive agent according to item 1277, wherein Basidiomycete cell is selected from the genus of *Chaetocarpus.*

1280. The bioactive agent according to item 1277, wherein Basidiomycete cell is selected from the genus of *Chaetodermella.*

1281. The bioactive agent according to item 1277, wherein Basidiomycete cell is selected from the genus of *Columnocystis.*

1282. The bioactive agent according to item 1277, wherein Basidiomycete cell is selected from the genus of *Grandinioides.*

1283. The bioactive agent according to item 1277, wherein Basidiomycete cell is selected from the genus of *Hirneola.*

1284. The bioactive agent according to item 1277, wherein Basidiomycete cell is selected from the genus of *Mycobonia.*

1285. The bioactive agent according to item 1277, wherein Basidiomycete cell is selected from the genus *Mycothele.*

1286. The bioactive agent according to item 1277, wherein Basidiomycete cell is selected from the genus of *Veluticeps.*

1287. The bioactive agent according to item 250, wherein said Basidiomycete cell belongs to a genus selected from the group consisting *Acantholichen, Aleurocorticium, Allosphaerium, Ambivina, Amylobasidium, Auricula, Bryochysium, Corticirama, Corticium, Cyanobasidium, Cytidia, Dendrocorticium, Dendrodontia, Dendrophysellum, Dendrothele, Dextrinodontia, Hemmesomyces, Laeticorticium, Laetisaria, Leptocorticium, Licrostroma, Limonomyces, Lindtneria, Lomatia, Lomatina, Lyomyces, Matula, Melzerodontia, Merulicium, Moniliopsis, Mutatoderma, Mycinema, Mycolindtneria, Necator, Nothocorticium, Papyrodiscus, Phaeophlebia, Pulcherricium, Punctularia, Rhizoctonia, Ripexicium, Thanatophytum* and *Vuilleminia.*

1288. The bioactive agent according to item 1287, wherein Basidiomycete cell is selected from the genus of *Acantholichen.*

1289. The bioactive agent according to item 1287, wherein Basidiomycete cell is selected from the genus of *Aleurocorticium.*

1290. The bioactive agent according to item 1287, wherein Basidiomycete cell is selected from the genus of *Allosphaerium.*

1291. The bioactive agent according to item 1287, wherein Basidiomycete cell is selected from the genus of *Ambivina.*

1292. The bioactive agent according to item 1287, wherein Basidiomycete cell is selected from the genus of *Amylobasidium.*

1293. The bioactive agent according to item 1287, wherein Basidiomycete cell is selected from the genus of *Auricula.*

1294. The bioactive agent according to item 1287, wherein Basidiomycete cell is selected from the genus of *Bryochysium.*

1295. The bioactive agent according to item 1287, wherein Basidiomycete cell is selected from the genus of *Corticirama.*

1296. The bioactive agent according to item 1287, wherein Basidiomycete cell is selected from the genus of *Corticium.*

1297. The bioactive agent according to item 1287, wherein Basidiomycete cell is selected from the genus of *Cyanobasidium.*

1298. The bioactive agent according to item 1287, wherein Basidiomycete cell is selected from the genus of *Cytidia.*

1299. The bioactive agent according to item 1287, wherein Basidiomycete cell is selected from the genus of *Dendrocorticium.*

1300. The bioactive agent according to item 1287, wherein Basidiomycete cell is selected from the genus of *Dendrodontia.*

1301. The bioactive agent according to item 1287, wherein Basidiomycete cell is selected from the genus of *Dendrophysellum.*

1302. The bioactive agent according to item 1287, wherein Basidiomycete cell is selected from the genus of *Dendrothele.*

1303. The bioactive agent according to item 1287, wherein Basidiomycete cell is selected from the genus of *Dextrinodontia*.
1304. The bioactive agent according to item 1287, wherein Basidiomycete cell is selected from the genus of *Hemmesomyces*.
1305. The bioactive agent according to item 1287, wherein Basidiomycete cell is selected from the genus of *Laeticorticium*.
1306. The bioactive agent according to item 1287, wherein Basidiomycete cell is selected from the genus of *Laetisaria*.
1307. The bioactive agent according to item 1287, wherein Basidiomycete cell is selected from the genus of *Leptocorticium*.
1308. The bioactive agent according to item 1287, wherein Basidiomycete cell is selected from the genus of *Licrostroma*.
1309. The bioactive agent according to item 1287, wherein Basidiomycete cell is selected from the genus of *Limonomyces*.
1310. The bioactive agent according to item 1287, wherein Basidiomycete cell is selected from the genus of *Lindtneria*.
1311. The bioactive agent according to item 1287, wherein Basidiomycete cell is selected from the genus of *Lomatia*.
1312. The bioactive agent according to item 1287, wherein Basidiomycete cell is selected from the genus of *Lomatina*.
1313. The bioactive agent according to item 1287, wherein Basidiomycete cell is selected from the genus of *Lyomyces*.
1314. The bioactive agent according to item 1287, wherein Basidiomycete cell is selected from the genus of *Matula*.
1315. The bioactive agent according to item 1287, wherein Basidiomycete cell is selected from the genus of *Meizerodontia*.
1316. The bioactive agent according to item 1287, wherein Basidiomycete cell is selected from the genus of *Merulicium*.
1317. The bioactive agent according to item 1287, wherein Basidiomycete cell is selected from the genus of *Moniliopsis*.
1318. The bioactive agent according to item 1287, wherein Basidiomycete cell is selected from the genus of *Mutatoderma*.
1319. The bioactive agent according to item 1287, wherein Basidiomycete cell is selected from the genus of *Mycinema*.
1320. The bioactive agent according to item 1287, wherein Basidiomycete cell is selected from the genus of *Mycolindtneria*.
1321. The bioactive agent according to item 1287, wherein Basidiomycete cell is selected from the genus of *Necator*.
1322. The bioactive agent according to item 1287, wherein Basidiomycete cell is selected from the genus of *Nothocorticium*.
1323. The bioactive agent according to item 1287, wherein Basidiomycete cell is selected from the genus of *Papyrodiscus*.
1324. The bioactive agent according to item 1287, wherein Basidiomycete cell is selected from the genus of *Phaeophlebia*.
1325. The bioactive agent according to item 1287, wherein Basidiomycete cell is selected from the genus of *Pulcherricium*.
1326. The bioactive agent according to item 1287, wherein Basidiomycete cell is selected from the genus of *Punctularia*.
1327. The bioactive agent according to item 1287, wherein Basidiomycete cell is selected from the genus of *Rhizoctonia*.
1328. The bioactive agent according to item 1287, wherein Basidiomycete cell is selected from the genus of *Ripexicium*.
1329. The bioactive agent according to item 1287, wherein Basidiomycete cell is selected from the genus of *Thanatophytum*.
1330. The bioactive agent according to item 1287, wherein Basidiomycete cell is selected from the genus of *Vuilleminia*.
1331. The bioactive agent according to item 251, wherein said Basidiomycete cell belongs to a genus selected from the group consisting of *Adustomyces, Asterocyphella, Catilla, Cyphella, Dendrocyphella, Flavophlebia, Globulicium, Gloeocorticium, Halocyphina, Hyphoradulum, Incrustocalyptella, Limnoperdon, Oxydontia, Phaeoporotheleum, Pseudolagarobasidium, Radulodon, Radulomyces, Rhodoarrhenia, Sarcodontia, Seticyphella, Sphaerobasidioscypha, Thujacorticium, Wiesnerina*, and *Woldmaria*.
1332. The bioactive agent according to item 1331, wherein Basidiomycete cell is selected from the genus of *Adustomyces*.
1333. The bioactive agent according to item 1331, wherein Basidiomycete cell is selected from the genus of *Asterocyphella*.
1334. The bioactive agent according to item 1331, wherein Basidiomycete cell is selected from the genus of *Catilla*.
1335. The bioactive agent according to item 1331, wherein Basidiomycete cell is selected from the genus of *Cyphella*.
1336. The bioactive agent according to item 1331, wherein Basidiomycete cell is selected from the genus of *Dendrocyphella*.
1337. The bioactive agent according to item 1331, wherein Basidiomycete cell is selected from the genus of *Flavophlebia*.
1338. The bioactive agent according to item 1331, wherein Basidiomycete cell is selected from the genus of *Globulicium*.
1339. The bioactive agent according to item 1331, wherein Basidiomycete cell is selected from the genus of *Gloeocorticium*.
1340. The bioactive agent according to item 1331, wherein Basidiomycete cell is selected from the genus of *Halocyphina*.
1341. The bioactive agent according to item 1331, wherein Basidiomycete cell is selected from the genus of *Hyphoradulum*.
1342. The bioactive agent according to item 1331, wherein Basidiomycete cell is selected from the genus of *Incrustocalyptella*.
1343. The bioactive agent according to item 1331, wherein Basidiomycete cell is selected from the genus of *Limnoperdon*.
1344. The bioactive agent according to item 1331, wherein Basidiomycete cell is selected from the genus of *Oxydontia*.
1345. The bioactive agent according to item 1331, wherein Basidiomycete cell is selected from the genus of *Phaeoporotheleum*.
1346. The bioactive agent according to item 1331, wherein Basidiomycete cell is selected from the genus of *Pseudolagarobasidium*.

1347. The bioactive agent according to item 1331, wherein Basidiomycete cell is selected from the genus of *Radulodon*.

1348. The bioactive agent according to item 1331, wherein Basidiomycete cell is selected from the genus of *Radulomyces*.

1349. The bioactive agent according to item 1331, wherein Basidiomycete cell is selected from the genus of *Rhodoarrhenia*.

1350. The bioactive agent according to item 1331, wherein Basidiomycete cell is selected from the genus of *Sarcodontia*.

1351. The bioactive agent according to item 1331, wherein Basidiomycete cell is selected from the genus of *Seticyphella*.

1352. The bioactive agent according to item 1331, wherein Basidiomycete cell is selected from the genus of *Sphaerobasidioscypha*.

1353. The bioactive agent according to item 1331, wherein Basidiomycete cell is selected from the genus of *Thujacorticium*.

1354. The bioactive agent according to item 1331, wherein Basidiomycete cell is selected from the genus of *Wiesnerina*.

1355. The bioactive agent according to item 1331, wherein Basidiomycete cell is selected from the genus of *Woldmaria*.

1356. The bioactive agent according to item 252, wherein said Basidiomycete cell belongs to a genus selected from the group consisting of *Cericium, Crustomyces, Cystidiodontia, Cystostereum, Dentocorticium, Parvobasidium, Physodontia* and *Pteridomyces*.

1357. The bioactive agent according to item 1356, wherein Basidiomycete cell is selected from the genus of *Cericium*.

1358. The bioactive agent according to item 1356, wherein Basidiomycete cell is selected from the genus of *Crustomyces*.

1359. The bioactive agent according to item 1356, wherein Basidiomycete cell is selected from the genus of *Cystidiodontia*.

1360. The bioactive agent according to item 1356, wherein Basidiomycete cell is selected from the genus of *Cystostereum*.

1361. The bioactive agent according to item 1356, wherein Basidiomycete cell is selected from the genus of *Dentocorticium*.

1362. The bioactive agent according to item 1356, wherein Basidiomycete cell is selected from the genus of *Parvobasidium*.

1363. The bioactive agent according to item 1356, wherein Basidiomycete cell is selected from the genus of *Physodontia*.

1364. The bioactive agent according to item 1356, wherein Basidiomycete cell is selected from the genus of *Pteridomyces*.

1365. The bioactive agent according to item 253, wherein said Basidiomycete cell belongs to a genus selected from the group consisting of *Epithele, Epithelopsis* and *Skeletohydnum*.

1366. The bioactive agent according to item 1365, wherein Basidiomycete cell is selected from the genus of *Epithele*.

1367. The bioactive agent according to item 1365, wherein Basidiomycete cell is selected from the genus of *Epithelopsis*.

1368. The bioactive agent according to item 1365, wherein Basidiomycete cell is selected from the genus of *Skeletohydnum*.

1369. The bioactive agent according to item 254, wherein said Basidiomycete cell belongs to a genus selected from the group consisting of *Agaricon, Agarico-pulpa, Agaricosuber, Agaricum, Agaricus, Amylocystis, Anomoporia, Auriporia, Buglossoporus, Daedalea, Donkioporia, Fomitopsis, Gilbertsonia, Hemidiscia, Laricifomes, Osteina, Parmastomyces, Phaeodaedalea, Pilatoporus, Piptoporus, Placoderma, Podoporia, Postia, Rhodofomes, Spelaeomyces, Spongiporus, Strangulidium, Striglia, Ungularia, Wolfiporia* and *Xylostroma*.

1370. The bioactive agent according to item 1369, wherein Basidiomycete cell is selected from the genus of *Agaricon*.

1371. The bioactive agent according to item 1369, wherein Basidiomycete cell is selected from the genus of *Agarico-pulpa*.

1372. The bioactive agent according to item 1369, wherein Basidiomycete cell is selected from the genus of *Agaricosuber*.

1373. The bioactive agent according to item 1369, wherein Basidiomycete cell is selected from the genus of *Agaricum*.

1374. The bioactive agent according to item 1369, wherein Basidiomycete cell is selected from the genus of *Agaricus*.

1375. The bioactive agent according to item 1369, wherein Basidiomycete cell is selected from the genus of *Amylocystis*.

1376. The bioactive agent according to item 1369, wherein Basidiomycete cell is selected from the genus of *Anomoporia*.

1377. The bioactive agent according to item 1369, wherein Basidiomycete cell is selected from the genus of *Auriporia*.

1378. The bioactive agent according to item 1369, wherein Basidiomycete cell is selected from the genus of *Buglossoporus*.

1379. The bioactive agent according to item 1369, wherein Basidiomycete cell is selected from the genus of *Daedalea*.

1380. The bioactive agent according to item 1369, wherein Basidiomycete cell is selected from the genus of *Donkioporia*.

1381. The bioactive agent according to item 1369, wherein Basidiomycete cell is selected from the genus of *Fomitopsis*.

1382. The bioactive agent according to item 1369, wherein Basidiomycete cell is selected from the genus of *Gilbertsonia*.

1383. The bioactive agent according to item 1369, wherein Basidiomycete cell is selected from the genus of *Hemidiscia*.

1384. The bioactive agent according to item 1369, wherein Basidiomycete cell is selected from the genus of *Laricifomes*.

1385. The bioactive agent according to item 1369, wherein Basidiomycete cell is selected from the genus of *Osteina*.

1386. The bioactive agent according to item 1369, wherein Basidiomycete cell is selected from the genus of *Parmastomyces*.

1387. The bioactive agent according to item 1369, wherein Basidiomycete cell is selected from the genus of *Phaeodaedalea*.

1388. The bioactive agent according to item 1369, wherein Basidiomycete cell is selected from the genus of *Pilatoporus*.

1389. The bioactive agent according to item 1369, wherein Basidiomycete cell is selected from the genus of *Piptoporus*.

1390. The bioactive agent according to item 1369, wherein Basidiomycete cell is selected from the genus of *Placoderma*.

1391. The bioactive agent according to item 1369, wherein Basidiomycete cell is selected from the genus of *Podoporia*.
1392. The bioactive agent according to item 1369, wherein Basidiomycete cell is selected from the genus of *Postia*.
1393. The bioactive agent according to item 1369, wherein Basidiomycete cell is selected from the genus of *Rhodofomes*.
1394. The bioactive agent according to item 1369, wherein Basidiomycete cell is selected from the genus of *Spelaeomyces*.
1395. The bioactive agent according to item 1369, wherein Basidiomycete cell is selected from the genus of *Spongiporus*.
1396. The bioactive agent according to item 1369, wherein Basidiomycete cell is selected from the genus of *Strangulidium*.
1397. The bioactive agent according to item 1369, wherein Basidiomycete cell is selected from the genus of *Striglia*.
1398. The bioactive agent according to item 1369, wherein Basidiomycete cell is selected from the genus of *Ungularia*.
1399. The bioactive agent according to item 1369, wherein Basidiomycete cell is selected from the genus of *Wolfiporia*.
1400. The bioactive agent according to item 1369, wherein Basidiomycete cell is selected from the genus of *Xylostroma*.
1401. The bioactive agent according to item 255, wherein said Basidiomycete cell belongs to a genus selected from the group consisting of *Amauroderma, Dendrophagus, Elfvingia, Friesia, Ganoderma, Haddowia, Humphreya, Lazulinospora, Magoderna, Thermophymatospora, Tomophagus, Trachyderma* and *Whitfordia*.
1402. The bioactive agent according to item 1401, wherein Basidiomycete cell is selected from the genus of *Amauroderma*.
1403. The bioactive agent according to item 1401, wherein Basidiomycete cell is selected from the genus of *Dendrophagus*.
1404. The bioactive agent according to item 1401, wherein Basidiomycete cell is selected from the genus of *Elfvingia*.
1405. The bioactive agent according to item 1401, wherein Basidiomycete cell is selected from the genus of *Friesia*.
1406. The bioactive agent according to item 1401, wherein Basidiomycete cell is selected from the genus of *Ganoderma*.
1407. The bioactive agent according to item 1401, wherein Basidiomycete cell is selected from the genus of *Haddowia*.
1408. The bioactive agent according to item 1401, wherein Basidiomycete cell is selected from the genus of *Humphreya*.
1409. The bioactive agent according to item 1401, wherein Basidiomycete cell is selected from the genus of *Lazulinospora*.
1410. The bioactive agent according to item 1401, wherein Basidiomycete cell is selected from the genus of *Magoderna*.
1411. The bioactive agent according to item 1401, wherein Basidiomycete cell is selected from the genus of *Thermophymatospora*.
1412. The bioactive agent according to item 1401, wherein Basidiomycete cell is selected from the genus of *Tomophagus*.
1413. The bioactive agent according to item 1401, wherein Basidiomycete cell is selected from the genus of *Trachyderma*.
1414. The bioactive agent according to item 1401, wherein Basidiomycete cell is selected from the genus of *Whitfordia*.
1415. The bioactive agent according to item 256, wherein said Basidiomycete cell belongs to a genus selected from the group consisting of *Anisomyces, Ceratophora, Gloeophyllum, Griseoporia, Lenzitina, Phaeocoriolellus, Reisneria, Serda* and *Sesia*.
1416. The bioactive agent according to item 1415, wherein Basidiomycete cell is selected from the genus of *Anisomyces*.
1417. The bioactive agent according to item 1415, wherein Basidiomycete cell is selected from the genus of *Ceratophora*.
1418. The bioactive agent according to item 1415, wherein Basidiomycete cell is selected from the genus of *Gloeophyllum*.
1419. The bioactive agent according to item 1415, wherein Basidiomycete cell is selected from the genus of *Griseoporia*.
1420. The bioactive agent according to item 1415, wherein Basidiomycete cell is selected from the genus of *Lenzitina*.
1421. The bioactive agent according to item 1415, wherein Basidiomycete cell is selected from the genus of *Phaeocoriolellus*.
1422. The bioactive agent according to item 1415, wherein Basidiomycete cell is selected from the genus of *Reisneria*.
1423. The bioactive agent according to item 1415, wherein Basidiomycete cell is selected from the genus of *Serda*.
1424. The bioactive agent according to item 1415, wherein Basidiomycete cell is selected from the genus of *Sesia*.
1425. The bioactive agent according to item 257, wherein said Basidiomycete cell belongs to a genus selected from the group consisting of *Grammothele, Hymenogramme, Porogramme, Theleporus* and *Tinctoporia*.
1426. The bioactive agent according to item 1425, wherein Basidiomycete cell is selected from the genus of *Grammothele*.
1427. The bioactive agent according to item 1425, wherein Basidiomycete cell is selected from the genus of *Hymenogramme*.
1428. The bioactive agent according to item 1425, wherein Basidiomycete cell is selected from the genus of *Porogramme*.
1429. The bioactive agent according to item 1425, wherein Basidiomycete cell is selected from the genus of *Theleporus*.
1430. The bioactive agent according to item 1425, wherein Basidiomycete cell is selected from the genus of *Tinctoporia*.
1431. The bioactive agent according to item 258, wherein said Basidiomycete cell belongs to a genus selected from the group consisting of *Aurantiporus, Bjerkandera, Ceraporus, Ceriporia, Ceriporiopsis, Climacocystis, Gelatoporia, Hapalopilus, Irpiciporus, Ischnoderma, Leptoporus, Myriadoporus, Porpomyces, Pouzaroporia, Sarcoporia, Somion* and *Spongipellis*.
1432. The bioactive agent according to item 1431, wherein Basidiomycete cell is selected from the genus of *Aurantiporus*.
1433. The bioactive agent according to item 1431, wherein Basidiomycete cell is selected from the genus of *Bjerkandera*.

1434. The bioactive agent according to item 1431, wherein Basidiomycete cell is selected from the genus of *Ceraporus*.
1435. The bioactive agent according to item 1431, wherein Basidiomycete cell is selected from the genus of *Ceriporia*.
1436. The bioactive agent according to item 1431, wherein Basidiomycete cell is selected from the genus *Ceriporiopsis*.
1437. The bioactive agent according to item 1431, wherein Basidiomycete cell is selected from the genus of *Climacocystis*.
1438. The bioactive agent according to item 1431, wherein Basidiomycete cell is selected from the genus of *Gelatoporia*.
1439. The bioactive agent according to item 1431, wherein Basidiomycete cell is selected from the genus of *Hapalopilus*.
1440. The bioactive agent according to item 1431, wherein Basidiomycete cell is selected from the genus of *Irpiciporus*.
1441. The bioactive agent according to item 1431, wherein Basidiomycete cell is selected from the genus of *Ischnoderma*.
1442. The bioactive agent according to item 1431, wherein Basidiomycete cell is selected from the genus of *Leptoporus*.
1443. The bioactive agent according to item 1431, wherein Basidiomycete cell is selected from the genus of *Myriadoporus*.
1444. The bioactive agent according to item 1431, wherein Basidiomycete cell is selected from the genus of *Porpomyces*.
1445. The bioactive agent according to item 1431, wherein Basidiomycete cell is selected from the genus of *Pouzaroporia*.
1446. The bioactive agent according to item 1431, wherein Basidiomycete cell is selected from the genus of *Sarcoporia*.
1447. The bioactive agent according to item 1431, wherein Basidiomycete cell is selected from the genus of *Somion*.
1448. The bioactive agent according to item 1431, wherein Basidiomycete cell is selected from the genus of *Spongipellis*.
1449. The bioactive agent according to item 259, wherein said Basidiomycete cell belongs to a genus selected from the group consisting of *Aegerita, Aegeritina, Aegeritopsis, Amaurohydnum, Amauromyces, Atheloderma, Brevicellicium, Bulbillomyces, Cerocorticium, Chrysoderma, Conohypha, Coronicium, Crocysporium, Cyanodontia, Dermosporium, Elaphocephala, Galzinia, Gloeohypochnicium, Hydnellum, Hyphoderma, Hyphodontiastra, Hyphodontiella, Hypochnicium, Intextomyces, Kneiffia, Kneiffiella, Lyomyces, Metulodontia, Neokneiffia, Nodotia, Odontiopsis, Pirex, Pycnodon, Subulicium, Subulicystidium, Uncobasidium* and *Xylodon*.
1450. The bioactive agent according to item 1449, wherein Basidiomycete cell is selected from the genus of *Aegerita*.
1451. The bioactive agent according to item 1449, wherein Basidiomycete cell is selected from the genus of *Aegeritina*.
1452. The bioactive agent according to item 1449, wherein Basidiomycete cell is selected from the genus of *Aegeritopsis*.
1453. The bioactive agent according to item 1449, wherein Basidiomycete cell is selected from the genus of *Amaurohydnum*.
1454. The bioactive agent according to item 1449, wherein Basidiomycete cell is selected from the genus of *Amauromyces*.
1455. The bioactive agent according to item 1449, wherein Basidiomycete cell is selected from the genus of *Atheloderma*.
1456. The bioactive agent according to item 1449, wherein Basidiomycete cell is selected from the genus of *Brevicellicium*.
1457. The bioactive agent according to item 1449, wherein Basidiomycete cell is selected from the genus of *Bulbillomyces*.
1458. The bioactive agent according to item 1449, wherein Basidiomycete cell is selected from the genus of *Cerocorticium*.
1459. The bioactive agent according to item 1449, wherein Basidiomycete cell is selected from the genus of *Chrysoderma*.
1460. The bioactive agent according to item 1449, wherein Basidiomycete cell is selected from the genus of *Conohypha*.
1461. The bioactive agent according to item 1449, wherein Basidiomycete cell is selected from the genus of *Coronicium*.
1462. The bioactive agent according to item 1449, wherein Basidiomycete cell is selected from the genus of *Crocysporium*.
1463. The bioactive agent according to item 1449, wherein Basidiomycete cell is selected from the genus of *Cyanodontia*.
1464. The bioactive agent according to item 1449, wherein Basidiomycete cell is selected from the genus of *Dermosporium*.
1465. The bioactive agent according to item 1449, wherein Basidiomycete cell is selected from the genus of *Elaphocephala*.
1466. The bioactive agent according to item 1449, wherein Basidiomycete cell is selected from the genus of *Galzinia*.
1467. The bioactive agent according to item 1449, wherein Basidiomycete cell is selected from the genus of *Gloeohypochnicium*.
1468. The bioactive agent according to item 1449, wherein Basidiomycete cell is selected from the genus of *Hydnellum*.
1469. The bioactive agent according to item 1449, wherein Basidiomycete cell is selected from the genus of *Hyphoderma*.
1470. The bioactive agent according to item 1449, wherein Basidiomycete cell is selected from the genus of *Hyphodontiastra*.
1471. The bioactive agent according to item 1449, wherein Basidiomycete cell is selected from the genus of *Hyphodontiella*.
1472. The bioactive agent according to item 1449, wherein Basidiomycete cell is selected from the genus of *Hypochnicium*.
1473. The bioactive agent according to item 1449, wherein Basidiomycete cell is selected from the genus of *Intextomyces*.
1474. The bioactive agent according to item 1449, wherein Basidiomycete cell is selected from the genus of *Kneiffia*.
1475. The bioactive agent according to item 1449, wherein Basidiomycete cell is selected from the genus of *Kneiffiella*.
1476. The bioactive agent according to item 1449, wherein Basidiomycete cell is selected from the genus of *Lyomyces*.

1477. The bioactive agent according to item 1449, wherein Basidiomycete cell is selected from the genus of *Metulodontia*.
1478. The bioactive agent according to item 1449, wherein Basidiomycete cell is selected from the genus of *Neokneiffia*.
1479. The bioactive agent according to item 1449, wherein Basidiomycete cell is selected from the genus of *Nodotia*.
1480. The bioactive agent according to item 1449, wherein Basidiomycete cell is selected from the genus of *Odontiopsis*.
1481. The bioactive agent according to item 1449, wherein Basidiomycete cell is selected from the genus of *Pirex*.
1482. The bioactive agent according to item 1449, wherein Basidiomycete cell is selected from the genus of *Pycnodon*.
1483. The bioactive agent according to item 1449, wherein Basidiomycete cell is selected from the genus of *Subulicium*.
1484. The bioactive agent according to item 1449, wherein Basidiomycete cell is selected from the genus of *Subulicystidium*.
1485. The bioactive agent according to item 1449, wherein Basidiomycete cell is selected from the genus of *Uncobasidium*.
1486. The bioactive agent according to item 1449, wherein Basidiomycete cell is selected from the genus of *Xylodon*.
1487. The bioactive agent according to item 260, wherein said Basidiomycete cell belongs to a genus selected from the group consisting of *Abortiporus, Antrodia, Bornetina, Cartilosoma, Cautinia, Cladodendron, Cladomeris, Coriolellus, Diacanthodes, Flabellopilus, Grifola, Henningsia, Heteroporus, Hydnopolyporus, Irpicium, Leucofomes, Loweomyces, Meripilus, Merisma, Physisporinus, Polypilus* and *Rigidoporus*.
1488. The bioactive agent according to item 1487, wherein Basidiomycete cell is selected from the genus of *Abortiporus*.
1489. The bioactive agent according to item 1487, wherein Basidiomycete cell is selected from the genus of *Antrodia*.
1490. The bioactive agent according to item 1487, wherein Basidiomycete cell is selected from the genus of *Bornetina*.
1491. The bioactive agent according to item 1487, wherein Basidiomycete cell is selected from the genus of *Cartilosoma*.
1492. The bioactive agent according to item 1487, wherein Basidiomycete cell is selected from the genus of *Cautinia*.
1493. The bioactive agent according to item 1487, wherein Basidiomycete cell is selected from the genus of *Cladodendron*.
1494. The bioactive agent according to item 1487, wherein Basidiomycete cell is selected from the genus of *Cladomeris*.
1495. The bioactive agent according to item 1487, wherein Basidiomycete cell is selected from the genus of *Coriolellus*.
1496. The bioactive agent according to item 1487, wherein Basidiomycete cell is selected from the genus of *Diacanthodes*.
1497. The bioactive agent according to item 1487, wherein Basidiomycete cell is selected from the genus of *Flabellopilus*.
1498. The bioactive agent according to item 1487, wherein Basidiomycete cell is selected from the genus of *Grifola*.
1499. The bioactive agent according to item 1487, wherein Basidiomycete cell is selected from the genus of *Henningsia*.
1500. The bioactive agent according to item 1487, wherein Basidiomycete cell is selected from the genus of *Heteroporus*.
1501. The bioactive agent according to item 1487, wherein Basidiomycete cell is selected from the genus of *Hydnopolyporus*.
1502. The bioactive agent according to item 1487, wherein Basidiomycete cell is selected from the genus of *Irpicium*.
1503. The bioactive agent according to item 1487, wherein Basidiomycete cell is selected from the genus of *Leucofomes*.
1504. The bioactive agent according to item 1487, wherein Basidiomycete cell is selected from the genus of *Loweomyces*.
1505. The bioactive agent according to item 1487, wherein Basidiomycete cell is selected from the genus of *Meripilus*.
1506. The bioactive agent according to item 1487, wherein Basidiomycete cell is selected from the genus of *Merisma*.
1507. The bioactive agent according to item 1487, wherein Basidiomycete cell is selected from the genus of *Physisporinus*.
1508. The bioactive agent according to item 1487, wherein Basidiomycete cell is selected from the genus of *Polypilus*.
1509. The bioactive agent according to item 1487, wherein Basidiomycete cell is selected from the genus of *Rigidoporus*.
1510. The bioactive agent according to item 261, wherein said Basidiomycete cell belongs to a genus selected from the group consisting of *Acia, Byssomerulius, Caloporia, Caloporus, Castanoporus, Ceraceohydnum, Ceraceomerulius, Chondrostereum, Climacodon, Columnodontia, Crustoderma, Cylindrobasidium, Dacryobolus, Donkia, Gloeocystidium, Gloeoporus, Gloeostereum, Himantia, Jacksonomyces, Meruliopsis, Merulius, Mycoacia, Mycoaciella, Phlebia, Resinicium, Ricnophora, Scopuloides, Skvortzovia* and *Trabecularia*.
1511. The bioactive agent according to item 1510, wherein Basidiomycete cell is selected from the genus of *Acia*.
1512. The bioactive agent according to item 1510, wherein Basidiomycete cell is selected from the genus of *Byssomerulius*.
1513. The bioactive agent according to item 1510, wherein Basidiomycete cell is selected from the genus of *Caloporia*.
1514. The bioactive agent according to item 1510, wherein Basidiomycete cell is selected from the genus of *Caloporus*.
1515. The bioactive agent according to item 1510, wherein Basidiomycete cell is selected from the genus of *Castanoporus*.
1516. The bioactive agent according to item 1510, wherein Basidiomycete cell is selected from the genus of *Ceraceohydnum*.
1517. The bioactive agent according to item 1510, wherein Basidiomycete cell is selected from the genus of *Ceraceomerulius*.
1518. The bioactive agent according to item 1510, wherein Basidiomycete cell is selected from the genus of *Chondrostereum*.
1519. The bioactive agent according to item 1510, wherein Basidiomycete cell is selected from the genus of *Climacodon*.

1520. The bioactive agent according to item 1510, wherein Basidiomycete cell is selected from the genus of *Columnodontia*.
1521. The bioactive agent according to item 1510, wherein Basidiomycete cell is selected from the genus of *Crustoderma*.
1522. The bioactive agent according to item 1510, wherein Basidiomycete cell is selected from the genus of *Cylindrobasidium*.
1523. The bioactive agent according to item 1510, wherein Basidiomycete cell is selected from the genus of *Dacryobolus*.
1524. The bioactive agent according to item 1510, wherein Basidiomycete cell is selected from the genus of *Donkia*.
1525. The bioactive agent according to item 1510, wherein Basidiomycete cell is selected from the genus of *Gloeocystidium*.
1526. The bioactive agent according to item 1510, wherein Basidiomycete cell is selected from the genus of *Gloeoporus*.
1527. The bioactive agent according to item 1510, wherein Basidiomycete cell is selected from the genus of *Gloeostereum*.
1528. The bioactive agent according to item 1510, wherein Basidiomycete cell is selected from the genus of *Himantia*.
1529. The bioactive agent according to item 1510, wherein Basidiomycete cell is selected from the genus of *Jacksonomyces*.
1530. The bioactive agent according to item 1510, wherein Basidiomycete cell is selected from the genus of *Meruliopsis*.
1531. The bioactive agent according to item 1510, wherein Basidiomycete cell is selected from the genus of *Merulius*.
1532. The bioactive agent according to item 1510, wherein Basidiomycete cell is selected from the genus of *Mycoacia*.
1533. The bioactive agent according to item 1510, wherein Basidiomycete cell is selected from the genus of *Mycoaciella*.
1534. The bioactive agent according to item 1510, wherein Basidiomycete cell is selected from the genus of *Phlebia*.
1535. The bioactive agent according to item 1510, wherein Basidiomycete cell is selected from the genus of *Resinicium*.
1536. The bioactive agent according to item 1510, wherein Basidiomycete cell is selected from the genus of *Ricnophora*.
1537. The bioactive agent according to item 1510, wherein Basidiomycete cell is selected from the genus of *Scopuloides*.
1538. The bioactive agent according to item 1510, wherein Basidiomycete cell is selected from the genus of *Skvortzovia*.
1539. The bioactive agent according to item 1510, wherein Basidiomycete cell is selected from the genus of *Trabecularia*.
1540. The bioactive agent according to item 262, wherein said Basidiomycete cell belongs to a genus selected from the group consisting of *Australicium, Botryodontia, Candelabrochaete, Ceraceomyces, Corticium, Efibula, Erythricium, Grandiniella, Gyrophanopsis, Hjortstamia, Hydnophlebia, Hyphodermella, Hyphodermopsis, Licentia, Lloydella, Lopharia, Membranicium, Odonticium, Phanerochaete, Phlebiopsis, Porostereum, Terana, Thwaitesiella* and *Xerocarpus*.
1541. The bioactive agent according to item 1540, wherein Basidiomycete cell is selected from the genus of *Australicium*.
1542. The bioactive agent according to item 1540, wherein Basidiomycete cell is selected from the genus of *Botryodontia*.
1543. The bioactive agent according to item 1540, wherein Basidiomycete cell is selected from the genus of *Candelabrochaete*.
1544. The bioactive agent according to item 1540, wherein Basidiomycete cell is selected from the genus of *Ceraceomyces*.
1545. The bioactive agent according to item 1540, wherein Basidiomycete cell is selected from the genus of *Corticium*.
1546. The bioactive agent according to item 1540, wherein Basidiomycete cell is selected from the genus of *Efibula*.
1547. The bioactive agent according to item 1540, wherein Basidiomycete cell is selected from the genus of *Erythricium*.
1548. The bioactive agent according to item 1540, wherein Basidiomycete cell is selected from the genus of *Grandiniella*.
1549. The bioactive agent according to item 1540, wherein Basidiomycete cell is selected from the genus of *Gyrophanopsis*.
1550. The bioactive agent according to item 1540, wherein Basidiomycete cell is selected from the genus of *Hjortstamia*.
1551. The bioactive agent according to item 1540, wherein Basidiomycete cell is selected from the genus of *Hydnophlebia*.
1552. The bioactive agent according to item 1540, wherein Basidiomycete cell is selected from the genus of *Hyphodermella*.
1553. The bioactive agent according to item 1540, wherein Basidiomycete cell is selected from the genus of *Hyphodermopsis*.
1554. The bioactive agent according to item 1540, wherein Basidiomycete cell is selected from the genus of *Licentia*.
1555. The bioactive agent according to item 1540, wherein Basidiomycete cell is selected from the genus of *Lloydella*.
1556. The bioactive agent according to item 1540, wherein Basidiomycete cell is selected from the genus of *Lopharia*.
1557. The bioactive agent according to item 1540, wherein Basidiomycete cell is selected from the genus of *Membranicium*.
1558. The bioactive agent according to item 1540, wherein Basidiomycete cell is selected from the genus of *Odonticium*.
1559. The bioactive agent according to item 1540, wherein Basidiomycete cell is selected from the genus of *Phanerochaete*.
1560. The bioactive agent according to item 1540, wherein Basidiomycete cell is selected from the genus of *Phlebiopsis*.
1561. The bioactive agent according to item 1540, wherein Basidiomycete cell is selected from the genus of *Porostereum*.
1562. The bioactive agent according to item 1540, wherein Basidiomycete cell is selected from the genus of *Terana*.
1563. The bioactive agent according to item 1540, wherein Basidiomycete cell is selected from the genus of *Thwaitesiella*.
1564. The bioactive agent according to item 1540, wherein Basidiomycete cell is selected from the genus of *Xerocarpus*.
1565. The bioactive agent according to item 263, wherein said Basidiomycete cell belongs to a genus selected from the group consisting of *Actinostroma, Aquascypha, Bec-* caria, Beccariella, Bresadolina, Caripia, Cladoderris, Coralloderma, Cotylidia, Craterella, Cymatoderma, Cyphellostereum, Granulobasidium, Inflatostereum, Podoscypha, Pseudolasiobolus, Stereogloeocystidium, Stereophyllum and Stereopsis.

1566. The bioactive agent according to item 1565, wherein Basidiomycete cell is selected from the genus of *Actinostroma*.
1567. The bioactive agent according to item 1565, wherein Basidiomycete cell is selected from the genus of *Aquascypha*.
1568. The bioactive agent according to item 1565, wherein Basidiomycete cell is selected from the genus of *Beccaria*.
1569. The bioactive agent according to item 1565, wherein Basidiomycete cell is selected from the genus of *Beccariella*.
1570. The bioactive agent according to item 1565, wherein Basidiomycete cell is selected from the genus of *Bresadolina*.
1571. The bioactive agent according to item 1565, wherein Basidiomycete cell is selected from the genus of *Caripia*.
1572. The bioactive agent according to item 1565, wherein Basidiomycete cell is selected from the genus of *Cladoderris*.
1573. The bioactive agent according to item 1565, wherein Basidiomycete cell is selected from the genus of *Coralloderma*.
1574. The bioactive agent according to item 1565, wherein Basidiomycete cell is selected from the genus of *Cotylidia*.
1575. The bioactive agent according to item 1565, wherein Basidiomycete cell is selected from the genus of *Craterella*.
1576. The bioactive agent according to item 1565, wherein Basidiomycete cell is selected from the genus of *Cymatoderma*.
1577. The bioactive agent according to item 1565, wherein Basidiomycete cell is selected from the genus of *Cyphellostereum*.
1578. The bioactive agent according to item 1565, wherein Basidiomycete cell is selected from the genus of *Granulobasidium*.
1579. The bioactive agent according to item 1565, wherein Basidiomycete cell is selected from the genus of *Inflatostereum*.
1580. The bioactive agent according to item 1565, wherein Basidiomycete cell is selected from the genus *Podoscypha*.
1581. The bioactive agent according to item 1565, wherein Basidiomycete cell is selected from the genus of *Pseudolasiobolus*.
1582. The bioactive agent according to item 1565, wherein Basidiomycete cell is selected from the genus of *Stereogloeocystidium*.
1583. The bioactive agent according to item 1565, wherein Basidiomycete cell is selected from the genus of *Stereophyllum*.
1584. The bioactive agent according to item 1565, wherein Basidiomycete cell is selected from the genus of *Stereopsis*.
1585. The bioactive agent according to item 264, wherein said Basidiomycete cell belongs to a genus selected from the group consisting of *Abundisporus, Agarico-igniarium, Agaricum, Amyloporia, Amyloporiella, Antromycopsis, Apoxona, Artolenzites, Asterochaete, Atroporus, Aurantiporellus, Australoporus, Austrolentinus, Bresadolia, Bridgeoporus, Bulliardia, Burgoa, Caloporus, Cellularia, Ceriomyces, Cerioporus, Cerrena, Choriphyllum, Cladoporus, Coriolopsis, Coriolus, Cryptomphalina, Cryptoporus, Cubamyces, Cyanosporus, Cystidiophorus, Cystostiptoporus, Daedaleopsis, Datronia, Dendrochaete, Dendropolyporus, Dextrinosporium, Dichomitus, Digitellus, Earliella, Echinochaete, Elfvingiella, Enslinia, Fabisporus, Faerberia, Favolus, Fibroporia, Flabellophora, Fomes, Fomitella, Funalia, Fuscocerrena, Gemmularia, Geopetalum, Globifomes, Grammothelopsis, Hansenia, Haploporus, Heliocybe, Hexagonia, Hirschioporus, Hornodermoporus, Incrustoporia, Laccocephalum, Laetifomes, Laetiporus, Lasiochlaena, Lentinopanus, Lentinus, Lentodiellum, Lentodium, Lentus, Lenzites, Leptopora, Leptoporellus, Leptotrimitus, Leucolenzites, Leucoporus, Lignosus, Lithopolyporales, Loweporus, Macrohyporia, Macroporia, Megasporoporia, Melanoporella, Melanoporia, Melanopus, Merulioporia, Microporellus, Microporus, Mollicarpus, Mycelithe, Navisporus, Neolentinus, Neolentiporus, Nigrofomes, Nigroporus, Oligoporus, Osmoporus, Pachykytospora, Pachyma, Panus, Paramyces, Perenniporia, Perenniporiella, Persooniana, Petaloides, Phaeolus, Phaeotrametes, Pherima, Phorima, Phyllodontia, Physisporus, Piloporia, Placodes, Pleuropus, Pocillaria, Podofomes, Pogonomyces, Polyporellus, Polyporus, Polyporus, Polyporus, Poria, Porodisculus, Porodiscus, Poronidulus, Poroptyche, Pseudofavolus, Pseudophaeolus, Pseudopiptoporus, Pseudotrametes, Ptychogaster, Pycnoporellus, Pycnoporus, Pyrofomes, Riopa, Romellia, Royoporus, Rubroporus, Ryvardenia, Scenidium, Sclerodepsis, Sistotrema, Skeletocutis, Sparsitubus, Spongiosus, Stiptophyllum, Tinctoporellus, Tomentoporus, Trametella, Trametes, Trichaptum, Truncospora, Tuberaster, Tyromyces, Ungulina, Vanderbylia, Velolentinus, Xerotinus, Xerotus, Xylometron* and *Xylopilus*.

1586. The bioactive agent according to item 1585, wherein Basidiomycete cell is selected from the genus of *Abundisporus*.
1587. The bioactive agent according to item 1585, wherein Basidiomycete cell is selected from the genus of *Agarico-igniarium*.
1588. The bioactive agent according to item 1585, wherein Basidiomycete cell is selected from the genus of *Agaricum*.
1589. The bioactive agent according to item 1585, wherein Basidiomycete cell is selected from the genus of *Amyloporia*.
1590. The bioactive agent according to item 1585, wherein Basidiomycete cell is selected from the genus of *Amyloporiella*.
1591. The bioactive agent according to item 1585, wherein Basidiomycete cell is selected from the genus of *Antromycopsis*.
1592. The bioactive agent according to item 1585, wherein Basidiomycete cell is selected from the genus of *Apoxona*.
1593. The bioactive agent according to item 1585, wherein Basidiomycete cell is selected from the genus of *Artolenzites*.
1594. The bioactive agent according to item 1585, wherein Basidiomycete cell is selected from the genus of *Asterochaete*.
1595. The bioactive agent according to item 1585, wherein Basidiomycete cell is selected from the genus of *Atroporus*.
1596. The bioactive agent according to item 1585, wherein Basidiomycete cell is selected from the genus of *Aurantiporellus*.
1597. The bioactive agent according to item 1585, wherein Basidiomycete cell is selected from the genus of *Australoporus*.

1598. The bioactive agent according to item 1585, wherein Basidiomycete cell is selected from the genus of *Austrolentinus*.
1599. The bioactive agent according to item 1585, wherein Basidiomycete cell is selected from the genus of *Bresadolia*.
1600. The bioactive agent according to item 1585, wherein Basidiomycete cell is selected from the genus of *Bridgeoporus*.
1601. The bioactive agent according to item 1585, wherein Basidiomycete cell is selected from the genus of *Bulliardia*.
1602. The bioactive agent according to item 1585, wherein Basidiomycete cell is selected from the genus of *Burgoa*.
1603. The bioactive agent according to item 1585, wherein Basidiomycete cell is selected from the genus of *Caloporus*.
1604. The bioactive agent according to item 1585, wherein Basidiomycete cell is selected from the genus of *Cellularia*.
1605. The bioactive agent according to item 1585, wherein Basidiomycete cell is selected from the genus of *Ceriomyces*.
1606. The bioactive agent according to item 1585, wherein Basidiomycete cell is selected from the genus of *Cerioporus*.
1607. The bioactive agent according to item 1585, wherein Basidiomycete cell is selected from the genus of *Cerrena*.
1608. The bioactive agent according to item 1585, wherein Basidiomycete cell is selected from the genus of *Choriphyllum*.
1609. The bioactive agent according to item 1585, wherein Basidiomycete cell is selected from the genus of *Cladoporus*.
1610. The bioactive agent according to item 1585, wherein Basidiomycete cell is selected from the genus of *Coriolopsis*.
1611. The bioactive agent according to item 1585, wherein Basidiomycete cell is selected from the genus of *Coriolus*.
1612. The bioactive agent according to item 1585, wherein Basidiomycete cell is selected from the genus of *Cryptomphalina*.
1613. The bioactive agent according to item 1585, wherein Basidiomycete cell is selected from the genus of *Cryptoporus*.
1614. The bioactive agent according to item 1585, wherein Basidiomycete cell is selected from the genus of *Cubamyces*.
1615. The bioactive agent according to item 1585, wherein Basidiomycete cell is selected from the genus of *Cyanosporus*.
1616. The bioactive agent according to item 1585, wherein Basidiomycete cell is selected from the genus of *Cystidiophorus*.
1617. The bioactive agent according to item 1585, wherein Basidiomycete cell is selected from the genus of *Cystostiptoporus*.
1618. The bioactive agent according to item 1585, wherein Basidiomycete cell is selected from the genus of *Daedaleopsis*.
1619. The bioactive agent according to item 1585, wherein Basidiomycete cell is selected from the genus of *Datronia*.
1620. The bioactive agent according to item 1585, wherein Basidiomycete cell is selected from the genus of *Dendrochaete*.
1621. The bioactive agent according to item 1585, wherein Basidiomycete cell is selected from the genus of *Dendropolyporus*.
1622. The bioactive agent according to item 1585, wherein Basidiomycete cell is selected from the genus of *Dextrinosporium*.
1623. The bioactive agent according to item 1585, wherein Basidiomycete cell is selected from the genus of *Dichomitus*.
1624. The bioactive agent according to item 1585, wherein Basidiomycete cell is selected from the genus of *Digitellus*.
1625. The bioactive agent according to item 1585, wherein Basidiomycete cell is selected from the genus of *Earliella*.
1626. The bioactive agent according to item 1585, wherein Basidiomycete cell is selected from the genus *Echinochaete*.
1627. The bioactive agent according to item 1585, wherein Basidiomycete cell is selected from the genus *Elfvingiella*.
1628. The bioactive agent according to item 1585, wherein Basidiomycete cell is selected from the genus of *Enslinia*.
1629. The bioactive agent according to item 1585, wherein Basidiomycete cell is selected from the genus of *Fabisporus*.
1630. The bioactive agent according to item 1585, wherein Basidiomycete cell is selected from the genus of *Faerberia*.
1631. The bioactive agent according to item 1585, wherein Basidiomycete cell is selected from the genus of *Favolus*.
1632. The bioactive agent according to item 1585, wherein Basidiomycete cell is selected from the genus of *Fibroporia*.
1633. The bioactive agent according to item 1585, wherein Basidiomycete cell is selected from the genus *Flabellophora*.
1634. The bioactive agent according to item 1585, wherein Basidiomycete cell is selected from the genus of *Fomes*.
1635. The bioactive agent according to item 1585, wherein Basidiomycete cell is selected from the genus of *Fomitella*.
1636. The bioactive agent according to item 1585, wherein Basidiomycete cell is selected from the genus of *Funalia*.
1637. The bioactive agent according to item 1585, wherein Basidiomycete cell is selected from the genus of *Fuscocerrena*.
1638. The bioactive agent according to item 1585, wherein Basidiomycete cell is selected from the genus of *Gemmularia*.
1639. The bioactive agent according to item 1585, wherein Basidiomycete cell is selected from the genus of *Geopetalum*.
1640. The bioactive agent according to item 1585, wherein Basidiomycete cell is selected from the genus *Globifomes*.
1641. The bioactive agent according to item 1585, wherein Basidiomycete cell is selected from the genus of *Grammothelopsis*.
1642. The bioactive agent according to item 1585, wherein Basidiomycete cell is selected from the genus of *Hansenia*.
1643. The bioactive agent according to item 1585, wherein Basidiomycete cell is selected from the genus of *Haploporus*.
1644. The bioactive agent according to item 1585, wherein Basidiomycete cell is selected from the genus of *Heliocybe*.
1645. The bioactive agent according to item 1585, wherein Basidiomycete cell is selected from the genus *Hexagonia*.
1646. The bioactive agent according to item 1585, wherein Basidiomycete cell is selected from the genus of *Hirschioporus*.

1647. The bioactive agent according to item 1585, wherein Basidiomycete cell is selected from the genus of *Hornodermoporus*.
1648. The bioactive agent according to item 1585, wherein Basidiomycete cell is selected from the genus of *Incrustoporia*.
1649. The bioactive agent according to item 1585, wherein Basidiomycete cell is selected from the genus of *Laccocephalum*.
1650. The bioactive agent according to item 1585, wherein Basidiomycete cell is selected from the genus of *Laetifomes*.
1651. The bioactive agent according to item 1585, wherein Basidiomycete cell is selected from the genus of *Laetiporus*.
1652. The bioactive agent according to item 1585, wherein Basidiomycete cell is selected from the genus of *Lasiochlaena*.
1653. The bioactive agent according to item 1585, wherein Basidiomycete cell is selected from the genus *Lentinopanus*.
1654. The bioactive agent according to item 1585, wherein Basidiomycete cell is selected from the genus *Lentinus*.
1655. The bioactive agent according to item 1585, wherein Basidiomycete cell is selected from the genus of *Lentodiellum*.
1656. The bioactive agent according to item 1585, wherein Basidiomycete cell is selected from the genus of *Lentodium*.
1657. The bioactive agent according to item 1585, wherein Basidiomycete cell is selected from the genus of *Lentus*.
1658. The bioactive agent according to item 1585, wherein Basidiomycete cell is selected from the genus of *Lenzites*.
1659. The bioactive agent according to item 1585, wherein Basidiomycete cell is selected from the genus of *Leptopora*.
1660. The bioactive agent according to item 1585, wherein Basidiomycete cell is selected from the genus of *Leptoporellus*.
1661. The bioactive agent according to item 1585, wherein Basidiomycete cell is selected from the genus of *Leptotrimitus*.
1662. The bioactive agent according to item 1585, wherein Basidiomycete cell is selected from the genus of *Leucolenzites*.
1663. The bioactive agent according to item 1585, wherein Basidiomycete cell is selected from the genus of *Leucoporus*.
1664. The bioactive agent according to item 1585, wherein Basidiomycete cell is selected from the genus *Lignosus*.
1665. The bioactive agent according to item 1585, wherein Basidiomycete cell is selected from the genus of *Lithopolyporales*.
1666. The bioactive agent according to item 1585, wherein Basidiomycete cell is selected from the genus of *Loweporus*.
1667. The bioactive agent according to item 1585, wherein Basidiomycete cell is selected from the genus of *Macrohyporia*.
1668. The bioactive agent according to item 1585, wherein Basidiomycete cell is selected from the genus of *Macroporia*.
1669. The bioactive agent according to item 1585, wherein Basidiomycete cell is selected from the genus of *Megasporoporia*.
1670. The bioactive agent according to item 1585, wherein Basidiomycete cell is selected from the genus of *Melanoporella*.
1671. The bioactive agent according to item 1585, wherein Basidiomycete cell is selected from the genus of *Melanoporia*.
1672. The bioactive agent according to item 1585, wherein Basidiomycete cell is selected from the genus of *Melanopus*.
1673. The bioactive agent according to item 1585, wherein Basidiomycete cell is selected from the genus of *Merulioporia*.
1674. The bioactive agent according to item 1585, wherein Basidiomycete cell is selected from the genus of *Meruliporia*.
1675. The bioactive agent according to item 1585, wherein Basidiomycete cell is selected from the genus of *Microporellus*.
1676. The bioactive agent according to item 1585, wherein Basidiomycete cell is selected from the genus of *Microporus*.
1677. The bioactive agent according to item 1585, wherein Basidiomycete cell is selected from the genus of *Mollicarpus*.
1678. The bioactive agent according to item 1585, wherein Basidiomycete cell is selected from the genus of *Mycelithe*.
1679. The bioactive agent according to item 1585, wherein Basidiomycete cell is selected from the genus of *Navisporus*.
1680. The bioactive agent according to item 1585, wherein Basidiomycete cell is selected from the genus of *Neolentinus*.
1681. The bioactive agent according to item 1585, wherein Basidiomycete cell is selected from the genus of *Neolentiporus*.
1682. The bioactive agent according to item 1585, wherein Basidiomycete cell is selected from the genus of *Nigrofomes*.
1683. The bioactive agent according to item 1585, wherein Basidiomycete cell is selected from the genus of *Nigroporus*.
1684. The bioactive agent according to item 1585, wherein Basidiomycete cell is selected from the genus *Oligoporus*.
1685. The bioactive agent according to item 1585, wherein Basidiomycete cell is selected from the genus of *Osmoporus*.
1686. The bioactive agent according to item 1585, wherein Basidiomycete cell is selected from the genus of *Pachykytospora*.
1687. The bioactive agent according to item 1585, wherein Basidiomycete cell is selected from the genus of *Pachyma*.
1688. The bioactive agent according to item 1585, wherein Basidiomycete cell is selected from the genus of *Panus*.
1689. The bioactive agent according to item 1585, wherein Basidiomycete cell is selected from the genus of *Paramyces*.
1690. The bioactive agent according to item 1585, wherein Basidiomycete cell is selected from the genus of *Perenniporia*.
1691. The bioactive agent according to item 1585, wherein Basidiomycete cell is selected from the genus of *Perenniporiella*.
1692. The bioactive agent according to item 1585, wherein Basidiomycete cell is selected from the genus of *Persooniana*.

1693. The bioactive agent according to item 1585, wherein Basidiomycete cell is selected from the genus of *Petaloides*.
1694. The bioactive agent according to item 1585, wherein Basidiomycete cell is selected from the genus of *Phaeolus*.
1695. The bioactive agent according to item 1585, wherein Basidiomycete cell is selected from the genus of *Phaeotrametes*.
1696. The bioactive agent according to item 1585, wherein Basidiomycete cell is selected from the genus of *Pherima*.
1697. The bioactive agent according to item 1585, wherein Basidiomycete cell is selected from the genus of *Phorima*.
1698. The bioactive agent according to item 1585, wherein Basidiomycete cell is selected from the genus of *Phyllodontia*.
1699. The bioactive agent according to item 1585, wherein Basidiomycete cell is selected from the genus of *Physisporus*.
1700. The bioactive agent according to item 1585, wherein Basidiomycete cell is selected from the genus of *Piloporia*.
1701. The bioactive agent according to item 1585, wherein Basidiomycete cell is selected from the genus of *Piloporia*.
1702. The bioactive agent according to item 1585, wherein Basidiomycete cell is selected from the genus of *Placodes*.
1703. The bioactive agent according to item 1585, wherein Basidiomycete cell is selected from the genus of *Pleuropus*.
1704. The bioactive agent according to item 1585, wherein Basidiomycete cell is selected from the genus of *Pocillaria*.
1705. The bioactive agent according to item 1585, wherein Basidiomycete cell is selected from the genus of *Podofomes*.
1706. The bioactive agent according to item 1585, wherein Basidiomycete cell is selected from the genus *Pogonomyces*.
1707. The bioactive agent according to item 1585, wherein Basidiomycete cell is selected from the genus of *Polyporellus*.
1708. The bioactive agent according to item 1585, wherein Basidiomycete cell is selected from the genus of *Polyporus*.
1709. The bioactive agent according to item 1585, wherein Basidiomycete cell is selected from the genus of *Poria*.
1710. The bioactive agent according to item 1585, wherein Basidiomycete cell is selected from the genus *Porodisculus*.
1711. The bioactive agent according to item 1585, wherein Basidiomycete cell is selected from the genus of *Porodiscus*.
1712. The bioactive agent according to item 1585, wherein Basidiomycete cell is selected from the genus of *Poronidulus*.
1713. The bioactive agent according to item 1585, wherein Basidiomycete cell is selected from the genus of *Poroptyche*.
1714. The bioactive agent according to item 1585, wherein Basidiomycete cell is selected from the genus of *Pseudofavolus*.
1715. The bioactive agent according to item 1585, wherein Basidiomycete cell is selected from the genus of *Pseudophaeolus*.
1716. The bioactive agent according to item 1585, wherein Basidiomycete cell is selected from the genus of *Pseudopiptoporus*.
1717. The bioactive agent according to item 1585, wherein Basidiomycete cell is selected from the genus *Pseudotrametes*.
1718. The bioactive agent according to item 1585, wherein Basidiomycete cell is selected from the genus of *Ptychogaster*.
1719. The bioactive agent according to item 1585, wherein Basidiomycete cell is selected from the genus of *Pycnoporellus*.
1720. The bioactive agent according to item 1585, wherein Basidiomycete cell is selected from the genus of *Pycnoporus*.
1721. The bioactive agent according to item 1585, wherein Basidiomycete cell is selected from the genus of *Pyrofomes*.
1722. The bioactive agent according to item 1585, wherein Basidiomycete cell is selected from the genus *Riopa*.
1723. The bioactive agent according to item 1585, wherein Basidiomycete cell is selected from the genus of *Romellia*.
1724. The bioactive agent according to item 1585, wherein Basidiomycete cell is selected from the genus of *Royoporus*.
1725. The bioactive agent according to item 1585, wherein Basidiomycete cell is selected from the genus of *Rubroporus*.
1726. The bioactive agent according to item 1585, wherein Basidiomycete cell is selected from the genus of *Ryvardenia*.
1727. The bioactive agent according to item 1585, wherein Basidiomycete cell is selected from the genus of *Scenidium*.
1728. The bioactive agent according to item 1585, wherein Basidiomycete cell is selected from the genus of *Sclerodepsis*.
1729. The bioactive agent according to item 1585, wherein Basidiomycete cell is selected from the genus of *Sistotrema*.
1730. The bioactive agent according to item 1585, wherein Basidiomycete cell is selected from the genus of *Skeletocutis*.
1731. The bioactive agent according to item 1585, wherein Basidiomycete cell is selected from the genus of *Sparsitubus*.
1732. The bioactive agent according to item 1585, wherein Basidiomycete cell is selected from the genus of *Spongiosus*.
1733. The bioactive agent according to item 1585, wherein Basidiomycete cell is selected from the genus of *Stiptophyllum*.
1734. The bioactive agent according to item 1585, wherein Basidiomycete cell is selected from the genus of *Tinctoporellus*.
1735. The bioactive agent according to item 1585, wherein Basidiomycete cell is selected from the genus *Tomentoporus*.
1736. The bioactive agent according to item 1585, wherein Basidiomycete cell is selected from the genus of *Trametella*.
1737. The bioactive agent according to item 1585, wherein Basidiomycete cell is selected from the genus of *Trametes*.
1738. The bioactive agent according to item 1585, wherein Basidiomycete cell is selected from the genus of *Trichaptum*.
1739. The bioactive agent according to item 1585, wherein Basidiomycete cell is selected from the genus of *Truncospora*.

1740. The bioactive agent according to item 1585, wherein Basidiomycete cell is selected from the genus of *Tuberaster*.
1741. The bioactive agent according to item 1585, wherein Basidiomycete cell is selected from the genus of *Tyromyces*.
1742. The bioactive agent according to item 1585, wherein Basidiomycete cell is selected from the genus of Ungulina.
1743. The bioactive agent according to item 1585, wherein Basidiomycete cell is selected from the genus of *Vanderbylia*.
1744. The bioactive agent according to item 1585, wherein Basidiomycete cell is selected from the genus of *Velolentinus*.
1745. The bioactive agent according to item 1585, wherein Basidiomycete cell is selected from the genus of *Xerotinus*.
1746. The bioactive agent according to item 1585, wherein Basidiomycete cell is selected from the genus of *Xerotus*.
1747. The bioactive agent according to item 1585, wherein Basidiomycete cell is selected from the genus of *Xylometron*.
1748. The bioactive agent according to item 1585, wherein Basidiomycete cell is selected from the genus of *Xylopilus*.
1749. The bioactive agent according to item 265, wherein said Basidiomycete cell belongs to a genus selected from the group consisting of *Cristelloporia, Echinotrema, Fibriciellum, Fibuloporia, Galziniella, Heptasporium, Hydnotrema, Ingoldiella, Minimedusa, Osteomorpha, Paullicorticium, Repetobasidiellum, Repetobasidium, Sistotrema, Sistotremastrum, Sistotremella, Sphaerobasidium, Tomentella, Trechispora* and *Urnobasidium*.
1750. The bioactive agent according to item 1749, wherein Basidiomycete cell is selected from the genus of *Cristelloporia*.
1751. The bioactive agent according to item 1749, wherein Basidiomycete cell is selected from the genus of *Echinotrema*.
1752. The bioactive agent according to item 1749, wherein Basidiomycete cell is selected from the genus of *Fibriciellum*.
1753. The bioactive agent according to item 1749, wherein Basidiomycete cell is selected from the genus of *Fibuloporia*.
1754. The bioactive agent according to item 1749, wherein Basidiomycete cell is selected from the genus of *Galziniella*.
1755. The bioactive agent according to item 1749, wherein Basidiomycete cell is selected from the genus of *Heptasporium*.
1756. The bioactive agent according to item 1749, wherein Basidiomycete cell is selected from the genus of *Hydnotrema*.
1757. The bioactive agent according to item 1749, wherein Basidiomycete cell is selected from the genus *Ingoldiella*.
1758. The bioactive agent according to item 1749, wherein Basidiomycete cell is selected from the genus of *Minimedusa*.
1759. The bioactive agent according to item 1749, wherein Basidiomycete cell is selected from the genus of *Osteomorpha*.
1760. The bioactive agent according to item 1749, wherein Basidiomycete cell is selected from the genus of *Paullicorticium*.
1761. The bioactive agent according to item 1749, wherein Basidiomycete cell is selected from the genus of *Repetobasidiellum*.
1762. The bioactive agent according to item 1749, wherein Basidiomycete cell is selected from the genus of *Repetobasidium*.
1763. The bioactive agent according to item 1749, wherein Basidiomycete cell is selected from the genus of *Sistotrema*.
1764. The bioactive agent according to item 1749, wherein Basidiomycete cell is selected from the genus of *Sistotremastrum*.
1765. The bioactive agent according to item 1749, wherein Basidiomycete cell is selected from the genus of *Sistotremella*.
1766. The bioactive agent according to item 1749, wherein Basidiomycete cell is selected from the genus of *Sphaerobasidium*.
1767. The bioactive agent according to item 1749, wherein Basidiomycete cell is selected from the genus of *Tomentella*.
1768. The bioactive agent according to item 1749, wherein Basidiomycete cell is selected from the genus of *Trechispora*.
1769. The bioactive agent according to item 1749, wherein Basidiomycete cell is selected from the genus of *Urnobasidium*.
1770. The bioactive agent according to item 266, wherein said Basidiomycete cell belongs to a genus selected from the group consisting of *Bondarcevomyces, Masseeola, Sparassiella* and *Sparassis*.
1771. The bioactive agent according to item 1770, wherein Basidiomycete cell is selected from the genus of *Bondarcevomyces*.
1772. The bioactive agent according to item 1770, wherein Basidiomycete cell is selected from the genus of *Masseeola*.
1773. The bioactive agent according to item 1770, wherein Basidiomycete cell is selected from the genus of *Sparassiella*.
1774. The bioactive agent according to item 1770, wherein Basidiomycete cell is selected from the genus of *Sparassis*.
1775. The bioactive agent according to item 267, wherein said Basidiomycete cell belongs to a genus selected from the group consisting of *Amethicium, Antrodiella, Aschersonia, Australohydnum, Baeostratoporus, Chaetoporus, Cinereomyces, Diplomitoporus, Etheirodon, Fibricium, Flaviporus, Flavodon, Irpex, Junghuhnia, Lamelloporus, Laschia, Leptodon, Metuloidea, Mycoleptodon, Mycoleptodonoides, Mycorrhaphium, Odontia, Odontina, Spathulina, Steccherinum* and *Stegiacantha*.
1776. The bioactive agent according to item 1775, wherein Basidiomycete cell is selected from the genus of *Amethicium*.
1777. The bioactive agent according to item 1775, wherein Basidiomycete cell is selected from the genus of *Antrodiella*.
1778. The bioactive agent according to item 1775, wherein Basidiomycete cell is selected from the genus of *Aschersonia*.
1779. The bioactive agent according to item 1775, wherein Basidiomycete cell is selected from the genus of *Australohydnum*.
1780. The bioactive agent according to item 1775, wherein Basidiomycete cell is selected from the genus of *Baeostratoporus*.
1781. The bioactive agent according to item 1775, wherein Basidiomycete cell is selected from the genus of *Chaetoporus*.

1782. The bioactive agent according to item 1775, wherein Basidiomycete cell is selected from the genus of *Cinereomyces*.
1783. The bioactive agent according to item 1775, wherein Basidiomycete cell is selected from the genus of *Diplomitoporus*.
1784. The bioactive agent according to item 1775, wherein Basidiomycete cell is selected from the genus of *Etheirodon*.
1785. The bioactive agent according to item 1775, wherein Basidiomycete cell is selected from the genus of *Fibricium*.
1786. The bioactive agent according to item 1775, wherein Basidiomycete cell is selected from the genus of *Flaviporus*.
1787. The bioactive agent according to item 1775, wherein Basidiomycete cell is selected from the genus of *Flavodon*.
1788. The bioactive agent according to item 1775, wherein Basidiomycete cell is selected from the genus of *Irpex*.
1789. The bioactive agent according to item 1775, wherein Basidiomycete cell is selected from the genus of *Junghuhnia*.
1790. The bioactive agent according to item 1775, wherein Basidiomycete cell is selected from the genus of *Lameloporus*.
1791. The bioactive agent according to item 1775, wherein Basidiomycete cell is selected from the genus of *Laschia*.
1792. The bioactive agent according to item 1775, wherein Basidiomycete cell is selected from the genus of *Leptodon*.
1793. The bioactive agent according to item 1775, wherein Basidiomycete cell is selected from the genus of *Metuloidea*.
1794. The bioactive agent according to item 1775, wherein Basidiomycete cell is selected from the genus of *Mycoleptodon*.
1795. The bioactive agent according to item 1775, wherein Basidiomycete cell is selected from the genus of *Mycoleptodonoides*.
1796. The bioactive agent according to item 1775, wherein Basidiomycete cell is selected from the genus of *Mycorrhaphium*.
1797. The bioactive agent according to item 1775, wherein Basidiomycete cell is selected from the genus of *Odontia*.
1798. The bioactive agent according to item 1775, wherein Basidiomycete cell is selected from the genus of *Odontina*.
1799. The bioactive agent according to item 1775, wherein Basidiomycete cell is selected from the genus of *Spathulina*.
1800. The bioactive agent according to item 1775, wherein Basidiomycete cell is selected from the genus *Steccherinum*.
1801. The bioactive agent according to item 1775, wherein Basidiomycete cell is selected from the genus of *Stegiacantha*.
1802. The bioactive agent according to item 268, wherein said Basidiomycete cell belongs to a genus selected from the group consisting of *Granulocystis, Leifia, Litschauerella, Tubulicium, Tubulicrinis* and *Tubulixenasma*.
1803. The bioactive agent according to item 1802, wherein Basidiomycete cell is selected from the genus of *Granulocystis*.
1804. The bioactive agent according to item 1802, wherein Basidiomycete cell is selected from the genus of *Leifia*.
1805. The bioactive agent according to item 1802, wherein Basidiomycete cell is selected from the genus of *Litschauerella*.
1806. The bioactive agent according to item 1802, wherein Basidiomycete cell is selected from the genus of *Tubulicium*.
1807. The bioactive agent according to item 1802, wherein Basidiomycete cell is selected from the genus of *Tubulicrinis*.
1808. The bioactive agent according to item 1802, wherein Basidiomycete cell is selected from the genus of *Tubulixenasma*.
1809. The bioactive agent according to item 268, wherein said Basidiomycete cell belongs to a genus selected from the group consisting of *Aphanobasidium, Clitopilina, Cunninghammyces, Lepidomyces, Phlebiella, Xenasma, Xenasmatella* and *Xenosperma*.
1810. The bioactive agent according to item 1809, wherein Basidiomycete cell is selected from the genus of *Aphanobasidium*.
1811. The bioactive agent according to item 1809, wherein Basidiomycete cell is selected from the genus of *Clitopilina*.
1812. The bioactive agent according to item 1809, wherein Basidiomycete cell is selected from the genus of *Cunninghammyces*.
1813. The bioactive agent according to item 1809, wherein Basidiomycete cell is selected from the genus of *Lepidomyces*.
1814. The bioactive agent according to item 1809, wherein Basidiomycete cell is selected from the genus of *Phlebiella*.
1815. The bioactive agent according to item 1809, wherein Basidiomycete cell is selected from the genus of *Xenasma*.
1816. The bioactive agent according to item 1809, wherein Basidiomycete cell is selected from the genus of *Xenasmatella*.
1817. The bioactive agent according to item 1809, wherein Basidiomycete cell is selected from the genus of *Xenosperma*.
1818. The bioactive agent according to item 363, wherein said Basidiomycete cell belongs to a species selected from the group consisting of *Agaricus arorae, Agaricus arvensis, Agaricus augustus, Agaricus benesi, Agaricus bernardii, Agaricus bitorquis, Agaricus californicus, Agaricus campestris, Agaricus comptulus, Agaricus cupreo-brunneus, Agaricus diminutivus, Agaricus fusco-fibrillosus, Agaricus fuscovelatus, Agaricus hondensis, Agaricus lilaceps, Agaricus micromegathus, Agaricus praeclaresquamosus, Agaricus pattersonae, Agaricus perobscurus, Agaricus semotus, Agaricus silvicola, Agaricus subrutilescens* and *Agaricus xanthodermus*.
1819. The bioactive agent according to item 1819, wherein Basidiomycete cell is *Agaricus arorae*.
1820. The bioactive agent according to item 1819, wherein Basidiomycete cell is *Agaricus arvensis*.
1821. The bioactive agent according to item 1819, wherein Basidiomycete cell is *Agaricus augustus*.
1822. The bioactive agent according to item 1819, wherein Basidiomycete cell is *Agaricus benesi*.
1823. The bioactive agent according to item 1819, wherein Basidiomycete cell is *Agaricus bernardii*.
1824. The bioactive agent according to item 1819, wherein Basidiomycete cell is *Agaricus bitorquis*.
1825. The bioactive agent according to item 1819, wherein Basidiomycete cell is *Agaricus californicus*.
1826. The bioactive agent according to item 1819, wherein Basidiomycete cell is *Agaricus campestris*.
1827. The bioactive agent according to item 1819, wherein Basidiomycete cell is *Agaricus comptulus*.

1828. The bioactive agent according to item 1819, wherein Basidiomycete cell is *Agaricus cupreo-brunneus.*
1829. The bioactive agent according to item 1819, wherein Basidiomycete cell is *Agaricus diminutivus.*
1830. The bioactive agent according to item 1819, wherein Basidiomycete cell is *Agaricus fusco-fibrillosus.*
1831. The bioactive agent according to item 1819, wherein Basidiomycete cell is *Agaricus fuscovelatus.*
1832. The bioactive agent according to item 1819, wherein Basidiomycete cell is *Agaricus hondensis.*
1833. The bioactive agent according to item 1819, wherein Basidiomycete cell is *Agaricus lilaceps.*
1834. The bioactive agent according to item 1819, wherein Basidiomycete cell is *Agaricus micromegathus.*
1835. The bioactive agent according to item 1819, wherein Basidiomycete cell is *Agaricus praeclaresquamosus.*
1836. The bioactive agent according to item 1819, wherein Basidiomycete cell is *Agaricus pattersonae.*
1837. The bioactive agent according to item 1819, wherein Basidiomycete cell is *Agaricus perobscurus.*
1838. The bioactive agent according to item 1819, wherein Basidiomycete cell is *Agaricus semotus.*
1839. The bioactive agent according to item 1819, wherein Basidiomycete cell is *Agaricus silvicola.*
1840. The bioactive agent according to item 1819, wherein Basidiomycete cell is *Agaricus subrutilescens.*
1841. The bioactive agent according to item 1819, wherein Basidiomycete cell is *Agaricus* xanthodermus.
1842. The bioactive agent according to item 925, wherein said Basidiomycete cell belongs to a species selected from the group consisting of *Schizophyllum album, Schizophyllum alneum, Schizophyllum alneum, Schizophyllum amplum, Schizophyllum brasiliense, Schizophyllum brevilamellatum, Schizophyllum commune, Schizophyllum egelingianum, Schizophyllum exiguum, Schizophyllum fasciatum, Schizophyllum flabellare, Schizophyllum leprieurii, Schizophyllum lobatum, Schizophyllum mexicanum, Schizophyllum multifidum, Schizophyllum murrayi, Schizophyllum mya, Schizophyllum palmatum, Schizophyllum radiatum, Schizophyllum umbrinum* and *Schizophyllum variabile.*
1843. The bioactive agent according to item 1842, wherein Basidiomycete cell is *Schizophyllum* album.
1844. The bioactive agent according to item 1842, wherein Basidiomycete cell is *Schizophyllum alneum.*
1845. The bioactive agent according to item 1842, wherein Basidiomycete cell is *Schizophyllum alneum.*
1846. The bioactive agent according to item 1842, wherein Basidiomycete cell is *Schizophyllum amplum.*
1847. The bioactive agent according to item 1842, wherein Basidiomycete cell is *Schizophyllum brasiliense.*
1848. The bioactive agent according to item 1842, wherein Basidiomycete cell is *Schizophyllum brevilamellatum.*
1849. The bioactive agent according to item 1842, wherein Basidiomycete cell is *Schizophyllum commune.*
1850. The bioactive agent according to item 1842, wherein Basidiomycete cell is *Schizophyllum egelingianum.*
1851. The bioactive agent according to item 1842, wherein Basidiomycete cell is *Schizophyllum exiguum.*
1852. The bioactive agent according to item 1842, wherein Basidiomycete cell is *Schizophyllum fasciatum.*
1853. The bioactive agent according to item 1842, wherein Basidiomycete cell is *Schizophyllum flabellare.*
1854. The bioactive agent according to item 1842, wherein Basidiomycete cell is *Schizophyllum leprieurii.*
1855. The bioactive agent according to item 1842, wherein Basidiomycete cell is *Schizophyllum lobatum.*
1856. The bioactive agent according to item 1842, wherein Basidiomycete cell is *Schizophyllum mexicanum.*
1857. The bioactive agent according to item 1842, wherein Basidiomycete cell is *Schizophyllum multifidum.*
1858. The bioactive agent according to item 1842, wherein Basidiomycete cell is *Schizophyllum murrayi.*
1859. The bioactive agent according to item 1842, wherein Basidiomycete cell is *Schizophyllum mya.*
1860. The bioactive agent according to item 1842, wherein Basidiomycete cell is *Schizophyllum palmatum.*
1861. The bioactive agent according to item 1842, wherein Basidiomycete cell is *Schizophyllum radiatum.*
1862. The bioactive agent according to item 1842, wherein Basidiomycete cell is *Schizophyllum umbrinum.*
1863. The bioactive agent according to item 1842, wherein Basidiomycete cell is *Schizophyllum variabile.*
1864. The bioactive agent according to item 1406, wherein said Basidiomycete cell belongs to a species selected from the group consisting of *Ganoderma adspersum, Ganoderma africanum, Ganoderma applanatum, Ganoderma arcuatum, Ganoderma areolatum, Ganoderma bakeri, Ganoderma balabacense, Ganoderma cacainum, Ganoderma calcigenum, Ganoderma calidophilum, Ganoderma camphoratum, Ganoderma cantharelloideum, Ganoderma capense, Ganoderma carnosum, Ganoderma cehengense, Ganoderma cervinum, Ganoderma chaffangeonii, Ganoderma chalceum, Ganoderma chaperi, Ganoderma chenhaiense, Ganoderma chilense, Ganoderma chiungchungense, Ganoderma chonoides, Ganoderma cochlear, Ganoderma coffeatum, Ganoderma colossus, Ganoderma comorense, Ganoderma comphoratum, Ganoderma concinnum, Ganoderma conicus, Ganoderma corrugatum, Ganoderma costatus, Ganoderma crebrostriatum, Ganoderma cupreolaccatum, Ganoderma cupreum, Ganoderma cupulatiprocerum, Ganoderma curranii, Ganoderma curtisii, Ganoderma dahlii, Ganoderma daiqingshanense, Ganoderma dejongii, Ganoderma densizonatum, Ganoderma diaoluoshanense, Ganoderma donkii, Ganoderma dorsale, Ganoderma dubio-cochlear, Ganoderma dussii, Ganoderma elmeri, Ganoderma elmerianum, Ganoderma eminii, Ganoderma endochrum, Ganoderma europaeum, Ganoderma exile, Ganoderma expallens, Ganoderma fasciatum, Ganoderma fasciculatum, Ganoderma fassii, Ganoderma fassioides, Ganoderma fici, Ganoderma flabelliforme, Ganoderma flaviporum, Ganoderma flexipes, Ganoderma formosanum, Ganoderma formosissimum, Ganoderma formicatum, Ganoderma frondosum, Ganoderma fulvellum, Ganoderma fuscum, Ganoderma galegense, Ganoderma gelsicola, Ganoderma ghesquierei, Ganoderma gibbosum, Ganoderma gilletii, Ganoderma guadelupense, Ganoderma guinanense, Ganoderma guizhouense, Ganoderma hainanense, Ganoderma henningsii, Ganoderma hildebrandii, Ganoderma hinnuleum, Ganoderma hoehnelianum, Ganoderma hollidayi, Ganoderma hoploides, Ganoderma hypoxanthum, Ganoderma impolitum, Ganoderma incrassatum, Ganoderma incrustatum, Ganoderma infulgens, Ganoderma infundibuliforme, Ganoderma insulare, Ganoderma intermedium, Ganoderma japonicum, Ganoderma jianfenglingense, Ganoderma koningsbergii, Ganoderma kosteri, Ganoderma kunmingense, Ganoderma laccatum, Ganoderma lamaoense, Ganoderma leptopum, Ganoderma leucocreas, Ganoderma leucophaeum, Ganoderma leytense, Ganoderma lignosum, Ganoderma limushanense, Ganoderma lingua, Ganoderma linhartii, Ganoderma lionnetii, Ganoderma lipsiense, Ganoderma lloydii, Ganoderma lobatoideum,*

*Ganoderma lobatum, Ganoderma longipes, Ganoderma longistipatum, Ganoderma longistipitatum, Ganoderma lorenzianum, Ganoderma lucidum, Ganoderma lusambilaense, Ganoderma luteicinctum, Ganoderma luteomarginatum, Ganoderma luteum, Ganoderma macer, Ganoderma magniporum, Ganoderma maitlandii, Ganoderma malayanum, Ganoderma malosporum, Ganoderma mangiferae, Ganoderma manoutchehrii, Ganoderma mastoporum, Ganoderma mediosinense, Ganoderma megaloma, Ganoderma megalosporum, Ganoderma meijangense, Ganoderma melanophaeum, Ganoderma meredithiae, Ganoderma microsporum, Ganoderma miniatocinctum, Ganoderma mirabile, Ganoderma mirivelutinum, Ganoderma mongolicum, Ganoderma multicornum, Ganoderma multipileum, Ganoderma multiplicatum, Ganoderma namutambalaense, Ganoderma neglectus, Ganoderma neojaponicum, Ganoderma neurosporum, Ganoderma nevadense, Ganoderma nigrolucidum, Ganoderma nitens, Ganoderma nitidum, Ganoderma noukahivense, Ganoderma nutans, Ganoderma obockense, Ganoderma obokensis, Ganoderma ochrolaccatum, Ganoderma oerstedii, Ganoderma omphalodes, Ganoderma opacum, Ganoderma orbiforme, Ganoderma oregonense, Ganoderma oroflavum, Ganoderma oroleucum, Ganoderma ostracodes, Ganoderma ostreatum, Ganoderma papillatum, Ganoderma parviungulatum, Ganoderma parvulum, Ganoderma pernanum, Ganoderma personatum, Ganoderma perturbatum, Ganoderma petchii, Ganoderma pfeifferi, Ganoderma philippii, Ganoderma platense, Ganoderma plicatum, Ganoderma polychromum, Ganoderma polymorphum, Ganoderma praelongum* Murrill, *Ganoderma praetervisum, Ganoderma preussii, Ganoderma pseudoboletus, Ganoderma pseudoferreum, Ganoderma puberulum, Ganoderma puglisii, Ganoderma pulchella, Ganoderma pullatum, Ganoderma pulverulentum, Ganoderma pygmoideum, Ganoderma ramosissimum, Ganoderma ravenelii, Ganoderma renidens, Ganoderma renii, Ganoderma resinaceum, Ganoderma reticulatosporum, Ganoderma rhacodes, Ganoderma rivulosum, Ganoderma rothwellii, Ganoderma rotundatum, Ganoderma rubeolum, Ganoderma rude, Ganoderma rufoalbum, Ganoderma rufobadium, Ganoderma rugosissimus, Ganoderma rugosum, Ganoderma sanmingense, Ganoderma sarasinii, Ganoderma schomburgkii, Ganoderma sculpturatum, Ganoderma septatum, Ganoderma sequoiae, Ganoderma sessile, Ganoderma sessiliforme, Ganoderma shandongense, Ganoderma shangsiens, Ganoderma sichuanense, Ganoderma sikorae, Ganoderma silveirae, Ganoderma simaoense, Ganoderma simulans, Ganoderma sinense, Ganoderma soniense, Ganoderma soyeri, Ganoderma sprucei, Ganoderma staneri, Ganoderma steyaertanum, Ganoderma stipitatum, Ganoderma stratoideum, Ganoderma subamboinense, Ganoderma subformicatum, Ganoderma subfulvum, Ganoderma subincrustatum, Ganoderma sublucidum, Ganoderma subperforatum, Ganoderma subrenatum, Ganoderma subresinosum, Ganoderma subrugosus, Ganoderma substipitata, Ganoderma subtornatum, Ganoderma subtuberculosum, Ganoderma subumbraculum, Ganoderma sulcatum, Ganoderma tenue, Ganoderma testaceum, Ganoderma theaecolum, Ganoderma tibetanum, Ganoderma tornatum, Ganoderma torosum, Ganoderma torrendii, Ganoderma trengganuense, Ganoderma triangulum, Ganoderma triviale, Ganoderma tropicum, Ganoderma trulla, Ganoderma trulliforme, Ganoderma tsugae, Ganoderma tsunodae, Ganoderma tuberculosum, Ganoderma tumidum, Ganoderma umbraculum, Ganoderma umbrinum, Ganoderma ungulatum, Ganoderma valesiacum, Ganoderma vanheurnii, Ganoderma vanmeelii, Ganoderma variabile, Ganoderma weberianum, Ganoderma williamsianum, Ganoderma wuhuense, Ganoderma wynaadense, Ganoderma xanthocreas, Ganoderma xingyiense, Ganoderma xylodes, Ganoderma xylonoides, Ganoderma zhenningense* and *Ganoderma zonatum.*

1865. The bioactive agent according to item 1864, wherein Basidiomycete cell is *Ganoderma adspersum*.
1866. The bioactive agent according to item 1864, wherein Basidiomycete cell is *Ganoderma africanum*.
1867. The bioactive agent according to item 1864, wherein Basidiomycete cell is *Ganoderma applanatum*.
1868. The bioactive agent according to item 1864, wherein Basidiomycete cell is *Ganoderma arcuatum*.
1869. The bioactive agent according to item 1864, wherein Basidiomycete cell is *Ganoderma areolatum*.
1870. The bioactive agent according to item 1864, wherein Basidiomycete cell is *Ganoderma bakeri*.
1871. The bioactive agent according to item 1864, wherein Basidiomycete cell is *Ganoderma balabacense*.
1872. The bioactive agent according to item 1864, wherein Basidiomycete cell is *Ganoderma cacainum*.
1873. The bioactive agent according to item 1864, wherein Basidiomycete cell is *Ganoderma cacainum*.
1874. The bioactive agent according to item 1864, wherein Basidiomycete cell is *Ganoderma calcigenum*.
1875. The bioactive agent according to item 1864, wherein Basidiomycete cell is *Ganoderma calidophilum*.
1876. The bioactive agent according to item 1864, wherein Basidiomycete cell is *Ganoderma camphoratum*.
1877. The bioactive agent according to item 1864, wherein Basidiomycete cell is *Ganoderma cantharelloideum*.
1878. The bioactive agent according to item 1864, wherein Basidiomycete cell is *Ganoderma capense*.
1879. The bioactive agent according to item 1864, wherein Basidiomycete cell is *Ganoderma carnosum*.
1880. The bioactive agent according to item 1864, wherein Basidiomycete cell is *Ganoderma cehengense*.
1881. The bioactive agent according to item 1864, wherein Basidiomycete cell is *Ganoderma cervinum*.
1882. The bioactive agent according to item 1864, wherein Basidiomycete cell is *Ganoderma chaffangeonii*.
1883. The bioactive agent according to item 1864, wherein Basidiomycete cell is *Ganoderma chalceum*.
1884. The bioactive agent according to item 1864, wherein Basidiomycete cell is *Ganoderma chaperi*.
1885. The bioactive agent according to item 1864, wherein Basidiomycete cell is *Ganoderma chenhaiense*.
1886. The bioactive agent according to item 1864, wherein Basidiomycete cell is *Ganoderma chilense*.
1887. The bioactive agent according to item 1864, wherein Basidiomycete cell is *Ganoderma chiungchungense*.
1888. The bioactive agent according to item 1864, wherein Basidiomycete cell is *Ganoderma chonoides*.
1889. The bioactive agent according to item 1864, wherein Basidiomycete cell is *Ganoderma cochlear*.
1890. The bioactive agent according to item 1864, wherein Basidiomycete cell is *Ganoderma coffeatum*.
1891. The bioactive agent according to item 1864, wherein Basidiomycete cell is *Ganoderma colossus*.
1892. The bioactive agent according to item 1864, wherein Basidiomycete cell is *Ganoderma comorense*.
1893. The bioactive agent according to item 1864, wherein Basidiomycete cell is *Ganoderma comphoratum*.

1894. The bioactive agent according to item 1864, wherein Basidiomycete cell is *Ganoderma concinnum*.
1895. The bioactive agent according to item 1864, wherein Basidiomycete cell is *Ganoderma conicus*.
1896. The bioactive agent according to item 1864, wherein Basidiomycete cell is *Ganoderma corrugatum*.
1897. The bioactive agent according to item 1864, wherein Basidiomycete cell is *Ganoderma costatus*.
1898. The bioactive agent according to item 1864, wherein Basidiomycete cell is *Ganoderma crebrostriatum*.
1899. The bioactive agent according to item 1864, wherein Basidiomycete cell is *Ganoderma cupreolaccatum*.
1900. The bioactive agent according to item 1864, wherein Basidiomycete cell is *Ganoderma curranii*.
1901. The bioactive agent according to item 1864, wherein Basidiomycete cell is *Ganoderma curtisii*.
1902. The bioactive agent according to item 1864, wherein Basidiomycete cell is *Ganoderma dahlii*.
1903. The bioactive agent according to item 1864, wherein Basidiomycete cell is *Ganoderma daiqingshanense*.
1904. The bioactive agent according to item 1864, wherein Basidiomycete cell is *Ganoderma dejongii*.
1905. The bioactive agent according to item 1864, wherein Basidiomycete cell is *Ganoderma densizonatum*.
1906. The bioactive agent according to item 1864, wherein Basidiomycete cell is *Ganoderma diaoluoshanense*.
1907. The bioactive agent according to item 1864, wherein Basidiomycete cell is *Ganoderma donkii*.
1908. The bioactive agent according to item 1864, wherein Basidiomycete cell is *Ganoderma dorsale*.
1909. The bioactive agent according to item 1864, wherein Basidiomycete cell is *Ganoderma dubio-cochlear*.
1910. The bioactive agent according to item 1864, wherein Basidiomycete cell is *Ganoderma dussii*.
1911. The bioactive agent according to item 1864, wherein Basidiomycete cell is *Ganoderma elmeri*.
1912. The bioactive agent according to item 1864, wherein Basidiomycete cell is *Ganoderma elmerianum*.
1913. The bioactive agent according to item 1864, wherein Basidiomycete cell is *Ganoderma eminii*.
1914. The bioactive agent according to item 1864, wherein Basidiomycete cell is *Ganoderma endochrum*.
1915. The bioactive agent according to item 1864, wherein Basidiomycete cell is *Ganoderma europaeum*.
1916. The bioactive agent according to item 1864, wherein Basidiomycete cell is *Ganoderma exile*.
1917. The bioactive agent according to item 1864, wherein Basidiomycete cell is *Ganoderma expallens*.
1918. The bioactive agent according to item 1864, wherein Basidiomycete cell is *Ganoderma fasciatum*.
1919. The bioactive agent according to item 1864, wherein Basidiomycete cell is *Ganoderma fassii*.
1920. The bioactive agent according to item 1864, wherein Basidiomycete cell is *Ganoderma fassioides*.
1921. The bioactive agent according to item 1864, wherein Basidiomycete cell is *Ganoderma fici*.
1922. The bioactive agent according to item 1864, wherein Basidiomycete cell is *Ganoderma flabelliforme*.
1923. The bioactive agent according to item 1864, wherein Basidiomycete cell is *Ganoderma flaviporum*.
1924. The bioactive agent according to item 1864, wherein Basidiomycete cell is *Ganoderma flexipes*.
1925. The bioactive agent according to item 1864, wherein Basidiomycete cell is *Ganoderma formosanum*.
1926. The bioactive agent according to item 1864, wherein Basidiomycete cell is *Ganoderma formosissimum*.
1927. The bioactive agent according to item 1864, wherein Basidiomycete cell is *Ganoderma formicatum*.
1928. The bioactive agent according to item 1864, wherein Basidiomycete cell is *Ganoderma frondosum*.
1929. The bioactive agent according to item 1864, wherein Basidiomycete cell is *Ganoderma fulvellum*.
1930. The bioactive agent according to item 1864, wherein Basidiomycete cell is *Ganoderma fuscum*.
1931. The bioactive agent according to item 1864, wherein Basidiomycete cell is *Ganoderma galegense*.
1932. The bioactive agent according to item 1864, wherein Basidiomycete cell is *Ganoderma gelsicola*.
1933. The bioactive agent according to item 1864, wherein Basidiomycete cell is *Ganoderma ghesquierei*.
1934. The bioactive agent according to item 1864, wherein Basidiomycete cell is *Ganoderma gibbosum*.
1935. The bioactive agent according to item 1864, wherein Basidiomycete cell is *Ganoderma gilletii*.
1936. The bioactive agent according to item 1864, wherein Basidiomycete cell is *Ganoderma guadelupense*.
1937. The bioactive agent according to item 1864, wherein Basidiomycete cell is *Ganoderma guinanense*.
1938. The bioactive agent according to item 1864, wherein Basidiomycete cell is *Ganoderma guizhouense*.
1939. The bioactive agent according to item 1864, wherein Basidiomycete cell is *Ganoderma hainanense*.
1940. The bioactive agent according to item 1864, wherein Basidiomycete cell is *Ganoderma henningsii*.
1941. The bioactive agent according to item 1864, wherein Basidiomycete cell is *Ganoderma hildebrandii*.
1942. The bioactive agent according to item 1864, wherein Basidiomycete cell is *Ganoderma hinnuleum*.
1943. The bioactive agent according to item 1864, wherein Basidiomycete cell is *Ganoderma hoehnelianum*.
1944. The bioactive agent according to item 1864, wherein Basidiomycete cell is *Ganoderma hollidayi*.
1945. The bioactive agent according to item 1864, wherein Basidiomycete cell is *Ganoderma hoploides*.
1946. The bioactive agent according to item 1864, wherein Basidiomycete cell is *Ganoderma hypoxanthum*.
1947. The bioactive agent according to item 1864, wherein Basidiomycete cell is *Ganoderma impolitum*.
1948. The bioactive agent according to item 1864, wherein Basidiomycete cell is *Ganoderma incrassatum*.
1949. The bioactive agent according to item 1864, wherein Basidiomycete cell is *Ganoderma incrustatum*.
1950. The bioactive agent according to item 1864, wherein Basidiomycete cell is *Ganoderma infulgens*.
1951. The bioactive agent according to item 1864, wherein Basidiomycete cell is *Ganoderma infundibuliforme*.
1952. The bioactive agent according to item 1864, wherein Basidiomycete cell is *Ganoderma insulare*.
1953. The bioactive agent according to item 1864, wherein Basidiomycete cell is *Ganoderma intermedium*.
1954. The bioactive agent according to item 1864, wherein Basidiomycete cell is *Ganoderma japonicum*.
1955. The bioactive agent according to item 1864, wherein Basidiomycete cell is *Ganoderma jianfenglingense*.
1956. The bioactive agent according to item 1864, wherein Basidiomycete cell is *Ganoderma koningsbergii*.
1957. The bioactive agent according to item 1864, wherein Basidiomycete cell is *Ganoderma kosteri*.
1958. The bioactive agent according to item 1864, wherein Basidiomycete cell is *Ganoderma kunmingense*.
1959. The bioactive agent according to item 1864, wherein Basidiomycete cell is *Ganoderma laccatum*.

1960. The bioactive agent according to item 1864, wherein Basidiomycete cell is *Ganoderma lamaoense.*

1961. The bioactive agent according to item 1864, wherein Basidiomycete cell is *Ganoderma leptopum.*

1962. The bioactive agent according to item 1864, wherein Basidiomycete cell is *Ganoderma leucocreas.*

1963. The bioactive agent according to item 1864, wherein Basidiomycete cell is *Ganoderma leucophaeum.*

1964. The bioactive agent according to item 1864, wherein Basidiomycete cell is *Ganoderma leytense.*

1965. The bioactive agent according to item 1864, wherein Basidiomycete cell is *Ganoderma lignosum.*

1966. The bioactive agent according to item 1864, wherein Basidiomycete cell is *Ganoderma limushanense.*

1967. The bioactive agent according to item 1864, wherein Basidiomycete cell is *Ganoderma lingua.*

1968. The bioactive agent according to item 1864, wherein Basidiomycete cell is *Ganoderma linhartii.*

1969. The bioactive agent according to item 1864, wherein Basidiomycete cell is *Ganoderma lionnetii.*

1970. The bioactive agent according to item 1864, wherein Basidiomycete cell is *Ganoderma lipsiense.*

1971. The bioactive agent according to item 1864, wherein Basidiomycete cell is *Ganoderma lloydii.*

1972. The bioactive agent according to item 1864, wherein Basidiomycete cell is *Ganoderma lobatoideum.*

1973. The bioactive agent according to item 1864, wherein Basidiomycete cell is *Ganoderma lobatum.*

1974. The bioactive agent according to item 1864, wherein Basidiomycete cell is *Ganoderma longipes.*

1975. The bioactive agent according to item 1864, wherein Basidiomycete cell is *Ganoderma longistipatum.*

1976. The bioactive agent according to item 1864, wherein Basidiomycete cell is *Ganoderma lorenzianum.*

1977. The bioactive agent according to item 1864, wherein Basidiomycete cell is *Ganoderma lucidum.*

1978. The bioactive agent according to item 1864, wherein Basidiomycete cell is *Ganoderma lusambilaense.*

1979. The bioactive agent according to item 1864, wherein Basidiomycete cell is *Ganoderma luteicinctum.*

1980. The bioactive agent according to item 1864, wherein Basidiomycete cell is *Ganoderma luteomarginatum.*

1981. The bioactive agent according to item 1864, wherein Basidiomycete cell is *Ganoderma luteum.*

1982. The bioactive agent according to item 1864, wherein Basidiomycete cell is *Ganoderma macer.*

1983. The bioactive agent according to item 1864, wherein Basidiomycete cell is *Ganoderma magniporum.*

1984. The bioactive agent according to item 1864, wherein Basidiomycete cell is *Ganoderma maitlandii.*

1985. The bioactive agent according to item 1864, wherein Basidiomycete cell is *Ganoderma malayanum.*

1986. The bioactive agent according to item 1864, wherein Basidiomycete cell is *Ganoderma malosporum.*

1987. The bioactive agent according to item 1864, wherein Basidiomycete cell is *Ganoderma mangiferae.*

1988. The bioactive agent according to item 1864, wherein Basidiomycete cell is *Ganoderma manoutchehrii.*

1989. The bioactive agent according to item 1864, wherein Basidiomycete cell is *Ganoderma mastoporum.*

1990. The bioactive agent according to item 1864, wherein Basidiomycete cell is *Ganoderma mediosinense.*

1991. The bioactive agent according to item 1864, wherein Basidiomycete cell is *Ganoderma megaloma.*

1992. The bioactive agent according to item 1864, wherein Basidiomycete cell is *Ganoderma megalosporum.*

1993. The bioactive agent according to item 1864, wherein Basidiomycete cell is *Ganoderma meijangense.*

1994. The bioactive agent according to item 1864, wherein Basidiomycete cell is *Ganoderma melanophaeum.*

1995. The bioactive agent according to item 1864, wherein Basidiomycete cell is *Ganoderma meredithiae.*

1996. The bioactive agent according to item 1864, wherein Basidiomycete cell is *Ganoderma microsporum.*

1997. The bioactive agent according to item 1864, wherein Basidiomycete cell is *Ganoderma miniatocinctum.*

1998. The bioactive agent according to item 1864, wherein Basidiomycete cell is *Ganoderma mirabile.*

1999. The bioactive agent according to item 1864, wherein Basidiomycete cell is *Ganoderma mirivelutinum.*

2000. The bioactive agent according to item 1864, wherein Basidiomycete cell is *Ganoderma mongolicum.*

2001. The bioactive agent according to item 1864, wherein Basidiomycete cell is *Ganoderma multicornum.*

2002. The bioactive agent according to item 1864, wherein Basidiomycete cell is *Ganoderma multipileum.*

2003. The bioactive agent according to item 1864, wherein Basidiomycete cell is *Ganoderma multiplicatum.*

2004. The bioactive agent according to item 1864, wherein Basidiomycete cell is *Ganoderma namutambalaense.*

2005. The bioactive agent according to item 1864, wherein Basidiomycete cell is *Ganoderma neglectus.*

2006. The bioactive agent according to item 1864, wherein Basidiomycete cell is *Ganoderma neojaponicum.*

2007. The bioactive agent according to item 1864, wherein Basidiomycete cell is *Ganoderma neurosporum.*

2008. The bioactive agent according to item 1864, wherein Basidiomycete cell is *Ganoderma nevadense.*

2009. The bioactive agent according to item 1864, wherein Basidiomycete cell is *Ganoderma nigrolucidum.*

2010. The bioactive agent according to item 1864, wherein Basidiomycete cell is *Ganoderma nitens.*

2011. The bioactive agent according to item 1864, wherein Basidiomycete cell is *Ganoderma nitidum.*

2012. The bioactive agent according to item 1864, wherein Basidiomycete cell *Ganoderma noukahivense.*

2013. The bioactive agent according to item 1864, wherein Basidiomycete cell is *Ganoderma nutans.*

2014. The bioactive agent according to item 1864, wherein Basidiomycete cell is *Ganoderma obockense.*

2015. The bioactive agent according to item 1864, wherein Basidiomycete cell is *Ganoderma obokensis.*

2016. The bioactive agent according to item 1864, wherein Basidiomycete cell is *Ganoderma ochrolaccatum.*

2017. The bioactive agent according to item 1864, wherein Basidiomycete cell is *Ganoderma oerstedii.*

2018. The bioactive agent according to item 1864, wherein Basidiomycete cell is *Ganoderma omphalodes.*

2019. The bioactive agent according to item 1864, wherein Basidiomycete cell is *Ganoderma opacum.*

2020. The bioactive agent according to item 1864, wherein Basidiomycete cell is *Ganoderma orbiforme.*

2021. The bioactive agent according to item 1864, wherein Basidiomycete cell is *Ganoderma oregonense.*

2022. The bioactive agent according to item 1864, wherein Basidiomycete cell is *Ganoderma oroflavum.*

2023. The bioactive agent according to item 1864, wherein Basidiomycete cell is *Ganoderma oroleucum.*

2024. The bioactive agent according to item 1864, wherein Basidiomycete cell is *Ganoderma ostracodes.*

2025. The bioactive agent according to item 1864, wherein Basidiomycete cell is *ostreatum.*

2026. The bioactive agent according to item 1864, wherein Basidiomycete cell is *Ganoderma papillatum*.
2027. The bioactive agent according to item 1864, wherein Basidiomycete cell is *Ganoderma parviungulatum*.
2028. The bioactive agent according to item 1864, wherein Basidiomycete cell is *Ganoderma parvulum*.
2029. The bioactive agent according to item 1864, wherein Basidiomycete cell is *Ganoderma pernanum*.
2030. The bioactive agent according to item 1864, wherein Basidiomycete cell is *Ganoderma personatum*.
2031. The bioactive agent according to item 1864, wherein Basidiomycete cell is *Ganoderma perturbatum*.
2032. The bioactive agent according to item 1864, wherein Basidiomycete cell is *Ganoderma petchii*.
2033. The bioactive agent according to item 1864, wherein Basidiomycete cell is *Ganoderma pfeifferi*.
2034. The bioactive agent according to item 1864, wherein Basidiomycete cell is *Ganoderma philippii*.
2035. The bioactive agent according to item 1864, wherein Basidiomycete cell is *Ganoderma platense*.
2036. The bioactive agent according to item 1864, wherein Basidiomycete cell is *Ganoderma plicatum*.
2037. The bioactive agent according to item 1864, wherein Basidiomycete cell is *Ganoderma polychromum*.
2038. The bioactive agent according to item 1864, wherein Basidiomycete cell is *Ganoderma polymorphum*.
2039. The bioactive agent according to item 1864, wherein Basidiomycete cell is *Ganoderma praelongum*.
2040. The bioactive agent according to item 1864, wherein Basidiomycete cell is *Ganoderma praetervisum*.
2041. The bioactive agent according to item 1864, wherein Basidiomycete cell is *Ganoderma preussii*.
2042. The bioactive agent according to item 1864, wherein Basidiomycete cell is *Ganoderma pseudoboletus*.
2043. The bioactive agent according to item 1864, wherein Basidiomycete cell is *Ganoderma pseudoferreum*.
2044. The bioactive agent according to item 1864, wherein Basidiomycete cell is *Ganoderma puberulum*.
2045. The bioactive agent according to item 1864, wherein Basidiomycete cell is *Ganoderma puglisii*.
2046. The bioactive agent according to item 1864, wherein Basidiomycete cell is *Ganoderma pulchella*.
2047. The bioactive agent according to item 1864, wherein Basidiomycete cell is *Ganoderma pullatum*.
2048. The bioactive agent according to item 1864, wherein Basidiomycete cell is *Ganoderma pulverulentum*.
2049. The bioactive agent according to item 1864, wherein Basidiomycete cell is *Ganoderma pygmoideum*.
2050. The bioactive agent according to item 1864, wherein Basidiomycete cell is *Ganoderma ramosissimum*.
2051. The bioactive agent according to item 1864, wherein Basidiomycete cell is *Ganoderma ravenehii*.
2052. The bioactive agent according to item 1864, wherein Basidiomycete cell is *Ganoderma renidens*.
2053. The bioactive agent according to item 1864, wherein Basidiomycete cell is *Ganoderma renii*.
2054. The bioactive agent according to item 1864, wherein Basidiomycete cell is *Ganoderma resinaceum*.
2055. The bioactive agent according to item 1864, wherein Basidiomycete cell is *Ganoderma reticulatosporum*.
2056. The bioactive agent according to item 1864, wherein Basidiomycete cell is *Ganoderma rhacode*.
2057. The bioactive agent according to item 1864, wherein Basidiomycete cell is *Ganoderma rivulosum*.
2058. The bioactive agent according to item 1864, wherein Basidiomycete cell is *Ganoderma rothwellii*.
2059. The bioactive agent according to item 1864, wherein Basidiomycete cell is *Ganoderma rotundatum*.
2060. The bioactive agent according to item 1864, wherein Basidiomycete cell is *Ganoderma rubeolum*.
2061. The bioactive agent according to item 1864, wherein Basidiomycete cell is *Ganoderma rude*.
2062. The bioactive agent according to item 1864, wherein Basidiomycete cell is *Ganoderma rufoalbum*.
2063. The bioactive agent according to item 1864, wherein Basidiomycete cell is *Ganoderma rufobadium*.
2064. The bioactive agent according to item 1864, wherein Basidiomycete cell is *Ganoderma rugosissimus*.
2065. The bioactive agent according to item 1864, wherein Basidiomycete cell is *Ganoderma rugosum*.
2066. The bioactive agent according to item 1864, wherein Basidiomycete cell is *Ganoderma sanmingense*.
2067. The bioactive agent according to item 1864, wherein Basidiomycete cell is *Ganoderma sarasinii*.
2068. The bioactive agent according to item 1864, wherein Basidiomycete cell is *Ganoderma schomburgkii*.
2069. The bioactive agent according to item 1864, wherein Basidiomycete cell is *Ganoderma sculpturatum*.
2070. The bioactive agent according to item 1864, wherein Basidiomycete cell is *Ganoderma septatum*.
2071. The bioactive agent according to item 1864, wherein Basidiomycete cell is *Ganoderma sequoiae*.
2072. The bioactive agent according to item 1864, wherein Basidiomycete cell is *Ganoderma sessile*.
2073. The bioactive agent according to item 1864, wherein Basidiomycete cell is *Ganoderma sessiliforme*.
2074. The bioactive agent according to item 1864, wherein Basidiomycete cell is *Ganoderma shandongense*.
2075. The bioactive agent according to item 1864, wherein Basidiomycete cell is *Ganoderma shangsiens*.
2076. The bioactive agent according to item 1864, wherein Basidiomycete cell is *Ganoderma sichuanense*.
2077. The bioactive agent according to item 1864, wherein Basidiomycete cell is *Ganoderma sikorae*.
2078. The bioactive agent according to item 1864, wherein Basidiomycete cell is *Ganoderma silveirae*.
2079. The bioactive agent according to item 1864, wherein Basidiomycete cell is *Ganoderma simaoense*.
2080. The bioactive agent according to item 1864, wherein Basidiomycete cell is *Ganoderma simulans*.
2081. The bioactive agent according to item 1864, wherein Basidiomycete cell is *Ganoderma sinense*.
2082. The bioactive agent according to item 1864, wherein Basidiomycete cell is *Ganoderma soniense*.
2083. The bioactive agent according to item 1864, wherein Basidiomycete cell is *Ganoderma soyeri*.
2084. The bioactive agent according to item 1864, wherein Basidiomycete cell is *Ganoderma sprucei*.
2085. The bioactive agent according to item 1864, wherein Basidiomycete cell is *Ganoderma staneri*.
2086. The bioactive agent according to item 1864, wherein Basidiomycete cell is *Ganoderma steyaertanum*.
2087. The bioactive agent according to item 1864, wherein Basidiomycete cell is *Ganoderma stipitatum*.
2088. The bioactive agent according to item 1864, wherein Basidiomycete cell is *Ganoderma stratoideum*.
2089. The bioactive agent according to item 1864, wherein Basidiomycete cell is *Ganoderma subamboinense*.
2090. The bioactive agent according to item 1864, wherein Basidiomycete cell is *Ganoderma subformicatum*.
2091. The bioactive agent according to item 1864, wherein Basidiomycete cell is *Ganoderma subfulvum*.

2092. The bioactive agent according to item 1864, wherein Basidiomycete cell is *Ganoderma subincrustatum*.
2093. The bioactive agent according to item 1864, wherein Basidiomycete cell is *Ganoderma sublucidum*.
2094. The bioactive agent according to item 1864, wherein Basidiomycete cell is *Ganoderma subperforatum*.
2095. The bioactive agent according to item 1864, wherein Basidiomycete cell is *Ganoderma subrenatum*.
2096. The bioactive agent according to item 1864, wherein Basidiomycete cell is *Ganoderma subresinosum*.
2097. The bioactive agent according to item 1864, wherein Basidiomycete cell is *Ganoderma subrugosus*.
2098. The bioactive agent according to item 1864, wherein Basidiomycete cell is *Ganoderma substipitata*.
2099. The bioactive agent according to item 1864, wherein Basidiomycete cell is *Ganoderma subtornatum*.
2100. The bioactive agent according to item 1864, wherein Basidiomycete cell is *Ganoderma subtuberculosum*.
2101. The bioactive agent according to item 1864, wherein Basidiomycete cell is *Ganoderma subumbraculum*.
2102. The bioactive agent according to item 1864, wherein Basidiomycete cell is *Ganoderma sulcatum*.
2103. The bioactive agent according to item 1864, wherein Basidiomycete cell is *Ganoderma tenue*.
2104. The bioactive agent according to item 1864, wherein Basidiomycete cell is *Ganoderma testaceum*.
2105. The bioactive agent according to item 1864, wherein Basidiomycete cell is *Ganoderma theaecolum*.
2106. The bioactive agent according to item 1864, wherein Basidiomycete cell is *Ganoderma tibetanum*.
2107. The bioactive agent according to item 1864, wherein Basidiomycete cell is *Ganoderma tornatum*.
2108. The bioactive agent according to item 1864, wherein Basidiomycete cell is *Ganoderma torosum*.
2109. The bioactive agent according to item 1864, wherein Basidiomycete cell is *Ganoderma torrendii*.
2110. The bioactive agent according to item 1864, wherein Basidiomycete cell is *Ganoderma trengganuense*.
2111. The bioactive agent according to item 1864, wherein Basidiomycete cell is *Ganoderma triangulum*.
2112. The bioactive agent according to item 1864, wherein Basidiomycete cell is *Ganoderma triviale*.
2113. The bioactive agent according to item 1864, wherein Basidiomycete cell is *Ganoderma tropicum*.
2114. The bioactive agent according to item 1864, wherein Basidiomycete cell is *Ganoderma trulla*.
2115. The bioactive agent according to item 1864, wherein Basidiomycete cell is *Ganoderma trulliforme*.
2116. The bioactive agent according to item 1864, wherein Basidiomycete cell is *Ganoderma tsugae*.
2117. The bioactive agent according to item 1864, wherein Basidiomycete cell is *Ganoderma tsunodae*.
2118. The bioactive agent according to item 1864, wherein Basidiomycete cell is *Ganoderma tuberculosum*.
2119. The bioactive agent according to item 1864, wherein Basidiomycete cell is *Ganoderma tumidum*.
2120. The bioactive agent according to item 1864, wherein Basidiomycete cell is *Ganoderma umbraculum*.
2121. The bioactive agent according to item 1864, wherein Basidiomycete cell is *Ganoderma umbrinum*.
2122. The bioactive agent according to item 1864, wherein Basidiomycete cell is *Ganoderma ungulatum*.
2123. The bioactive agent according to item 1864, wherein Basidiomycete cell is *Ganoderma valesiacum*.
2124. The bioactive agent according to item 1864, wherein Basidiomycete cell is *Ganoderma vanheurnii*.
2125. The bioactive agent according to item 1864, wherein Basidiomycete cell is *Ganoderma vanmeehii*.
2126. The bioactive agent according to item 1864, wherein Basidiomycete cell is *Ganoderma variabile*.
2127. The bioactive agent according to item 1864, wherein Basidiomycete cell is *Ganoderma weberianum*.
2128. The bioactive agent according to item 1864, wherein Basidiomycete cell is *Ganoderma williamsianum*.
2129. The bioactive agent according to item 1864, wherein Basidiomycete cell is *Ganoderma wuhuense*.
2130. The bioactive agent according to item 1864, wherein Basidiomycete cell is *Ganoderma wynaadense*.
2131. The bioactive agent according to item 1864, wherein Basidiomycete cell is *Ganoderma xanthocreas*.
2132. The bioactive agent according to item 1864, wherein Basidiomycete cell is *Ganoderma xingyiense*.
2133. The bioactive agent according to item 1864, wherein Basidiomycete cell is *Ganoderma xylodes*.
2134. The bioactive agent according to item 1864, wherein Basidiomycete cell is *Ganoderma xylonoides*.
2135. The bioactive agent according to item 1864, wherein Basidiomycete cell is *Ganoderma zhenningense*.
2136. The bioactive agent according to item 1864, wherein Basidiomycete cell is *Ganoderma zonatum*.
2137. The bioactive agent according to item 1498, wherein said Basidiomycete cell belongs to a species selected from the group consisting of *Grifola acanthoides, Grifola albicans, Grifola armeniaca, Grifola badia, Grifola colensoi, Grifola eos, Grifola fractipes, Grifola frondosa, Grifola gargal, Grifola gigantea, Grifola intybacea, Grifola lentifrondosa, Grifola obducta, Grifola platypora, Grifola rosularis, Grifola sordulenta, Grifola sulphurea, Grifola sumstinei* and *Grifola tuckahoe*.
2138. The bioactive agent according to item 2137, wherein Basidiomycete cell is *Grifola acanthoides*.
2139. The bioactive agent according to item 2137, wherein Basidiomycete cell is *Grifola albicans*.
2140. The bioactive agent according to item 2137, wherein Basidiomycete cell is *Grifola armeniaca*.
2141. The bioactive agent according to item 2137, wherein Basidiomycete cell is *Grifola badia*.
2142. The bioactive agent according to item 2137, wherein Basidiomycete cell is *Grifola colensoi*.
2143. The bioactive agent according to item 2137, wherein Basidiomycete cell is *Grifola eos*.
2144. The bioactive agent according to item 2137, wherein Basidiomycete cell is *Grifola fractipes*.
2145. The bioactive agent according to item 2137, wherein Basidiomycete cell is *Grifola frondosa*.
2146. The bioactive agent according to item 2137, wherein Basidiomycete cell is *Grifola gargal*.
2147. The bioactive agent according to item 2137, wherein Basidiomycete cell is *Grifola gigantea*.
2148. The bioactive agent according to item 2137, wherein Basidiomycete cell is *Grifola intybacea*.
2149. The bioactive agent according to item 2137, wherein Basidiomycete cell is *Grifola lentifrondosa*.
2150. The bioactive agent according to item 2137, wherein Basidiomycete cell is *Grifola obducta*.
2151. The bioactive agent according to item 2137, wherein Basidiomycete cell is *Grifola platypora*.
2152. The bioactive agent according to item 2137, wherein Basidiomycete cell is *Grifola rosularis*.
2153. The bioactive agent according to item 2137, wherein Basidiomycete cell is *Grifola sordulenta*.
2154. The bioactive agent according to item 2137, wherein Basidiomycete cell is *Grifola sulphurea*.

2155. The bioactive agent according to item 2137, wherein Basidiomycete cell is *Grifola sumstinei*.
2156. The bioactive agent according to item 2137, wherein Basidiomycete cell is *Grifola tuckahoe*.
2157. The bioactive agent according to item 1654, wherein said Basidiomycete cell belongs to a species selected from the group consisting of *Lentinus albovelutinus, Lentinus anthocephalus, Lentinus badius, Lentinus castoreus, Lentinus chrysopeplus, Lentinus cochleatus, Lentinus concinnus, Lentinus delicatus, Lentinus edodes, Lentinus fasciatus, Lentinus hyracinus, Lentinus lepideus sensu, Lentinus lepideus, Lentinus novaezelandiae, Lentinus pulvinulus, Lentinus punctaticeps, Lentinus punctaticeps, Lentinus pygmaeus, Lentinus sajor-caju, Lentinus squarrulosus, Lentinus strigosus, Lentinus suffrutescens, Lentinus tuber-regium* and *Lentinus zelandicus*.
2158. The bioactive agent according to item 2157, wherein Basidiomycete cell is *Lentinus albovelutinus*.
2159. The bioactive agent according to item 2157, wherein Basidiomycete cell is *Lentinus albovelutinus*.
2160. The bioactive agent according to item 2157, wherein Basidiomycete cell is *Lentinus anthocephalus*.
2161. The bioactive agent according to item 2157, wherein Basidiomycete cell is *Lentinus badius*.
2162. The bioactive agent according to item 2157, wherein Basidiomycete cell is *Lentinus castoreus*.
2163. The bioactive agent according to item 2157, wherein Basidiomycete cell is *Lentinus chrysopeplus*.
2164. The bioactive agent according to item 2157, wherein Basidiomycete cell is *Lentinus cochleatus*.
2165. The bioactive agent according to item 2157, wherein Basidiomycete cell is *Lentinus concinnus*.
2166. The bioactive agent according to item 2157, wherein Basidiomycete cell is *Lentinus delicatus*.
2167. The bioactive agent according to item 2157, wherein Basidiomycete cell is *Lentinus edodes*.
2168. The bioactive agent according to item 2157, wherein Basidiomycete cell is *Lentinus fasciatus*.
2169. The bioactive agent according to item 2157, wherein Basidiomycete cell is *Lentinus hyracinus*.
2170. The bioactive agent according to item 2157, wherein Basidiomycete cell is *Lentinus lepideus* sensu.
2171. The bioactive agent according to item 2157, wherein Basidiomycete cell is *Lentinus lepideus*.
2172. The bioactive agent according to item 2157, wherein Basidiomycete cell is *Lentinus novaezelandiae*.
2173. The bioactive agent according to item 2157, wherein Basidiomycete cell is *Lentinus pulvinulus*.
2174. The bioactive agent according to item 2157, wherein Basidiomycete cell is *Lentinus punctaticeps*.
2175. The bioactive agent according to item 2157, wherein Basidiomycete cell is *Lentinus pygmaeus*.
2176. The bioactive agent according to item 2157, wherein Basidiomycete cell is *Lentinus sajor-caju*.
2177. The bioactive agent according to item 2157, wherein Basidiomycete cell is *Lentinus squarrulosus*.
2178. The bioactive agent according to item 2157, wherein Basidiomycete cell is *Lentinus strigosus*.
2179. The bioactive agent according to item 2157, wherein Basidiomycete cell is *Lentinus suffrutescens*.
2180. The bioactive agent according to item 2157, wherein Basidiomycete cell is *Lentinus tuber-regium*.
2181. The bioactive agent according to item 2157, wherein Basidiomycete cell is *Lentinus zelandicus*.
2182. The bioactive agent according to item 1737, wherein said Basidiomycete cell belongs to a species selected from the group consisting of *Trametes cervina, Trametes cingulata, Trametes cotonea, Trametes gibbosa, Trametes hirsuta, Trametes incerta, Trametes lactine, Trametes maxima, Trametes meyenii, Trametes morganii, Trametes ochracea, Trametes pubescens, Trametes robiniophila, Trametes suaveolens, Trametes subsinuosa, Trametes tegularis, Trametes tenuis, Trametes trabea, Trametes umbrina, Trametes unicolor, Trametes versicolor, Trametes villosa* and *Trametes zonata*.
2183. The bioactive agent according to item 2182, wherein Basidiomycete cell is *Trametes cervina*.
2184. The bioactive agent according to item 2182, wherein Basidiomycete cell is *Trametes cingulata*.
2185. The bioactive agent according to item 2182, wherein Basidiomycete cell is *Trametes cotonea*.
2186. The bioactive agent according to item 2182, wherein Basidiomycete cell is *Trametes gibbosa*.
2187. The bioactive agent according to item 2182, wherein Basidiomycete cell is *Trametes hirsuta*.
2188. The bioactive agent according to item 2182, wherein Basidiomycete cell is *Trametes incerta*.
2189. The bioactive agent according to item 2182, wherein Basidiomycete cell is *Trametes lactine*.
2190. The bioactive agent according to item 2182, wherein Basidiomycete cell is *Trametes maxima*.
2191. The bioactive agent according to item 2182, wherein Basidiomycete cell is *Trametes meyenii*.
2192. The bioactive agent according to item 2182, wherein Basidiomycete cell is *Trametes morganii*.
2193. The bioactive agent according to item 2182, wherein Basidiomycete cell is *Trametes ochracea*.
2194. The bioactive agent according to item 2182, wherein Basidiomycete cell is *Trametes pubescens*.
2195. The bioactive agent according to item 2182, wherein Basidiomycete cell is *Trametes robiniophila*.
2196. The bioactive agent according to item 2182, wherein Basidiomycete cell is *Trametes suaveolens*.
2197. The bioactive agent according to item 2182, wherein Basidiomycete cell is *Trametes subsinuosa*.
2198. The bioactive agent according to item 2182, wherein Basidiomycete cell is *Trametes tegularis*.
2199. The bioactive agent according to item 2182, wherein Basidiomycete cell is *Trametes tenuis*.
2200. The bioactive agent according to item 2182, wherein Basidiomycete cell is *Trametes trabea*.
2201. The bioactive agent according to item 2182, wherein Basidiomycete cell is *Trametes umbrina*.
2202. The bioactive agent according to item 2182, wherein Basidiomycete cell is *Trametes unicolor*.
2203. The bioactive agent according to item 2182, wherein Basidiomycete cell is *Trametes versicolor*.
2204. The bioactive agent according to item 2182, wherein Basidiomycete cell is *Trametes villosa*.
2205. The bioactive agent according to item 2182, wherein Basidiomycete cell is *Trametes zonata*.
2206. A composition comprising the bioactive agent according to any of the items above and a physiologically acceptable carrier.
2207. A pharmaceutical composition comprising the bioactive agent according to any of the items above and a pharmaceutically acceptable carrier.
2208. Use of the pharmaceutical composition according to item 2207 in the manufacture of a medicament.

In one embodiment, the bioactive agent is an *Agaricus* bioactive agent. A bioactive agent from any of the below *Agaricus* species may be used in the present invention, such as any bioactive agents from the group consisting of: *Agaricus arorae, Agaricus arvensis, Agaricus augustus, Agaricus* benesi, *Agaricus bernardii, Agaricus bisporus, Agaricus bitorquis, Agaricus blazei* Murill yh (has reclassified as *Agaricus brasiliensis*), *Agaricus californicus, Agaricus campestris, Agaricus comptulus, Agaricus cupreo-brunneus, Agaricus diminutives, Agaricus fusco-fibrillosus, Agaricus fuscovelatus, Agaricus hondensis, Agaricus lilaceps, Agaricus micromegathus, Agaricus praeclaresquamosus, Agaricus pattersonae, Agaricus perobscurus, Agaricus semotus, Agaricus silvicola, Agaricus subrutilescens, Agaricus xanthodermus.*

It is preferred that the *Agaricus* bioactive agent is from any of the following: *A. blazei, A. blazei* Murill, *A. bisporus, A. hortensis, A. campestris*.

In a particularly preferred embodiment of the present invention, the *Agaricus* bioactive agent is from *A. blazei*, preferably *A. blazei* Murill.

In another preferred embodiment of the present invention, the *Agaricus* bioactive agent is from *A. bisporus*. In another preferred embodiment of the present invention, the *Agaricus* bioactive agent is from *A. hortensis*. In another preferred embodiment of the present invention, the *Agaricus* bioactive agent is from *A. campestris*

Accordingly, in a preferred embodiment of the present invention the compositions disclosed herein have been produced by an *Agaricus* fungus. Preferably, the compositions have been purified from the extracellular environment of an *Agaricus* fungus. Even more preferably the fungus, preferably a fungal mycelium, has been cultivated in a liquid growth medium and said composition has been purified from said liquid growth medium.

It is thus preferred that the composition of the invention has been produced by a method comprising the steps of
  i) cultivating an *Agaricus* fungus, such as an *Agaricus* fungal mycelium, in a liquid growth medium, and
  ii) isolating the composition from said liquid growth medium By fungal mycelium is intended any fungal biomass, which can be grown in a submerged culture. The fungal biomass may be in the form of single hyphae, spores, aggregates of mycelium, and partly differentiated mycelium.

The liquid growth medium may be any of the liquid growth media described herein below.

The *Agaricus* bioactive agent comprised in the kit of parts according to the present invention may be in solid or liquid form.

In one preferred embodiment, the *Agaricus* bioactive agent is selected from the group consisting of:
  agents comprising or consisting of an oligosaccharide,
  agents comprising or consisting of a polysaccharide,
  agents comprising or consisting of an optionally glycosylated peptide,
  agents comprising or consisting of an optionally glycosylated polypeptide,
  agents comprising or consisting of an oligonucleotide,
  agents comprising or consisting of a polynucleotide,
  agents comprising or consisting of a lipid,
  agents comprising or consisting of a fatty acid,
  agents comprising or consisting of a fatty acid ester and
  agents comprising or consisting of secondary metabolites.

Thus, in one preferred embodiment of the present invention, the *Agaricus* bioactive agent is selected from the group consisting of: an agent selected from an oligosaccharide, a polysaccharide and an optionally glycosylated polypeptide.

In another preferred embodiment of the present invention, the *Agaricus* bioactive agent is a polysaccharide.

In another preferred embodiment of the present invention, the *Agaricus* bioactive agent is an oligosaccharide.

In another preferred embodiment of the present invention, the *Agaricus* bioactive agent is an optionally glycosylated polypeptide.

In another preferred embodiment of the present invention, the *Agaricus* bioactive agent is a homopolymer In another preferred embodiment of the present invention, the *Agaricus* bioactive agent is a heteropolymer Further Characterisation of the *Agaricus* Bioactive Species:

In one preferred embodiment of the present invention, the *Agaricus* bioactive agent comprises or consists of an optionally glycosylated peptide.

In another preferred embodiment of the present invention, the *Agaricus* bioactive agent comprises or consists of a polypeptide In another preferred embodiment of the present invention, the *Agaricus* bioactive agent comprises or consists of an oligonucleotide In another preferred embodiment of the present invention, the *Agaricus* bioactive agent comprises or consists of a polynucleotide.

In another preferred embodiment of the present invention, the *Agaricus* bioactive agent comprises or consists of a lipid.

In another preferred embodiment of the present invention, the *Agaricus* bioactive agent comprises or consists of a fatty acid.

In another preferred embodiment of the present invention, the *Agaricus* bioactive agent comprises or consists of fatty acid esters.

In another preferred embodiment of the present invention, the *Agaricus* bioactive agent comprises or consists of secondary metabolite(s), such as steroids, shikimic acids, alkaloids and benzodiazepins.

In one embodiment, the *Agaricus* bioactive agent is a polysaccharide, such as a polysaccharide having a molar ratio of galactose:mannose:glucose of 1:10 to 20:30 to 50, such as 1:12 to 18:35 to 45; for example 1:14 to 16:38 to 42, such as 1:about 15:about 40, for example 1:15:40.

Accordingly, the *Agaricus* bioactive agent may in one embodiment comprise one or more polypeptides and/or a mixture of polysaccharides, wherein the majority of the polysaccharides of the composition has a molecular weight of at least 10,000 Da and wherein said one or more polypeptides and/or said mixture of polysaccharides comprises the monosaccharides galactose, mannose and glucose in the ratio (galactose:mannose:glucose) of 1:0 to 25:1 to 50, such as 1:10 to 20:30 to 50, such as 1:12 to 18:35 to 45; for example 1:14 to 16:38 to 42, such as 1:about 15:about 40, for example 1:15:40.

In another one embodiment, the *Agaricus* bioactive agent according to the present invention has a molar ratio of galactose:mannose:glucose of 1:0.5 to 5:6 to 12, such as 1:1 to 4:7 to 11; for example 1:1.5 to 3.5:7.5 to 10, such as 1:2.0 to 3.0:7.5 to 9.5, for example 1:2.2 to 2.8:8.0 to 9.0, such as 1:about 2.5:8.0 to 9.0, for example 1:2.5:8.0 to 9.0, such as 1:2.5:8.6.

Accordingly, the *Agaricus* bioactive agent according to the present invention can comprise one or more polypeptides and/or a mixture of polysaccharides, wherein the majority of the polysaccharides of the composition has a molecular weight of at least 10,000 Da and wherein said one or more polysaccharides and/or said mixture of polysaccharides comprises the monosaccharides galactose, mannose and glucose in the ratio (galactose:mannose:glucose) of 1:0 to 25:1 to 50, for example 1:0.5 to 5:6 to 12, such as 1:1 to 4:7 to 11; for example 1:1.5 to 3.5:7.5 to 10, such as 1:2.0 to 3.0:7.5 to 9.5, for example 1:2.2 to 2.8:8.0 to 9.0, such as 1:about 2.5:8.0 to 9.0, for example 1:2.5:8.0 to 9.0, such as 1:2.5:8.6.

Particularly Preferred Embodiments of the *Agaricus* Bioactive Agent

Particularly preferred embodiments of the *Agaricus* bioactive agent for use in the present invention are described below:

(1) In one preferred embodiment of the present invention, the *Agaricus* bioactive agent comprises or consists of the (1-4)-alpha D glucan and/or (1-6)-beta-D-glucan described by Fujimiya et al., ("Selective Tumoricial effect of soluble proteoglucan extracted from the basidiomycete, *Agaricus blazei* Murill, mediated via natural killer cell activation and apoptosis, Cancer Immunol Immunother (1998) 46: 147-159)

(2) In another preferred embodiment of the present invention, the *Agaricus* bioactive agent comprises or consists of the soluble beta-(1-6)-glucans described by Fujimiya et al., ("Peroral effect on tumour progression of soluble beta-(1,6)-glucans prepared by acid treatment from *Agaricus blazei*. Murr (Agaricaceae, Higher basidiomycetes). International Journal of Medicinal Mushrooms 2, 43-49).

(3) In another preferred embodiment of the present invention, the *Agaricus* bioactive agent comprises or consists of any of the following compounds described by Smith et al., ("Medicinal mushrooms: their therapeutic properties and current medical usage with special emphasis on cancer treatments.", downloadable from http://sci.cancerresearchuk.org/labs/med_mush/med_mush.html): $FI_1$-a-beta (beta-glucan from the fruiting body), FIII2-beta (beta glucan-protein from the fruiting body), FA-1a-beta (hetero-beta glucan from the fruiting body), FA-2b-beta (RNA from the fruiting body), FV-1 (insoluble beta-glucan from the fruiting body), ATOM (glucomannan-protein, isolated from submerged cultured mycelial biomass), AB-FP (mannan protein, isolated from the liquid cultured broth), Beta (1-6)-D-glucan.

(4) In another preferred embodiment of the present invention, the *Agaricus* bioactive agent comprises or consists of the beta-(1-6)-D:-glucan described by Kobayashi et al., ("Suppressing effects of daily oral supplementation of beta-glucan extracted from *Agaricus blazei* Murill on spontaneous and peritoneal disseminated metastasis in mouse model", J Cancer Res Clin Oncol. 2005 May 10)

(5) In another preferred embodiment of the present invention, the *Agaricus* bioactive agent comprises or consists of the HM3-G (molecular mass 380 kDa), mainly (1-4)-alpha D glucan with (1-6)-beta branching, described by Fujimiya et al., ("Selective Tumoricial effect of soluble proteoglucan extracted from the basidiomycete, *Agaricus blazei* Murill, mediated via natural killer cell activation and apoptosis, Cancer Immunol Immunother (1998) 46: 147-159).

(6) In another preferred embodiment of the present invention, the *Agaricus* bioactive agent comprises or consists of Glucomannan with a main chain of beta-1,2-linked D-mannopyranosyl residues and beta-D-glucopyranosyl-3-O-beta-D-glucopyranosyl residues as a side chain described by Mizuno et al. ("Anti-tumor polysaccharide from the mycelium of liquid-cultured *Agaricus blazei* mill", Biochem Mol Biol Int. 1999 April; 47(4):707-14)

(7) In another preferred embodiment of the present invention, the *Agaricus* bioactive agent comprises or consists of the polysaccharide fraction prepared using cold or hot NaOH extraction described by Ohno et al., (Antitumor beta glucan from the cultured fruit body of *Agaricus blazei*. Biol Pharm Bull. 2001 July; 24(7):820-8).

(8) In another preferred embodiment of the present invention, the *Agaricus* bioactive agent comprises or consists of the Glucomannan with a main chain of beta-1,2-linked D-mannopyranosyl residues and beta-D-glucopyranosyl-3-O-beta-D-glucopyranosyl residues as a side chain described by Mizuno et al. ("Anti-tumor polysaccharide from the mycelium of liquid-cultured *Agaricus blazei* mill", Biochem Mol Biol Int. 1999 April; 47(4):707-14)

(9) In another preferred embodiment of the present invention, the *Agaricus* bioactive agent comprises or consists of the alpha-1,4-glucan-beta-1,6-glucan complex with an average molecular weight of 20 kDa described by Fujimiya et al., (Tumor-specific cytocidal and immunopotentiating effects of relatively low molecular weight products derived from the basidiomycete, *Agaricus blazei* Murill. Anticancer Res. 1999 January-February; 19(1A):113-8)

(10) In another preferred embodiment of the present invention, the *Agaricus* bioactive agent comprises or consists of the complex of alpha-1,6- and alpha-1,4-glucan described by Mizuno et al., (Polysaccharides from *Agaricus blazei* stimulate lymphocyte T-cell subsets in mice. Biosci Biotechnol Biochem. 1998 March; 62(3):434-7)

(11) In another preferred embodiment of the present invention, the *Agaricus* bioactive agent comprises or consists of the ergosterol described by Takaku et al., (Isolation of an antitumor compound from *Agaricus blazei* Murill and its mechanism of action. J. Nutr. 2001 May; 131(5):1409-13)

(12) In another preferred embodiment of the present invention, the *Agaricus* bioactive agent comprises or consists of ATOM (glucomannan-protein, isolated from submerged cultured mycelial biomass) described by Ito et al., "Antitumour effects of a new polysaccharide-protein complex (ATOM) prepared from *Agaricus blazei* (Iwade strain 101) "Himematsutake" and its mechanisms in tumor-bearing mice", Anticancer research 17:277-284 (1997)

(13) In another preferred embodiment of the present invention, the *Agaricus* bioactive agent comprises or consists of the FIII-2-b ((1-6)-beta-D-glucan complex) described by Kawagishi et al. ("Formolysis of a potent antitumor (1-6)-beta-D-glucan-protein complex from *Agaricus blazei* fruiting bodies and antitumor activity of the resulting products. Carbohydr polymers 12:393-403, 1990)

(14) In another preferred embodiment of the present invention, the *Agaricus* bioactive agent comprises or consists of the Isoflavone-beta-D-glucan, produced by culturing *Agaricus blazei* mycelia in isoflavone-containing liquid medium described in US2005069989.

(15) In another preferred embodiment of the present invention, the *Agaricus* bioactive agent comprises or consists of the Glucomannan having a mannose chain of −1, −2 bonds as its primary chain described in JP 11080206.

(16) In another preferred embodiment of the present invention, the *Agaricus* bioactive agent comprises or consists of the polysaccharide described by Fan et al., "Production of polysaccharide by culinary-medicinal mushroom *Agaricus brasiliensis* S Wasser et al. LPB 03 (Agaricomycetideae) in submerged fermentation and its antitumor effect", International Journal of Medicinal Mushrooms 2003), 5(1), 17-23.

(17) In another preferred embodiment of the present invention, the *Agaricus* bioactive agent comprises or consists of the Linoleic acid; and/or 13-hydroxy cis-9, trans-11-octadecadienoic acid (13ZE-LOH) described in "Fruit body of a basidiomycete *Agaricus-Blazei*", Yakugaku Zasshi-Journal of the Pharmaceutical Society of Japan 1994

(18) In another preferred embodiment of the present invention, the *Agaricus* bioactive agent comprises or consists of the Ab-FP described by Liu et al., ("Fractionation of extracellular polysaccharide from *Agaricus blazei* murill and its antitumor activity", Shipin Yu Fajiao Gongye (2001), 27(11), 27-29;)

(19) In another preferred embodiment of the present invention, the *Agaricus* bioactive agent comprises or consists of the Glucan-protein complex described by Gonzaga et al., ("Isolation and characterisation of polysaccharides from *Agaricus blazei* Murill", Carbohydrate polymers 2005, Vol. 60, Iss 1, p 43-49)

(20) In another preferred embodiment of the present invention, the *Agaricus* bioactive agent comprises or consists of the Ap-MP (water-soluble mycelia polysaccharide) described by Liu et al., "Study on antitumor activity of *Agaricus blazei*".

(21) In another preferred embodiment of the present invention, the *Agaricus* bioactive agent comprises or consists of the 1SY16 described by Lee et al. ("1SY16 isolated from *Agaricus blazei* Murill K as a potent multipotential chemopreventative agent", Cancer Epidemiology Biomarkers and Prevention 2004, Vol 13, Iss 11, p 1861S).

(22) In another preferred embodiment of the present invention, the *Agaricus* bioactive agent comprises or consists of the Sodium pyroglutamate described by Kimura et al. ("Isolation of an anti-angiogenic substance from *Agaricus blazei* Murill: Its antitumor and antimetastatic actions", Cancer Science 2004, Vol 95, Iss 9, p 758-764).

(23) In another preferred embodiment of the present invention, the *Agaricus* bioactive agent comprises or consists of the Blazeispirane derivatives described by Hirotani et al., ("Blazeispirane and protoblazeispirane derivatives from the cultured mycelia of the fungus *Agaricus blazei*", Phytochemistry 2002, Vol. 61, Iss 5, p 589-595).

(24) In another preferred embodiment of the present invention, the *Agaricus* bioactive agent comprises or consists of any of the basidiolipids BI-1, BI-2, BI-3 or BI-4 as described by Jennemann et al., "Novel glycoinositolphosphosphingolipds, basidiolipds, from *Agaricus*", Eur. J. Biochem. 259, 331-338 (1999).

(25) In another preferred embodiment of the present invention, the *Agaricus* bioactive agent is a composition comprising one or more polypeptides and a mixture of polysaccharides, wherein the majority of the polysaccharides of the composition has a molecular weight of at least 10,000 Da and wherein said mixture of polysaccharides comprises the monosaccharides galactose, mannose and glucose in the ratio 1:0 to 25:1 to 50.

In another preferred embodiment of the present invention, the compound may be Beta-(1-3)-D-glucan, Beta-(1-4)-a-D-glucan or Beta-(1-6)-D-glucan.

The bioactive agent can be obtained from the extracellular medium after having been subjected to at least one further method step selected from a purification step or a precipitation step, such as precipitation by mixing the extracellular medium with an alcohol. The mycelium is removed from the liquid growth medium prior to the isolation of the bioactive agent. The fungal mycelium can be removed e.g. by filtration or centrifugation.

The bioactive agent can also be precipitated by ultracentrifugation. The bioactive agent can be size fractionated prior to precipitation or centrifugation and the bioactive agent can be further purified by one or more steps involving washing, desalting, size fractionation, and affinity chromatography, such as ion-exchange chromatography. In one embodiment, the bioactive agent is further purified by washing and ion-exchange chromatography.

The precipitated immune stimulating agent can also be further purified by size exclusion chromatography or gel filtration.

In one embodiment, the bioactive agent isolatable from the liquid growth medium is also produced intracellularly in said *Basidiomycete* sp. The bioactive agent isolatable from the liquid growth medium can be immunologically distinct from an intracellularly produced bioactive variant of the agent having essentially the same activity.

The liquid growth medium can comprise one or more of malt extract, yeast extract, peptone, glucose, sucrose, salts providing phosphate, magnesium and potassium, corn-steep liquor and vitamins, such as thiamine. In one embodiment, the liquid growth medium comprises malt extract, yeast extract, peptone, and glucose. The liquid growth medium is agitated and supplied with an oxygen source and the growth temperature is preferably in the range of from 23° C. to 32° C.

Modulation of the Immune System

The compositions according to the invention may be immune modulating, preferably, the compositions are immune stimulating. The stimulation of the immune system can be demonstrated by e.g. increased antibody production, by activation of helper T-cells, or by increased production of interleukins such as Interleukin 1 and Interleukin 2.

Any assay known to the skilled person, which is suitable for testing whether a composition is immune modulating may be employed to test whether a composition of the present invention is immune modulating. Such an assay may be an in vitro or an in vivo assay.

One preferred assay is to test whether the composition is capable of inducing IL-1 production, such as IL1-α and/or IL1-β production. Thus, in a preferred embodiment of the invention, the composition according to the present invention is capable of inducing IL-1 production from at least one kind of IL-1 producing cells in an in-vitro assay. The cells may be any IL-1 producing cells, such as P388 mouse macrophage cells. IL-1 production may be determined using any suitable assay. In general, assays involving the use of specific IL-1 antibodies, such as specific IL1-α and/or IL1-β antibodies, are useful. Such assays may for example be Western blotting, ELISA or similar assays. The assay may be performed as described in example 4.

Because it is difficult to calibrate an IL1 assay, the assay is preferably performed using a specific composition as reference. Thus in one preferred embodiment of the present invention, the composition is capable of inducing production of at least 1.5, preferably at least 2, such as at least 4, for example at least 6, such as at least 8, for example at least 10, such as at least 15, for example at least 20, such as at least 30, for example at least 40 times more IL1-α, than the amount of IL1-α induced using the commercially available Lentinan for injection (Eureka Bio-Chemicals Pty, Little Collins Street. Melbourne 3000, Australia) in a reference experiment performed in parallel. In one preferred embodiment of the present invention, the composition is capable of inducing production of at least 1.5, preferably at least 2, such as at least 4, for example at least 6, such as at least 8, for example at least 10, such as at least 15, for example at least 20 times more IL1-β, than the amount of IL1-β induced using Lentinan for injection from Eureka Biochemicals Pty. in a reference experiment performed in parallel. Preferably, the aforementioned assays are performed as described in example 4. It is most preferred that the composition induced production of both IL1α and IL1β as described above.

In another embodiment of the invention, the composition is capable of enhancing antibody production in a mammal, when administered to said mammal. The mammal may for example be a mouse, rat, rabbit or even a human being. Preferably such an assay is performed by administering the composition to a mammal prior to and simultaneously with administration of an antigen, optionally in the presence of an adjuvant. Preferably, the composition is administered in the range of 1 to 30 days, preferably in the range of 1 to 10 days, more preferably in the range of 1 to 3 days prior to administration of the antigen. Subsequently, antibody production in the mammal may be determined. The composition is preferably capable of inducing production of at least 1.5, more preferably at least 2, even more preferably at least 2.5, such as at least 3, for example at least 4, such as 6 times more antibody compared to the amount of antibody produced without administration of the composition. An example of such an assay is outlined in example 6.

It is preferred that the composition is immune modulating in more than one assay system, such as in a combination of any of the assay systems described herein above.

Manufacture of an *Agaricus* Bioactive Agent

Methods of manufacture of the bioactive agent for use in the present invention are well-known to those skilled in the art, such as disclosed in any of the following references, incorporated herein by reference: Fujimiya et al., ("Selective Tumoricial effect of soluble proteoglucan extracted from the basidiomycete, *Agaricus blazei* Murill, mediated via natural killer cell activation and apoptosis, Cancer Immunol Immunother (1998) 46: 147-159); Fujimiya et al., ("Peroral effect on tumour progression of soluble beta-(1,6)-glucans prepared by acid treatment from *Agaricus blazei*. Murr (Agaricaceae, Higher basidiomycetes). International Journal of Medicinal Mushrooms 2, 43-49); Smith et al., ("Medicinal mushrooms: their therapeutic properties and current medical usage with special emphasis on cancer treatments.", downloadable from http://sci.cancerresearchuk.org/labs/med_mush/med_mush.html); Kobayashi et al., ("Suppressing effects of daily oral supplementation of beta-glucan extracted from *Agaricus blazei* Murill on spontaneous and peritoneal disseminated metastasis in mouse model", J Cancer Res Clin Oncol. 2005 May 10); Fujimiya et al., ("Selective Tumoricial effect of soluble proteoglucan extracted from the basidiomycete, *Agaricus blazei* Murill, mediated via natural killer cell activation and apoptosis, Cancer Immunol Immunother (1998) 46: 147-159); Mizuno et al. ("Anti-tumor polysaccharide from the mycelium of liquid-cultured *Agaricus blazei* mill", Biochem Mol Biol Int. 1999 April; 47(4):707-14); Ohno et al., (Antitumor beta glucan from the cultured fruit body of *Agaricus blazei*. Biol Pharm Bull. 2001 July; 24(7):820-8); Mizuno et al. ("Anti-tumor polysaccharide from the mycelium of liquid-cultured *Agaricus blazei* mill", Biochem Mol Biol Int. 1999 April; 47(4):707-14); Fujimiya et al., (Tumor-specific cytocidal and immunopotentiating effects of relatively low molecular weight products derived from the basidiomycete, *Agaricus blazei* Murill. Anticancer Res. 1999 January-February; 19(1A):113-8); Mizuno et al., (Polysaccharides from *Agaricus blazei* stimulate lymphocyte T-cell subsets in mice. Biosci Biotechnol Biochem. 1998 March; 62(3):434-7); Takaku et al., (Isolation of an antitumor compound from *Agaricus blazei* Murill and its mechanism of action. J. Nutr. 2001 May; 131(5):1409-13); Ito et al., "Antitumour effects of a new polysaccharide-protein complex (ATOM) prepared from *Agaricus blazei* (Iwade strain 101) "Himematsutake" and its mechanisms in tumor-bearing mice", Anticancer research 17:277-284 (1997); Kawagishi et al. ("Formolysis of a potent antitumor (1-6)-beta-D-glucan-protein complex from *Agaricus blazei* fruiting bodies and antitumor activity of the resulting products. Carbohydr polymers 12:393-403, 1990); US2005069989; JP 11080206; Fan et al., "Production of polysaccharide by culinary-medicinal mushroom *Agaricus brasiliensis* S Wasser et al. LPB 03 (Agaricomycetideae) in submerged fermentation and its antitumor effect", International Journal of Medicinal Mushrooms 2003), 5(1), 17-23; "Fruit body of a basidiomycete *Agaricus-Blazei*", Yakugaku Zasshi-Journal of the Pharmaceutical Society of Japan 1994; Liu et al., ("Fractionation of extracellular polysaccharide from *Agaricus blazei* murill and its antitumor activity", Shipin Yu Fajiao Gongye (2001), 27(11), 27-29;); Gonzaga et al., ("Isolation and characterisation of polysaccharides from *Agaricus blazei* Murill", Carbohydrate polymers 2005, Vol. 60, Iss 1, p 43-49); Liu et al., "Study on antitumor activity of *Agaricus blazei*"; Lee et al. ("1SY16 isolated from *Agaricus blazei* Murill K as a potent multipotential chemopreventative agent", Cancer Epidemiology Biomarkers and Prevention 2004, Vol 13, Iss 11, p 1861S); Kimura et al. ("Isolation of an anti-angiogenic substance from *Agaricus blazei* Murill: Its antitumor and antimetastatic actions", Cancer Science 2004, Vol 95, Iss 9, p 758-764); Hirotani et al., ("Blazeispirane and protoblazeispirane derivatives from the cultured mycelia of the fungus *Agaricus blazei*", Phytochemistry 2002, Vol. 61, Iss 5, p 589-595); Jennemann et al., "Novel glycoinositolphosphosphingolipds, basidiolipds, from *Agaricus*", Eur. J. Biochem. 259, 331-338 (1999).

It is preferred that the *Agaricus* species is produced in a liquid medium using submerged fermentation techniques. The liquid growth medium may in one embodiment comprise one or more of malt extract, yeast extract, peptone, glucose, sucrose, salts providing phosphate, magnesium and potassium, corn-steep liquor and vitamins, such as thiamine. *Agaricus* may also be grown in a liquid growth medium comprising malt extract, yeast extract, peptone, and glucose.

For use in the present invention, the *Agaricus* may be grown in a liquid growth medium which is agitated and supplied with an oxygen source.

For use in the present invention, the *Agaricus* may be grown at a temperature in the range of from 23° C. to 32° C.

For use in the present invention, the *Agaricus* mycelium may be removed from the liquid growth medium prior to the isolation of the *Agaricus* bioactive agent.

For use in the present invention, the *Agaricus* fungal mycelium may be removed from the initial *Agaricus* culture by filtration or centrifugation.

Individual Treated Using the Compositions of the Present Invention

Any individual may be treated using the kit-of-parts according to the invention, for example in any of the uses or methods described herein. Preferably, said individual is a mammal, such as a human being. In one embodiment of the present invention, the individual is immunocompromised.

In one embodiment of the present invention, said individual is elderly, such as 60-120 years old, for example 70-120 years old, such as 80-120 years old, for instance 90-120 years old. In another embodiment of the present invention, said individual is 20-60 years old, such as 30-50 years old. In another embodiment of the present invention, said individual is a child, such as from 0-20 years old, for example 0-15 years old, such as 0-10 years old, for example 0-5 years old, such as 0-1 years old, such as a newborn child less than 2 months old.

Pharmaceutical Composition

While it is possible for the compounds or salts thereof useful in the present invention to be administered as the raw chemical, it is preferred to present them in the form of a pharmaceutical composition. The anti-cancer compound and *Agaricus* bioactive agent may be co-formulated as two separate pharmaceutical compositions.

In one particular embodiment the invention relates to the use of a pharmaceutical composition comprising a mixture of at least two different *Agaricus* bioactive compounds and/or at least one or two anti-cancer medicaments.

The pharmaceutical composition may comprise any anti-cancer agent and/or *Agaricus* bioactive agent or a pharmaceutically acceptable salt thereof, and pharmaceutically acceptable carriers, vehicles and/or excipients. Said composition may further optionally comprise transport molecules. The transport molecules are primarily added in order to increase the half-life of the compound(s). Transport molecules act by having incorporated into or anchored to it the compound according to the invention.

Any suitable transport molecules known to the skilled person may be used, such as liposomes, micelles, and/or microspheres.

Conventional liposomes are typically composed of phospholipids (neutral or negatively charged) and/or cholesterol. The liposomes are vesicular structures based on lipid bilayers surrounding aqueous compartments. They can vary in their physiochemical properties such as size, lipid composition, surface charge and number and fluidity of the phospholipids bilayers. The most frequently used lipid for liposome formation are: 1,2-Dilauroyl-sn-Glycero-3-Phosphocholine (DLPC), 1,2-Dimyristoyl-sn-Glycero-3-Phosphocholine (DMPC), 1,2-Dipalmitoyl-sn-Glycero-3-Phosphocholine (DPPC), 1,2-Distearoyl-sn-Glycero-3-Phosphocholine (DSPC), 1,2-Dioleoyl-sn-Glycero-3-Phosphocholine (DOPC), 1,2-Dimyristoyl-sn-Glycero-3-Phosphoethanolamine (DMPE), 1,2-Dipalmitoyl-sn-Glycero-3-Phosphoethanolamine (DPPE), 1,2-Dioleoyl-sn-Glycero-3-Phosphoethanolamine (DOPE), 1,2-Dimyristoyl-sn-Glycero-3-Phosphate (Monosodium Salt) (DMPA), 1,2-Dipalmitoyl-sn-Glycero-3-Phosphate (Monosodium Salt) (DPPA), 1,2-Dioleoyl-sn-Glycero-3-Phosphate (Monosodium Salt) (DOPA), 1,2-Dimyristoyl-sn-Glycero-3-[Phospho-rac-(1-glycerol)] (Sodium Salt) (DMPG), 1,2-Dipalmitoyl-sn-Glycero-3-[Phospho-rac-(1-glycerol)] (Sodium Salt) (DPPG), 1,2-Dioleoyl-sn-Glycero-3-[Phospho-rac-(1-glycerol)] (Sodium Salt) (DOPG), 1,2-Dimyristoyl-sn-Glycero-3-[Phospho-L-Serine] (Sodium Salt) (DMPS), 1,2-Dipalmitoyl-sn-Glycero-3-[Phospho-L-Serine) (Sodium Salt) (DPPS), 1,2-Dioleoyl-sn-Glycero-3-[Phospho-L-Serine] (Sodium Salt) (DOPS), 1,2-Dioleoyl-sn-Glycero-3-Phosphoethanolamine-N-(glutaryl) (Sodium Salt) and 1,1',2,2'-Tetramyristoyl Cardiolipin (Ammonium Salt). Formulations composed of DPPC in combination with other lipid or modifiers of liposomes are preferred e.g. in combination with cholesterol and/or phosphatidylcholine.

Long-circulating liposomes are characterized by their ability to extravasate at body sites where the permeability of the vascular wall is increased. The most popular way to produce long circulating liposomes is to attach hydrophilic polymer polyethylene glycol (PEG) covalently to the outer surface of the liposome. Some of the preferred lipids are: 1,2-Dipalmitoyl-sn-Glycero-3-Phosphoethanolamine-N-[Methoxy (Polyethylene glycol)-2000] (Ammonium Salt), 1,2-Dipalmitoyl-sn-Glycero-3-Phosphoethanolamine-N-[Methoxy (Polyethylene glycol)-5000] (Ammonium Salt), 1,2-Dioleoyl-3-Trimethylammonium-Propane (Chloride Salt) (DOTAP).

A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837, 028, all of which are incorporated herein by reference. One method is described in example 9. Another method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder like form. This film is covered with an aqueous solution of the targeted drug and the targeting component and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate. Additionally, the liposome suspension may include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

Micelles are formed by surfactants (molecules that contain a hydrophobic portion and one or more ionic or otherwise strongly hydrophilic groups) in aqueous solution. As the concentration of a solid surfactant increases, its monolayers adsorbed at the air/water or glass/water interfaces become so tightly packed that further occupancy requires excessive compression of the surfactant molecules already in the two monolayers. Further increments in the amount of dissolved surfactant beyond that concentration cause amounts equivalent to the new molecules to aggregate into micelles. This process begins at a characteristic concentration called "critical micelle concentration".

The shape of micelles formed in dilute surfactant solutions is approximately spherical. The polar head groups of the surfactant molecules are arranged in an outer spherical shell whereas their hydrocarbon chains are oriented toward the center, forming a spherical core for the micelle. The hydrocarbon chains are randomly coiled and entangled and the micellar interior has a nonpolar, liquid-like character. In the micelles of polyoxyethylated non-ionic detergents, the polyoxyethlene moieties are oriented outward and permeated by water. This arrangement is energetically favourable since the hydrophilic head groups are in contact with water and the hydrocarbon moieties are removed from the aqueous medium and partly shielded from contact with water by the polar head groups. The hydrocarbon tails of the surfactant molecules, located in the interior of the micelle, interact with one another by weak van der Waals forces.

The size of a micelle or its aggregation number is governed largely by geometric factors. The radius of the hydrocarbon core cannot exceed the length of the extended hydrocarbon chain of the surfactant molecule. Therefore, increasing the chain length or ascending homologous series increases the aggregation number of spherical micelles. If the surfactant concentration is increased beyond a few percent and if electrolytes are added (in the case of ionic surfactants) or the temperature is raised (in the case of non-ionic surfactants), the micelles increase in size. Under these conditions, the micelles are too large to remain spherical and become ellipsoidal, cylindrical or finally lamellar in shape.

Common surfactants well known to one of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127 (Wyandotte Chemicals Corp.). Preferred surfactants are nonionic polyoxyethylene and polyoxypropylene detergents compatible with IV injection such as, TWEEN-80., PLURONIC F-68., n-octyl-.beta.-D-glucopyranoside, and the like. In addition, phospholipids, such as those described for use in the production of liposomes, may also be used for micelle formation.

In another preferred embodiment, the compounds of the present invention are formulated as described in the literature for an administration route selected from: buccal delivery, sublingual delivery, transdermal delivery, inhalation and needle-free injection, such as using the methods developed by Powderjet.

For inhalation, the compounds of the present invention can be formulated as using methods known to those skilled in the art, for example an aerosol, dry powder or solubilized such as in micro droplets, preferably in a device intended for such delivery (such as commercially available from Aradigm, Alkerme or Nektar).

Pharmaceutical compositions of the present invention may contain a physiologically tolerable carrier together with at least one compound according to the present invention, dissolved or dispersed therein as an active ingredient.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. It is preferred that the formulation has a pH within the range of 3.5-8, such as in the range 4.5-7.5, such as in the range 5.5-7, such as in the range 6-7.5, most preferably around 7.3. However, as is understood by one skilled in the art, the pH range may be adjusted according to the individual treated and the administration procedure. For example, in another preferred embodiment of the invention the formulation has a pH within the range 3.5-7, such as 4-6, such as 5-6, such as 5.3-5.7, such as 5.5.

The pharmaceutical composition of the present invention can include pharmaceutically acceptable salts of the compounds therein. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by e.g. oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

Other suitable pharmaceutically acceptable salts include the acid addition salts (formed with the free amino groups of the polypeptide). Other examples of salts include pharmaceutically acceptable acid addition salts, pharmaceutically acceptable metal salts, ammonium salts and alkylated ammonium salts. Acid addition salts include salts of inorganic acids as well as organic acids. Representative examples of suitable inorganic acids include hydrochloric, hydrobromic, hydriodic, phosphoric, sulfuric and nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, ethylenediaminetetraacetic (EDTA), p-aminobenzoic, glutamic, benzenesulfonic and ptoluenesulfonic acids and the like. Further examples of pharmaceutically acceptable inorganic or organic acid addition salts include the pharmaceutical acceptable salts listed in J. Pharm. Sci. 1977, 66, 2, which is incorporated herein by reference. Examples of metal salts include lithium, sodium, potassium and magnesium salts and the like.

Examples of ammonium and alkylated ammonium salts include ammonium, methylammonium, dimethylammonium, trimethylammonium, ethylammonium, hydroxyethylammonium, diethylammonium, butylammonium and tetramethylammonium salts and the like.

Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Also included within the scope of compounds or pharmaceutical acceptable acid addition salts thereof in the context of the present invention are any hydrates (hydrated forms) thereof.

For parenteral administration, solutions of the present compounds in sterile aqueous solution, aqueous propylene glycol or sesame or peanut oil may be employed. Such aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Administered by nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

The pharmaceutical compositions formed by combining the compounds of the invention and the pharmaceutical acceptable carriers are then readily administered in a variety of dosage forms suitable for the disclosed routes of administration. The formulations may conveniently be presented in unit dosage form by methods known in the art of pharmacy.

In a preferred embodiment of the invention the formulation comprises the compound or salt(s) thereof as a lyophilisate and the formulation further comprises a solvent, said lyophilisate and said solvent being in separate compartments until administration.

Administration

The components of the kit-of-parts according to the present invention do not have to be administered concurrently, however in one preferred embodiment the anti-cancer medicament is administered simultaneously with the administration of the *Agaricus* bioactive agent, such as in a co-formulation. In another preferred embodiment, the anti-cancer medicament and the bioactive agent are administered sequentially, in any order, such as first the *Agaricus* bioactive agent and then the anti-cancer medicament.

In one preferred embodiment of the present invention, the medicament and/or agent are administered subcutaneously.

In another preferred embodiment of the present invention, the medicament and/or agent are administered nasally.

In another preferred embodiment of the present invention, the medicament and/or agent are administered via the pulmonary route, such as via aerosol administration.

In another preferred embodiment of the present invention, the medicament and/or agent are administered via parenteral administration.

In another preferred embodiment of the present invention, said medicament and/or agent are administered orally.

In another preferred embodiment of the present invention, said medicament and/or agent are administered topically.

In another preferred embodiment of the present invention, said medicament and/or agent are co-formulated in a composition.

The kit-of-parts according to the present invention may comprise two or more administration types, but co-formulation or at least the same administration route is preferred for all the elements in the kit-of-parts.

In another aspect the *Agaricus* agent and/or anti-cancer medicament is administered as a bolus, wherein the administration form may be any suitable parenteral form.

In a preferred embodiment the *Agaricus* agent and/or anti-cancer medicament is administered subcutaneously in a bolus.

Pharmaceutical compositions for parenteral administration include sterile aqueous and non-aqueous injectable solutions, dispersions, suspensions or emulsions, as well as sterile powders to be reconstituted in sterile injectable solutions or dispersions prior to use.

Other suitable administration forms include suppositories, sprays, ointments, cremes, gels, inhalants, dermal patches, implants, pills, tablets, lozenges and capsules.

The compounds of the present invention may be formulated for nasal administration. The solutions or suspensions are applied directly to the nasal cavity by conventional means, for example with a dropper, pipette or spray. The compositions may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Compositions administered by aerosols may be prepared, for example, as solutions in saline, employing benzyl alcohol or other suitable preservatives, absorption promoters to enhance bioavailability, employing fluorocarbons, and/or employing other solubilizing or dispersing agents.

Compositions for Oral Administration

Those compound types capable of remaining biologically active in an individual after oral administration (such as e.g. small molecules and short peptides) can be formulated in a wide range of oral administration dosage forms. The pharmaceutical compositions and dosage forms may comprise the compounds of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, wetting agents, tablet disintegrating agents, or an encapsulating material.

Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. The powders and tablets preferably containing from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the composition of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

Other forms suitable for oral administration include liquid form preparations including emulsions, syrups, elixirs, aqueous solutions, aqueous suspensions, toothpaste, gel dentifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavours, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilizers, buffers, artificial and natural sweeteners, dispersants, thickeners, solubilizing agents, and the like.

Compositions for Parenteral Administration

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water. Aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Solutions of the compound(s) or pharmaceutically acceptable salt(s) thereof, (and for example antigenic epitopes and protease inhibitors) can be prepared in water or saline, and optionally mixed with a nontoxic surfactant. Compositions for intravenous or intra-arterial administration may include sterile aqueous solutions that may also contain buffers, liposomes, diluents and other suitable additives.

Oils useful in parenteral compositions include petroleum, animal, vegetable, or synthetic oils. Specific examples of oils useful in such compositions include peanut, soybean, sesame, cottonseed, corn, olive, petrolatum, and mineral. Suitable fatty acids for use in parenteral compositions include oleic acid, stearic acid, and isostearic acid. Ethyl oleate and isopropyl myristate are examples of suitable fatty acid esters.

Suitable soaps for use in parenteral compositions include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-.beta.-aminopropionates, and 2-alkyl-imidazoline quaternary ammonium salts, and (e) mixtures thereof.

The parenteral compositions typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such compositions will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral compositions can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The pharmaceutical dosage forms suitable for injection or infusion can include sterile aqueous solutions or dispersions comprising the active ingredient that are adapted for administration by encapsulation in liposomes. In all cases, the ultimate dosage form must be sterile, fluid and stable under the conditions of manufacture and storage.

Sterile injectable solutions are prepared by incorporating the compound or pharmaceutically acceptable salt thereof in the required amount in the appropriate solvent with various of the other ingredients enumerated above, as required, followed by filter sterilization.

Compositions for Topical Administration

The compounds of the invention can also be delivered topically. Regions for topical administration include the skin surface and also mucous membrane tissues of the rectum, nose, mouth, and throat. Compositions for topical administration via the skin and mucous membranes should not give rise to signs of irritation, such as swelling or redness.

The topical composition may include a pharmaceutically acceptable carrier adapted for topical administration. Thus, the composition may take the form of a suspension, solution, ointment, lotion, cream, foam, aerosol, spray, suppository, implant, inhalant, tablet, capsule, dry powder, syrup, balm or lozenge, for example. Methods for preparing such compositions are well known in the pharmaceutical industry.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Compositions suitable for topical administration in the mouth include lozenges comprising active agents in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Creams, ointments or pastes according to the present invention are semi-solid compositions of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The composition may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

The compounds described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987). Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

A variety of types of transdermal patches will find use in the methods described herein. For example, a simple adhesive patch can be prepared from a backing material and an acrylate adhesive. The compound(s) are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the compound(s). The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

The liquid reservoir patch will also find use in the methods described herein. This patch comprises an impermeable or semipermeable, heat sealable backing material, a heat sealable membrane, an acrylate based pressure sensitive skin adhesive, and a siliconized release liner. The backing is heat sealed to the membrane to form a reservoir which can then be filled with a solution of the complex, enhancers, gelling agent, and other excipients.

Foam matrix patches are similar in design and components to the liquid reservoir system, except that the gelled compound solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system. See U.S. Pat. Nos. 4,816,258; 4,927,408; 4,904,475; 4,588,580, 4,788,062; and the like. The rate of drug delivery will be dependent, in part, upon the nature of the membrane. For example, the rate of drug delivery across membranes within the body is generally higher than across dermal barriers. The rate at which the compound(s) is delivered from the device to the membrane is most advantageously controlled by the use of rate-limiting membranes which are placed between the reservoir and the skin. Assuming that the skin is sufficiently permeable to the compound (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

Compositions for Administration as Suppositories

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The active compound may be formulated into a suppository comprising, for example, about 0.5% to about 50% of a compound of the invention, disposed in a polyethylene glycol (PEG) carrier (e.g., PEG 1000 [96%] and PEG 4000 [4%].

Dosage

Suitable dosing regimens for the various compounds and methods of the present invention are preferably determined taking into account factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug.

The compositions of the invention may be administered using any suitable administration form; usually however, administration will be oral or parenteral. Oral administration in the form of a syrup comprising the composition and/or a capsule containing a syrup comprising the composition or in a powder form of the composition is preferred.

The dosage requirements will vary with the particular composition employed, the route of administration and the particular individual being treated. Ideally, an individual to be treated by the present method will receive a pharmaceutically effective amount of the compound in the maximum tolerated dose.

In general the daily (preferably oral) dosage regimen may be about 0.001 to about 100 mg/kg, preferably in the range of 0.01 to 50 mg/kg, more preferably in the range of 0.1 to 10, even more preferably in the range of 1 to 2 mg/kg of total body weight. It will also be recognised by one skilled in the art that the optimal quantity and spacing of individual dosages of the composition will be determined by the nature and extent of the condition being treated, the form, route and site of administration, and the particular patient being treated, and that such optimums can be determined by conventional techniques. It will also be appreciated by one skilled in the art that the optimal course of treatment, i.e., the number of doses of the composition given per day for a defined number of days, can be ascertained by those skilled in the art using conventional course of treatment determination tests.

It is preferred that the kit according to the present invention comprises dosage regime instructions with guidelines for dose and time administration.

Medical Methods and Use

One aspect of the present invention relates to use of any of the anti-cancer medicaments described herein and any of the *Agaricus* bioactive agents described herein for the manufacture of a kit of parts suitable for administration to an individual in need thereof, preferably for treatment or prophylaxis of a neoplastic disease, such as any of the diseases described herein.

In one preferred embodiment of the present invention, the *Agaricus* bioactive agent stimulates the immune system of an animal or a human when administered to said animal or human in a pharmaceutically active amount. Preferably, said agent is capable of stimulating in an individual in need of such stimulation, the production of one or more of antibodies, such as IgG, IgA, and IgE, T helper cells, interleukins, such as IL-1 and IL-2, interferon, such as IFN-gamma, natural killer cells, and macrophages.

It is further envisaged that any of the uses and products described herein may be used in a method for the treatment of a neoplastic disease in an individual, said method comprising the steps of
  a. providing any of the kit of parts as described herein, and
  b. administering any of the anti-cancer medicaments and *Agaricus* bioactive agents described herein to said individual.

EXAMPLES

The following examples describe illustrative embodiments of the invention and should not be regarded as limiting for the invention.

Example 1

Protocol for cultivation of Basidiomycete cells according to the present invention. The protocol is used in the further examples unless otherwise stated.

Cultivation Conditions:
Temperature: 25° C.±1° C.
pH: Medium pH
Water: Tap water
Medium: Glucose 30 g/l;
  Mycological peptone 10 g/l;
  Yeast extract 6 g/l
  Malt extract 6 g/l Plate Cultivation of Basidiomycete Cells 15 cm Petri dishes containing about 60 ml of the medium+agar at a concentration corresponding to 15 g/l. Inoculate the plates by scraping off the top layer of mycelium on a Petri dish using a sterile scalpel and spread it onto the new plate. One Petri dish will yield enough mycelium to inoculate three new plates. Cultivate the plates at 25° C. for at least three weeks prior to use. They can be kept at this temperature for a total of 7 more weeks before they should be discarded.

Shake Flask Cultivation of Basidiomycete Cells 500 ml Ehrlenmeyer flasks containing 200 ml of medium. Scrape off the top layer of mycelium on two plates using a sterile scalpel and place in a 300 ml Ehrlenmeyer flask containing 100 ml of medium. Homogenise the resulting mixture. Inoculate the 500 ml flasks with 50 ml of the homogenised material per flask. Put on orbital shaker at 25° C. and 140 rpm and leave for 7-10 days. If required, longer fermentation periods can also be used, such as e.g. 15-30 days.

Fermenter (3 Liters) Cultivation of Basidiomycete Cells

Place 1.7 liters of the medium in the fermenter and sterilise at 121° C. for 20 mins. Set the fermentation conditions: 25° C., 200-300 rpm and air at 0.2-0.5 vvm. Decant as much liquid as possible from two shake flasks and inoculate the fermenter with the remaining broth (this will normally amount to 300-500 ml). Add a suitable antifoam agent when required (normally throughout the run). Harvests after 6-8 days. If required, longer fermentation periods can also be used, such as e.g. 15-30 days.

Harvesting of Basidiomycete Cells

Biomass: Remove the biomass from the broth using a nylon cloth with pore size 45 as a filter medium. Wash the biomass thoroughly with water and dry in a microwave oven set at defrost until dry (normal sample size will require about 15 mins). Store in a desiccator until cool and weigh.

Fermentation liquor: The concentration of bioactive agent in the fermentation liquor is determined by precipitation with abs ethanol. Sterile, distilled water is added if necessary to adjust the concentration to the desired level. The resulting liquid is autoclave and stored.

Medical grade: Pass the biomass-free fermentation liquor through a UF filter having a suitable cut-off value, such as e.g. a cut-off value of 300 kD. When 70-80% of the liquid has been removed add water to the retentate to wash the solution. Repeat until the solution has lost much (at least most of) its colour and appears clean.

Example 2

Protocol for cultivation of *Trametes* sp.—and polysaccharides obtained from such a cultivation.

*Trametes versicolour*

A *Trametes* sp. fermentation, in the cultivation medium used in Example 1, takes about 7 days. The initial pH is 4.7, final pH is 3. The final biomass concentration is about 7 g/l and precipitated compound is about 0.3 g/l, the monosaccharide composition of which is about 1:0.15:1:4 (glucose:galactose:mannose). The fermentation liquid contains, after removal of biomass, no detectable free glucose, Example 3

Protocol for cultivation of *Schizophyllum* sp.—and polysaccharides obtained from such a cultivation.

*Schizophyllum commune*

This fermentation, using the same medium as in example 1, takes about 3 days. pH falls from 4.7 to 3.3 and the biomass concentration at the end of the fermentation is about 8 g/l. The fermentation broth, after removal of biomass, contains no detectable free glucose. The precipitated product concentration is about 0.6 g/l. The monosaccharide composition is about 1:0.1:0.65.

Example 4

Bacteriostatic Effect

In this example it is demonstrated that the bioactive agent obtained by the method as described in example 1 (precipitated from the Fermentation liquor) has a bacteriostatic effect on *E. coli* K12.

Method:

The bacteriostatic effect of the bioactive agent was determined by measuring the cell-density of *E. coli* K12 cultures grown in Antibiotic assay medium 3 with different dilutions of the bioactive agent. A culture without the bioactive agent in the medium was used as control.

Cells were grown in a 50 ml conical flask at 34° C. for 26 h. The dilutions of the bioactive agent in the growth medium were 1:10, 1:20 and 1:40. The optical density was measured robotically every 2 h at 660 nm.

Results:

Results are shown in FIG. 1. The optical density significantly decreased in the cultures with a 1:10 and 1:20 dilution of the bioactive agent in the stationary phase (between 15 and 26 h). The incubation with a 1:40 dilution of the bioactive agent does not lead to a significant decrease in optical density in comparison with the control.

Conclusion:

The bioactive agent is shown to have a bacteriostatic effect on *E. coli* K12.

Example 5

Anti-Tumor Effect

In this example it is demonstrated that human and mouse cancer cell lines are sensitive to treatment with bioactive agent obtained by the method as described in example 1 (precipitated from the Fermentation liquor).

Method:

The anti-tumor effect of the bioactive agent was determined by measuring the cell-viability of different human and mouse cell lines after exposure to different concentrations of Lentinex. The MRC-5 cell line from normal human fetal lung fibroblasts was used as control.

Cells were grown in a 96 well dish to a sub confluent cell layer. The medium was removed and the cells washed with PBS. Fresh medium without the bioactive agent (negative control) or containing 0.1; 0.2; 0, 3 or 0.4 mg/ml bioactive agent was added and cells were incubated for 24 h at 37° C.

A MTT-Assay, which measures the activity of the mitochondrial succinate-dehydrogenase, was used to determine the cytotoxic effect of the bioactive agent. In living cells this enzyme converts the yellow water-soluble 3-(4,5-dimethylthiazol-2-yl)-2,5-diphenyl-tetrazolium-bromide (MTT) to blue water-insoluble formazan, whereas there is no conversion in dead cells. Thus the amount of formazan directly correlates to the number of living cells.

10 µl MTT solution was added to each well and the plates were incubated for additional 2 h. 70 µl of supernatant were removed from each well and 100 µl acidic isopropanol was added to extract the formazan. After 1 h the absorption was measured at 590 nm.

Results:

Results are shown in FIG. 2. The number of viable cells was significantly decreased in all cancer cell lines after incubation with the bioactive agent for 24 h. This effect increased with the concentration of the bioactive agent in the medium. In all cancer cell lines, fewer than 50% of the cells were viable after incubation with 0.4 mg/ml bioactive agent for 24 h. The most severe effect of the bioactive agent was observed in the mouse colon cancer cell line C-26, where there were almost no viable cells after the incubation with 0.4 mg/ml bioactive agent for 24 h.

Conclusion:

The bioactive agent is shown to have a cytotoxic effect specifically directed against cancer cells, and not normal cells.

Example 7

For a determination of immunostimulating characteristics, the following method may be used: 12 weeks old Sprague Dawley rats receives 1 mg of the composition according to the invention in 0.5 ml 0.09 saline (i.p.) 2 days before the immunisation. Control animals receives 1 mg casein. The animals are immunised with BSA (0.5 mg) in 0.25 "Freunds Complete Adjuvant" and blood samples are obtained after 11 days for measurement of the antibody response. The specific anti-BSA antibody concentration is determined against an absolute standard of antibody BSA by means of "sandwich" ELISA.

The invention claimed is:

1. A pharmaceutical kit of parts comprising
    a) an anti-cancer medicament, and
    b) a Basidiomycete bioactive agent, said Basidiomycete being of the genus *Lentinus*, in solid or liquid form,
wherein said bioactive agent comprises a heteropolymeric polysaccharide comprising the monosaccharide units glucose, galactose and mannose,
wherein said heteropolymeric polysaccharide has a molecular weight in the size range of from 100,000 g/mol to 1,000,000 g/mol,
wherein said bioactive agent is isolated from the liquid growth medium of a liquid culture of the genus *Lentinus* after the mycelium has been removed from said liquid culture, and wherein said liquid growth medium is not subjected to alcohol precipitation.

2. The kit according to claim 1, wherein the bioactive agent is precipitated by ultracentrifugation.

3. The kit according to claim 1, wherein said anticancer medicament is suitable for administration simultaneously with the administration of the bioactive agent.

4. The kit of claim 1, further comprising instructions for a dosing regime.

5. The kit of claim 1, wherein said polysaccharide does not comprise a peptide or a polypeptide.

6. A method of treatment comprising the step of administering the anti-cancer medicament and the bioactive agent of the pharmaceutical kit of parts according to claim 1 to an individual in need thereof according to a set dosage regime.

7. The method of claim 6, wherein the anti-cancer medicament and the bioactive agent are administered simultaneously.

8. The method of claim 7, wherein the anti-cancer medicament and the bioactive agent are administered as a co-formulation.

9. The method of claim 6, wherein the anti-cancer medicament and the bioactive agent are administered sequentially.

10. The kit of claim 1, wherein the bioactive agent is obtainable from *Lentinus edodes*.

* * * * *